United States Patent
Martinez Botella et al.

(10) Patent No.: US 12,071,453 B2
(45) Date of Patent: Aug. 27, 2024

(54) NEUROACTIVE STEROIDS, COMPOSITIONS, AND USES THEREOF

(71) Applicant: Sage Therapeutics, Inc., Cambridge, MA (US)

(72) Inventors: Gabriel Martinez Botella, Wayland, MA (US); Boyd L. Harrison, Princeton Junction, NJ (US); Albert Jean Robichaud, Boston, MA (US); Francesco G. Salituro, Marlborough, MA (US); Robert Jason Herr, Voorheesville, NY (US); Robert Borbo Kargbo, Guilderland, NY (US)

(73) Assignee: Sage Therapeutics, Inc., Cambridge, MA (US)

( * ) Notice: Subject to any disclaimer, the term of this patent is extended or adjusted under 35 U.S.C. 154(b) by 0 days.

(21) Appl. No.: 17/952,694

(22) Filed: Sep. 26, 2022

(65) Prior Publication Data

US 2023/0279044 A1   Sep. 7, 2023
US 2024/0239836 A9   Jul. 18, 2024

Related U.S. Application Data

(63) Continuation of application No. 16/843,822, filed on Apr. 8, 2020, now Pat. No. 11,498,940, which is a continuation of application No. 14/913,920, filed as application No. PCT/US2014/052417 on Aug. 22, 2014, now abandoned.

(60) Provisional application No. 62/014,018, filed on Jun. 18, 2014, provisional application No. 61/869,440, filed on Aug. 23, 2013, provisional application No. 61/869,446, filed on Aug. 23, 2013.

(51) Int. Cl.
| | |
|---|---|
| C07J 43/00 | (2006.01) |
| A61K 31/58 | (2006.01) |
| A61K 45/06 | (2006.01) |
| C07J 7/00 | (2006.01) |
| C07J 1/00 | (2006.01) |
| C07J 13/00 | (2006.01) |
| C07J 21/00 | (2006.01) |

(52) U.S. Cl.
CPC ............ *C07J 43/003* (2013.01); *A61K 31/58* (2013.01); *A61K 45/06* (2013.01); *C07J 1/0059* (2013.01); *C07J 7/002* (2013.01); *C07J 7/007* (2013.01); *C07J 7/0085* (2013.01); *C07J 13/007* (2013.01); *C07J 21/00* (2013.01); *C07J 21/008* (2013.01)

(58) Field of Classification Search
CPC . C07J 1/0059; C07J 7/002; C07J 7/007; C07J 13/007; C07J 43/003; A61K 31/58
See application file for complete search history.

(56) References Cited

U.S. PATENT DOCUMENTS

| | | |
|---|---|---|
| 2,856,415 A | 10/1958 | Mihina |
| 3,169,134 A | 2/1965 | Klimstra et al. |
| 3,206,459 A | 9/1965 | Cross |
| 3,580,937 A | 5/1971 | Campbell et al. |
| 3,943,124 A | 3/1976 | Phillipps et al. |
| 3,983,111 A | 9/1976 | Phillipps et al. |
| 3,998,829 A | 12/1976 | Phillips et al. |
| 4,029,777 A | 6/1977 | Engelfried et al. |
| 4,071,625 A | 1/1978 | Grunwell et al. |
| 4,179,336 A | 12/1979 | Weber et al. |
| 4,192,871 A | 3/1980 | Phillipps et al. |
| 4,389,345 A | 6/1983 | Lenz |
| 5,593,983 A | 1/1997 | Campbell |
| 5,721,227 A | 2/1998 | Melloni et al. |
| 5,925,630 A | 7/1999 | Upasani et al. |

(Continued)

FOREIGN PATENT DOCUMENTS

| | | |
|---|---|---|
| CA | 2831054 A1 | 12/2013 |
| CN | 1190404 A | 8/1998 |

(Continued)

OTHER PUBLICATIONS

Adams et al., "The estrogenic activity and enzymic oxidation of 17b-estradiol-17a-d1", Steroids, Elsevier Science Publishers, (1965), pp. 75-84.

(Continued)

*Primary Examiner* — Barbara P Badio
(74) *Attorney, Agent, or Firm* — Honigman LLP; Andrew N. Weber; Jonathan P. O'Brien

(57) ABSTRACT

Described herein are neuroactive steroids of the Formula (I): or a pharmaceutically acceptable salt thereof; wherein ------, $R^1$, $R^2$, $R^3$, A and L are as defined herein. Such compounds are envisioned, in certain embodiments, to behave as GABA modulators. The present invention also provides pharmaceutical compositions comprising a compound of the present invention and methods of use and treatment, e.g., such for inducing sedation and/or anesthesia.

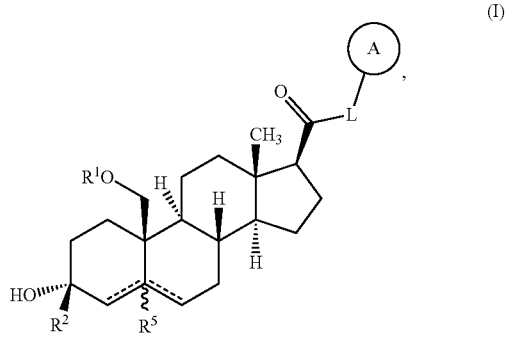

33 Claims, No Drawings

(56) References Cited

U.S. PATENT DOCUMENTS

| | | |
|---|---|---|
| 5,935,545 A | 8/1999 | Leary et al. |
| 5,939,545 A | 8/1999 | Upasani et al. |
| 6,133,280 A | 10/2000 | Brodie et al. |
| 6,143,736 A | 11/2000 | Upasani et al. |
| 6,277,838 B1 | 8/2001 | Upasani et al. |
| 6,717,002 B2 | 4/2004 | Yano et al. |
| 6,844,456 B2 | 1/2005 | Covey |
| 7,064,116 B2 | 6/2006 | Calogeropoulou et al. |
| 7,781,421 B2 | 8/2010 | Covey et al. |
| 8,759,330 B2 | 6/2014 | Covey et al. |
| 8,939,545 B2 | 1/2015 | Tunmore et al. |
| 9,156,876 B2 | 10/2015 | Covey |
| 9,365,611 B2 | 6/2016 | Martinez Botella et al. |
| 9,512,165 B2 | 12/2016 | Martinez Botella et al. |
| 9,630,986 B2 | 4/2017 | Covey et al. |
| 9,725,481 B2 | 8/2017 | Martinez Botella et al. |
| 9,765,110 B2 | 9/2017 | Covey |
| 10,246,482 B2 | 4/2019 | Harrison et al. |
| 10,329,320 B2 | 6/2019 | Robichaud et al. |
| 2002/0091112 A1 | 7/2002 | Menzenbach et al. |
| 2005/0176976 A1 | 8/2005 | Calogeropoulou et al. |
| 2006/0094696 A1 | 5/2006 | Leese et al. |
| 2007/0014719 A1 | 1/2007 | Reading et al. |
| 2008/0269183 A1 | 10/2008 | Mellon et al. |
| 2009/0048218 A1 | 2/2009 | Kuhnke et al. |
| 2010/0152840 A1 | 6/2010 | Seguin et al. |
| 2010/0234335 A1 | 9/2010 | Gravanis et al. |
| 2010/0317638 A1 | 12/2010 | Covey et al. |
| 2011/0152840 A1 | 6/2011 | Lee et al. |
| 2011/0172242 A1 | 7/2011 | Helton et al. |
| 2014/0017675 A1 | 1/2014 | Ito |
| 2014/0050789 A1 | 2/2014 | Rogawski et al. |
| 2014/0094619 A1 | 4/2014 | Runyon et al. |
| 2014/0148412 A1 | 5/2014 | Hogenkamp |
| 2014/0235600 A1 | 8/2014 | Covey et al. |
| 2014/0249120 A1 | 9/2014 | Covey et al. |
| 2014/0275241 A1 | 9/2014 | Covey |
| 2015/0291654 A1 | 10/2015 | Upasani et al. |
| 2015/0315230 A1 | 11/2015 | Covey et al. |
| 2016/0068563 A1 | 3/2016 | Martinez Botella et al. |
| 2016/0083418 A1 | 3/2016 | Martinez Botella et al. |
| 2016/0108080 A1 | 4/2016 | Martinez Botella et al. |
| 2016/0229887 A1 | 8/2016 | Martinez Botella et al. |
| 2017/0240589 A1 | 8/2017 | Martinez Botella et al. |
| 2017/0247406 A1 | 8/2017 | Harrison et al. |
| 2018/0071315 A1 | 3/2018 | Cashman et al. |
| 2019/0160078 A1 | 5/2019 | Masuoka et al. |
| 2019/0177358 A1 | 6/2019 | Martinez Botella et al. |
| 2019/0337975 A1 | 11/2019 | Bryson et al. |

FOREIGN PATENT DOCUMENTS

| | | |
|---|---|---|
| CN | 101412742 A | 4/2009 |
| CN | 101624414 A | 1/2010 |
| CN | 104136452 A | 11/2014 |
| CN | 108727453 A | 11/2018 |
| DE | 2330342 A1 | 1/1974 |
| DE | 2526373 A1 | 12/1976 |
| DE | 2700267 A1 | 7/1977 |
| DE | 2632677 A1 | 1/1978 |
| EP | 0104489 A1 | 4/1984 |
| EP | 0554436 A1 | 8/1993 |
| EP | 0656365 A1 | 6/1995 |
| EP | 0701444 A1 | 3/1996 |
| EP | 1038880 A2 | 9/2000 |
| FR | 1994 M | 9/1963 |
| GB | 1380246 A | 1/1975 |
| GB | 1430942 A | 4/1976 |
| GB | 1494097 A | 12/1977 |
| GB | 1538869 A | 1/1979 |
| GB | 1570394 A | 7/1980 |
| GB | 1581234 A | 12/1980 |
| GB | 1581235 A | 12/1980 |
| RU | 2194712 C2 | 12/2002 |
| RU | 2243232 C2 | 12/2004 |
| RU | 2010/100334 A | 7/2011 |
| RU | 2675855 C2 | 12/2018 |
| WO | 1991/016897 A1 | 11/1991 |
| WO | 1993/03732 A1 | 3/1993 |
| WO | 1993/05786 A1 | 4/1993 |
| WO | 1993/18053 A1 | 9/1993 |
| WO | 1994/27608 A1 | 12/1994 |
| WO | 1995/021617 A1 | 8/1995 |
| WO | 1996/003421 A1 | 2/1996 |
| WO | 1996/016076 A1 | 5/1996 |
| WO | 1996/40043 A2 | 12/1996 |
| WO | 1998/005337 A1 | 2/1998 |
| WO | 2000/066614 A1 | 11/2000 |
| WO | 2005/051972 A1 | 6/2005 |
| WO | 2005/105822 A2 | 11/2005 |
| WO | 2006/037016 A2 | 4/2006 |
| WO | 2006/131392 A1 | 12/2006 |
| WO | 2008/151745 A1 | 12/2008 |
| WO | 2008/157460 A1 | 12/2008 |
| WO | 2010/003391 A2 | 1/2010 |
| WO | 2010/054158 A2 | 5/2010 |
| WO | 2010/107815 A1 | 9/2010 |
| WO | 2012/013816 A2 | 7/2011 |
| WO | 2012/083090 A2 | 6/2012 |
| WO | 2012/109752 A1 | 8/2012 |
| WO | 2012/110010 A1 | 8/2012 |
| WO | 2012/116290 A2 | 8/2012 |
| WO | 2013/019711 A2 | 2/2013 |
| WO | 2013/036835 A1 | 3/2013 |
| WO | 2013/056181 A1 | 4/2013 |
| WO | 2013/188792 A2 | 12/2013 |
| WO | 2013/192097 A1 | 12/2013 |
| WO | 2014/058736 A1 | 4/2014 |
| WO | 2014/071449 A1 | 5/2014 |
| WO | 2014/100228 A1 | 6/2014 |
| WO | 2014/108808 A2 | 7/2014 |
| WO | 2014/122480 A1 | 8/2014 |
| WO | 2014/169831 A1 | 10/2014 |
| WO | 2014/169832 A1 | 10/2014 |
| WO | 2014/169833 A1 | 10/2014 |
| WO | 2014/169836 A1 | 10/2014 |
| WO | 2015/010054 A2 | 1/2015 |
| WO | 2015/027227 A1 | 2/2015 |
| WO | 2015/180679 A1 | 12/2015 |
| WO | 2015/195962 A1 | 12/2015 |
| WO | 2016/134301 A1 | 2/2016 |
| WO | 2016/036724 A1 | 3/2016 |
| WO | 2016/061527 A1 | 4/2016 |
| WO | 2016/061537 A1 | 4/2016 |
| WO | 2016/082789 A1 | 6/2016 |
| WO | 2016/123056 A1 | 8/2016 |
| WO | 2016/131414 A1 | 8/2016 |
| WO | 2016/209847 A1 | 12/2016 |
| WO | 2017/044659 A1 | 3/2017 |
| WO | 2017/066626 A1 | 4/2017 |
| WO | 2017/087864 A1 | 5/2017 |
| WO | 2017/156103 A1 | 9/2017 |
| WO | 2017/156418 A1 | 9/2017 |
| WO | 2018/013613 A1 | 1/2018 |
| WO | 2018/013615 A1 | 1/2018 |
| WO | 2018/039378 A1 | 3/2018 |
| WO | 2019/018119 A1 | 1/2019 |
| WO | 2019/045121 A1 | 3/2019 |
| WO | 2019/051264 A1 | 3/2019 |
| WO | 2019094724 A1 | 5/2019 |

OTHER PUBLICATIONS

Anderson et al., "Anesthetic Activity of Novel Water-Soluble 2b-Morpholinyl Steroids and Their Modulatory Effects at GABA-A Receptors", Journal of Medicinal Chemistry., 1997, vol. 40, pp. 1668-1681.

Anderson et al., "Conformationally Constrained Anesthetic Steroids That Modulate GABAA Receptors," Journal of Medicinal Chemistry, 2000, vol. 43, No. 22, pp. 4118-4125.

Anonymous: "Archive History for NCT03000530", Aug. 4, 2017, Retrieved from the Internet: <URL:https://www.clinicaltrials.gov/

(56) References Cited

OTHER PUBLICATIONS ct2/his> tory/NCT03000530?V_6=View#StudyPageTop; [retrieved on Nov. 20, 2018].
Atack, "Development of Subtype-Selective GABAA Receptor Compounds for the Treatment of Anxiety, Sleep Disorders and Epilepsy", GABA and Sleep. Molecular, Functional and Clinical Aspects. 2010, pp. 25-72.
Banday et al., "D-ring substituted 1,2,3-triazolyl 20-keto pregnenanes as potential anticancer agents: Synthesis and biological evaluation", Steroids, (2010), vol. 75, No. 12, pp. 801-804, Abstract.
Bandyopadhyaya et al., "Neurosteroid Analogs. 15. A Comparative Study of the Anesthetic and GABAergic Actions of Alphaxalone, D16-Alphaxalone and TheirCorresponding 17-Carbonitrile Analogs," Bioorganic & Medicinal Chemistry Letters 20:6680-6684 (2010).
Berge et al., J. Pharmaceutical Sciences, 1977, vol. 66, pp. 1-19.
Bernstein, BE., "Rett Syndrome Medication" [online], Updated Feb. 6, 2017, [retrieved on May 3, 2018]. Retrieved from the website Medscape, using internet URL: <https://emedicine.medscape.com/article/916377-medication>.
Bjorkhem et al., "Steroid hormone metabolism in developing rates", Eur. J.Biochem., 1972, vol. 27, No. 2, pp. 318-326.
Botella et al., "Neuroactive Steroids. 1. Positive Allosteric Modulators of the (g-Aminobutyric Acid)A Receptor: Structure-Activity Relationships of Heterocyclic Substitution at C-21", Journal of Medical Chemistry, 2015, pp. 3500-3511.
Botella et al., "Neuroactive Steroids. 2. 3a-Hydroxy-3b-methyl-21-(4-cyano-1H-pyrazol-1-yl)-19-nor-5b-pregnan-20-one (SAGE-217): A Clinical Next Generation Neuroactive Steroid Positive Allosteric Modulator of the (g-Aminobutyric Acid) A Receptor" Journal of Medical Chemistry, 2017, 10 pp. A-J.
CAS Registry No. 1040410-23-8 [Database Registry in STN]; STN Entry Date: Aug. 12, 2008; Chemical Name: 1-((3S,8R,9S,10S,13S,14S,17S)-3-hydroxy-10, 13-dimethyl-2,3,4,5,8,9, 10, 11, 12, 13, 14, 15, 16, 17-tetradecahydro-1H-cyclopenta[a]phenanthren-17-yl)ethan-1-one.
CAS Registry No. 162882-77-1 [Database Registry in STN]; STN Entry Date: May 11, 1995; Chemical Name: (3a,5b)-3-Hydroxy-3-methyl-19-norpregnan-20-one.
CAS Registry No. 162883-68-3 [Database Registry in STN]; STN Entry Date: May 11, 1995; Chemical Name: 19-Norpregnan-20-one, 3-hydroxy-3-methyl-, (3a,5a) -.
Caspi et al., "Stereochemistry of 19-hydroxy-19alpha-methyl steroids," Chemical Communications, 1966, vol. 7, pp. 209-210.
Cerny et al., "Syntheses of 19-[O-(carboxymethyl)oxime] haptens of epipregnanolone and pregnanolone", Steroids, 2006, vol. 71(2), pp. 120-128.
Cerny et al., "Synthetic approach to 5alpha-pregnanolone 19-[0-(carboxymethyl) oxime] derivatives", Collection of Czechoslovak Chemical Communications, 2004, vol. 69, No. 9, pp. 1805-1817.
Chen C Y et al: "The mechanism investigation in substitution of 21-bromo-3@a-hydroxyl-3@b-methoxymethyl-5@a-pregnan-20-one with nucleophiles", Steroids, vol. 71, No. 11-12, Nov. 1, 2006 (Nov. 1, 2006), pp. 942-948.
Chisari, Magiangela et al., "The Influence of Neuroactive Steroid Lipophilicity on GABA Receptor Modulation: Evidence for a Low-Affinity Interaction", Journal of Neurophysiology (2009), vol. 102, pp. 1254-1264.
Chodounska et al., "Epalons: Synthesis of 3a, 7a-Dihydroxy-5a-Pregnan-20-One", Collection Symposium Series, vol. 63, No. 10, (1998), pp. 1543-1548.
Database CAPLUS in STN, Acc. No. 1995:986323, Upasani et al., WO 9521617 A1 (Aug. 17, 1995) (abstract). [Upasani, Ravindra B. "Androstanes and pregnanes for allosteric modulation of GABA receptor, and preparation and therapeutic uses of compounds".].
Database CAPLUS in STN, Acc. No. 1998:112239, Lan, WO 9805337 A1 (Feb. 12, 1998) (abstract). [Lan, Nancy C., "Use of GABA agonists and NMDA receptor antagonists for the treatment of migraine headache".].

Database Medline, US National Library of Medicine, Bethesda, MD, 1984, Welling: "Interactions affecting drug absorption", Database accession No. NLM6388952, abstract.
Deluca et al., "Synthesis of 3b-Hydroxy[21-14C] -5b-pregn-8(14)-en-20-one from Chenodeoxycholic Acid", Helvetica Chemica Acta, vol. 69, (1986), pp. 1844-1850.
Deniau et al., "Synthesis of fluorinated analogues of the neurosteroid GABA receptor antagonist, 17-PA", Journal of Fluorine Chemistry, (2008), vol. 129, No. 9, pp. 881-887.
D'hulst et al., "Expression of the GABAergic system in animal models for fragile X syndrome and fragile X associated tremor/ataxia syndrome (FXTAS)", Brain Research, 2008, vol. 1253, pp. 176-183.
Dorwald, "Side Reactions in Organic Synthesis", 2005, Wiley-VCH, Preface, p. IX.
Durán et al., "Synthesis of 6-thia analogs of the natural neurosteroid allopregnanolone", Tetrahedron, Elsevier Science Publishers, 2006, vol. 62, No. 20, pp. 4762-4768.
Edgar et al., "CCD-3693: An Orally Bioavailable Analog of the Endogenous Neuroactive Steroid, Pregnanolone, Demonstrates Potent Sedative Hypnotic Actions in the Rat" The Journal of Pharmacology and Experimental Therapeutics (1997) vol. 282, No. 1, pp. 420-429.
Eimon et al., "Brain activity patterns in high-throughput electrophysiology screen predict both drug efficacies and side effects", Nature Communications, (2018) 9:219, pp. 1-14.
Evers et al., "A Synthetic 18-Norsleroid Distinguishes Between Two Neuroactive Steroid Binding Sites on GABAA Receptors", Journal of Pharmacology and Experimental Therapeutics, 2010, vol. 333, No. 2, pp. 404-413.
Extended European Search Report for application 14785712.2 PCT/CN2014075594 dated Aug. 26, 2016.
Extended European Search Report for application 14786089.4; PCT/CN2014075593 dated Aug. 26, 2016.
Fajkos et al., "Steroids. XXIII. Synthesis and configuration of the two stereoisomeric 3b-hydroxy-16-acetylandrostanes", Chemicke Listy pro Vedu a Prumysl, 1956, vol. 50, pp. 791-799.
Fesik et al., "Geometric Requirements for Membrance Perturbation and Anesthetic Activity", Molecular Pharmacology, 1985, vol. 27, pp. 624-629.
Galofre et al., "GABAA receptor and cell membrane potential as functional endpoints in cultured neurons to evaluate chemicals for human acute toxicity", Neurotoxicology and Teratology, (2009), vol. 32, pp. 52-61.
Gasior et al., "Neuroactive steroids: potential therapeutic use in neurological and psychiatric disorders", Trends in Pharmacological Science, (1999), vol. 20, No. 3, pp. 107-112.
Gottesmann, "GABA Mechanisms and Sleep", Neuroscience, (2002), vol. 111, No. 2, pp. 231-239.
Green et al., "The nonfeminizing enantiomer of 17b-estradiol exerts protective effects in neuronal cultures and a rat model of cerebral ischemia", Endocrinology, 2001, vol. 142, pp. 400-406.
Guardia et al., "GABAergic and Glutamatergic Modulation in Binge Eating: Therapeutic Approach", Current pharmaceutical design, 2011, vol. 17, No. 14, pp. 1396-1409.
Gunduz-Bruce et al., "Sage-217 in Major Depressive Disorder: A Multicenter, Randomized, Double-Blind, Phase 2 Placebo-Controlled Trial", European Nueuropsychopharmacology, vol. 29, 2019, pp. S59-S-60, Abstract.
Gunduz-Bruce et al., "Sage-217 in Subjects with Major Depressive Disorder: Efficacy and Safety Results from Open-Label Part A of a Phase 2a Study", Poster, (Presented on Sep. 2-5, 2017 at the 30th ECNP Congress, Paris, France.
Gustafsson et al., "Steroid excretion patterns in urine from ovariectomized and adrenalectomized rats", Biochmica ET Biophysica ACTA—Lipids and Lipid Metabolism, Elsevier Science BV, 1972, vol. 280, No. 1, pp. 182-186.
Gustafsson et al., "Steroids in Germfree and Conventional Rats. 7. Identification of C19 and C21 Steroids in faeces from Conventional Rats", European Journal of Biochemistry, 1968, vol. 6, No. 2, pp. 248-255.
Gyermek et al., "Steroids, CCCX. 1 Structure-Activity Relationship of Some Steroidal Hypnotic Agents", Journal of Medicinal Chemistry, 1968, vol. 11, No. 1, pp. 117-125.

(56) References Cited

OTHER PUBLICATIONS

Han et al., "Neurosteroid Analogs. 3. The Synthesis and Electrophysiological Evaluation of Benz[e]indene Congeners of Neuroactive Steroids Having the 5b-Configuration", Journal of of Medicinal Chemistry, 1995, vol. 38, No. 22, pp. 4548-4556.

Han et al., "Neurosteroid Analogues. 4. The Effect of Methyl Substitution at the C-5 and C-10 Positions of Neurosteroids on Electrophysiological Activity at GABAA Receptors", Journal of Medicinal Chemistry, (1996), vol. 39, pp. 4218-4232.

Harrison et al., "Structure-Activity Relationships for Steroid Interaction with the y-Aminobutyric AcidA Receptor Complex" The Journal of Pharmacology and Experimental Therapeutics (1987) vol. 241, No. 1, pp. 346-353.

Hauser et al., "Steroids. CCV. Fragmentations and intramolecular abstractions of tertiary hydrogen atoms by primary oxy radicals with fixed reaction centers", Helv. Chim. Acta, 1964, vol. 47, pp. 1961-1979.

Hawkins et al., "The synthetic neuroactive steroid SGE-516 reduces seizure burden and improves survival in a Dravet syndrome mouse model", Science Reports, (2017), pp. 1-8.

Hawkinson et al., "3a-Hydroxy-3b-trifluoromethyl-5a-pregnan-20-one (Co 2-1970): A Partial Agonist at the Neuroactive Steroid Site of the y-Aminobutyric acidA Receptor" Molecular Pharmacology (1996) vol. 49, pp. 897-906.

Hawkinson et al., "Correlation of Neuroactive Steroid Modulation of [35S]t-Butylbicyclophosphorothionate and [3H] Flunitrazepam Binding and y-Aminobutyric AcidA Receptor Function", Molecular Pharmacology (1994) vol. 46, pp. 977-985.

Hawkinson et al., "Substituted 3b-Phenylethynyl Derivatives of 3a-Hydroxy-5a-pregnan-20-one: Remarkably Potent Neuroactive Steroid Modulators of y-Aminobutyric AcidA Receptors", The Journal of Pharmacology and Experimental Therapeutics(1998), vol. 287, No. 1, pp. 198-207.

Heard et al., "Steroids. VII. Preparation of of androstan-3(b)-ol-7-one from from dehydroisoandrosterone", Journal of Biological Chemistry, 1946, vol. 165, pp. 677-685.

Hewett et al., "Amino steroids. Part III. 2- and 3-Amino-5a-androstanes", Journal of the Chemical Society, 1968, vol. 9, pp. 1134-1140.

Hill et al., "Pholochemische Reaktionen. 32 Milleilung. UV-Bestrahlung von gesattigten und bela, gamma- ngesalligten, homoallylisch konjugierten steroidaldehyden", Helvetica Chimica Acta, 1946, vol. 49, No. 1, pp. 292-311.

Hogenkamp et al., "Pharmacological profile of a 17b-heteroaryl-substituted neuroactive steroid", Psychopharmacology, vol. 231, (2014), pp. 3517-3524.

Hogenkamp et al., "Synthesis and in Vitro Activity of 3b-Substituted-3a-hydroxypregnan-20-ones: Allosteric Modulators of the GABAA Receptor", Journal of Medicinal Chemistry, (1997), vol. 40, pp. 61-72.

Hu et al., "Neurosteroid analogues. Part 5. Enantiomers of neuroactive steroids and benz[e]indenes: total synthesis, 18 electrophysiological effects on GABAA receptor function and anesthetic actions in tadpoles", J. Chem. Soc. Perkin Trans 1, 1997, pp. 3665-3671.

Hu et al., "Neurosteroid Analogues: Structure-Activity Studies of Benz(e] indene Modulators of GABAA Receptor Function. 1. The Effect of 6-Melhyl Substitution on the Electrophysiological Activity of 7-Substituted Benz[e]indene-3-carbonitriles", Journal of Medicinal Chemistry, (1993), pp. 3956-3967.

Im et al., "Studies on the Mechanism of Interactions between Anesthetic Steroids and y-Aminobutyric AcidA Receptors", Molecular Pharmacology (1990), 37(3), pp. 429-434.

International Search Report and Written Opinion for Corresponding International Application No. PCT/CN2014/078820 dated Feb. 27, 2015.

International Search Report and Written Opinion for Corresponding International Application No. PCT/CN2015/080216 dated Aug. 3, 2015.

International Search Report and Written Opinion for Corresponding International Application No. PCT/CN2015/095765 dated Mar. 4, 2016.

International Search Report and Written Opinion for Corresponding International Application No. PCT/US15/56054 dated Feb. 9, 2016.

International Search Report and Written Opinion for Corresponding International Application No. PCT/US2013/076214 dated Jun. 5, 2014.

International Search Report and Written Opinion for Corresponding International Application No. PCT/US2014/052417 dated Nov. 19, 2014.

International Search Report and Written Opinion for Corresponding International Application No. PCT/US2014/092369 dated Aug. 25, 2015.

International Search Report and Written Opinion for Corresponding International Application No. PCT/US2015/036500 dated Sep. 11, 2015.

International Search Report and Written Opinion for Corresponding International Application No. PCT/US2015/056066 dated Feb. 8, 2016.

International Search Report and Written Opinion for Corresponding International Application No. PCT/US2016/014835 dated Jun. 9, 2016.

International Search Report and Written Opinion for Corresponding International Application No. PCT/US2016/018748 dated Aug. 29, 2016.

International Search Report and Written Opinion for Corresponding International Application No. PCT/US2016/062874 dated Jan. 30, 2017.

International Search Report and Written Opinion for Corresponding International Application No. PCT/US2017/041600 dated Dec. 1, 2017.

International Search Report and Written Opinion for Corresponding International Application No. PCT/US2017/041605 dated Dec. 12, 2017.

International Search Report and Written Opinion for Corresponding International Application No. PCT/US2017/048267 dated Aug. 29, 2016.

International Search Report and Written Opinion for Corresponding International Application No. PCT/US2018/050012 dated Dec. 7, 2018.

International Search Report and Written Opinion for Corresponding International Application No. PCT/US2018/051048 dated Jan. 11, 2019.

International Search Report and Written Opinion for Corresponding International Application No. PCT/US2018/064546 dated Apr. 9, 2019.

International Search Report and Written Opinion for Corresponding International Application No. PCT/US2019/036848 dated Aug. 22, 2019.

International Search Report and Written Opinion for International Application No. PCT/CN2013/074312 dated Jan. 23, 2014.

International Search Report and Written Opinion for International Application No. PCT/CN2013/074319 dated Jan. 23, 2014.

International Search Report and Written Opinion for International Application No. PCT/CN2013/074323 dated Jan. 30, 2014.

International Search Report and Written Opinion for International Application No. PCT/CN2013/074325 dated Jan. 23, 2014.

International Search Report and Written Opinion for International Application No. PCT/CN2014/075585 dated Aug. 4, 2014.

International Search Report and Written Opinion for International Application No. PCT/CN2014/075593 dated Jul. 22, 2014.

International Search Report and Written Opinion for International Application No. PCT/CN2014/075594 dated Jul. 16, 2014.

International Search Report and Written Opinion for International Application No. PCT/CN2014/075600 dated Jul. 29, 2014.

International Search Report and Written Opinion for International Application No. PCT/US14/47246, mailed Jan. 22, 2015.

International Search Report and Written Opinion for International Application No. PCT/US2018/067277 dated May 24, 2019.

International Search Report and Written Opinion for International Application No. PCT/US2018/067306 dated May 28, 2019.

(56) References Cited

OTHER PUBLICATIONS

International Search Report and Written Opinion for International Application No. PCT/US2019/013315 dated Jun. 14, 2019.
International Search Report for International Application No. PCT/US2012/060136 dated Mar. 27, 2013.
Itoh et al., "On the acid-catalyzed d-homoannulation of pregnanetriol 20-sulfate and its c-20 isomeric sulfate", Chemical and Pharmaceutical Bulletin. 1994, vol. 42, No. 9, pp. 1736-1744.
Jiang et al., "Neurosteroid analogues. 9. Conformationally constrained pregnanes: structure-activity studies of 13,24-cyclo-18, 21-dinorcholane analogues of the GABA modulatory and anesthetic steroids (3a,5a)- and (3a,5a)-3-hydroxypregnan-20-one", Journal of Medicinal Chemistry, 2003, vol. 46, pp. 5334-5348.
Jungmann et al., "7-Keto-5b-ätiansäure-Derivate. über Gallensäuren und verwandte Stoffe, 51. Mitteilung [Bile acids and related substances. LI. 7-0xo-5. beta.-etianic acid derivatives]", Helvetica Chimica Acta, vol. 41, No. 5, (1958), pp. 1206-1233.
Kaji et al., "Synthesis of 3-epi-6, 7-dideoxyxestobergsterol A", Chem. & Pharm. Bulletin, 2000, vol. 48, No. 10, pp. 1480-1483.
Kanes et al., "A multiple-ascending dose study of the neuroactive steroid Sage-217", Biological Psychiatry, vol. 81, No. 10, 2017, pp. S347.
Kanes et al., "A single-ascending dose study of the neuroactive steroid Sage-217", Biological Psychiatry, vol. 81, No. 10, 2017, pp. S31.
Kasal et al., "Neurosteroid analogues: synthesis of 6-aza-allopregnanolone", Tetrahedron, Elsevier Science Publishers, 2005, vol. 61, No. 9, pp. 2269-2278.
Katona et al., "Neurosteroid analogues. 12. Potent enhancement of GABA-mediated chloride currents at GABAA receptors by ent-androgens", European Journal of Medicinal Chemistry, 2008, vol. 43, No. 1, pp. 107-113.
Knox et al., "Steroids. CCLXXVIII. Reductions of 19-substituted androst-4-en-3-ones and related compounds", Journal of Organic Chemistry, 1965, vol. 30, No. 7, pp. 2198-2205.
Krafft et al., "Synthesis of the C/D/E and A/B Rings of Xestobergsterol—(A)", Journal of Organic Chemistry, American Chemical Society, vol. 64, No. 7, (1999), pp. 2475-2485.
Krishnan et al., "Neurosteroid Analogues. Chapter 17. Inverted Binding Orientations of Androsterone Enantiomers at the Steroid Potentiation Site on y-Aminobutyric Acid Type A Receptors", Journal of Medicinal Chemistry, 2012, vol. 55, No. 3, pp. 1334-1345.
Lehmann et al., "Schweinegallensäuren Der Abbau von Hyocholsäure zu Pregnanderivaten", vol. 32, No. 3-4, (1966), pp. 217-224.
Lewbart et al., "Oxidation of Steroidal a-Ketols to Glyoxals with Cupric Acetate", Journal of Organic Chemistry, (1963), vol. 28, No. 8, pp. 2001-2006.
Li et al., "Neuroactive Steroids and Human Recombinant p1 GABAc Receptors", Journal of Pharmacology and Experimental Therapeutics, (2007), vol. 323, pp. 236-247.
Mangialasche et al., "Alzheimer's disease: clinical trials and drug development", Lance Neurology, vol. 9 (2010), pp. 702-716.
Matsui et al., "Comparative fate of testosterone and testosterone sulfate in female rats: C19O2 and C19O3 steroid metabolites in the bile", Journal of Steroid Biochemistry, 1977, 8(4), pp. 323-328.
Möhler, "The GABA system in anxiety and depression and its therapeutic potential", Neuropharmacology, (2012) 62; pp. 42-53.
Mok et al., "Evidence that 5a-pregnan-3a-ol-20-one is the metabolite responsible for progesterone anesthesia", Brain Research (1990), 533(1), pp. 42-45.
Morrow et al., "Characterization of Steroid Interactions with gamma-Aminobutyric Acid Receptor-Gated Chloride Ion Channels: Evidence for Multiple Steroid Recognition Sites", 1989, Molecular Pharmacology, 37, pp. 263-270.
Nicoletti et al., "Synthesis and GABAA receptor activity of 6-oxa-analogs of neurosteroids", Steroids, Elsevier Science Publishers 2000, vol. 65, No. 6, pp. 349-356.
Nilsson et al., "Neurosteroid analogues. 6. The synthesis and GABAA receptor pharmacology of enantiomers of dehydroepiandrosterone sulfate, pregnenolone sulfate, and (3a,5b)-3-hydroxypregnan-20-one sulfate", Journal of Medicinal Chemistry, 1998, vol. 41, pp. 2604-2613.
Notification of Transmittal of the International Search Report and the Written Opinion of the International Searching authority, or the Declaration, International Application No. PCT/US13/45933, Dec. 3, 2013, 5 Pages.
Paradiso et al., "Steroid Inhibition of Rat Neuronal Nicotinic a4B2 Receptors Expressed in HEK 293 Cells", Journal of Molecular Pharmacology, (2000), vol. 58, pp. 341-351.
Paul et al., "Neuroactive Steroids", The Journal of the Federation of American Societies for Experimental Biology, (1992), pp. 2311-2322.
Peart et al., "Hydroxylation of steroids by Fusarium oxysporum, Exophiala jeanselmei and Ceratocystis paradoxa", Steroids, vol. 76, No. 12, (2011), pp. 1317-1330.
Pechet et al., "Metabolism of 19-hydroxycorticosterone. Isolation and characterization of three metabolites", Journal of Biological Chemistry, Jan. 1, 1961, vol. 236, No. 10, pp. PC68-PC69.
Phillipps et al., "A New Series of Steroidal Antidysrhythmic Agents," J. Steroid Biochem. 19(1):759-765 (1983).
Phillipps et al., "Water-soluble Steroidal Anaesthetics", Journal of Steroid Biochemistry 11:79-86 (1979).
Phillipps, "Structure-Activity Relationships in Steroidal Anaesthetics", Journal of Steroid Biochemistry, (1975), vol. 6, pp. 607-613.
Phillipps, "Structure-Activity Relationships in Steroidal Anaesthetics", Nol. Mech. Gen. Anaesth. Glaxo Symposium, (1974), pp. 32-47.
PubChem CID: 70249446, [database online], created Dec. 1, 2012 [retrieved on Mar. 21, 2018]. Retrieved from the National Center for Biotechnology Information, PubChem Compound Database, using internet URL: <https://pubchem.ncbi.nlm.nih.gov/compound/70249446>.
Purdy et al., "Synthesis, Metabolism, and Pharmacological Activity of 3a-Hydroxy Steroids Which Potentiate GABA-Receptor-Mediated Chloride Ion Uptake in Rat Cerebral Cortical Synaptoneurosomes", Journal of Medicinal Chemistry, (1990), vol. 33, pp. 1572-1581.
Qian et al., "Neurosteroid Analogues, 18. Structure-Activity Studies of ent-Steroid Potentiators of y-Aminobutyric Acid Type A Receptors and Comparison of Their Activities with Those of Alphaxalone and Allopregnanolone", Journal of MedicinalChemistry, 2014, vol. 57, No. 1, pp. 171-190.
Qian et al., "The efficient and enantiospecific total synthesis of cyclopenta[b]phenanthrenes structurally related to neurosteroids", Adv. Syn. & Cata., 2010, vol. 352, Nos. 11-12, pp. 2057-2061.
Rogawski et al. (Sep. 2013) "Neuroactive Steroids for the Treatment of Status Epilepticus," Epilepsia, Author manuscript; available in PMC Sep. 1, 2014, 54(0 6):93-98, doi: 10.1111/epi.12289.
Rongone et al., "In vivo metabolism of d-homotestosterone", Steroids, vol. 1, No. 6, 1963, pp. 664-669.
Runyon et al., "17b-Nitro-5a-androstan-3a-ol and its 3b-methyl derivative: Neurosteroid analogs with potent anticonvulsant and anxiolytic activities", European Journal of Pharmacology 617, (2009), pp. 68-73.
Ruzicka et al., "Steroids and sex hormones. CXXXIX. The relation between constitution and odor of steroids. Methylandrostane and allopregnane derivatives", Helvetica Chimica Acta, 1947, vol. 30, pp. 867-878.
Rychnovsky et al., "Synthesis of ent-cholesterol, the unnatural enantiomer", Journal of Organic Chemistry, 1992, vol. 57, No. 9, pp. 2732-2736.
Sage Therapeutics: "Sage Therapeutics Advances SAGE-217 into Placebo-Controlled Phase 2 Clinical Trial in Major Depressive Disorder", Feb. 13, 2017, Retrieved from the Internet: <URL:https://investor.sagerx.com/static-fil>es/80fllf35-fc4c-4eb2-9456-3228ec891a59; [retrieved on Dec. 21, 2018].
Santaniello & Caspi, "Reduction of certain steroidal 19-sulfonic esters with metal hydrides", J. Of Ster. Biochem, 1976, vol. 7, No. 3, pp. 223-227.
Saporito et al., "Intravenously Administered Ganaxolone Blocks Diazepam-Resistant Lithium-Pilocarpine-Induced Status Epilepticus

(56) References Cited

OTHER PUBLICATIONS in Rats: Comparison with Allopregnanolone", Journal of Pharmacology Exp. Ther. 2019, 368(3), pp. 326-327.
Sarett., "A new method for the preparation of 17(alpha)-hydroxy-20-ketopregnanes", J. Am. Chem. Soc., 1948, vol. 70, pp. 1454-1458.
Scaglione et al., "Neurosteroid Analogues. 14. Alternative Ring System Scaffolds: GABA Modulatory and Anesthetic Actions of Cyclopenta[b]phenanthrenes and Cyclopenta[b]anthracenes", 2008, Journal of Medicinal Chemistry, vol. 51, pp. 1309-1318.
Shen et al., "Microbial aromatization of 19-hydroxymethylepidehydroandrosterone acetate by Corynebacterium simplex", Huaxue Xuebao, 1983, vol. 41, No. 5, pp. 473-474.
Shu et al., "Characteristics of concatemeric GABA receptors containing alpha4/d subunits expressed in Xenopus oocytes" British Journal of Pharmacology (2012) 165, 2228-2243.
Shu et al., "Photodynamic effects of steroid-conjugated fluorophores on gabaa receptors", Molecular Pharmacology, 2009, vol. 76, No. 4, pp. 754-765.
Slavíková et al., "Allopregnanolone (3a-Hydroxy-5a-pregnan-20-one) Derivatives with a Polar Chain in Position 16a: Synthesis and Activity", Journal of Medicinal Chemistry, vol. 52, No. 7, (2009), 2119-2125.
Spiegel et al., "Use of Nonaqueous Solvents in Parenteral Products", Journal of Pharmaceutical Sciences, 1963, vol. 52, No. 10, pp. 917-927.
Starnes et al., "Thin-Layer Chromatography of 17-Kelosteroid 2,4-Dinitrophenylhydrazones", Journal of Clinical Endocrinology and Metabolism, 1966, vol. 26, No. 11, pp. 1245-1250.
Stastna et al., "Neurosteroid Analogues. 16. A New Explanation for the Lack of Anesthetic Effects in D16—Alphaxalone and Identification of a D17(20) Analogue with Potent Anesthetic Activity", Journal of Medicinal Chemistry, 2011, vol. 54, No. 11, pp. 3926-3934.
Stastna et al., "Stereoselectivity of sodium borohydride reduction of saturated steroidal ketones utilizing conditions of Luche reduction", Steroids, 2010, vol. 75, No. 10, pp. 721-725.
Stastna et al., "Synthesis of C3, C5, and C7 pregnane derivatives and their effect on NMDA receptor responses in cultured rat hippocampal neurons", Steroids, Elsevier Science Publishers, vol. 74, No. 2, (2008), pp. 256-263.
Stastna et al., "The use of symmetry in enantioselective synthesis: Four pairs of chrysene enantiomers prepared from 19-nortestosterone", Org. Biomol. Chem., 2011, vol. 9, pp. 4685-4694.
Sunôl et al., "Activity of b-nor analogues of neurosteroids on the gabaa receptor in primary neuronal cultures", Journal of Medicinal Chemistry, 2006, vol. 49, No. 11, pp. 3225-3234.
Supplemental European Search Report, European Patent Application No. 14826212.4, mailed Feb. 16, 2017.
Suthoff et al., "Assessment of Health-Related Quality of Life by the SF36V2 in a Phase 2, Randomized Placebo-Controlled Trial of the GABA A Receptor Positive Allosteric Modulator Sage-217 in Major Depressive Disorder", Value in Health, vol. 21, No. Suppl. 3, 2018, Abstract.
Tsai et al., "Synthesis and antiproliferative activity of 3a-hydroxyl-3b-methoxymethyl-5a-pregnan-20-one with a C-21 hydrophilic substituent", Heteroatom Chemistry, (2017), pp. 1-9.

Upasani et al., "3a-Hydroxy-3β-(phenylethynyl)-5β-pregnan-20-ones: Synthesis and Pharmacological Activity of Neuroactive Steroids with High Affinity for GABAA Receptors", J. Med. Chem. (1997) vol. 40, No. 1, pp. 73-84.
Vanover et al., "Behavioral characterization of Co 134444 (3a-hydroxy-21-(1'-imidazolyl)-3b-methoxymethyl-5a-pregnan-20-one), a novel sedative-hypnotic neuroactive steroid", Psychopharmacology (2001), vol. 155, pp. 285-291.
Vanover et al., "Characterization of the Anxiolytic Properties of a Novel Neuroactive Steroid, Co 2-6749 (GMA-839; WAY-141839; 3a, 21-Dihydroxy-3b-trifluoromethyl-19-nor-5b-pregnan-20-one), a Selective Modulator of y-Aminobutyric AcidA Receptors", The Journal of Pharmacology and Experimental Therapeutics, (2000), vol. 295, No. 1, pp. 337-345.
Vanover et al., "Response-Rate Suppression in Operant Paradigm as Predictor of Soporific Potency in Rats and Identification of Three Novel Sedative-Hypnotic Neuroactive Steroids", The Journal of Pharmacology and Experimental Therapeutics, (1999), vol. 291, No. 3, pp. 1317-1323.
Veleiro et al., "Structure-activity relationships of neuroactive steroids acting on the gabaa receptor", Current Medicinal Chemistry, 2009, vol. 16, No. 4, pp. 455-472.
Veleiro et al., "Synthesis and GABAA Receptor Acitivity of a6, 19-Oxido Analogue of Pregnanolone", Bioorganic & Medicinal Chemistry Letters, (2003), vol. 13, pp. 343-345.
Welling, "Interactions affecting drug absorption", Clinical Pharmacokinetics, vol. 9, No. 5, Sep. 1984 (Sep. 1984), pp. 404-434.
Wicha et al., "Transformations of steroidal neopentyl systems. II. Migration of acetate from the 3beta- to the 19-hydroxyl in delta 5 and A/B-trans steroids", Canadian Journal of Chemistry, 1967, vol. 45, No. 7, pp. 707-711.
Wicha et al., "Transformations of steroidal neopentyl systems. IV. Stereochemistry of Products of Reaction of Methyllithium with Steroidal A5-19-aldehydes", Journal of the Chemical Society (Section) C: Organic, 1968, vol. 14, 1740-1746.
Wicha et al., "Transformations of steroidal neopentyl systems. V. Synthesis and proof of the configuration of 19amethyl-19β-alcohols", Journal of the Chemical Society [Section] C: Organic, 1969, vol. 6, pp. 947-951.
Wicha et al., "Transformations of steroidal neopentyl systems. VI. Intramolecular Claisen condensation of 19R-acetoxy-19A-methyl-3-ones of the 5alpha series", Tetrahedron, 1969, vol. 25, No. 17, pp. 3961-3968.
Wicha et al., "Transformations of steroidal neopentyl systems. VII. Mechanism of the transformation of (19R)-(19)-hydroxy-19-methyl-3-oxo-5alpha-to 3alpha-hydroxy-19-methyl-19--oxo-5alpha-analogs", Journal of Organic Chemistry, 1973, vol. 38 No. 7, pp. 1280-1283.
Wu, "A New Classification of Prodrugs: Regulatory Perspectives", Pharmaceuticals, 2009, vol. 2, pp. 77-81.
Zeng et al., "Neurosteroid Analogues. 10. The Effect of Methyl Group Substitution at the C-6 and C-7 Positions on the GABA Modulatory and Anesthetic Actions of (3a,5a) -and (3a, 5b)-3-Hydroxypregnan-20-one", Journal of Medicinal Chemistry, (2005). vol. 48, pp. 3051-3059.
Zonana et al., "The Neurobiology of Postpartum Depression", CNS Spectrums, (2005), pp. 792-799, 805.
Zorumski et al., "Enantioselective Modulation of GABAergic Synaptic Transmission by Steroids and Benz[dindenes in Hippocampal Microcultures", Synapse, (1998), vol. 29, pp. 162-171.

NEUROACTIVE STEROIDS, COMPOSITIONS, AND USES THEREOF

RELATED APPLICATIONS

The present application claims priority under 35 U.S.C. § 119(e) to U.S. provisional patent applications, U.S. Ser. No. 61/869,440 filed Aug. 23, 2013, U.S. Ser. No. 61/869,446 filed Aug. 23, 2013, and U.S. Ser. No. 62/014,018 filed Jun. 18, 2014, each of which are incorporated herein by reference.

BACKGROUND OF THE INVENTION

Brain excitability is defined as the level of arousal of an animal, a continuum that ranges from coma to convulsions, and is regulated by various neurotransmitters. In general, neurotransmitters are responsible for regulating the conductance of ions across neuronal membranes. At rest, the neuronal membrane possesses a potential (or membrane voltage) of approximately −70 mV, the cell interior being negative with respect to the cell exterior. The potential (voltage) is the result of ion ($K^+$, $Na^+$, $Cl^-$, organic anions) balance across the neuronal semipermeable membrane. Neurotransmitters are stored in presynaptic vesicles and are released under the influence of neuronal action potentials. When released into the synaptic cleft, an excitatory chemical transmitter such as acetylcholine will cause membrane depolarization, e.g., a change of potential from −70 mV to −50 mV. This effect is mediated by postsynaptic nicotinic receptors which are stimulated by acetylcholine to increase membrane permeability to $Na^+$ ions. The reduced membrane potential stimulates neuronal excitability in the form of a postsynaptic action potential.

In the case of the GABA receptor complex (GRC), the effect on brain excitability is mediated by GABA, a neurotransmitter. GABA has a profound influence on overall brain excitability because up to 40% of the neurons in the brain utilize GABA as a neurotransmitter. GABA regulates the excitability of individual neurons by regulating the conductance of chloride ions across the neuronal membrane. GABA interacts with its recognition site on the GRC to facilitate the flow of chloride ions down an electrochemical gradient of the GRC into the cell. An intracellular increase in the levels of this anion causes hyperpolarization of the transmembrane potential, rendering the neuron less susceptible to excitatory inputs, i.e., reduced neuron excitability. In other words, the higher the chloride ion concentration in the neuron, the lower the brain excitability and level of arousal.

It is well-documented that the GRC is responsible for the mediation of anxiety, seizure activity, and sedation. Thus, GABA and drugs that act like GABA or facilitate the effects of GABA (e.g., the therapeutically useful barbiturates and benzodiazepines (BZs), such as diazepam (VALIUM®)) produce their therapeutically useful effects by interacting with specific regulatory sites on the GRC. Accumulated evidence has now indicated that in addition to the benzodiazepine and barbiturate binding site, the GRC contains a distinct site for neuroactive steroids. See, e.g., Lan, N. C. et al., *Neurochem. Res.* (1991) 16:347-356.

Neuroactive steroids can occur endogenously. The most potent endogenous neuroactive steroids are 3α-hydroxy-5-reduced pregnan-20-one and 3α-21-dihydroxy-5-reduced pregnan-20-one, metabolites of hormonal steroids progesterone and deoxycorticosterone, respectively. The ability of these steroid metabolites to alter brain excitability was recognized in 1986 (Majewska, M. D. et al., *Science* 232: 1004-1007 (1986); Harrison, N. L. et al., *J Pharmacol. Exp. Ther.* 241:346-353 (1987)).

The ovarian hormone progesterone and its metabolites have been demonstrated to have profound effects on brain excitability (Backstrom, T. el al., *Acta Obstet. Gynecol. Scand. Suppl.* 130:19-24 (1985); Pfaff, D. W and McEwen, B. S., *Science* 219:808-814 (1983); Gyermek et al., *J Med Chem.* 11: 117 (1968); Lambert, J. el al., *Trends Pharmacol. Sci.* 8:224-227 (1987)). The levels of progesterone and its metabolites vary with the phases of the menstrual cycle. It has been well documented that the levels of progesterone and its metabolites decrease prior to the onset of menses. The monthly recurrence of certain physical symptoms prior to the onset of menses has also been well documented. These symptoms, which have become associated with premenstrual syndrome (PMS), include stress, anxiety, and migraine headaches (Dalton, K., *Premenstrual Syndrome and Progesterone Therapy*, 2nd edition, Chicago Yearbook, Chicago (1984)). Subjects with PMS have a monthly recurrence of symptoms that are present in premenses and absent in postmenses.

In a similar fashion, a reduction in progesterone has also been temporally correlated with an increase in seizure frequency in female epileptics, i.e., catamenial epilepsy (Laidlaw, J., *Lancet*, 1235-1237 (1956)). A more direct correlation has been observed with a reduction in progesterone metabolites (Rosciszewska et al., *J. Neurol. Neurosurg. Psych.* 49:47-51 (1986)). In addition, for subjects with primary generalized petit mal epilepsy, the temporal incidence of seizures has been correlated with the incidence of the symptoms of premenstrual syndrome (Backstrom, T. et al., *J. Psychosom. Obstet. Gynaecol.* 2:8-20 (1983)). The steroid deoxycorticosterone has been found to be effective in treating subjects with epileptic spells correlated with their menstrual cycles (Aird, R. B. and Gordan, G., *J. Amer. Med. Soc.* 145:715-719 (1951)).

A syndrome also related to low progesterone levels is postnatal depression (PND). Immediately after birth, progesterone levels decrease dramatically leading to the onset of PND. The symptoms of PND range from mild depression to psychosis requiring hospitalization. PND is also associated with severe anxiety and irritability. PND-associated depression is not amenable to treatment by classic antidepressants, and women experiencing PND show an increased incidence of PMS (Dalton, K., *Premenstrual Syndrome and Progesterone Therapy*, 2nd edition, Chicago Yearbook, Chicago (1984)).

Collectively, these observations imply a crucial role for progesterone and deoxycorticosterone and more specifically their metabolites in the homeostatic regulation of brain excitability, which is manifested as an increase in seizure activity or symptoms associated with catamenial epilepsy, PMS, and PND. The correlation between reduced levels of progesterone and the symptoms associated with PMS, PND, and catamenial epilepsy (Backstrom, T. et al., *J Psychosom. Obstet. Gynaecol.* 2:8-20 (1983)); Dalton, K., Premenstrual Syndrome and Progesterone Therapy, 2nd edition, Chicago Yearbook, Chicago (1984)) has prompted the use of progesterone in their treatment (Mattson et al., "Medroxyprogesterone therapy of catamenial epilepsy," in *Advances in Epileptology: XVth Epilepsy International Symposium*, Raven Press, New York (1984), pp. 279-282, and Dalton, K., *Premenstrual Syndrome and Progesterone Therapy*, 2nd edition, Chicago Yearbook, Chicago (1984)). However, progesterone is not consistently effective in the treatment of the aforementioned syndromes. For example, no dose-response relationship exists for progesterone in the treatment of PMS (Maddocks et al., *Obstet. Gynecol.* 154:573-581 (1986); Dennerstein et al., *Brit. Med J* 290:16-17 (1986)).

New and improved neuroactive steroids are needed that act as modulating agents for brain excitability, as well as agents for the prevention and treatment of CNS-related diseases. The compounds, compositions, and methods described herein are directed toward this end.

SUMMARY OF THE INVENTION

Provided herein are C21-substituted neuroactive steroids designed, for example, to act as GABA modulators. In certain embodiments, such compounds are envisioned to be useful as therapeutic agents for the inducement of anesthesia and/or sedation in a subject. In some embodiments, such compounds are envisioned to be useful as therapeutic agents for treating a CNS-related disorder (e.g., sleep disorder, a mood disorder, a schizophrenia spectrum disorder, a convulsive disorder, a disorder of memory and/or cognition, a movement disorder, a personality disorder, autism spectrum disorder, pain, traumatic brain injury, a vascular disease, a substance abuse disorder and/or withdrawal syndrome, or tinnitus) in a subject in need (e.g., a subject with Rett syndrome, Fragile X syndrome, or Angelman syndrome).

In one aspect, provided is a compound of Formula (I):

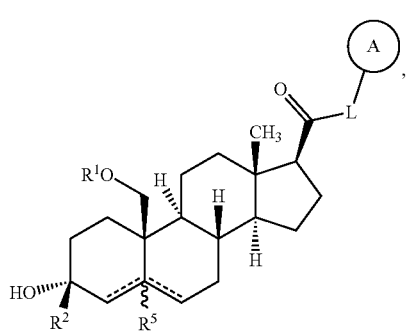

(I)

a pharmaceutically acceptable salt thereof, wherein: A is an optionally substituted nitrogen-containing heteroaryl or heterocyclyl; L is —C($R^3$)($R^3$)—, —O—, —S—, or —$NR^3$—; $R^1$ is hydrogen or $C_1$-$C_6$ alkyl, $C_1$-$C_6$ alkenyl, $C_1$-$C_6$ alkynyl, carbocyclyl, or heterocyclyl; $R^2$ is hydrogen, $C_1$-$C_6$ alkyl (e.g., $C_1$-$C_6$ haloalkyl), or $C_1$-$C_6$ alkoxy; each $R^3$ is independently hydrogen or $C_1$-$C_6$ alkyl; $R^5$ is absent or hydrogen; and ----- represents a single or double bond, wherein when one of ----- is a double bond, the other ----- is a single bond; and when one of the ----- is a double bond, $R^5$ is absent.

The present invention also provides pharmaceutical compositions comprising a compound of the present invention and methods of use and treatment, e.g., such as for inducing sedation and/or anesthesia, for treating a CNS-related disorder.

Steroids of Formula (I), sub-genera thereof, and pharmaceutically acceptable salts thereof are collectively referred to herein as "compounds of the present invention."

In another aspect, provided is a pharmaceutical composition comprising a compound of the present invention and a pharmaceutically acceptable excipient. In certain embodiments, the compound of the present invention is provided in an effective amount in the pharmaceutical composition. In certain embodiments, the compound of the present invention is provided in a therapeutically effective amount. In certain embodiments, the compound of the present invention is provided in a prophylactically effective amount.

Compounds of the present invention as described herein, act, in certain embodiments, as GABA modulators, e.g., effecting the $GABA_A$ receptor in either a positive or negative manner. As modulators of the excitability of the central nervous system (CNS), as mediated by their ability to modulate $GABA_A$ receptor, such compounds are expected to have CNS-activity.

Thus, in another aspect, provided are methods of treating a CNS-related disorder in a subject in need thereof, comprising administering to the subject an effective amount of a compound of the present invention. In certain embodiments, the CNS-related disorder is selected from the group consisting of a sleep disorder, a mood disorder, a schizophrenia spectrum disorder, a convulsive disorder, a disorder of memory and/or cognition, a movement disorder, a personality disorder, autism spectrum disorder, pain, traumatic brain injury, a vascular disease, a substance abuse disorder and/or withdrawal syndrome, and tinnitus. In certain embodiments, the compound is administered orally, subcutaneously, intravenously, or intramuscularly. In certain embodiments, the compound is administered chronically. In certain embodiments, the compound is administered continuously, e.g., by continuous intravenous infusion.

Other objects and advantages will become apparent to those skilled in the art from a consideration of the ensuing Detailed Description, Examples, and Claims.

Definitions

Chemical Definitions

Definitions of specific functional groups and chemical terms are described in more detail below. The chemical elements are identified in accordance with the Periodic Table of the Elements, CAS version, *Handbook of Chemistry and Physics*, 75th Ed., inside cover, and specific functional groups are generally defined as described therein. Additionally, general principles of organic chemistry, as well as specific functional moieties and reactivity, are described in Thomas Sorrell, *Organic Chemistry*, University Science Books, Sausalito, 1999; Smith and March, *March's Advanced Organic Chemistry*, 5th Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3rd Edition, Cambridge University Press, Cambridge, 1987.

Compounds described herein can comprise one or more asymmetric centers, and thus can exist in various isomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, *Stereochemistry of Carbon Compounds* (McGraw-Hill, N Y, 1962); and Wilen, Tables of Resolving Agents and Optical Resolutions p. 268 (E. L. Eliel, Ed., Univ. of Notre Dame Press, Notre Dame, IN 1972). The invention additionally encompasses compounds described herein as individual isomers substantially free of other isomers, and alternatively, as mixtures of various isomers.

As used herein a pure enantiomeric compound is substantially free from other enantiomers or stereoisomers of the compound (i.e., in enantiomeric excess). In other words, an "S" form of the compound is substantially free from the "R" form of the compound and is, thus, in enantiomeric excess of the "R" form. The term "enantiomerically pure" or "pure enantiomer" denotes that the compound comprises more than 75% by weight, more than 80% by weight, more than 85% by weight, more than 90% by weight, more than 91% by weight, more than 92% by weight, more than 93% by weight, more than 94% by weight, more than 95% by weight, more than 96% by weight, more than 97% by weight, more than 98% by weight, more than 98.5% by weight, more than 99% by weight, more than 99.2% by weight, more than 99.5% by weight, more than 99.6% by weight, more than 99.7% by weight, more than 99.8% by weight or more than 99.9% by weight, of the enantiomer. In certain embodiments, the weights are based upon total weight of all enantiomers or stereoisomers of the compound.

In the compositions provided herein, an enantiomerically pure compound can be present with other active or inactive ingredients. For example, a pharmaceutical composition comprising enantiomerically pure R-compound can comprise, for example, about 90% excipient and about 10% enantiomerically pure R-compound. In certain embodiments, the enantiomerically pure R-compound in such compositions can, for example, comprise, at least about 95% by weight R-compound and at most about 5% by weight S-compound, by total weight of the compound. For example, a pharmaceutical composition comprising enantiomerically pure S-compound can comprise, for example, about 90% excipient and about 10% enantiomerically pure S-compound. In certain embodiments, the enantiomerically pure S-compound in such compositions can, for example, comprise, at least about 95% by weight S-compound and at most about 5% by weight R-compound, by total weight of the compound. In certain embodiments, the active ingredient can be formulated with little or no excipient or carrier.

Compound described herein may also comprise one or more isotopic substitutions. For example, H may be in any isotopic form, including $^1H$, $^2H$ (D or deuterium), and $^3H$ (T or tritium); C may be in any isotopic form, including $^{12}C$, $^{13}C$, and $^{14}C$; O may be in any isotopic form, including $^{16}O$ and $^{18}O$; and the like.

The articles "a" and "an" may be used herein to refer to one or to more than one (i.e. at least one) of the grammatical objects of the article. By way of example "an analogue" means one analogue or more than one analogue.

When a range of values is listed, it is intended to encompass each value and sub-range within the range. For example "$C_{1-6}$alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

The following terms are intended to have the meanings presented therewith below and are useful in understanding the description and intended scope of the present invention.

"Alkyl" refers to a radical of a straight-chain or branched saturated hydrocarbon group having from 1 to 20 carbon atoms ("$C_{1-20}$ alkyl"). In some embodiments, an alkyl group has 1 to 12 carbon atoms ("$C_{1-12}$ alkyl"). In some embodiments, an alkyl group has 1 to 8 carbon atoms ("$C_{1-8}$ alkyl"). In some embodiments, an alkyl group has 1 to 6 carbon atoms ("$C_{1-6}$ alkyl", also referred to herein as "lower alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$alkyl"). Examples of $C_{1-6}$ alkyl groups include methyl ($C_1$), ethyl ($C_2$), n-propyl ($C_3$), isopropyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), and n-hexyl ($C_6$). Additional examples of alkyl groups include n-heptyl ($C_7$), n-octyl ($C_8$) and the like. Unless otherwise specified, each instance of an alkyl group is independently optionally substituted, i.e., unsubstituted (an "unsubstituted alkyl") or substituted (a "substituted alkyl") with one or more substituents; e.g., for instance from 1 to 5 substituents, 1 to 3 substituents, or 1 substituent. In certain embodiments, the alkyl group is unsubstituted $C_{1-10}$ alkyl (e.g., —$CH_3$). In certain embodiments, the alkyl group is substituted $C_{1-10}$ alkyl. Common alkyl abbreviations include Me (—$CH_3$), Et (—$CH_2CH_3$), iPr (—$CH(CH_3)_2$), nPr (—$CH_2CH_2CH_3$), n-Bu (—$CH_2CH_2CH_2CH_3$), or i-Bu (—$CH_2CH(CH_3)_2$).

"Alkenyl" refers to a radical of a straight-chain or branched hydrocarbon group having from 2 to 20 carbon atoms, one or more carbon-carbon double bonds, and no triple bonds ("$C_{2-20}$ alkenyl"). In some embodiments, an alkenyl group has 2 to 10 carbon atoms ("$C_{2-10}$ alkenyl"). In some embodiments, an alkenyl group has 2 to 8 carbon atoms ("$C_{2-8}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like. Unless otherwise specified, each instance of an alkenyl group is independently optionally substituted, i.e., unsubstituted (an "unsubstituted alkenyl") or substituted (a "substituted alkenyl") with one or more substituents e.g., for instance from 1 to 5 substituents, 1 to 3 substituents, or 1 substituent. In certain embodiments, the alkenyl group is unsubstituted $C_{2-10}$ alkenyl. In certain embodiments, the alkenyl group is substituted $C_{2-10}$ alkenyl.

"Alkynyl" refers to a radical of a straight-chain or branched hydrocarbon group having from 2 to 20 carbon atoms, one or more carbon-carbon triple bonds, and optionally one or more double bonds ("$C_{2-20}$ alkynyl"). In some embodiments, an alkynyl group has 2 to 10 carbon atoms ("$C_{2-10}$ alkynyl"). In some embodiments, an alkynyl group has 2 to 8 carbon atoms ("$C_{2-8}$ alkynyl"). In some embodiments, an alkynyl group has 2 to 6 carbon atoms ("$C_{2-4}$ alkynyl"). In some embodiments, an alkynyl group has 2 to 5 carbon atoms ("$C_{2-5}$ alkynyl"). In some embodiments, an alkynyl group has 2 to 4 carbon atoms ("$C_{2-4}$ alkynyl"). In some embodiments, an alkynyl group has 2 to 3 carbon atoms ("$C_{2-3}$ alkynyl"). In some embodiments, an alkynyl group has 2 carbon atoms ("$C_2$ alkynyl"). The one or more carbon-carbon triple bonds can be internal (such as in 2-butynyl) or terminal (such as in 1-butynyl). Examples of $C_{2-4}$ alkynyl groups include, without limitation, ethynyl ($C_2$), 1-propynyl ($C_3$), 2-propynyl ($C_3$), 1-butynyl ($C_4$), 2-butynyl ($C_4$), and the like. Examples of $C_{2-4}$ alkenyl groups include the aforementioned $C_{2-4}$ alkynyl groups as well as pentynyl (C), hexynyl (C), and the like. Additional examples of alkynyl include heptynyl ($C_7$), octynyl ($C_8$), and the like. Unless otherwise specified, each instance of an alkynyl group is independently optionally substituted, i.e., unsubstituted (an "unsubstituted alkynyl") or substituted (a "substituted alkynyl") with one or more substituents; e.g., for instance from 1 to 5 substituents, 1 to 3 substituents, or 1 substituent. In certain embodiments, the alkynyl group is unsubstituted $C_{2-10}$ alkynyl. In certain embodiments, the alkynyl group is substituted $C_{2-10}$ alkynyl.

"Aryl" refers to a radical of a monocyclic or polycyclic (e.g., bicyclic or tricyclic) 4n+2 aromatic ring system (e.g., having 6, 10, or 14 π electrons shared in a cyclic array) having 6-14 ring carbon atoms and zero heteroatoms provided in the aromatic ring system ("$C_{6-14}$ aryl"). In some embodiments, an aryl group has six ring carbon atoms ("$C_6$ aryl"; e.g., phenyl). In some embodiments, an aryl group has ten ring carbon atoms ("$C_{10}$ aryl"; e.g., naphthyl such as 1-naphthyl and 2-naphthyl). In some embodiments, an aryl group has fourteen ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Aryl groups include, but are not limited to, phenyl, naphthyl, indenyl, and tetrahydronaphthyl. Unless otherwise specified, each instance of an aryl group is independently optionally substituted, i.e., unsubstituted (an "unsubstituted aryl") or substituted (a "substituted aryl") with one or more substituents. In certain embodiments, the aryl group is unsubstituted $C_{6-14}$ aryl. In certain embodiments, the aryl group is substituted $C_{6-14}$ aryl.

In certain embodiments, an aryl group substituted with one or more of groups selected from halo, $C_1$-$C_8$ alkyl, $C_1$-$C_8$ haloalkyl, cyano, hydroxy, $C_1$-$C_8$ alkoxy, and amino.

Examples of representative substituted aryls include the following

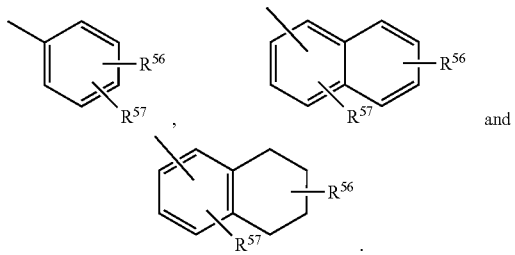

wherein one of $R^{56}$ and $R^{57}$ may be hydrogen and at least one of $R^{56}$ and $R^7$ is each independently selected from $C_1$-$C_8$ alkyl, $C_1$-$C_8$ haloalkyl, 4-10 membered heterocyclyl, alkanoyl, $C_1$-$C_8$ alkoxy, heteroaryloxy, alkylamino, arylamino, heteroarylamino, $NR^{5R}COR^{59}$, $NR^{58}SOR^{59}NR^{58}SO_2R^{59}$, COOalkyl, COOaryl, $CONR^{58}R^{59}$, $CONR^{58}OR^{59}$, $NR^{58}R^{59}$, $SO_2NR^{58}R^{59}$, S-alkyl, SOalkyl, $SO_2$alkyl, Saryl, SOaryl, $SO_2$aryl; or $R^{56}$ and $R^{57}$ may be joined to form a cyclic ring (saturated or unsaturated) from 5 to 8 atoms, optionally containing one or more heteroatoms selected from the group N, O, or S. $R^{60}$ and $R^{61}$ are independently hydrogen, $C_1$-$C_8$ alkyl, $C_1$-$C_4$ haloalkyl, $C_3$-$C_{10}$ cycloalkyl, 4-10 membered heterocyclyl, $C_6$-$C_{10}$ aryl, substituted $C_6$-$C_{10}$ aryl, 5-10 membered heteroaryl, or substituted 5-10 membered heteroaryl.

Other representative aryl groups having a fused heterocyclyl group include the following:

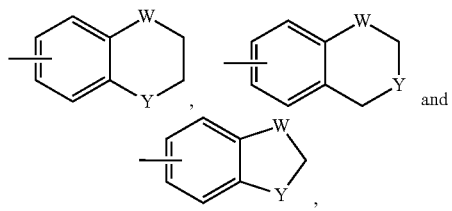

wherein each W is selected from $C(R^{66})_2$, $NR^{66}$, O, and S; and each Y is selected from carbonyl, $NR^{66}$, O and S; and $R^{66}$ is independently hydrogen, $C_1$-$C_8$ alkyl, $C_3$-$C_{10}$ cycloalkyl, 4-10 membered heterocyclyl, $C_6$-$C_{10}$ aryl, and 5-10 membered heteroaryl.

"Halo" or "halogen," independently or as part of another substituent, mean, unless otherwise stated, a fluorine (F), chlorine (Cl), bromine (Br), or iodine (I) atom. The term "halide" by itself or as part of another substituent, refers to a fluoride, chloride, bromide, or iodide atom. In certain embodiments, the halo group is either fluorine or chlorine.

"Haloalkyl" and "haloalkoxy" can include alkyl and alkoxy structures that are substituted with one or more halo groups or with combinations thereof. For example, the terms "fluoroalkyl" and "fluoroalkoxy" include haloalkyl and haloalkoxy groups, respectively, in which the halo is fluorine.

"Heteroaryl" refers to a radical of a 5-10 membered monocyclic or bicyclic 4n+2 aromatic ring system (e.g., having 6 or 10 π electrons shared in a cyclic array) having ring carbon atoms and 1-4 ring heteroatoms provided in the aromatic ring system, wherein each heteroatom is independently selected from nitrogen, oxygen and sulfur ("5-10 membered heteroaryl"). In heteroaryl groups that contain one or more nitrogen atoms, the point of attachment can be a carbon or nitrogen atom, as valency permits. Heteroaryl bicyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused (aryl/heteroaryl) ring system. Bicyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently optionally substituted, i.e., unsubstituted (an "unsubstituted heteroaryl") or substituted (a "substituted heteroaryl") with one or more substituents. In certain embodiments, the heteroaryl group is unsubstituted 5-14 membered heteroaryl. In certain embodiments, the heteroaryl group is substituted 5-14 membered heteroaryl.

Exemplary 5-membered heteroaryl groups containing one heteroatom include, without limitation, pyrrolyl, furanyl and thiophenyl. Exemplary 5-membered heteroaryl groups containing two heteroatoms include, without limitation, imidazolyl, pyrazolyl, oxazolyl, isoxazolyl, thiazolyl, and isothiazolyl. Exemplary 5-membered heteroaryl groups containing three heteroatoms include, without limitation, triazolyl, oxadiazolyl, and thiadiazolyl. Exemplary 5-membered heteroaryl groups containing four heteroatoms include, without limitation, tetrazolyl. Exemplary 6-membered beteroaryl groups containing one heteroatom include, without limitation, pyridinyl. Exemplary 6-membered heteroaryl groups containing two heteroatoms include, without limitation, pyridazinyl, pyrimidinyl, and pyrazinyl. Exemplary 6-membered heteroaryl groups containing three or four heteroatoms include, without limitation, triazinyl and tetrazinyl, respectively. Exemplary 7-membered heteroaryl groups containing one heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic beteroaryl groups include, without limitation, naphthyridinyl, pteridinyl, quinolinyl, isoquinolinyl, cinnolinyl, quinoxalinyl, phthalazinyl, and quinazolinyl.

Examples of representative heteroaryls include the following formulae:

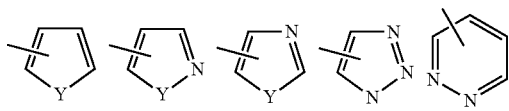

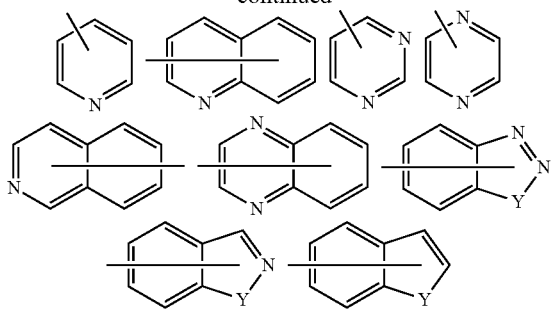

wherein each Y is selected from carbonyl, N, $NR^{65}$, O, and S; and $R^{65}$ is independently hydrogen, $C_1$-$C_8$ alkyl, $C_3$-$C_{10}$ cycloalkyl, 4-10 membered heterocyclyl, $C_6$-$C_{10}$ aryl, and 5-10 membered heteroaryl.

"Carbocyclyl" or "carbocyclic" refers to a radical of a non-aromatic cyclic hydrocarbon group having from 3 to 10 ring carbon atoms ("$C_{3-10}$ carbocyclyl") and zero heteroatoms in the non-aromatic ring system. In some embodiments, a carbocyclyl group has 3 to 8 ring carbon atoms ("$C_{3-8}$ carbocyclyl"). In some embodiments, a carbocyclyl group has 3 to 6 ring carbon atoms ("$C_{3-6}$ carbocyclyl"). In some embodiments, a carbocyclyl group has 3 to 6 ring carbon atoms ("$C_{3-6}$ carbocyclyl"). In some embodiments, a carbocyclyl group has 5 to 10 ring carbon atoms ("$C_{5-10}$ carbocyclyl"). Exemplary $C_{3-6}$carbocyclyl groups include, without limitation, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. Exemplary $C_{3-8}$ carbocyclyl groups include, without limitation, the aforementioned $C_3$_6 carbocyclyl groups as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), bicyclo[2.2.1]heptanyl ($C_7$), bicyclo[2.2.2]octanyl ($C_8$), and the like. Exemplary $C_{3-10}$ carbocyclyl groups include, without limitation, the aforementioned $C_{3-8}$ carbocyclyl groups as well as cyclononyl ($C_9$), cyclononenyl ($C_9$), cyclodecyl ($C_{10}$), cyclodecenyl ($C_{10}$), octahydro-1H-indenyl ($C_9$), decahydronaphthalenyl ($C_{10}$), spiro[4.5]decanyl ($C_{10}$), and the like. As the foregoing examples illustrate, in certain embodiments, the carbocyclyl group is either monocyclic ("monocyclic carbocyclyl") or contain a fused, bridged or spiro ring system such as a bicyclic system ("bicyclic carbocyclyl") and can be saturated or can be partially unsaturated. "Carbocyclyl" also includes ring systems wherein the carbocyclyl ring, as defined above, is fused with one or more aryl or heteroaryl groups wherein the point of attachment is on the carbocyclyl ring, and in such instances, the number of carbons continue to designate the number of carbons in the carbocyclic ring system. Unless otherwise specified, each instance of a carbocyclyl group is independently optionally substituted, i.e., unsubstituted (an "unsubstituted carbocyclyl") or substituted (a "substituted carbocyclyl") with one or more substituents. In certain embodiments, the carbocyclyl group is unsubstituted $C_{3-10}$ carbocyclyl. In certain embodiments, the carbocyclyl group is a substituted $C_{3-10}$ carbocyclyl.

In some embodiments, "carbocyclyl" is a monocyclic, saturated carbocyclyl group having from 3 to 10 ring carbon atoms ("$C_{3-10}$ cycloalkyl"). In some embodiments, a cycloalkyl group has 3 to 8 ring carbon atoms ("$C_{3-8}$ cycloalkyl"). In some embodiments, a cycloalkyl group has 3 to 6 ring carbon atoms ("$C_{3-6}$ cycloalkyl"). In some embodiments, a cycloalkyl group has 5 to 6 ring carbon atoms ("$C_{5-6}$ cycloalkyl"). In some embodiments, a cycloalkyl group has 5 to 10 ring carbon atoms ("$C_{5-10}$ cycloalkyl"). Examples of $C_{5-6}$, cycloalkyl groups include cyclopentyl ($C_5$) and cyclohexyl ($C_6$). Examples of $C_{3-6}$ cycloalkyl groups include the aforementioned $C_{5-6}$ cycloalkyl groups as well as cyclopropyl ($C_3$) and cyclobutyl ($C_4$). Examples of $C_{3-8}$ cycloalkyl groups include the aforementioned $C_{3-6}$ cycloalkyl groups as well as cycloheptyl ($C_7$) and cyclooctyl ($C_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is unsubstituted $C_{3-10}$ cycloalkyl. In certain embodiments, the cycloalkyl group is substituted $C_{3-10}$ cycloalkyl.

"Heterocyclyl" or "heterocyclic" refers to a radical of a 3- to 10-membered non-aromatic ring system having ring carbon atoms and 1 to 4 ring heteroatoms, wherein each heteroatom is independently selected from nitrogen, oxygen, sulfur, boron, phosphorus, and silicon ("3-10 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or a fused, bridged or spiro ring system such as a bicyclic system ("bicyclic heterocyclyl"), and can be saturated or can be partially unsaturated. Heterocyclyl bicyclic ring systems can include one or more heteroatoms in one or both rings. "Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. Unless otherwise specified, each instance of heterocyclyl is independently optionally substituted, i.e., unsubstituted (an "unsubstituted heterocyclyl") or substituted (a "substituted heterocyclyl") with one or more substituents. In certain embodiments, the heterocyclyl group is unsubstituted 3-10 membered heterocyclyl. In certain embodiments, the heterocyclyl group is substituted 3-10 membered heterocyclyl.

In some embodiments, a heterocyclyl group is a 5-10 membered non-aromatic ring system having ring carbon atoms and 1-4 ring heteroatoms, wherein each heteroatom is independently selected from nitrogen, oxygen, sulfur, boron, phosphorus, and silicon ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has one ring heteroatom selected from nitrogen, oxygen, and sulfur.

Exemplary 3-membered heterocyclyl groups containing one heteroatom include, without limitation, azirdinyl, oxiranyl, thiorenyl. Exemplary 4-membered heterocyclyl groups containing one heteroatom include, without limitation, azetidinyl, oxetanyl and thietanyl. Exemplary 5-membered heterocyclyl groups containing one heteroatom include, without limitation, tetrahydrofuranyl, dihydrofuranyl, tetrahydrothiophenyl, dihydrothiophenyl, pyrrolidinyl, dihydropyrrolyl and pyrrolyl-2,5-dione. Exemplary 5-membered heterocyclyl groups containing two heteroatoms include, without limitation, dioxolanyl, oxasulfuranyl, disulfuranyl, and oxazolidin-2-one. Exemplary 5-membered heterocyclyl groups containing three heteroatoms include, without limitation, triazolinyl, oxadiazolinyl, and thiadiazolinyl. Exemplary 6-membered heterocyclyl groups containing one heteroatom include, without limitation, piperidinyl, tetrahydropyranyl, dihydropyridinyl, and thianyl. Exemplary 6-membered heterocyclyl groups containing two heteroatoms include, without limitation, piperazinyl, morpholinyl, dithianyl, dioxanyl. Exemplary 6-membered heterocyclyl groups containing two heteroatoms include, without limitation, triazinanyl. Exemplary 7-membered heterocyclyl groups containing one heteroatom include, without limitation, azepanyl, oxepanyl and thiepanyl. Exemplary 8-membered heterocyclyl groups containing one heteroatom include, without limitation, azocanyl, oxecanyl and thiocanyl. Exemplary 5-membered heterocyclyl groups fused to a $C_6$ aryl ring (also referred to herein as a 5,6-bicyclic heterocyclic ring) include, without limitation, indolinyl, isoindolinyl, dihydrobenzofuranyl, dihydrobenzothienyl, benzoxazolinonyl, and the like. Exemplary 6-membered heterocyclyl groups fused to an aryl ring (also referred to herein as a 6,6-bicyclic heterocyclic ring) include, without limitation, tetrahydroquinolinyl, tetrahydroisoquinolinyl, and the like.

Particular examples of heterocyclyl groups are shown in the following illustrative examples:

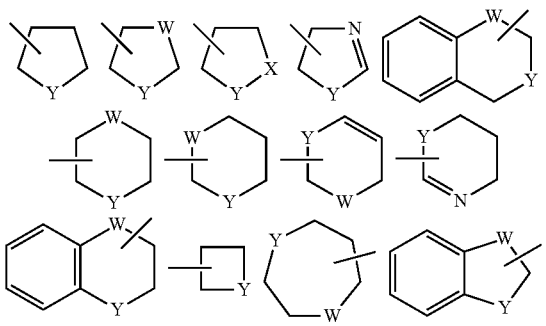

wherein each W is selected from $CR^{67}$, $C(R^{67})_2$, $NR^{67}$, O, and S; and each Y is selected from $NR^{67}$, O, and S; and $R^{67}$ is independently hydrogen, $C_1$-$C_8$ alkyl, $C_3$-$C_{10}$ cycloalkyl, 4-10 membered heterocyclyl, $C_6$-$C_{10}$ aryl, and 5-10-membered heteroaryl. These heterocyclyl rings may be optionally substituted with one or more groups selected from the group consisting of acyl, acylamino, acyloxy, alkoxy, alkoxycarbonyl, alkoxycarbonylamino, amino, substituted amino, aminocarbonyl (e.g., amido), aminocarbonylamino, aminosulfonyl, sulfonylamino, aryl, aryloxy, azido, carboxyl, cyano, cycloalkyl, halogen, hydroxy, keto, nitro, thiol, —S-alkyl, —S-aryl, —S(O)-alkyl, —S(O)-aryl, —S(O)$_2$-alkyl, and —S(O)$_2$-aryl. Substituting groups include carbonyl or thiocarbonyl which provide, for example, lactam and urea derivatives.

"Acyl" refers to a radical —C(O)R$^{20}$, where R$^{20}$ is hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl, as defined herein. "Alkanoyl" is an acyl group wherein R$^{20}$ is a group other than hydrogen. Representative acyl groups include, but are not limited to, formyl (—CHO), acetyl (—C(=O)CH$_3$), cyclohexylcarbonyl, cyclohexylmethylcarbonyl, benzoyl (—C(=O)Ph), benzylcarbonyl (—C(=O)CH$_2$Ph), —C(O)—C$_1$-C$_8$ alkyl, —C(O)—(CH$_2$)$_t$(C$_6$-C$_{10}$ aryl), —C(O)—(CH$_2$)$_t$(5-10 membered heteroaryl), —C(O)—(CH$_2$)(C$_3$-C$_{10}$ cycloalkyl), and —C(O)—(CH$_2$)$_t$(4-10 membered heterocyclyl), wherein t is an integer from 0 to 4. In certain embodiments, R$^{21}$ is C$_1$-C$_8$ alkyl, substituted with halo or hydroxy; or C$_3$-C$_{10}$ cycloalkyl, 4-10 membered heterocyclyl, C$_6$-C$_{10}$ aryl, arylalkyl, 5-10 membered heteroaryl or heteroarylalkyl, each of which is substituted with unsubstituted C$_1$-C$_4$ alkyl, halo, unsubstituted C$_1$-C$_4$ alkoxy, unsubstituted C$_1$-C$_4$ haloalkyl, unsubstituted C$_1$-C$_4$ hydroxyalkyl, or unsubstituted C$_1$-C$_4$ haloalkoxy or hydroxy.

"Acylamino" refers to a radical —NR$^{22}$C(O)R$^{23}$, where each instance of R$^{22}$ and R$^{23}$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl, as defined herein, or R$^{22}$ is an amino protecting group. Exemplary "acylamino" groups include, but are not limited to, formylamino, acetylamino, cyclohexylcarbonylamino, cyclohexylmethyl-carbonylamino, benzoylamino and benzylcarbonylamino. Particular exemplary "acylamino" groups are —NR$^{24}$C(O)—C$_1$-C$_8$ alkyl, —NR$^{24}$C(O)—(CH$_2$)$_t$(C$_6$-C$_{10}$ aryl), —NR$^{24}$C(O)—(CH$_2$)$_t$(5-10 membered heteroaryl), —NR$^{24}$C(O)(CH$_2$)(C$_3$-C$_{10}$ cycloalkyl), and —NR$^{24}$C(O)—(CH$_2$)$_t$(4-10 membered heterocyclyl), wherein t is an integer from 0 to 4, and each R$^{24}$ independently represents hydrogen or C$_1$-C$_8$ alkyl. In certain embodiments, R$^5$ is H, C$_1$-C$_8$ alkyl, substituted with halo or hydroxy; C$_3$-C$_{10}$ cycloalkyl, 4-10 membered heterocyclyl, C$_6$-C$_{10}$ aryl, arylalkyl, 5-10 membered heteroaryl or heteroarylalkyl, each of which is substituted with unsubstituted C$_1$-C$_4$ alkyl, halo, unsubstituted C$_1$-C$_4$ alkoxy, unsubstituted C$_1$-C$_4$ haloalkyl, unsubstituted C$_1$-C$_4$ hydroxyalkyl, or unsubstituted C$_1$-C$_4$ haloalkoxy or hydroxy; and R$^{26}$ is H, C$_1$-C$_8$ alkyl, substituted with halo or hydroxy; C$_3$-C$_{10}$ cycloalkyl, 4-10-membered heterocyclyl, C$_6$-C$_{10}$ aryl, arylalkyl, 5-10-membered heteroaryl or heteroarylalkyl, each of which is substituted with unsubstituted C$_1$-C$_4$ alkyl, halo, unsubstituted C$_1$-C$_4$ alkoxy, unsubstituted C$_1$-C$_4$ haloalkyl, unsubstituted C$_1$-C$_4$ hydroxyalkyl, or unsubstituted C$_1$-C$_4$ haloalkoxy or hydroxy; provided at least one of R$^2$ and R$^{26}$ is other than H.

"Acyloxy" refers to a radical —OC(O)R$^{27}$, where R$^{27}$ is hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl, as defined herein. Representative examples include, but are not limited to, formyl, acetyl, cyclohexylcarbonyl, cyclohexylmethylcarbonyl, benzoyl, and benzylcarbonyl. In certain embodiments, R$^{2'}$ is C$_1$-C$_8$ alkyl, substituted with halo or hydroxy; C$_3$-C$_{10}$ cycloalkyl, 4-10-membered heterocyclyl, C$_6$-C$_{10}$ aryl, arylalkyl, 5-10-membered heteroaryl or heteroarylalkyl, each of which is substituted with unsubstituted C$_1$-C$_4$ alkyl, halo, unsubstituted C$_1$-C$_4$ alkoxy, unsubstituted C$_1$-C$_4$ haloalkyl, unsubstituted C$_1$-C$_4$ hydroxyalkyl, or unsubstituted C$_1$-C$_4$ haloalkoxy or hydroxy.

"Alkoxy" refers to the group —OR$^{29}$ where R$^{29}$ is substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl. Particular alkoxy groups are methoxy, ethoxy, n-propoxy, isopropoxy, n-butoxy, tert-butoxy, sec-butoxy, n-pentoxy, n-hexoxy, and 1,2-dimethylbutoxy. Particular alkoxy groups are lower alkoxy, i.e., with between 1 and 6 carbon atoms. Further particular alkoxy groups have between 1 and 4 carbon atoms.

In certain embodiments, R$^{29}$ is a group that has 1 or more substituents, for instance from 1 to 5 substituents, and particularly from 1 to 3 substituents, in particular 1 substituent, selected from the group consisting of amino, substituted amino, C$_6$-C$_{10}$ aryl, aryloxy, carboxyl, cyano, C$_3$-C$_{10}$ cycloalkyl, 4-10 membered heterocyclyl, halogen, 5-10 membered heteroaryl, hydroxy, nitro, thioalkoxy, thioaryloxy, thiol, alkyl-S(O)—, aryl-S(O)—, alkyl-S(O)$_2$—and aryl-S(O)$_2$—. Exemplary "substituted alkoxy" groups include, but are not limited to, —O—(CH$_2$)$_t$(C$_6$-C$_{10}$ aryl), —O—(CH$_2$)$_t$(5-10 membered heteroaryl), —O—(CH$_2$)$_t$(C$_3$-C$_{10}$ cycloalkyl), and —O—(CH$_2$)$_t$(4-10 membered heterocyclyl), wherein t is an integer from 0 to 4 and any aryl, heteroaryl, cycloalkyl or heterocyclyl groups present, may themselves be substituted by unsubstituted C$_1$-C$_4$ alkyl, halo, unsubstituted C$_1$-C$_4$ alkoxy, unsubstituted C$_1$-C$_4$ haloalkyl, unsubstituted C$_1$-C$_4$ hydroxyalkyl, or unsubstituted C$_1$-C$_4$ haloalkoxy or hydroxy. Particular exemplary 'substituted alkoxy' groups are —OCF$_3$, —OCH$_2$CF$_3$, —OCH$_2$Ph, —OCH$_2$-cyclopropyl, —OCH$_2$CH$_2$OH, and —OCH$_2$CH$_2$NMe$_2$.

"Amino" refers to the radical —NH$_2$.

"Substituted amino" refers to an amino group of the formula —N(R$^{38}$)$_2$ wherein R$^{38}$ is hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or an amino protecting group, wherein at least one of R$^{38}$ is not a hydrogen. In certain embodiments, each R$^{38}$ is independently selected from hydrogen, C$_1$-C$_8$ alkyl, C$_3$-C$_5$ alkenyl, C$_3$-C$_8$ alkynyl, C$_6$-C$_{10}$ aryl, 5-10 membered heteroaryl, 4-10 membered heterocyclyl, or C$_3$-C$_{10}$ cycloalkyl; or C$_1$-C$_8$ alkyl, substituted with halo or hydroxy; C$_3$-C$_8$ alkenyl, substituted with halo or hydroxy; C$_3$-C$_8$ alkynyl, substituted with halo or hydroxy, or —(CH$_2$)$_t$(C$_6$-C$_{10}$ aryl), —(CH$_2$)(5-10 membered heteroaryl), —(CH$_2$)(C$_3$-C$_{10}$ cycloalkyl), or —(CH$_2$)$_t$(4-10 membered heterocyclyl), wherein t is an integer between 0 and 8, each of which is substituted by unsubstituted C$_1$-C$_4$ alkyl, halo, unsubstituted C$_1$-C$_4$ alkoxy, unsubstituted C$_1$-C$_4$ haloalkyl, unsubstituted C$_1$-C$_4$ hydroxyalkyl, or unsubstituted C$_1$-C$_4$ haloalkoxy or hydroxy; or both R$^{38}$ groups are joined to form an alkylene group.

Exemplary "substituted amino" groups include, but are not limited to, —NR$^{39}$—C$_1$-C$_8$ alkyl, —NR$^{39}$—(CH$_2$)$_t$(C$_6$-C$_{10}$ aryl), —NR$^{39}$—(CH$_2$)$_t$(5-10 membered heteroaryl), —NR$^{39}$—(CH$_2$)$_t$(C$_3$-C$_{10}$ cycloalkyl), and —NR$^{39}$—(CH$_2$)$_t$(4-10 membered heterocyclyl), wherein t is an integer from 0 to 4, for instance 1 or 2, each R$^{39}$ independently represents hydrogen or C$_1$-C$_8$ alkyl; and any alkyl groups present, may themselves be substituted by halo, substituted or unsubstituted amino, or hydroxy; and any aryl, heteroaryl, cycloalkyl, or heterocyclyl groups present, may themselves be substituted by unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy. For the avoidance of doubt the term 'substituted amino' includes the groups alkylamino, substituted alkylamino, alkylarylamino, substituted alkylarylamino, arylamino, substituted arylamino, dialkylamino, and substituted dialkylamino as defined below. Substituted amino encompasses both monosubstituted amino and disubstituted amino groups.

"Azido" refers to the radical —$N_3$.

"Carbamoyl" or "amido" refers to the radical —C(O)$NH_2$.

"Substituted carbamoyl" or "substituted amido" refers to the radical —C(O)N($R^{62}$)$_2$ wherein each $R^{62}$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or an amino protecting group, wherein at least one of $R^{62}$ is not a hydrogen. In certain embodiments, $R^{62}$ is selected from H, $C_1$-$C_8$ alkyl, $C_3$-$C_{10}$cycloalkyl, 4-10 membered heterocyclyl, $C_6$-$C_{10}$ aryl, and 5-10 membered heteroaryl; or $C_1$-$C_8$ alkyl substituted with halo or hydroxy; or $C_3$-$C_{10}$ cycloalkyl, 4-10 membered heterocyclyl, $C_6$-$C_{10}$ aryl, or 5-10 membered heteroaryl, each of which is substituted by unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy; provided that at least one $R^{62}$ is other than H.

"Carboxy" refers to the radical —C(O)OH.

"Cyano" refers to the radical —CN.

"Hydroxy" refers to the radical —OH.

"Nitro" refers to the radical —$NO_2$.

"Ethenyl" refers to substituted or unsubstituted —(C═C)—. "Ethylene" refers to substituted or unsubstituted —(C—C)—. "Ethynyl" refers to —(C≡C)—.

"Nitrogen-containing heterocyclyl" group means a 4- to 7-membered non-aromatic cyclic group containing at least one nitrogen atom, for example, but without limitation, morpholine, piperidine (e.g. 2-piperidinyl, 3-piperidinyl and 4-piperidinyl), pyrrolidine (e.g. 2-pyrrolidinyl and 3-pyrrolidinyl), azetidine, pyrrolidone, imidazoline, imidazolidinone, 2-pyrazoline, pyrazolidine, piperazine, and N-alkyl piperazines such as N-methyl piperazine. Particular examples include azetidine, piperidone and piperazone.

Alkyl, alkenyl, alkynyl, carbocyclyl, heterocyclyl, aryl, and heteroaryl groups, as defined herein, are optionally substituted (e.g., "substituted" or "unsubstituted" alkyl, "substituted" or "unsubstituted" alkenyl, "substituted" or "unsubstituted" alkynyl, "substituted" or "unsubstituted" carbocyclyl, "substituted" or "unsubstituted" heterocyclyl, "substituted" or "unsubstituted" aryl or "substituted" or "unsubstituted" beteroaryl group). In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, any of the substituents described herein that results in the formation of a stable compound. The present invention contemplates any and all such combinations in order to arrive at a stable compound. For purposes of this invention, heteroatoms such as nitrogen may have hydrogen substituents and/or any suitable substituent as described herein which satisfy the valencies of the heteroatoms and results in the formation of a stable moiety.

Exemplary carbon atom substituents include, but are not limited to, halogen, —CN, —$NO_2$, —$N_3$, —$SO_2H$, —$SO_3H$, —OH, —$OR^{aa}$, —ON($R^{bb}$)$_2$, —N($R^{bb}$)$_2$, —N($R^{bb}$)$_3$$^+$$X^-$, —N(OR$^{cc}$)$R^{bb}$, —SH, —$SR^{aa}$, —$SSR^{cc}$, —C(═O)$R^{aa}$, —$CO_2H$, —CHO, —C(O$R^{cc}$)$_2$, —$CO_2R^{aa}$, —OC(═O)$R^{aa}$, —$OCO_2R^{aa}$, —C(═O)N($R^{bb}$)$_2$, —OC(═O)N($R^{bb}$)$_2$, —$NR^{bb}$C(═O)$R^{aa}$, —$NR^{bb}$$CO_2R^{aa}$, —$NR^{bb}$C(═O)N($R^{bb}$)$_2$, —C(═$NR^{bb}$)$R^{aa}$, —C(═$NR^{bb}$)$OR^{aa}$, —OC(═$NR^{bb}$)$R^{aa}$, —OC(═$NR^{bb}$)$OR^{aa}$, —C(═$NR^{bb}$)N($R^{bb}$)$_2$, —OC(═$NR^{bb}$)N($R^{bb}$)$_2$, —$NR^{bb}$C(═$NR^{bb}$)N($R^{bb}$)$_2$, —C(═O)$NR^{bb}$$SO_2R^{aa}$, —$NR^{bb}$$SO_2R^{aa}$, —$SO_2$N($R^{bb}$)$_2$, —$SO_2R^{aa}$, —$SO_2OR^{aa}$, —$OSO_2R^{aa}$, —S(═O)$R^{aa}$, —OS(═O)$R^{aa}$, —Si($R^{aa}$)$_3$, —OSi($R^{aa}$)$_3$—C(═S)N($R^{bb}$)$_2$, —C(═S)$SR^{aa}$, —C(═S)$SR^{aa}$, —SC(═S)$SR^{aa}$, —SC(═O)$SR^{aa}$, —OC(═O)$SR^{aa}$, —SC(═O)$OR^{aa}$, —SC(═O)$R^{aa}$, —P(═O)$_2R^{aa}$, —OP(═O)$_2R^{aa}$, —P(═O)($R^{aa}$)$_2$, —OP(═O)($R^{aa}$)$_2$, —OP(═O)(O$R^{cc}$)$_2$, —P(═O)$_2$N($R^{bb}$)$_2$, —OP(═O)$_2$N($R^{bb}$)$_2$, —P(═O)(N$R^{bb}$)$_2$, —OP(═O)(N$R^{bb}$)$_2$, —$NR^{bb}$P(═O)(O$R^{cc}$)$_2$, —$NR^{bb}$P(═O)(N$R^{bb}$)$_2$, —P($R^{cc}$)$_2$, —P($R^{cc}$)$_3$, —OP($R^{cc}$)$_2$, —OP($R^{cc}$)$_3$, —B($R^{aa}$)$_2$, —B(O$R^{cc}$)$_2$, —B$R^{aa}$(O$R^{cc}$), $C_{1-10}$ alkyl, $C_{1-10}$ perhaloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, wherein each alkyl, alkenyl, alkynyl, carbocyclyl, heterocyclyl, aryl, and heteroaryl is independently substituted with 0, 1, 2, 3, 4, or 5 $R^{dd}$ groups;

each instance of $R^{aa}$ is, independently, selected from $C_{1-10}$ alkyl, $C_{1-10}$ perhaloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, or two $R^{aa}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups;

each instance of $R^{bb}$ is, independently, selected from hydrogen, —OH, —$OR^{aa}$, —N($R^{cc}$)$_2$, —CN, —C(═O)$R^{aa}$, —C(═O)N($R^{cc}$)$_2$, —$CO_2R^{aa}$, —$SO_2R^{aa}$, —C(═$NR^{cc}$)$OR^{aa}$, —C(═$NR^{cc}$)N($R^{cc}$)$_2$, —$SO_2$N($R^{cc}$)$_2$, —$SO_2R^{cc}$, —$SO_2OR^{cc}$, —$SOR^{aa}$, —C(═S)N($R^{cc}$)$_2$, —C(═O)$SR^{cc}$, —C(═S)$SR^{cc}$, —P(═O)$_2R^{aa}$, —P(═O)($R^{aa}$)$_2$, —P(═O)$_2$N($R^{cc}$)$_2$, —P(═O)(N$R^{cc}$)$_2$, $C_{1-10}$ alkyl, $C_{1-10}$ perhaloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, or two $R^{bb}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups;

each instance of $R^{cc}$ is, independently, selected from hydrogen, $C_{1-10}$ alkyl, $C_{1-10}$ perhaloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, or two $R^{cc}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups;

each instance of $R^{dd}$ is, independently, selected from halogen, —CN, —NO$_2$, —N$_3$, —SO$_2$H, —SO$_3$H, —OH, —OR$^{cc}$, —ON(R$^{ff}$)$_2$, —N(R$^{ff}$)$_2$, —N(R$^{ff}$)$_3$$^+$X$^-$, —N(OR$^{ee}$)R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O)R$^{ee}$, —NR$^{ff}$CO$_2$R$^{ee}$, —NR$^{ff}$C(=O)N(R$^{ff}$)$_2$, —C(=NR$^{ff}$)OR$^{ee}$, —OC(=NR$^{ff}$)R$^{ee}$, —OC(=NR$^{ff}$)OR$^{ee}$, —C(=NR$^{ff}$)N(R$^{ff}$)$_2$, —OC(=NR$^{ff}$)N(R$^{ff}$)$_2$, —NR$^{ff}$C(=NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(=O)R, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O)$_2$R$^{ee}$, —P(=O)(R$^{ee}$)$_2$, —OP(=O)(R$^{ee}$)$_2$, —OP(=O)(OR$^{ee}$)$_2$, $C_{1-6}$ alkyl, $C_{1-6}$ perhaloalkyl, $C_{2-6}$ alkenyl, $C_{2-6}$ alkynyl, $C_{3-10}$ carbocyclyl, 3-10 membered heterocyclyl, $C_{6-10}$ aryl, 5-10 membered heteroaryl, wherein each alkyl, alkenyl, alkynyl, carbocyclyl, heterocyclyl, aryl, and heteroaryl is independently substituted with 0, 1, 2, 3, 4, or 5 $R^{gg}$ groups;

each instance of $R^{ee}$ is, independently, selected from $C_{1-6}$ alkyl, $C_{1-6}$ perhaloalkyl, $C_{2-6}$ alkenyl, $C_{2-6}$ alkynyl, $C_{3-10}$ carbocyclyl, $C_{6-10}$ aryl, 3-10 membered heterocyclyl, and 3-10 membered heteroaryl, wherein each alkyl, alkenyl, alkynyl, carbocyclyl, heterocyclyl, aryl, and heteroaryl is independently substituted with 0, 1, 2, 3, 4, or 5 $R^{gg}$ groups;

each instance of $R^{ff}$ is, independently, selected from hydrogen, $C_{1-6}$ alkyl, $C_{1-6}$ perhaloalkyl, $C_{2-6}$ alkenyl, $C_{2-6}$ alkynyl, $C_{3-10}$ carbocyclyl, 3-10 membered heterocyclyl, $C_{6-10}$ aryl and 5-10 membered heteroaryl, or two $R^{ff}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{gg}$ groups; and each instance of $R^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3$$^+$X$^-$, —NH(C$_{1-6}$ alkyl)$_2$$^+$X$^-$, —NH$_2$(C$_{1-6}$ alkyl)$^+$ X$^-$, —NH$_3$$^+$X$^-$, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O)(C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO$_2$(C$_{1-6}$ alkyl), —NHC(=O)N(C$_{1-6}$ alkyl)$_2$, —NHC(=O)NH(C$_{1-6}$ alkyl), —NHC(=O)NH$_2$, —C(=NH)O(C$_{1-6}$ alkyl), —OC(=NH)(C$_{1-6}$ alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(NH)NH(C$_{1-6}$ alkyl), —OC(NH)NH$_2$, —NHC(NH)N(C$_{1-6}$alkyl)$_2$, —NHC(=NH)NH$_2$, —NHSO$_2$(C$_{1-6}$ alkyl), —SO$_2$N(C$_{1-6}$ alkyl)$_2$, —SO$_2$NH(C$_{1-6}$ alkyl), —SO$_2$NH$_2$, —SO$_2$C$_{1-6}$ alkyl, —SO$_2$OC$_{1-6}$ alkyl, —OSO$_2$C$_{1-6}$ alkyl, —SOC$_{1-6}$ alkyl, —Si(C$_{1-6}$ alkyl)$_3$, —OSi(C$_{1-6}$ alkyl)$_3$ —C(=S)N(C$_{1-6}$ alkyl)$_2$, C(=S)NH(C$_{1-6}$ alkyl), C(=S)NH$_2$, —C(=O)S(C$_{1-6}$ alkyl), —C(=S)SC$_{1-6}$ alkyl, —SC(=S)SC$_{1-6}$ alkyl, —P(=O)$_2$(C$_{1-6}$ alkyl), —P(=O)(C$_{1-6}$ alkyl)$_2$, —OP(=O)(C$_{1-6}$ alkyl)$_2$, —OP(=O)(OC$_{1-6}$ alkyl)$_2$, $C_{1-6}$ alkyl, $C_{1-6}$ perhaloalkyl, $C_{2-6}$ alkenyl, $C_{2-6}$ alkynyl, $C_{3-10}$ carbocyclyl, $C_{6-10}$ aryl, 3-10 membered heterocyclyl, 5-10 membered heteroaryl; wherein X$^-$ is a counterion.

A "counterion" or "anionic counterion" is a negatively charged group associated with a cationic quaternary amino group in order to maintain electronic neutrality. Exemplary counterions include halide ions (e.g., F$^-$, Cl$^-$, Br$^-$, I$^-$), NO$_3$$^-$, ClO$_4$$^-$, OH$^-$, H$_2$PO$_4$$^-$, HSO$_4$$^-$, sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), and carboxylate ions (e.g., acetate, ethanoate, propanoate, benzoate, glycerate, lactate, tartrate, glycolate, and the like).

Nitrogen atoms can be substituted or unsubstituted as valency permits, and include primary, secondary, tertiary, and quarternary nitrogen atoms. Exemplary nitrogen atom substitutents include, but are not limited to, hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{bb}$)R$^{aa}$, —C(=NR$^{cc}$)OR$^{aa}$, —C(=NR$^{cc}$)N(R$^{cc}$), —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R$^{aa}$, —P(=O)(R$^{aa}$)$_2$, —P(=O)$_2$N(R$^{cc}$)$_2$, —P(=O)(NR$^{cc}$)$_2$, $C_{1-10}$ alkyl, $C_{3-10}$ perhaloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14-membered heteroaryl, or two $R^{cc}$ groups attached to a nitrogen atom are joined to form a 3-14-membered heterocyclyl or 5-14-membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups, and wherein $R^{aa}$, $R^{bb}$, $R^{cc}$ and $R^{dd}$ are as defined above.

In certain embodiments, the substituent present on a nitrogen atom is an amino protecting group (also referred to herein as a nitrogen protecting group). Amino protecting groups include, but are not limited to, —OH, —OR$^{aa}$, —N(R$^{cc}$)$_2$, —C(=O)R$^{aa}$, —C(=O)OR$^{aa}$, —C(=O)N(R$^{cc}$)$_2$, —S(=O)$_2$R$^{aa}$, —C(=NR$^{cc}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, $C_{1-10}$ alkyl, $C_{2-10}$ alkenyl, $C_{2-10}$ alkynyl, $C_{3-10}$ carbocyclyl, 3-14-membered heterocyclyl, $C_{6-14}$ aryl, and 5-14-membered heteroaryl groups, wherein each alkyl, alkenyl, alkynyl, carbocyclyl, heterocyclyl, aryl, and heteroaryl is independently substituted with 0, 1, 2, 3, 4, or 5 $R^{dd}$ groups, and wherein $R^{aa}$, $R^{bb}$, $R^{cc}$ and $R^{dd}$ are as defined herein. Amino protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

Exemplary amino protecting groups include, but are not limited to amide groups (e.g., —C(=O)R$^{aa}$), which include, but are not limited to, formamide and acetamide; carbamate groups (e.g., —C(=O)OR$^{aa}$), which include, but are not limited to, 9-fluorenylmethyl carbamate (Fmoc), t-butyl carbamate (BOC), and benzyl carbamate (Cbz); sulfonamide groups (e.g., —S(=O)$_2$R$^{aa}$), which include, but are not limited to, p-toluenesulfonamide (Ts), methanesulfonamide (Ms), and N-[2-(trimethylsilyl)ethoxy]methylamine (SEM).

In certain embodiments, the substituent present on an oxygen atom is an oxygen protecting group (also referred to as a hydroxyl protecting group). Oxygen protecting groups include, but are not limited to, —R$^{aa}$, —N(R$^{bb}$)$_2$, —C(=O)SR$^{aa}$, —C(=O)R$^{aa}$, —CO$_2$R$^{aa}$, —C(=O)N(R$^{bb}$)$_2$, —C(=NR$^{bb}$)R$^{aa}$, —C(=NR$^{bb}$)OR$^{aa}$, —C(=NR$^{bb}$)N $(R^{bb})_2$, $-S(=O)R^{aa}$, $-SO_2R^{aa}$, $-Si(R^{aa})_3$, $-P(R^{cc})_2$, $-P(R^{cc})_3$, $-P(=O)_2R^{aa}$, $-P(=O)R^{aa})_2$, $-P(=O)(OR^{cc})_2$, $-P(=O)_2N(R^{bb})_2$, and $-P(=O)(NR^{bb})_2$, wherein $R^{aa}$, $R^{bb}$, and $R^{cc}$ are as defined herein. Oxygen protecting groups are well known in the art and include those described in detail in *Protecting Groups in Organic Synthesis*, T. W. Greene and P. G. M. Wuts, 3rd edition, John Wiley & Sons, 1999, incorporated herein by reference.

Exemplary oxygen protecting groups include, but are not limited to, methyl, methoxylmethyl (MOM), 2-methoxyethoxymethyl (MEM), benzyl (Bn), triisopropylsilyl (TIPS), t-butyldimethylsilyl (TBDMS), t-butylmethoxyphenylsilyl (TBMPS), methanesulfonate (mesylate), and tosylate (Ts).

In certain embodiments, the substituent present on an sulfur atom is an sulfur protecting group (also referred to as a thiol protecting group). Sulfur protecting groups include, but are not limited to, $-R^{aa}$, $-N(R^{bb})_2$, $-C(=O)SR^{aa}$, $-C(=O)R^{aa}$, $-CO_2R^{aa}$, $-C(=O)N(R^{bb})_2$, $-C(=NR^{bb})R^{aa}$, $-C(=NR^{bb})OR^{aa}$, $-C(=NR^{bb})N(R^{bb})_2$, $-S(=O)R^{aa}$, $-SO_2R^{aa}$, $-Si(R^{aa})_3$, $-P(R^{cc})_2$, $-P(R^{cc})_3$, $-P(=O)_2R^{aa}$, $-P(=O)R^{aa})_2$, $-P(=O)(OR^{cc})_2$, $-P(=O)_2N(R^{bb})_2$, and $-P(=O)(NR^{bb})_2$, wherein $R^{aa}$, $R^{bb}$, and $R^{cc}$ are as defined herein. Sulfur protecting groups are well known in the art and include those described in detail in *Protecting Groups in Organic Synthesis*, T. W. Greene and P. G. M. Wuts, 3rd edition, John Wiley & Sons, 1999, incorporated herein by reference.

These and other exemplary substituents are described in more detail in the Detailed Description, Examples, and Claims. The invention is not intended to be limited in any manner by the above exemplary listing of substituents.

Other Definitions

As used herein, the term "modulation" refers to the inhibition or potentiation of GABA receptor function. A "modulator" (e.g., a modulator compound) may be, for example, an agonist, partial agonist, antagonist, or partial antagonist of the GABA receptor.

"Pharmaceutically acceptable" means approved or approvable by a regulatory agency of the Federal or a state government or the corresponding agency in countries other than the United States, or that is listed in the U.S. Pharmacopoeia or other generally recognized pharmacopoeia for use in animals, and more particularly, in humans.

"Pharmaceutically acceptable salt" refers to a salt of a compound of the invention that is pharmaceutically acceptable and that possesses the desired pharmacological activity of the parent compound. In particular, such salts are non-toxic may be inorganic or organic acid addition salts and base addition salts. Specifically, such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, N-methylglucamine and the like. Salts further include, by way of example only, sodium, potassium, calcium, magnesium, ammonium, tetraalkylammonium, and the like; and when the compound contains a basic functionality, salts of non-toxic organic or inorganic acids, such as hydrochloride, hydrobromide, tartrate, mesylate, acetate, maleate, oxalate and the like. The term "pharmaceutically acceptable cation" refers to an acceptable cationic counterion of an acidic functional group. Such cations are exemplified by sodium, potassium, calcium, magnesium, ammonium, tetraalkylammonium cations, and the like. See, e.g., Berge, el al., *J. Pharm. Sci.* (1977) 66(1): 1-79.

"Solvate" refers to forms of the compound that are associated with a solvent or water (also referred to as "hydrate"), usually by a solvolysis reaction. This physical association includes hydrogen bonding. Conventional solvents include water, ethanol, acetic acid, and the like. The compounds of the invention may be prepared e.g. in crystalline form and may be solvated or hydrated. Suitable solvates include pharmaceutically acceptable solvates, such as hydrates, and further include both stoichiometric solvates and non-stoichiometric solvates. In certain instances the solvate will be capable of isolation, for example when one or more solvent molecules are incorporated in the crystal lattice of the crystalline solid. "Solvate" encompasses both solution-phase and isolable solvates. Representative solvates include hydrates, ethanolates and methanolates.

As used herein, the term "isotopic variant" refers to a compound that contains unnatural proportions of isotopes at one or more of the atoms that constitute such compound. For example, an "isotopic variant" of a compound can contain one or more non-radioactive isotopes, such as for example, deuterium ($^2H$ or D), carbon-13 ($^{13}C$), nitrogen-15 ($^{15}N$), or the like. It will be understood that, in a compound where such isotopic substitution is made, the following atoms, where present, may vary, so that for example, any hydrogen may be $^2H$/D, any carbon may be $^{13}C$, or any nitrogen may be $^{15}N$, and that the presence and placement of such atoms may be determined within the skill of the art. Likewise, the invention may include the preparation of isotopic variants with radioisotopes, in the instance for example, where the resulting compounds may be used for drug and/or substrate tissue distribution studies. The radioactive isotopes tritium, i.e., $^3H$, and carbon-14, i.e., $^{14}C$, are particularly useful for this purpose in view of their ease of incorporation and ready means of detection. Further, compounds may be prepared that are substituted with positron emitting isotopes, such as $^{11}C$, $^{18}F$, $^{15}O$, and $^{13}N$, and would be useful in Positron Emission Topography (PET) studies for examining substrate receptor occupancy. All isotopic variants of the compounds provided herein, radioactive or not, are intended to be encompassed within the scope of the invention.

"Stereoisomers": It is also to be understood that compounds that have the same molecular formula but differ in the nature or sequence of bonding of their atoms or the arrangement of their atoms in space are termed "isomers." Isomers that differ in the arrangement of their atoms in space are termed "stereoisomers." Stereoisomers that are not mirror images of one another are termed "diastereomers" and those that are non-superimposable mirror images of each other are termed "enantiomers." When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

"Tautomers" refer to compounds that are interchangeable forms of a particular compound structure, and that vary in the displacement of hydrogen atoms and electrons. Thus, two structures may be in equilibrium through the movement of n electrons and an atom (usually H). For example, enols and ketones are tautomers because they are rapidly interconverted by treatment with either acid or base. Another example of tautomerism is the aci- and nitro-forms of phenylnitromethane, that are likewise formed by treatment with acid or base. Tautomeric forms may be relevant to the attainment of the optimal chemical reactivity and biological activity of a compound of interest.

A "subject" to which administration is contemplated includes, but is not limited to, humans (i.e., a male or female of any age group, e.g., a pediatric subject (e.g, infant, child, adolescent) or adult subject (e.g., young adult, middle-aged adult or senior adult)) and/or a non-human animal, e.g., a mammal such as primates (e.g., cynomolgus monkeys, rhesus monkeys), cattle, pigs, horses, sheep, goats, rodents, cats, and/or dogs. In certain embodiments, the subject is a human. In certain embodiments, the subject is a non-human animal. The terms "human," "patient," and "subject" are used interchangeably herein.

Disease, disorder, and condition are used interchangeably herein.

As used herein, and unless otherwise specified, the terms "treat," "treating" and "treatment" contemplate an action that occurs while a subject is suffering from the specified disease, disorder or condition, which reduces the severity of the disease, disorder or condition, or retards or slows the progression of the disease, disorder or condition ("therapeutic treatment"), and also contemplates an action that occurs before a subject begins to suffer from the specified disease, disorder or condition ("prophylactic treatment").

In general, the "effective amount" of a compound refers to an amount sufficient to elicit the desired biological response, e.g., to treat a CNS-related disorder, is sufficient to induce anesthesia or sedation. As will be appreciated by those of ordinary skill in this art, the effective amount of a compound of the invention may vary depending on such factors as the desired biological endpoint, the pharmacokinetics of the compound, the disease being treated, the mode of administration, and the age, weight, health, and condition of the subject. An effective amount encompasses therapeutic and prophylactic treatment.

As used herein, and unless otherwise specified, a "therapeutically effective amount" of a compound is an amount sufficient to provide a therapeutic benefit in the treatment of a disease, disorder or condition, or to delay or minimize one or more symptoms associated with the disease, disorder or condition. A therapeutically effective amount of a compound means an amount of therapeutic agent, alone or in combination with other therapies, which provides a therapeutic benefit in the treatment of the disease, disorder or condition. The term "therapeutically effective amount" can encompass an amount that improves overall therapy, reduces or avoids symptoms or causes of disease or condition, or enhances the therapeutic efficacy of another therapeutic agent.

As used herein, and unless otherwise specified, a "prophylactically effective amount" of a compound is an amount sufficient to prevent a disease, disorder or condition, or one or more symptoms associated with the disease, disorder or condition, or prevent its recurrence. A prophylactically effective amount of a compound means an amount of a therapeutic agent, alone or in combination with other agents, which provides a prophylactic benefit in the prevention of the disease, disorder or condition. The term "prophylactically effective amount" can encompass an amount that improves overall prophylaxis or enhances the prophylactic efficacy of another prophylactic agent.

DETAILED DESCRIPTION OF CERTAIN EMBODIMENTS OF THE INVENTION

As generally described herein, the present invention provides C21-substituted neuroactive steroids designed, for example, to act as GABA modulators. In certain embodiments, such compounds are envisioned to be useful as therapeutic agents for the induction of anesthesia and/or sedation in a subject. In certain embodiments, such compounds are envisioned to be useful as therapeutic agents for treating a CNS-related disorder.

Compounds

In one aspect, provided is a compound of Formula (I):

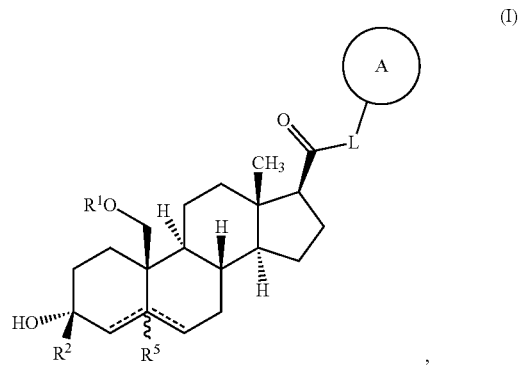

a pharmaceutically acceptable salt thereof, wherein: A is an optionally substituted nitrogen-containing heteroaryl or heterocyclyl; L is —C(R$^3$)(R$^3$)—, —O—, —S—, or —NR$^3$—; R$^1$ is hydrogen or C$_1$-C$_6$ alkyl, C$_1$-C$_6$ alkenyl, C$_1$-C$_6$ alkynyl, carbocyclyl, or heterocyclyl; R$^2$ is hydrogen, C$_1$-C$_6$ alkyl (e.g., C$_1$-C$_6$ haloalkyl), or C$_1$-C$_6$ alkoxy; each R$^3$ is independently hydrogen or C$_1$-C$_6$ alkyl; R$^5$ is absent or hydrogen; and ≡≡≡≡≡ represents a single or double bond, wherein when one of ≡≡≡≡≡ is a double bond, the other ≡≡≡≡≡ is a single bond; and when one of the ≡≡≡≡≡ is a double bond, R$^5$ is absent.

In one aspect, provided is a compound of Formula (Ia):

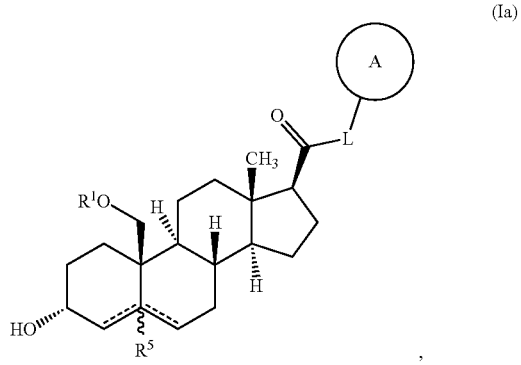

a pharmaceutically acceptable salt thereof, wherein: A is an optionally substituted nitrogen-containing heteroaryl or heterocyclyl; L is —C(R³)(R³)—, —O—, —S—, or —NR³—; R¹ is hydrogen or C₁-C₆ alkyl, C₁-C₆ alkenyl, C₁-C₆ alkynyl, carbocyclyl, or heterocyclyl; each R³ is independently hydrogen or C₁-C₆ alkyl; R⁵ is absent or hydrogen; and ----- represents a single or double bond wherein when one of ----- is a double bond, the other ----- is a single bond; and when one of the ----- is a double bond, R⁵ is absent.

In some embodiments, the compound is of the Formula (Ia-1):

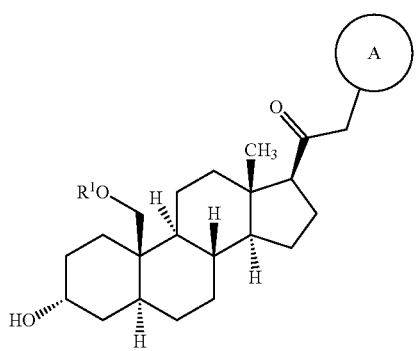

(Ia-1)

In some embodiments, the compound is of the Formula (Ia-2):

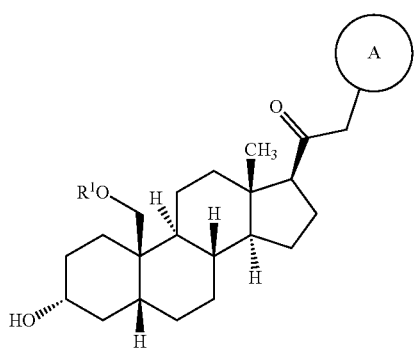

(Ia-2)

In some embodiments, A is monocyclic or bicyclic.

In some embodiments, A is monocyclic. In some aspects of these embodiments, A is attached through a nitrogen. In some embodiments, A is a heteroaryl. In some aspects of these embodiments, the heteroaryl comprising up to five nitrogen atoms. In some embodiments, A is a 5-membered heteroaryl or heterocyclyl. In some embodiments, A is a 5-membered heteroaryl or heterocyclyl comprising up to four nitrogen atoms. In some embodiments, A is a 5-membered heteroaryl or heterocyclyl comprising 2, 3, or 4 nitrogen atoms. In some embodiments, A is pyrazole, triazole, or tetrazole. In some embodiments, A is unsubstituted pyrazole, triazole, or tetrazole. In some embodiments, A is

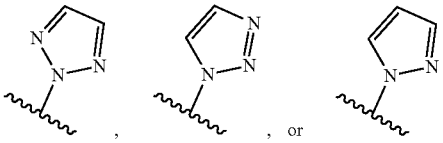

In some embodiments, A is unsubstituted triazole. In some embodiments, A is

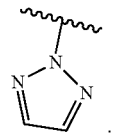

In some embodiments, A is bicyclic. In some aspects of these embodiments, A is attached through a nitrogen. In some embodiments, A is a heteroaryl. In some aspects of these embodiments, the heteroaryl comprises up to five nitrogen atoms. In some embodiments, the heteroaryl comprises at least two nitrogen atoms. In some embodiments, A is a heteroaryl comprising up to four nitrogen atoms. In some embodiments, A is a heteroaryl comprising up to three nitrogen atoms. In some embodiments, A is a heteroaryl comprising 2, 3, or 4 nitrogen atoms. In some embodiments, the heteroaryl is benzotriazole, azabenzotriazole, diazabenzotriazole, benzopyrazole, azabenzopyrazole, or diazabenzopyrazole.

In some embodiments, the compound is of the Formula (Ia-3):

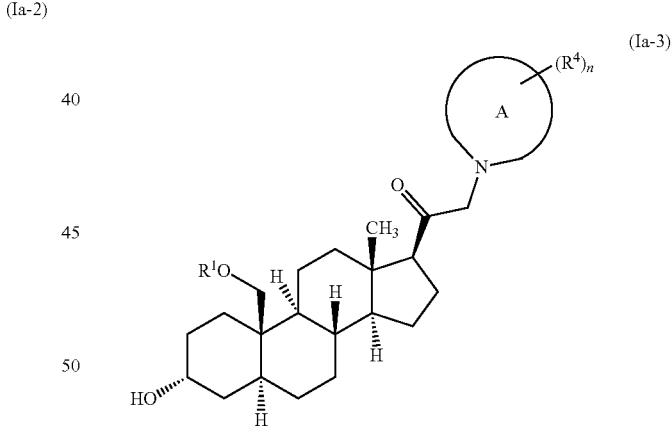

(Ia-3)

wherein R⁴ is cyano, nitro, hydroxy, halo, C₁-C₆ alkyl, C₁-C₆ alkoxy, —C(O)Rᵃ, —C(O)N(Rᵇ)(Rᶜ), —C(O)ORᵃ, —N(Rᵇ)(Rᶜ), —OC(O)N(Rᵇ)(Rᶜ), —OC(O)ORᵃ, —OC(O)Rᵃ, —S(O)₀₋₂Rᵃ, —S(O)₀₋₂ORᵃ, or —S(O)₀₋₂N(Rᵇ)(Rᶜ); each Rᵃ is hydrogen or C₁-C₆ alkyl; each Rᵇ and Rᶜ is independently hydrogen, C₁-C₆ alkyl, carbocyclyl, heterocyclyl, aryl, heteroaryl, or Rᵇ and Rᶜ, together with the nitrogen atom to which they are bound to form a ring (e.g., a 3-7-membered ring, e.g., a 5-7-membered ring; a ring containing at least one heteroatom, e.g., a nitrogen, oxygen, or sulfur atom); and n is 0, 1, 2, or 3.

In some embodiments, the compound is of the Formula (Ia-4):

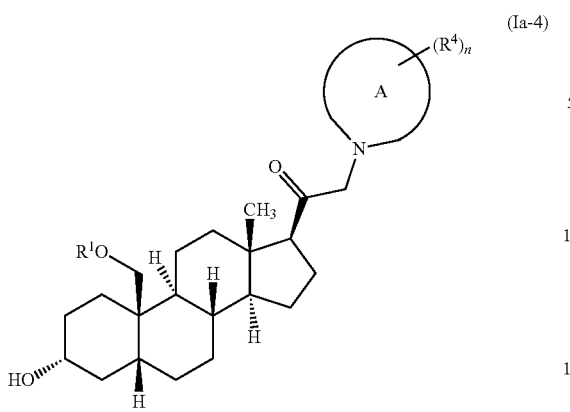

(Ia-4)

wherein $R^4$ is cyano, nitro, hydroxy, halo, $C_1$-$C_6$ alkyl, $C_1$-$C_6$ alkoxy, —C(O)$R^a$, —C(O)N($R^b$)($R^c$), —C(O)O$R^a$, —N($R^b$)($R^c$), —OC(O)N($R^b$($R^c$), —OC(O)O$R^a$, —OC(O)$R^a$, —S(O)$_{0-2}$$R^a$, —S(O)$_{0-2}$O$R^a$, or —S(O)$_{0-2}$N($R^b$)($R^c$); each $R^a$ is hydrogen or $C_1$-$C_6$ alkyl; each $R^b$ and $R^c$ is independently hydrogen, $C_1$-$C_6$ alkyl, carbocyclyl, heterocyclyl, aryl, heteroaryl, or $R^b$ and $R^c$ together with the nitrogen atom to which they are bound to form a ring (e.g., a 3-7-membered ring, e.g., a 5-7-membered ring; a ring containing at least one heteroatom, e.g., a nitrogen, oxygen, or sulfur atom); and n is 0, 1, 2, or 3.

In some embodiments, n is 0.

In some embodiments, in is 1. In some aspects of these embodiments, $R^4$ is cyano, nitro, hydroxy, halo, $C_1$-$C_6$ alkyl, $C_1$-$C_6$ alkoxy, —C(O)$R^a$, —C(O)O$R^a$, or —S(O)$_{0-2}$$R^a$. In some embodiments, n is 1 and $R^4$ is cyano, nitro, hydroxy, halo, $C_1$-$C_6$ alkyl, $C_1$-$C_6$ alkoxy, —C(O)$R^a$, —C(O)O$R^a$, or —S(O)$_{0-2}$$R^a$. In some aspects of these embodiments, $R^4$ is halo (e.g., F, Cl, Br). In some embodiments, $R^4$ is F. In some embodiments, $R^4$ is Cl. In some embodiments, $R^4$ is Br. In some embodiments, $R^4$ is $C_1$-$C_6$ alkoxy (e.g., —OCH$_3$, —OCH$_2$CH$_3$). In some embodiments, $R^4$ is cyano. In some embodiments, $R^4$ is —C(O)$R^a$ or —C(O)O$R^a$. In some aspects of these embodiments, $R^a$ is $C_1$-$C_6$ alkyl (e.g., —CH$_3$, —CH$_2$CH$_3$). In some embodiments, $R^4$ is —S(O)$_{0-2}$$R^a$. In some embodiments, $R^4$ is —S(O)$_2$$R^a$, and $R^a$ is $C_1$-$C_6$ alkyl. In some aspects of these embodiments, $R^a$ is —CH$_3$. In some embodiments, $R^4$ is —S(O)$_2$CH$_3$. In some embodiments, $R^4$ is $C_1$-$C_6$ alkyl (e.g., —CH$_3$, —CH$_2$CH$_3$).

In some embodiments, n is 2. In some aspects of these embodiments, $R^4$ is cyano, nitro, hydroxy, halo, $C_1$-$C_6$ alkyl, $C_1$-$C_6$ alkoxy, —C(O)$R^a$,—C(O)O$R^a$, or —S(O)$_{0-2}$$R^a$. In some embodiments, n is 2 and $R^4$ is cyano, nitro, hydroxy, halo, $C_1$-$C_6$ alkyl, $C_1$-$C_6$ alkoxy, —C(O)$R^a$, —C(O)O$R^a$, or —S(O)$_{0-2}$$R^a$. In some aspects of these embodiments, $R^4$ is halo (e.g., F, Cl, Br). In some embodiments, $R^4$ is F. In some embodiments, $R^4$ is Cl. In some embodiments, $R^4$ is Br. In some embodiments, $R^4$ is $C_1$-$C_6$ alkoxy (e.g., —OCH$_3$, —OCH$_2$CH$_3$). In some embodiments, $R^4$ is cyano. In some embodiments, $R^4$ is —C(O)$R^a$ or —C(O)O$R^a$. In some aspects of these embodiments, $R^a$ is $C_1$-$C_6$ alkyl (e.g., —CH$_3$, —CH$_2$CH$_3$). In some embodiments, $R^4$ is —S(O)$_{0-2}$$R^a$. In some embodiments, $R^4$ is —S(O)$_2$$R^a$, and $R^a$ is $C_1$-$C_6$ alkyl. In some aspects of these embodiments, $R^a$ is —CH$_3$. In some embodiments, $R^4$ is $C_1$-$C_6$ alkyl (e.g., —CH$_3$, —CH$_2$CH$_3$).

In some embodiments, n is 1 or 2, and $R^4$ is $C_1$-$C_6$ alkyl or C(O)O$R^a$. In some embodiments, the compound $R^4$ is methyl. In some embodiments, the compound $R^a$ is $C_1$-$C_6$ alkyl. In some embodiments, $R^a$ is ethyl.

In some embodiments, $R^1$ is hydrogen or $C_1$-$C_6$ alkyl, and $R^4$ is —C(O)O$R^a$.

In some embodiments, $R^1$ is $C_1$-$C_6$ alkyl, $C_1$-$C_6$ alkenyl, $C_1$-$C_6$ alkynyl, carbocyclyl, or heterocyclyl. In some embodiments, the compound $R^1$ is $C_1$-$C_6$ alkyl. In some embodiments, the compound $R^1$ is methyl, ethyl, or isopropyl.

In some embodiments, $R^1$ is methyl and $R^4$ is —C(O)OEt.

In some embodiments, the compound is selected from:

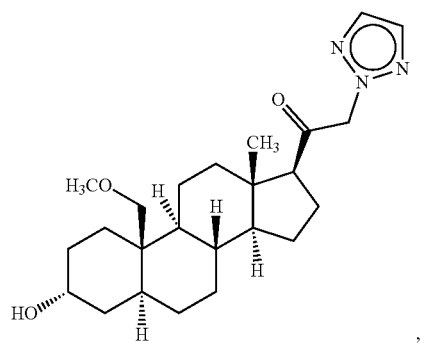

,

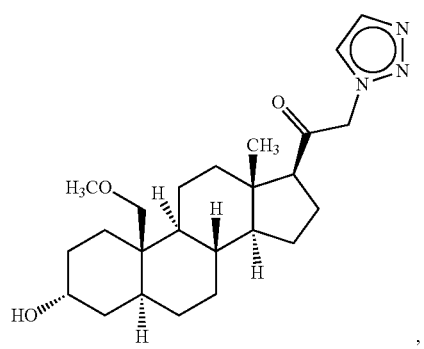

,

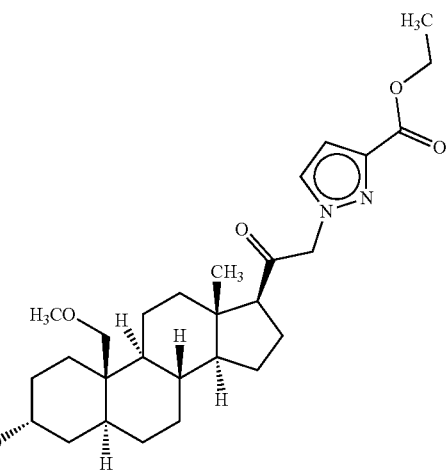

,

-continued

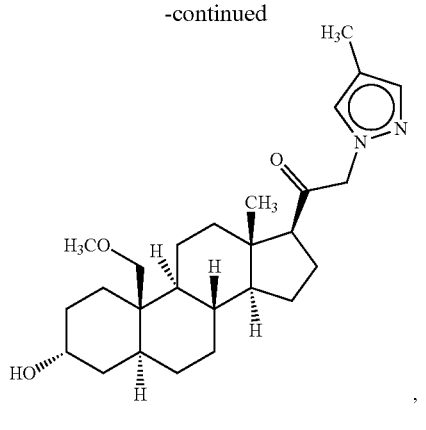

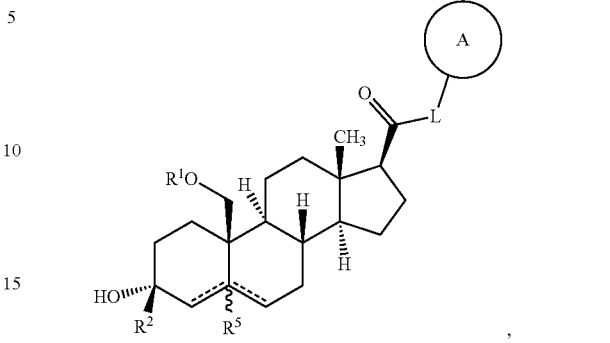

In one aspect, provided is a compound of Formula (Ib):

(Ib-2)

a pharmaceutically acceptable salt thereof, wherein: A is an optionally substituted nitrogen-containing heteroaryl or heterocyclyl; L is —C($R^3$)($R^3$)—, —O—, —S—, or —N$R^3$—; $R^1$ is hydrogen or $C_1$-$C_6$ alkyl, $C_1$-$C_6$ alkenyl, $C_1$-$C_6$ alkynyl, carbocyclyl, or heterocyclyl; $R^2$ is $C_1$-$C_6$ alkyl (e.g., $C_1$-$C_6$ haloalkyl) or $C_1$-$C_6$ alkoxy; each $R^3$ is independently hydrogen or $C_1$-$C_6$ alkyl; $R^5$ is absent or hydrogen; and ⁃⁃⁃⁃⁃ represents a single or double bond, wherein when one of ⁃⁃⁃⁃⁃ is a double bond, the other ⁃⁃⁃⁃⁃ is a single bond and when one of the ⁃⁃⁃⁃⁃ is a double bond, $R^5$ is absent.

In some embodiments, the compound is of the Formula (Ib-1):

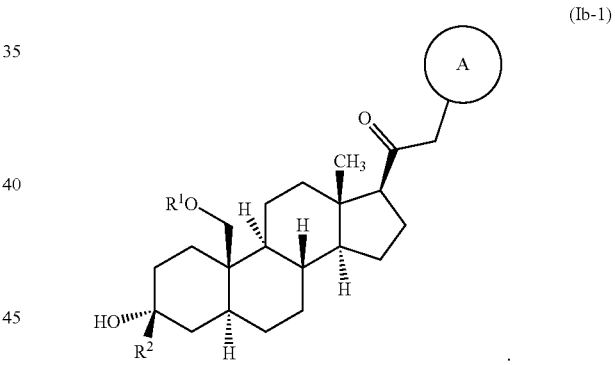

(Ib-1)

, and

In some embodiments, the compound is of the Formula (Ib-2):

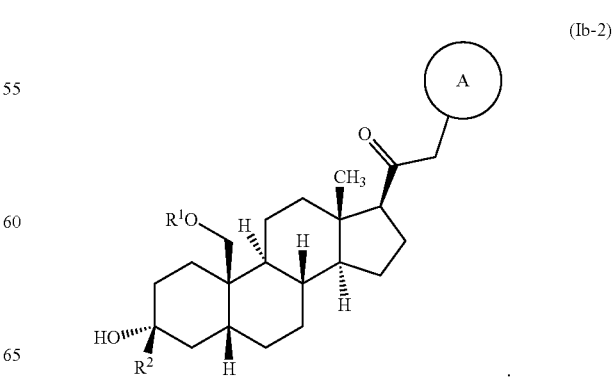

(Ib-2)

.

In some embodiments, the compound is of the Formula (Ib-3)

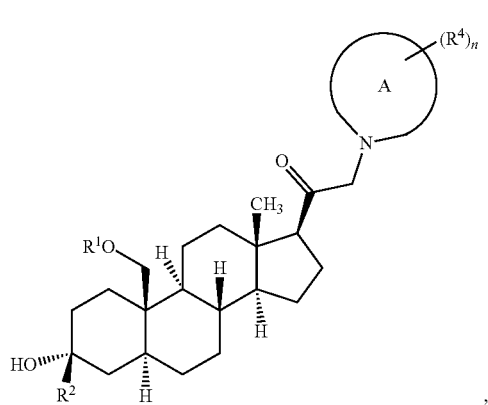
(Ib-3)

wherein $R^4$ is cyano, nitro, hydroxy, halo, $C_1$-$C_6$ alkyl, $C_1$-$C_6$ alkoxy, —C(O)$R^a$, —C(O)N(RN)$R^c$), —C(O)O$R^a$, —N($R^b$)($R^c$), —OC(O)N($R^b$)($R^c$), —OC(O)O$R^a$, —OC(O)$R^a$, —S(O)$_{0-2}R^a$, —S(O)$_{0-2}R^a$, or —S(O)$_{0-2}$N($R^b$)($R^c$); each $R^a$ is hydrogen or $C_1$-$C_6$ alkyl; each $R^b$ and $R^c$ is independently hydrogen, $C_1$-$C_6$ alkyl, carbocyclyl, heterocyclyl, aryl, heteroaryl, or $R^b$ and $R^c$, together with the nitrogen atom to which they are bound to form a ring (e.g., a 3-7-membered ring, e.g., a 5-7-membered ring; a ring containing at least one heteroatom, e.g., a nitrogen, oxygen, or sulfur atom); and n is 0, 1, 2, or 3.

In some embodiments the compound is of the Formula (Ib-4

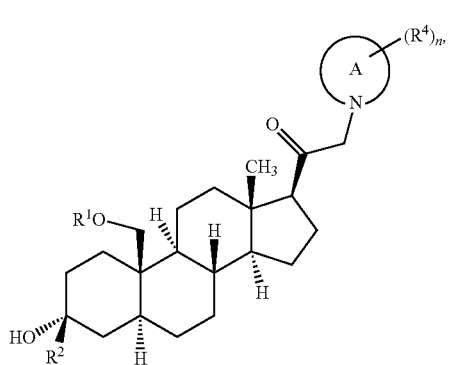
(Ib-4)

wherein $R^4$ is cyano, nitro, hydroxy, halo, $C_1$-$C_6$ alkyl, $C_1$-$C_6$ alkoxy, —C(O)$R^a$, —C(O)N($R^b$)($R^c$), —C(O)O$R^a$, —N($R^b$)($R^c$), —OC(O)N($R^b$)($R^c$), —OC(O)O$R^a$, —OC(O)$R^a$, —S(O)$_{0-2}R^a$, —S(O)$_{0-2}R^a$, or —S(O)$_{0-2}$N($R^b$)($R^c$); each $R^a$ is hydrogen or $C_1$-$C_6$ alkyl; each $R^b$ and $R^c$ is independently hydrogen, $C_1$-$C_6$ alkyl, carbocyclyl, heterocyclyl, aryl, heteroaryl, or $R^b$ and $R^c$, together with the nitrogen atom to which they are bound to form a ring (e.g., a 3-7-membered ring, e.g., a 5-7-membered ring; a ring containing at least one heteroatom, e.g., a nitrogen, oxygen, or sulfur atom); and n is 0, 1, 2, or 3.

In some embodiments, A is monocyclic.
In some embodiments, A is bicyclic.
In some embodiments, A is attached through a nitrogen.
In some embodiments, A is a 5-membered or 6-membered heteroaryl or heterocyclyl. In some embodiments, A is a 5-membered or 6-membered heteroaryl or heterocyclyl comprising up to four nitrogen atoms. In some embodiments, A is a 5-membered or 6-membered heteroaryl or heterocyclyl comprising 1, 2, 3, or 4 nitrogen atoms.

In some embodiments, A is a heterocyclyl. In some embodiments, A is morpholine or piperazine. In some embodiments, A is

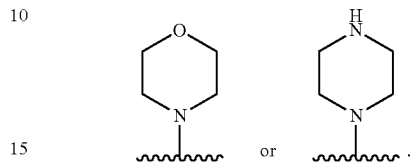

In some embodiments, A is a heteroaryl. In some aspects of these embodiments, the heteroaryl comprises up to five nitrogen atoms. In some embodiments, the heteroaryl is benzotriazole, azabenzotriazole, diazabenzotriazole, benzopyrazole, azabenzopyrazole, or diazabenzopyrazole. In some embodiments, A is

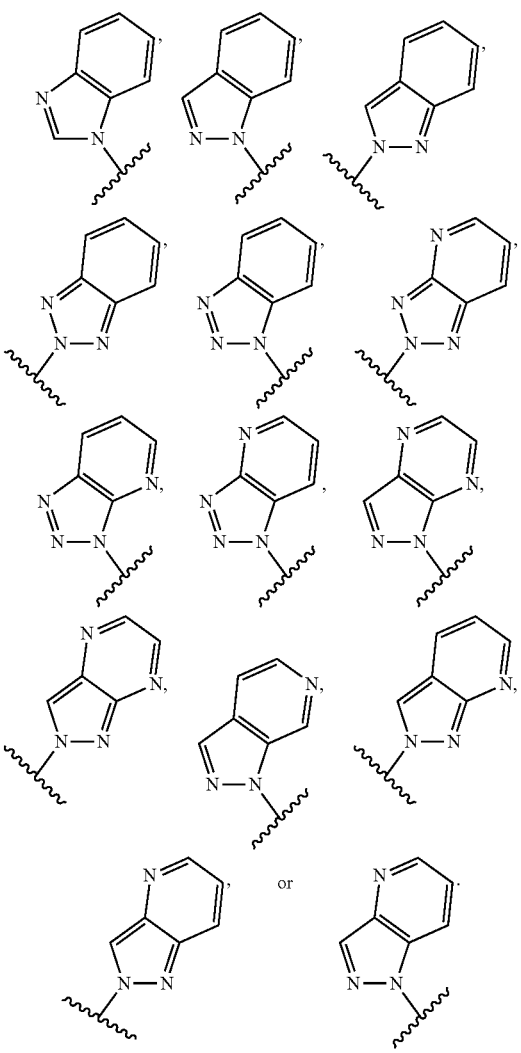

In some embodiments, the heteroaryl is 5-membered.

In some embodiments, A comprises up to four nitrogen atoms. In some embodiments, A comprises 2, 3, or 4 nitrogen atoms. In some embodiments, A is pyrazole, triazole, or tetrazole. In some embodiments, A is unsubstituted pyrazole, triazole, or tetrazole. In some embodiments, A is

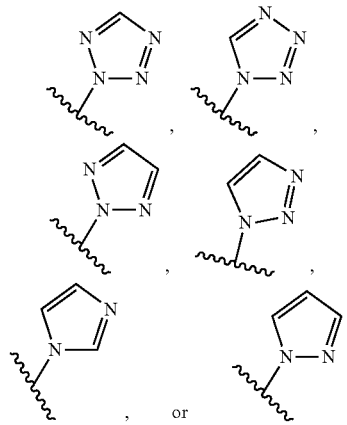

In some embodiments, A is unsubstituted triazole. In some embodiments, A is

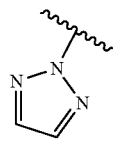

In some embodiments, $R^1$ is $C_1$-$C_6$ alkyl, $C_1$-$C_6$ alkenyl, $C_1$-$C_6$ alkynyl, carbocyclyl, or heterocyclyl. In some embodiments, $R^1$ is $C_1$-$C_6$ alkyl. In some embodiments, $R^1$ is methyl, ethyl, or isopropyl. In some embodiments, $R^1$ is methyl. In some embodiments, $R^1$ is ethyl.

In some embodiments, $R^2$ is $C_1$-$C_6$alkyl. In some embodiments, $R^2$ is methyl. In some embodiments, $R^2$ is $C_1$-$C_6$haloalkyl. In some embodiments, $R^2$ is —$CF_3$.

In some embodiments, n is 0.

In some embodiments, n is 1 or 2, and $R^4$ is cyano, halo, $C_1$-$C_6$ alkyl, $C_1$-$C_6$ alkoxy, —$C(O)R^a$, or —$S(O)_{0-2}R^a$.

In some embodiments, $R^4$ is Br, Cl, or F. In some embodiments, $R^4$ is F. In some embodiments, $R^4$ is Cl. In some embodiments, $R^4$ is Br. In some embodiments, $R^4$ is —$OCH_3$. In some embodiments, $R^4$ is —$OCF_3$. In some embodiments, $R^4$ is cyano. In some embodiments, $R^4$ is $C_1$-$C_6$ alkyl. In some embodiments, $R^4$ is methyl. In some embodiments, $R^4$ is —$C(O)R^a$. In some embodiments, $R^a$ is $C_1$-$C_6$ alkyl. In some embodiments, $R^a$ is methyl. In some embodiments, $R^4$ is —$CF_3$. In some embodiments, $R^4$ is —$S(O)_2R^a$. In some embodiments, $R^a$ is methyl.

In some embodiments, $R^1$ is $C_1$-$C_6$ alkyl and $R^4$ is —$C(O)R^a$. In some embodiments, $R^1$ is methyl and $R^4$ is —$C(O)$Me.

In some embodiments, n is 2, and $R^4$ is cyano, halo, $C_1$-$C_6$ alkyl, $C_1$-$C_6$ alkoxy, —$C(O)R^a$, or —$S(O)_{0-2}R^a$. In some embodiments, n is 2, one $R^4$ is F and one $R^4$ is F. In some embodiments, n is 2, one $R^4$ is F and one $R^4$ is Cl. In some embodiments, in is 2, one $R^4$ is —$OCH_3$ and one $R^4$ is —$OCH_3$.

In some embodiments, n is 0 or 1; $R^1$ is hydrogen or $C_1$-$C_6$ alkyl; and $R^2$ is methyl.

In some embodiments, $R^1$ is methyl, ethyl, or isopropyl. In some embodiments, $R^1$ is methyl.

In some embodiments, $R^4$ is $C_1$-$C_6$ alkyl, —$C(O)R^a$, or —$S(O)_{0-2}R^a$. In some embodiments, $R^4$ is methyl. In some embodiments, $R^4$ is —$C(O)$Me. In some embodiments, $R^4$ is —$S(O)_2$Me. In some embodiments, $R^4$ is cyano.

In some embodiments, the compound is selected from:

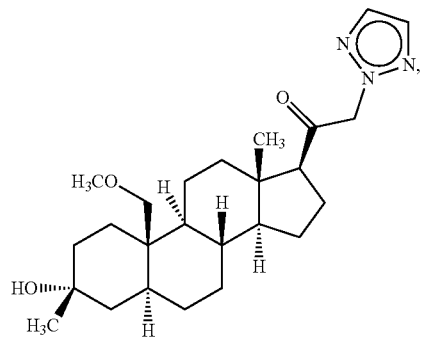

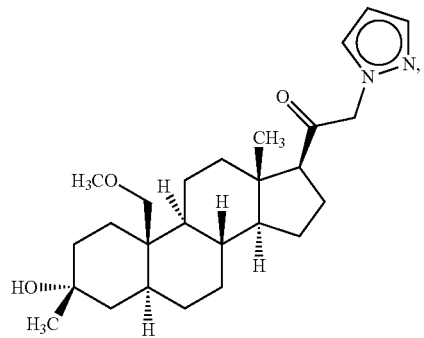

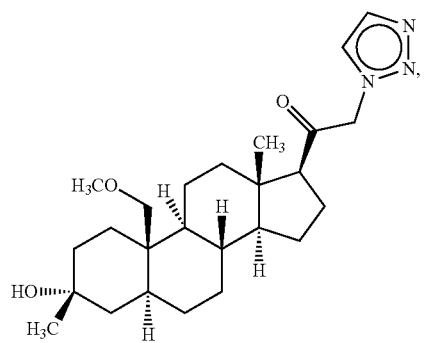

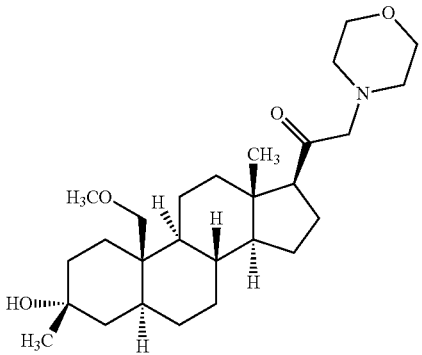

33
-continued
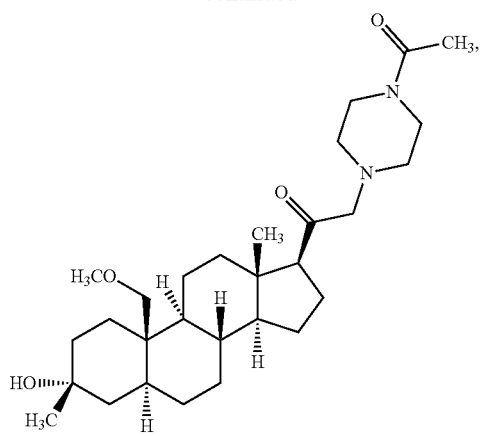
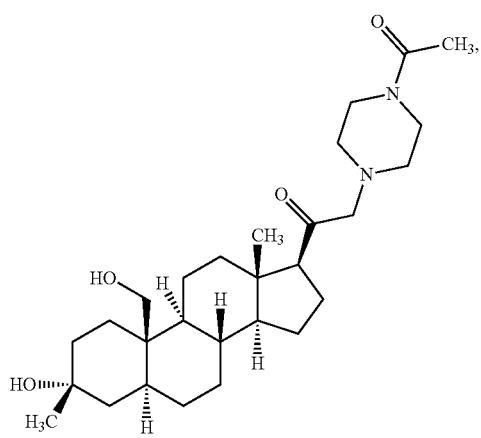
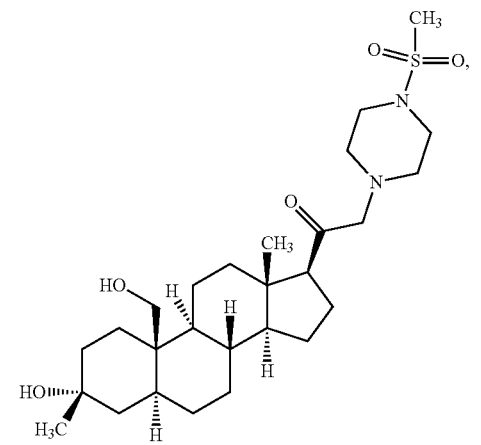
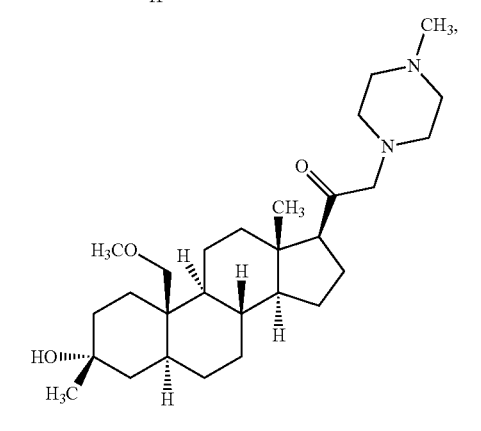
34
-continued
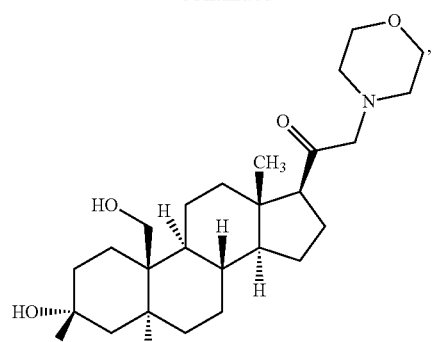
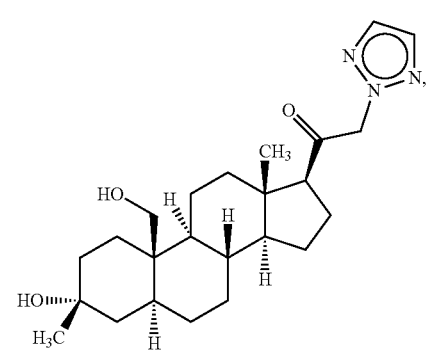
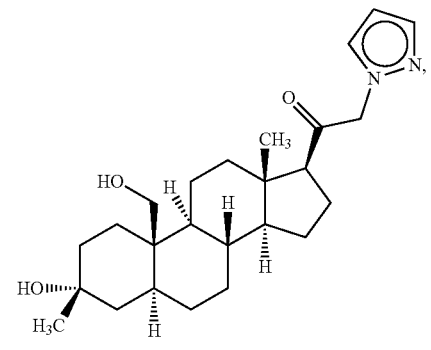
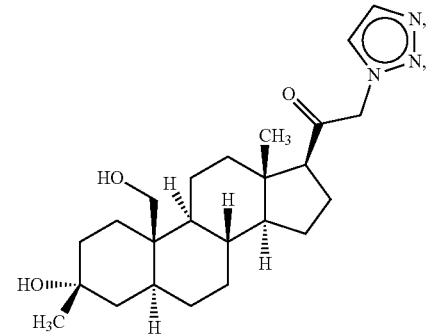
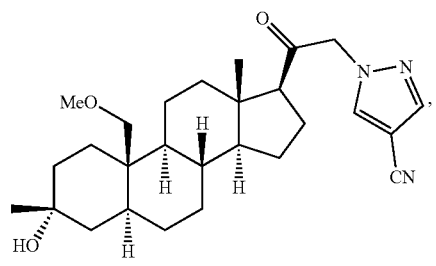

35
-continued
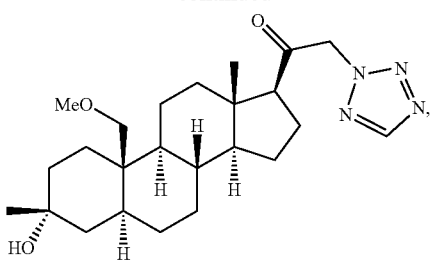
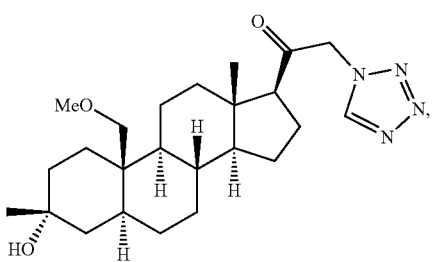
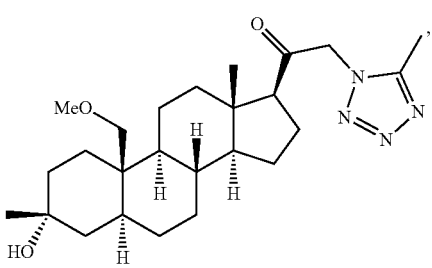
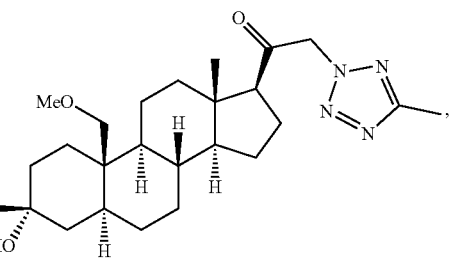
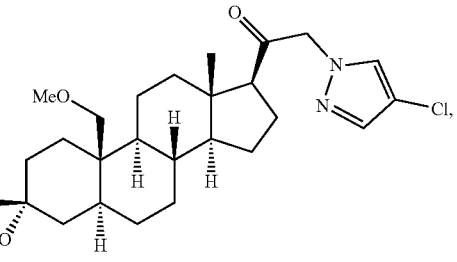
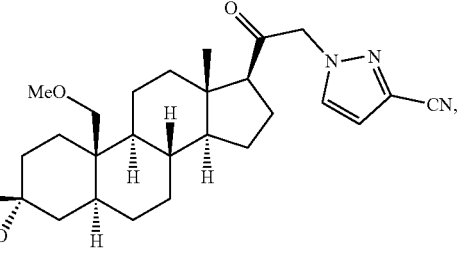
36
-continued
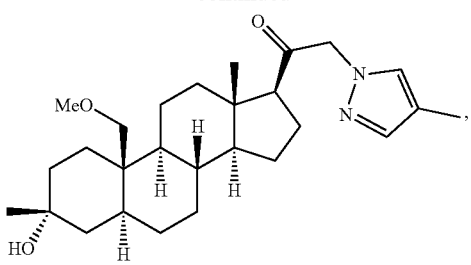
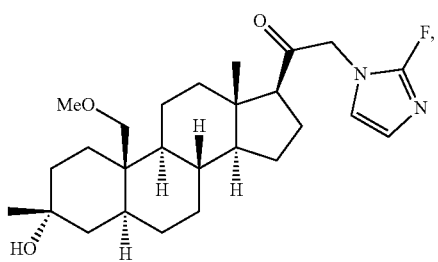
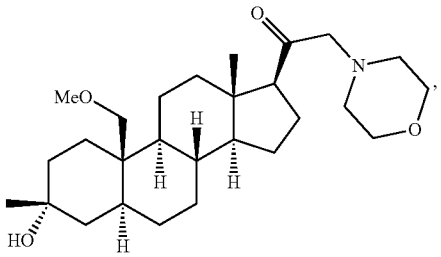
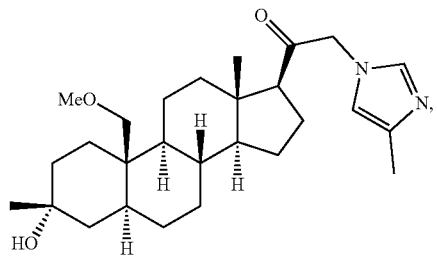
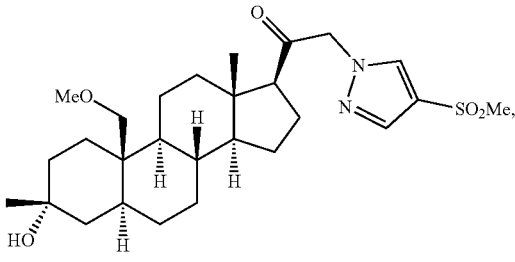
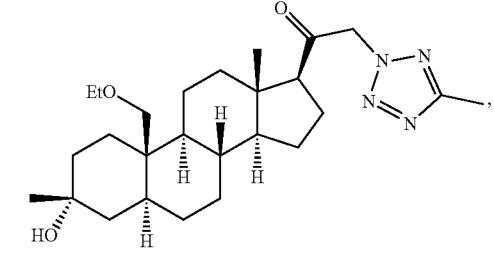

37
-continued
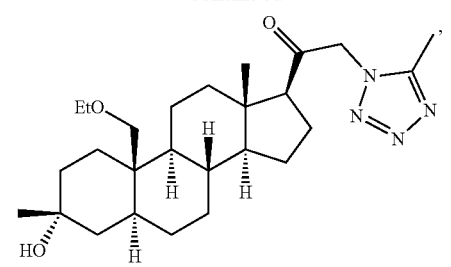
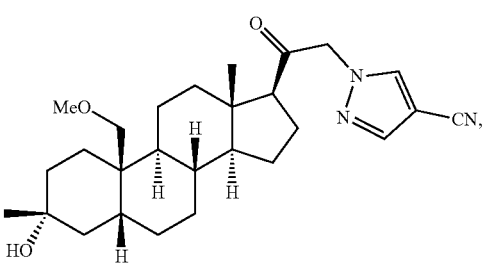
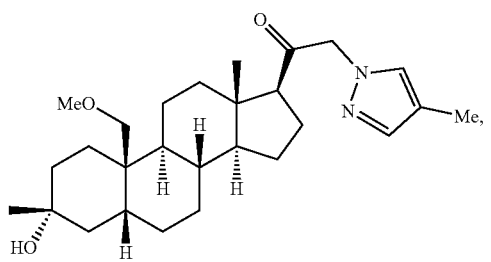
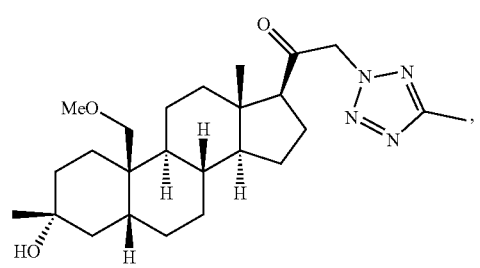
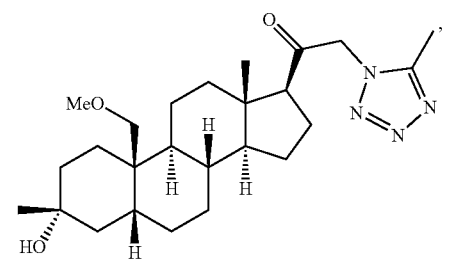
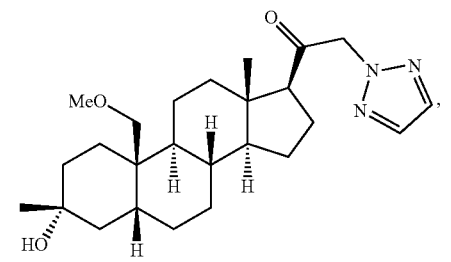
38
-continued
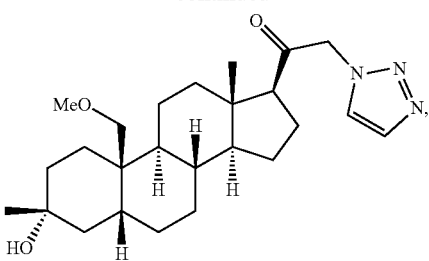
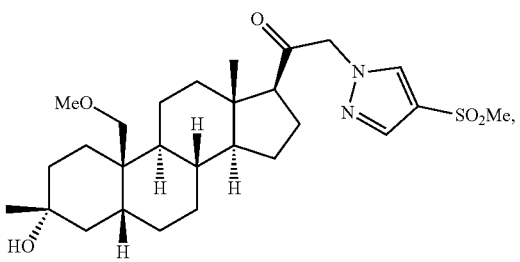
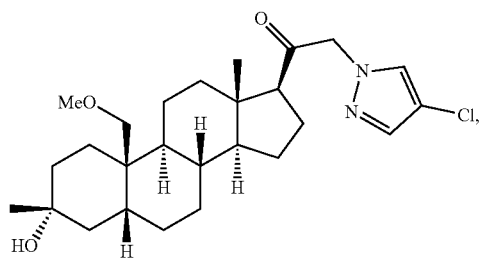
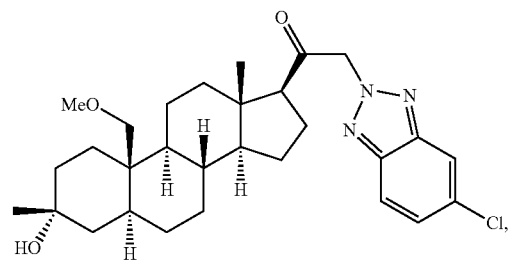
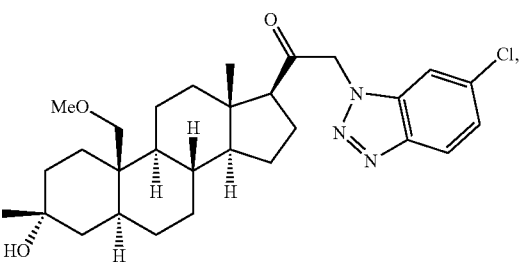
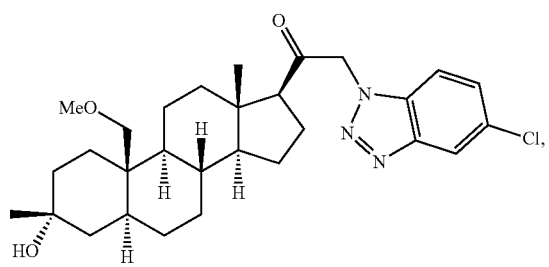

39
-continued
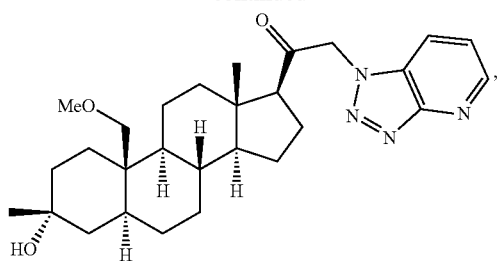
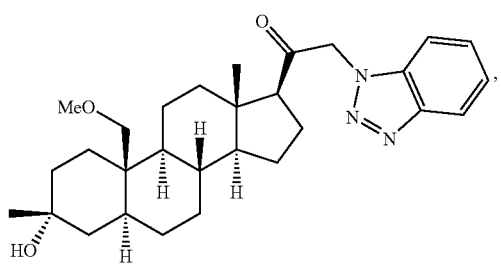
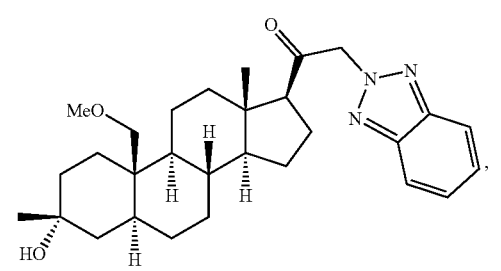
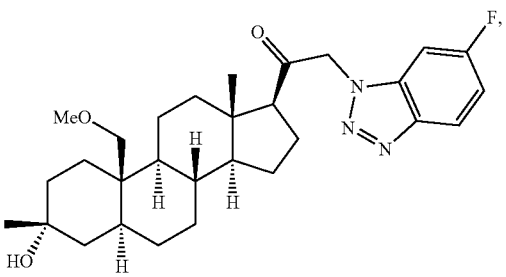
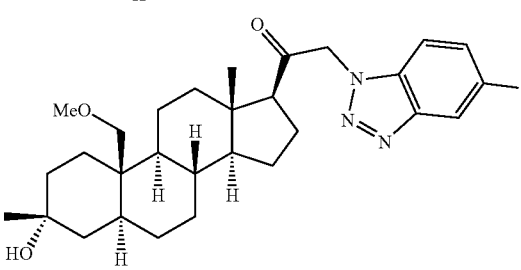
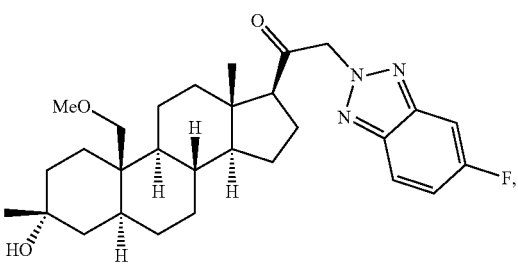
40
-continued
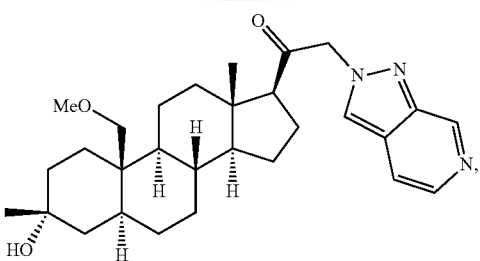
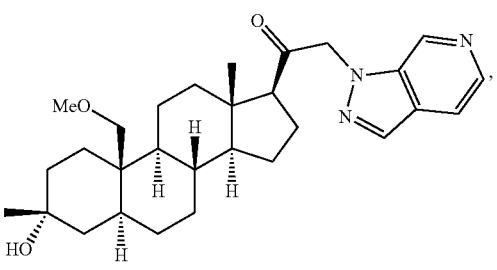
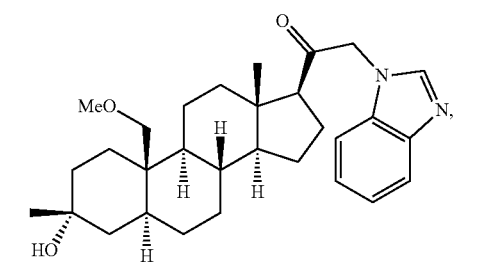
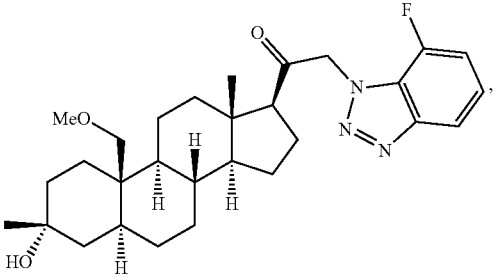
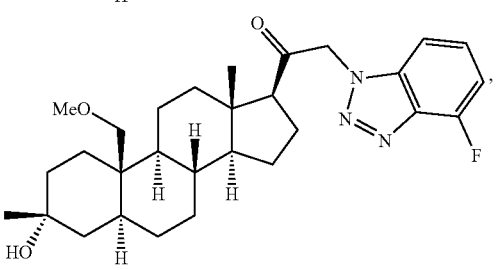
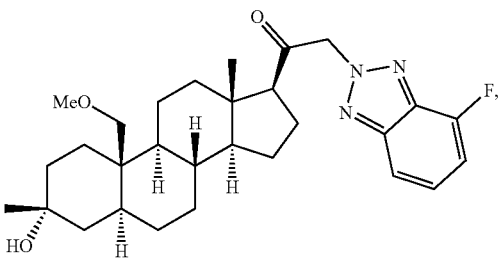

41
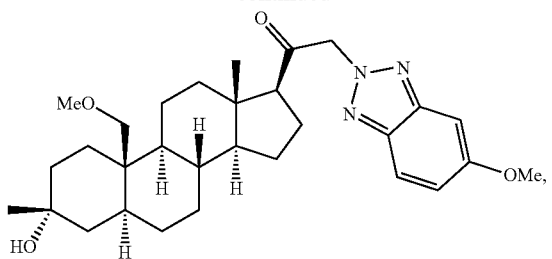
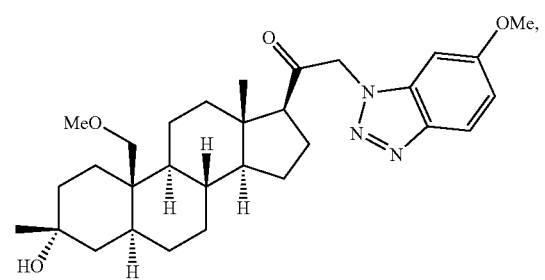
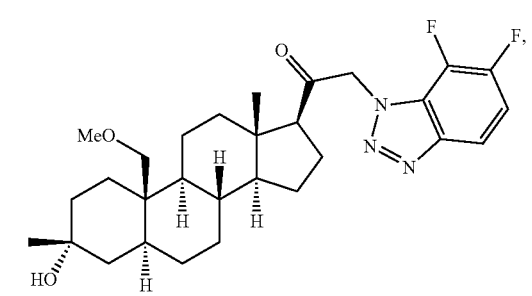
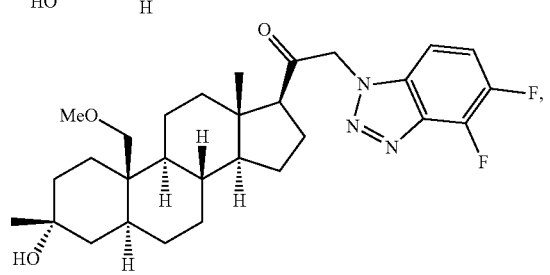
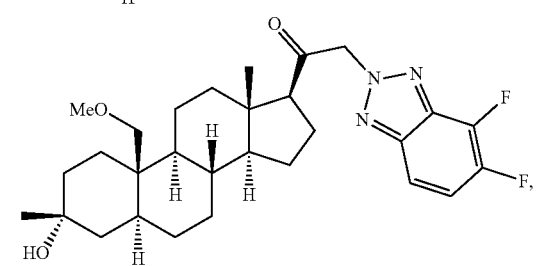
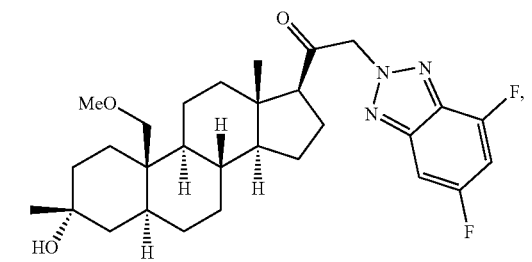
42
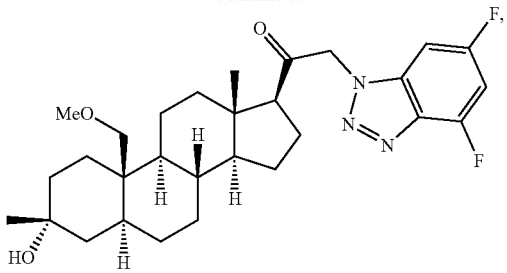
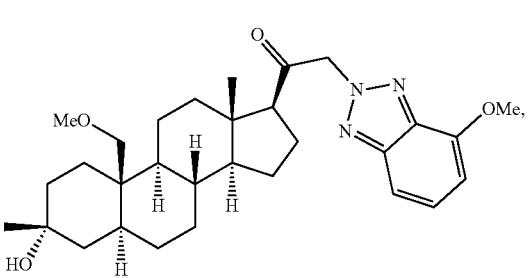
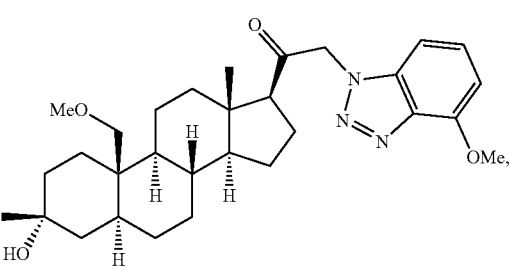
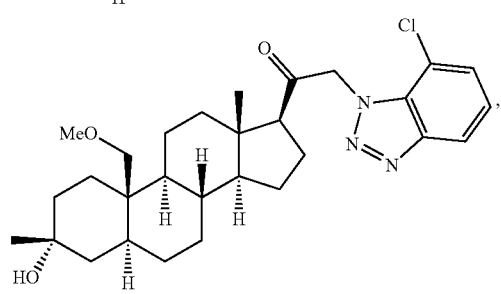
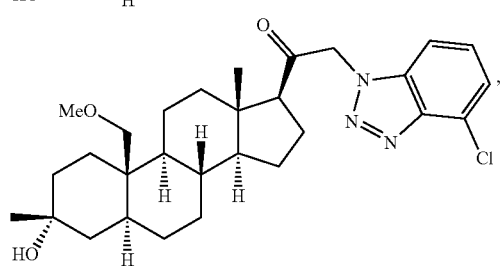
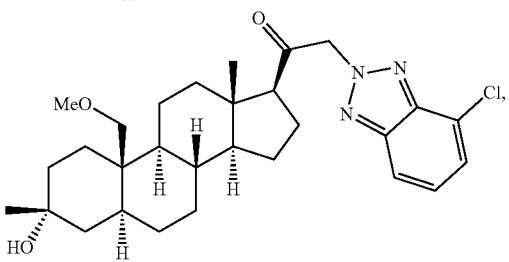

-continued
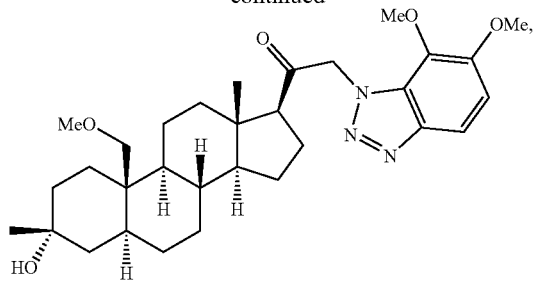
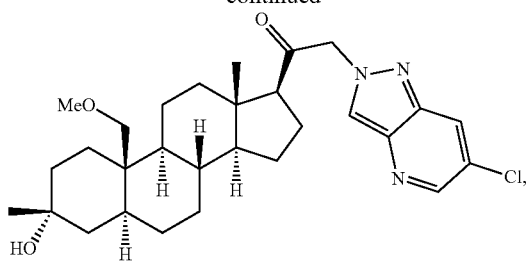
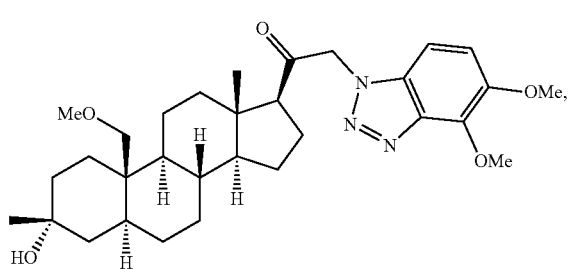
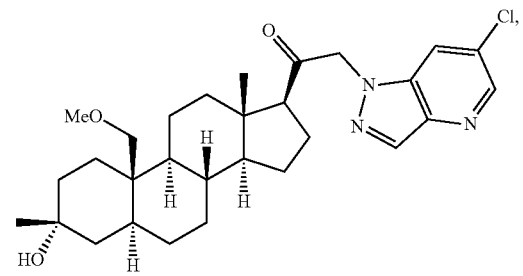
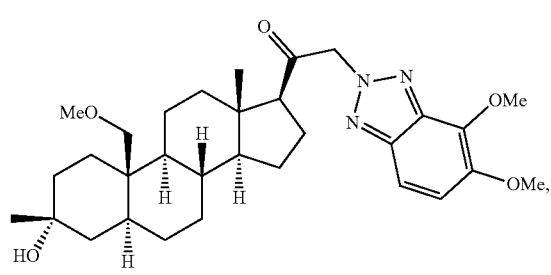
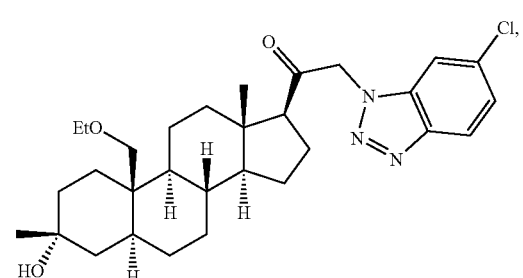
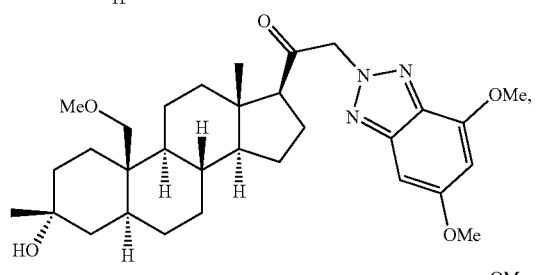
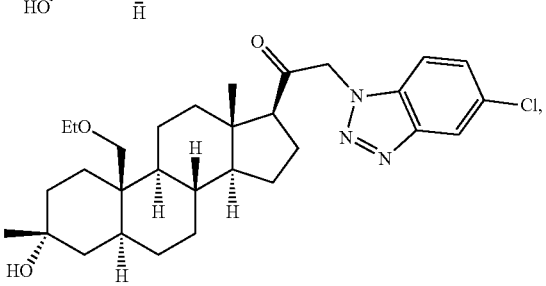
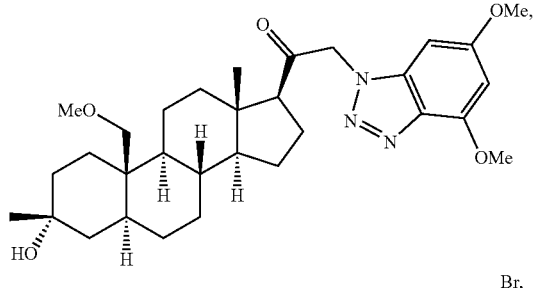
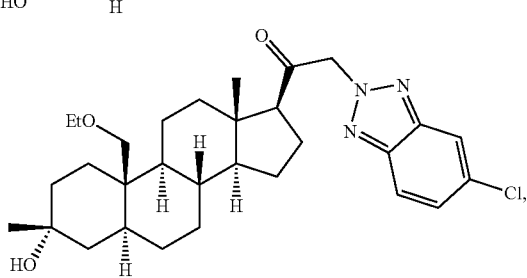
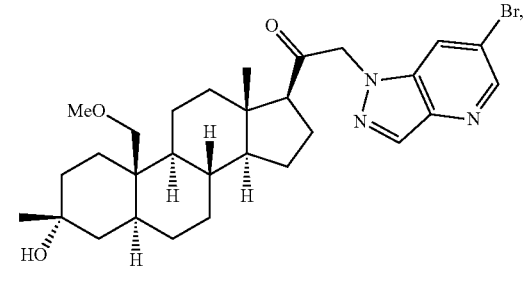
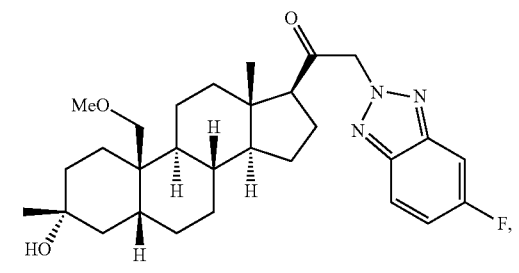

45
-continued
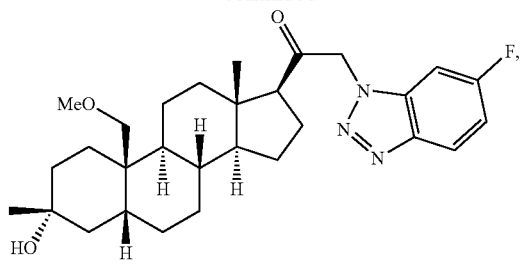
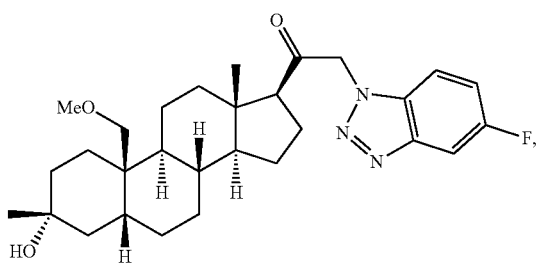
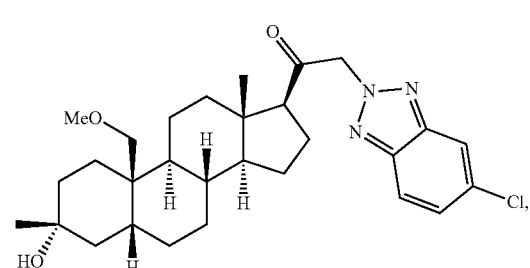
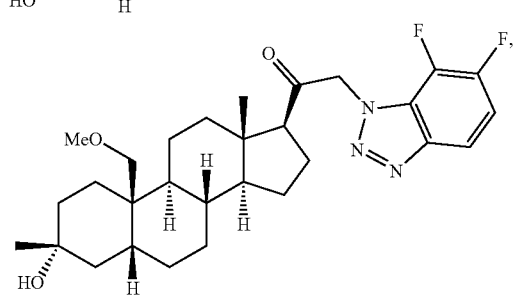
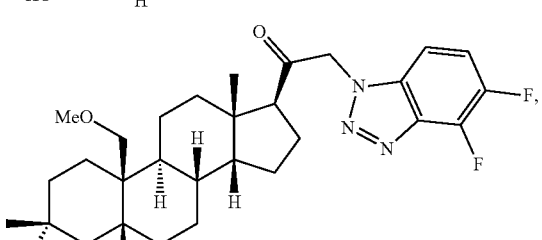
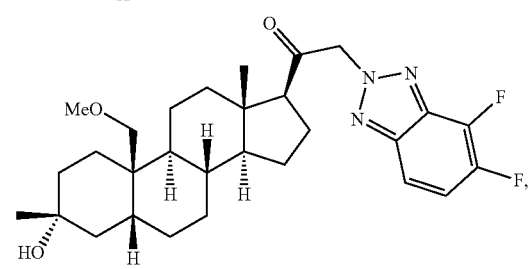
46
-continued
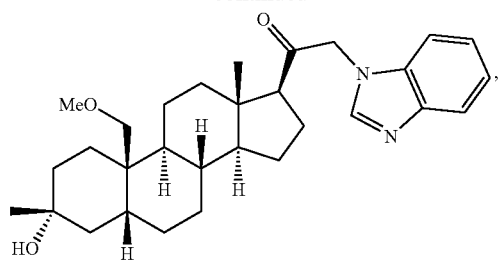
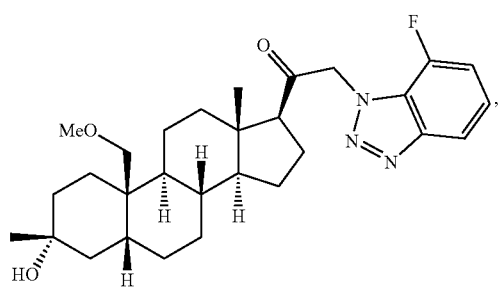
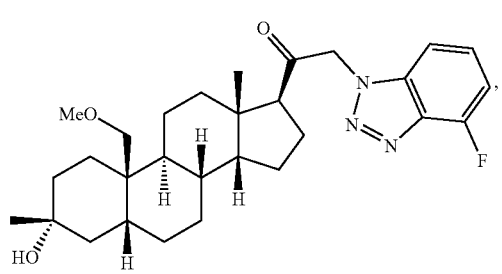
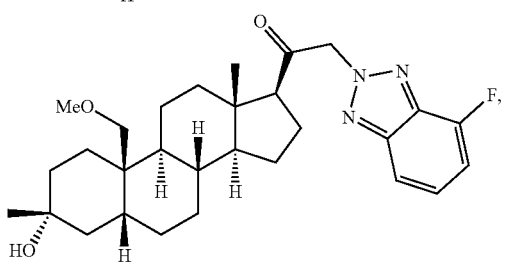
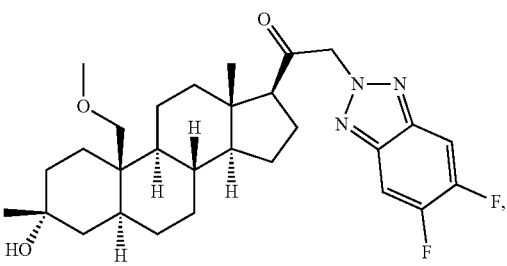
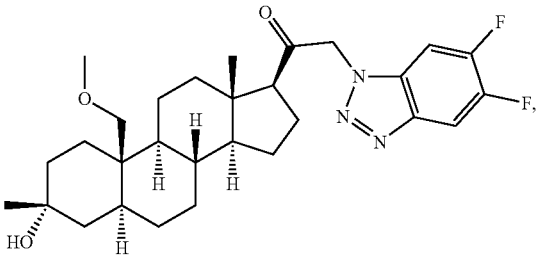

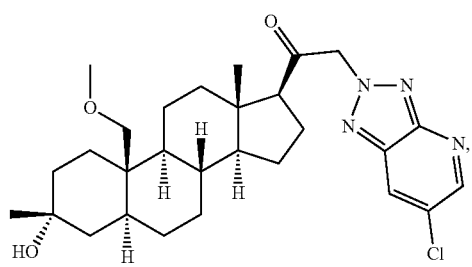
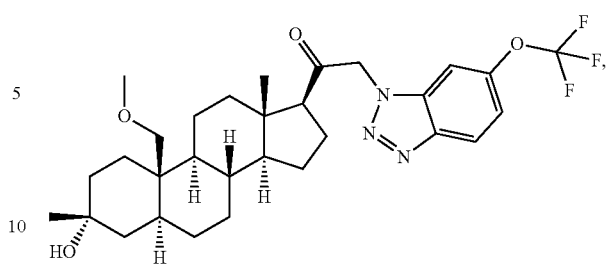
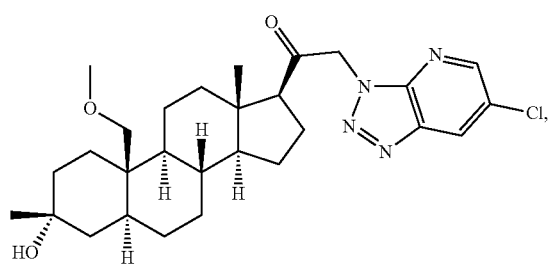
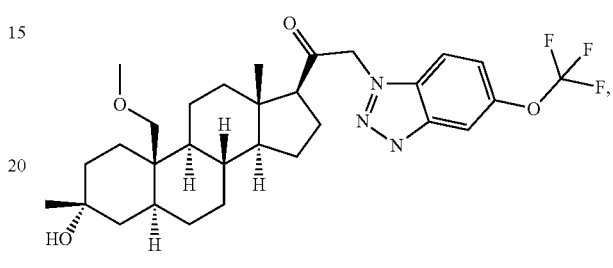
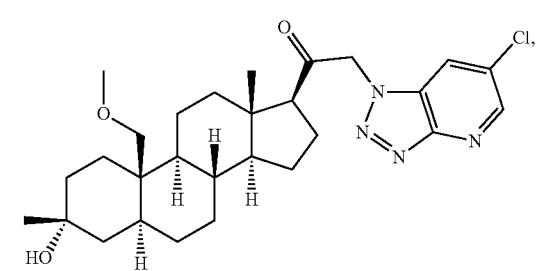
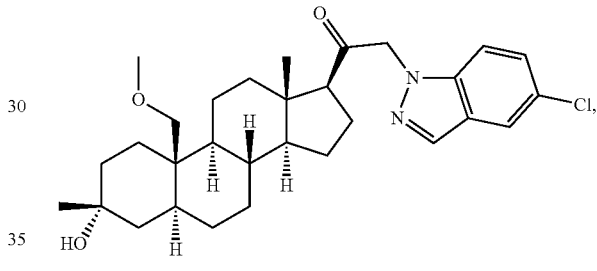
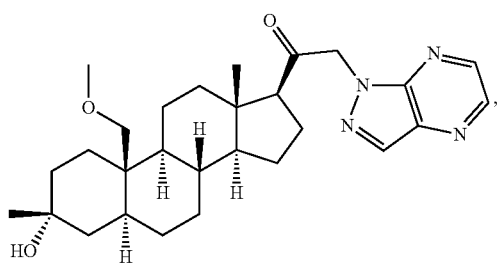
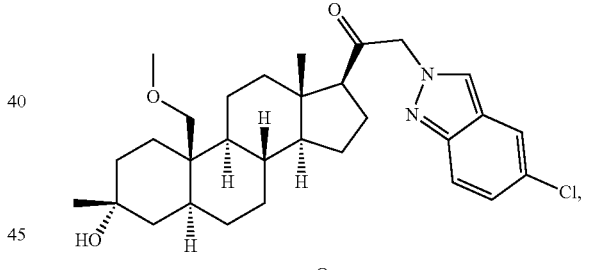
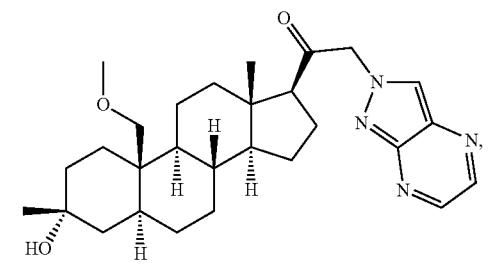
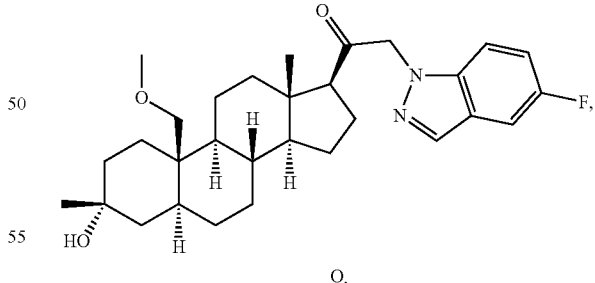
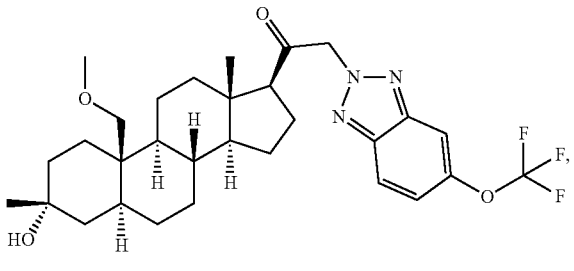
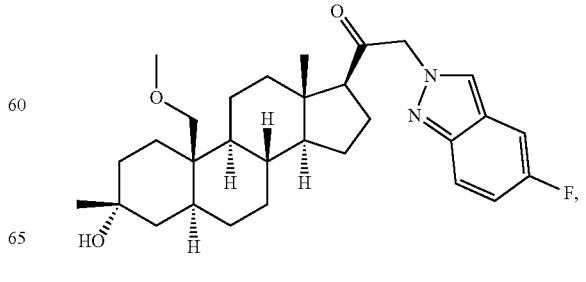

-continued
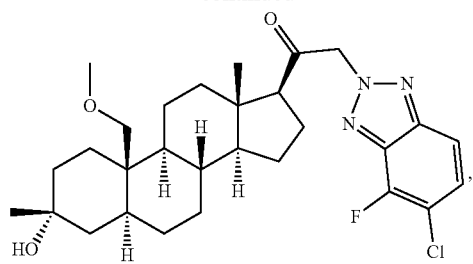
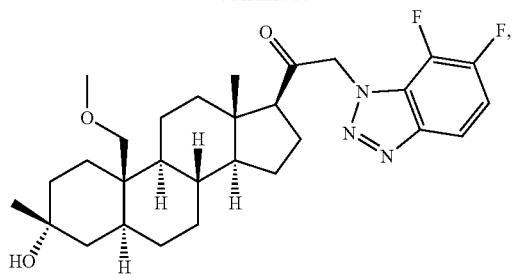
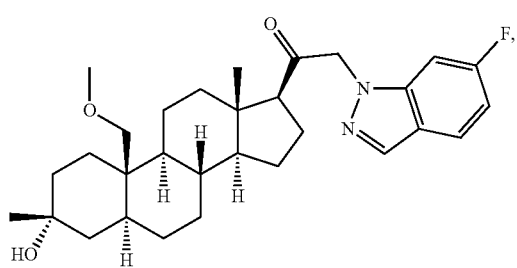
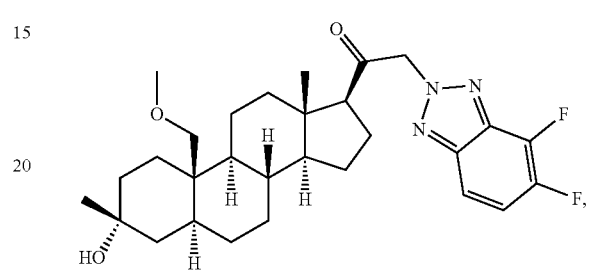
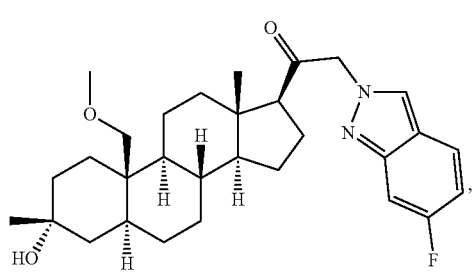
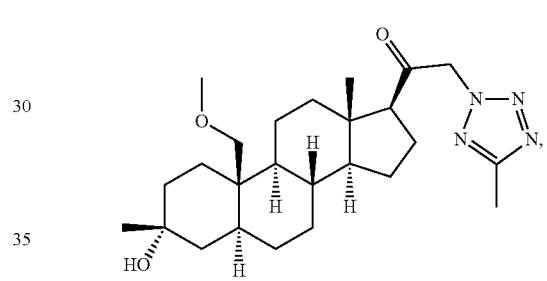
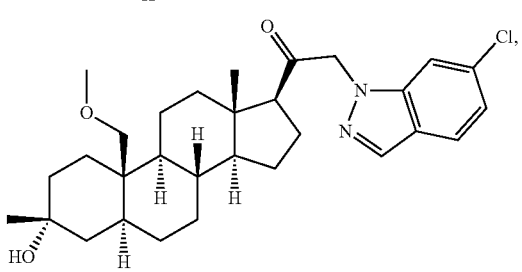
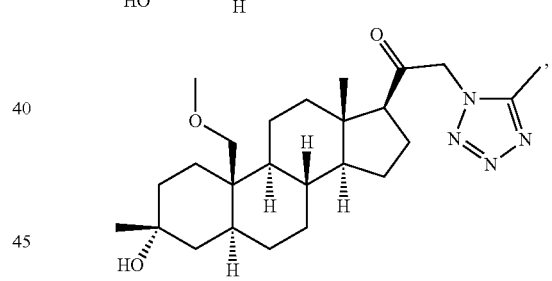
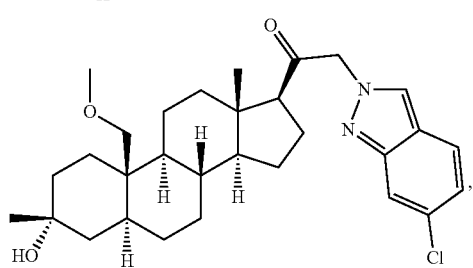
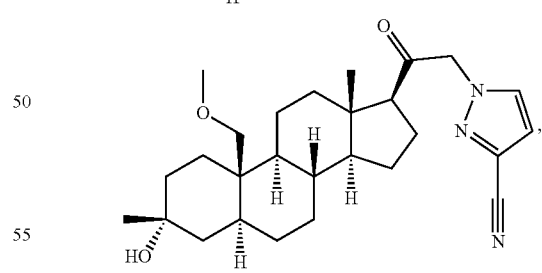
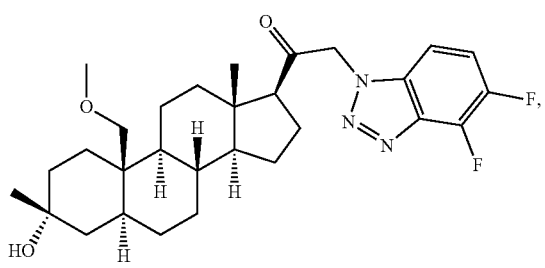
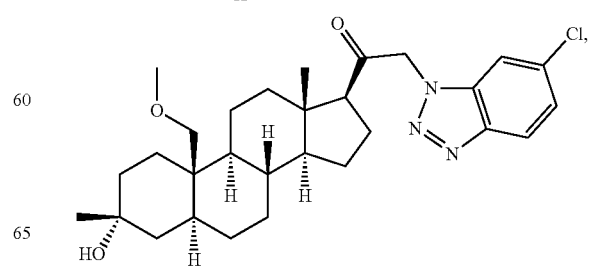

51
-continued
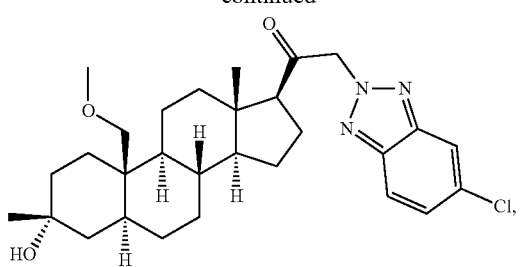
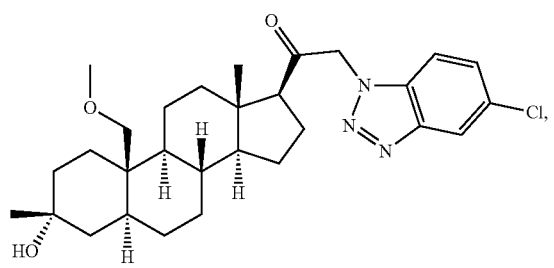
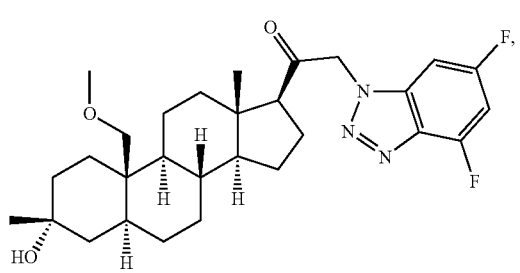
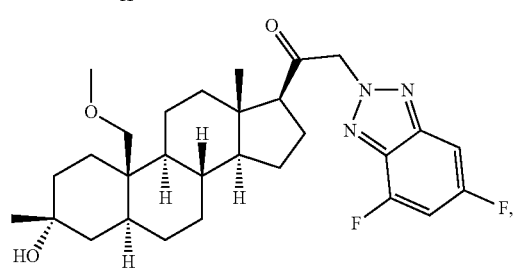
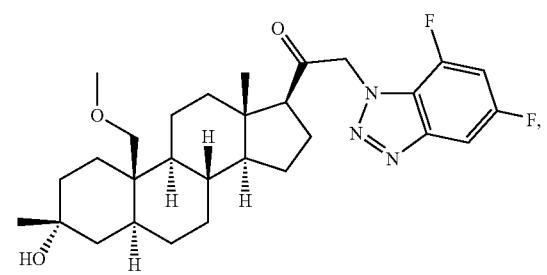
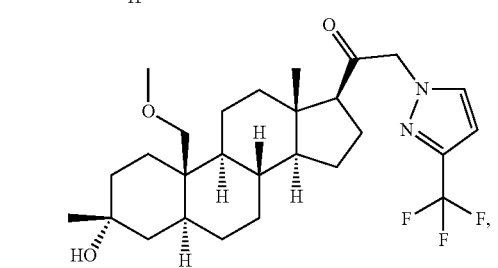
52
-continued
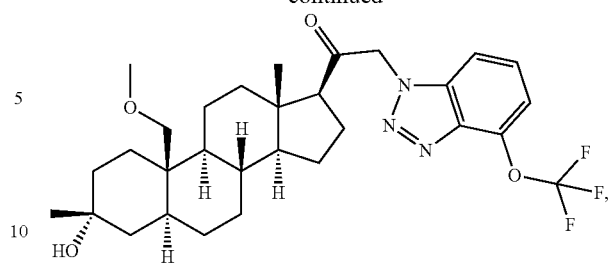
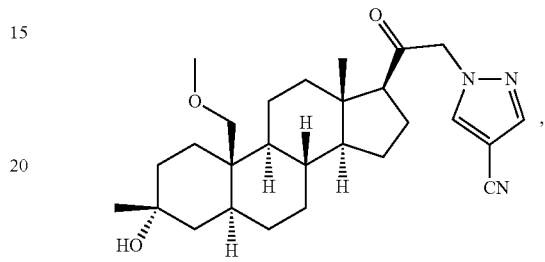
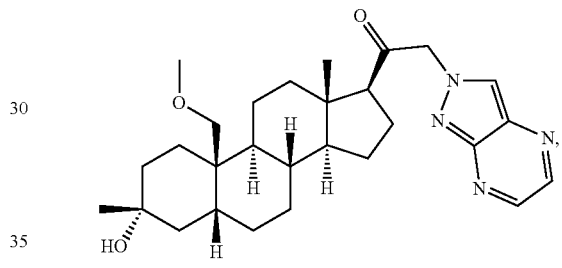
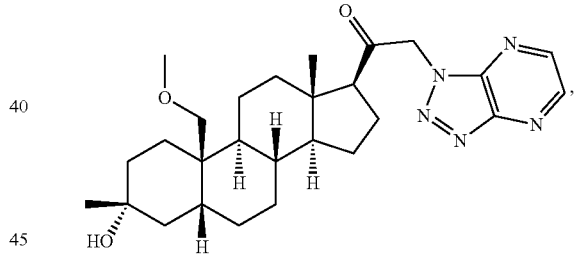
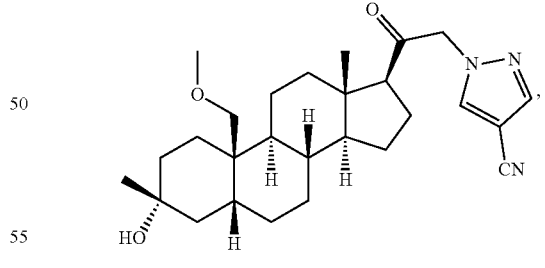
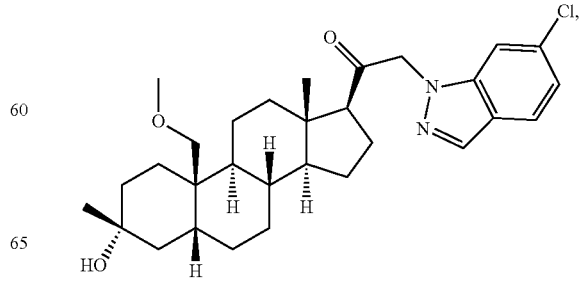

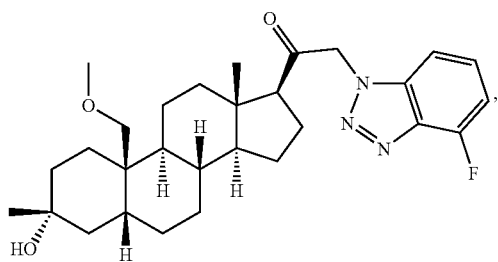
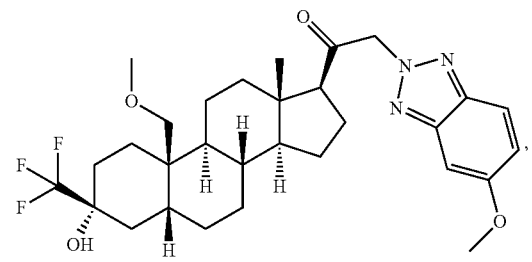
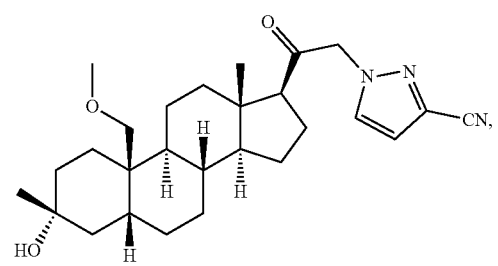
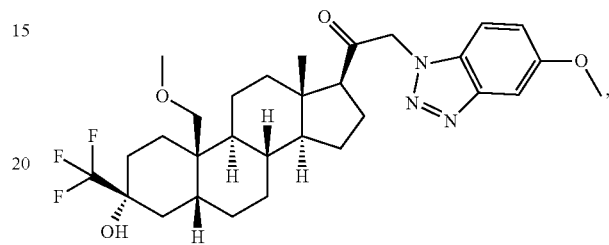
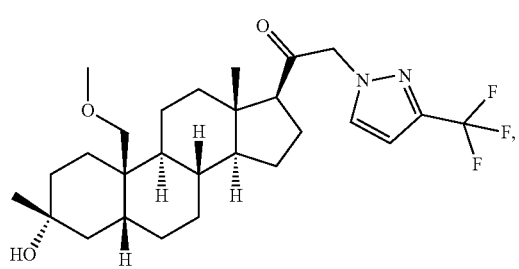
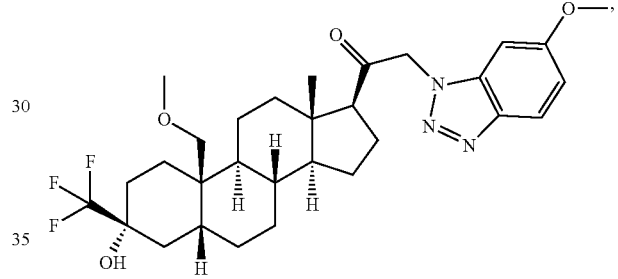
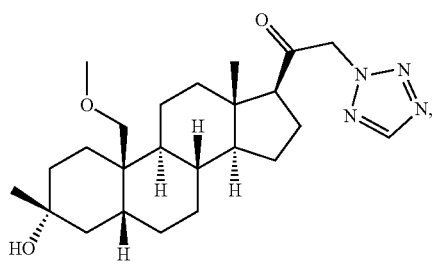
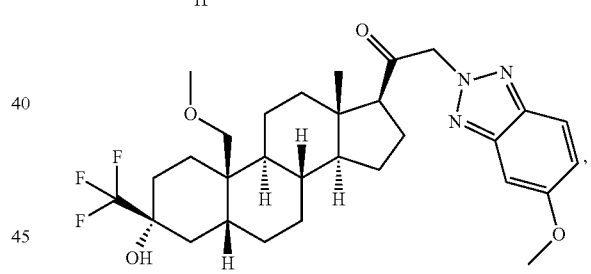
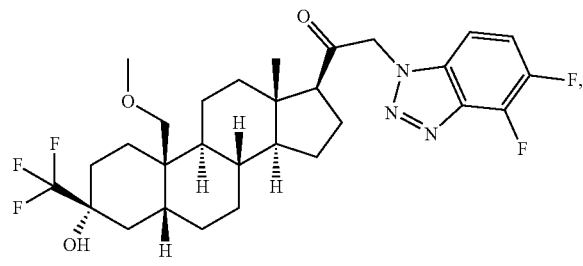
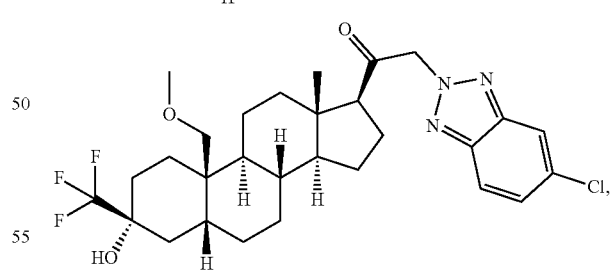
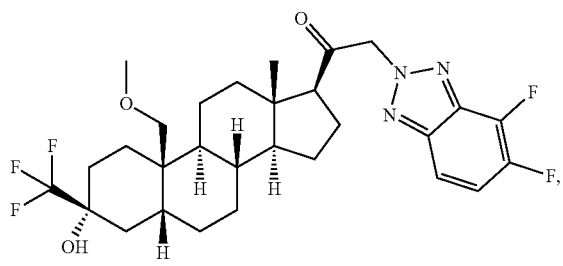
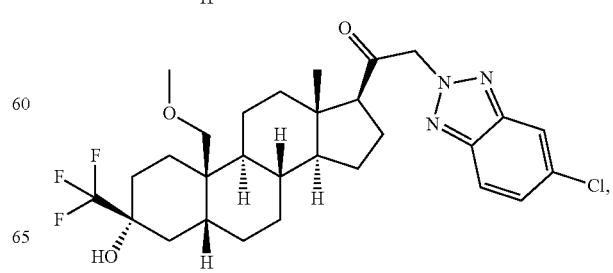

-continued

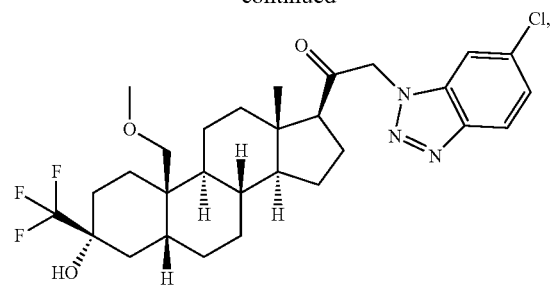

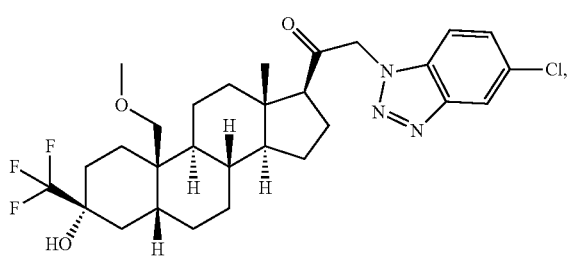

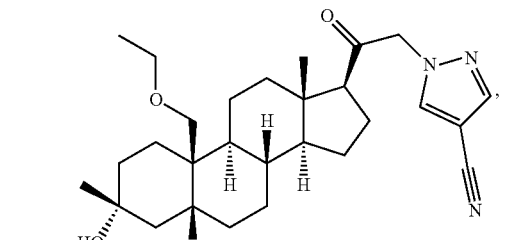

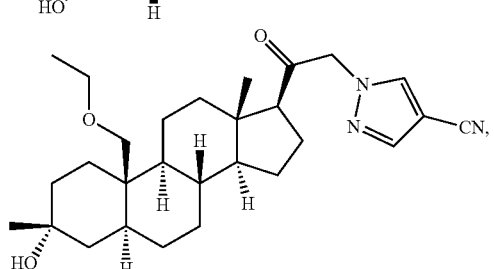

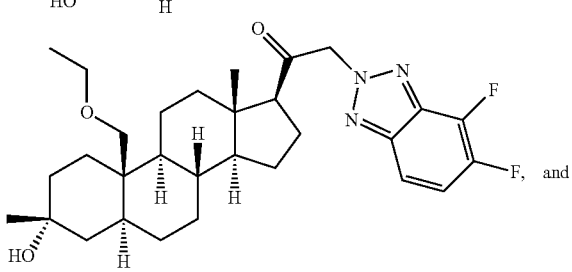

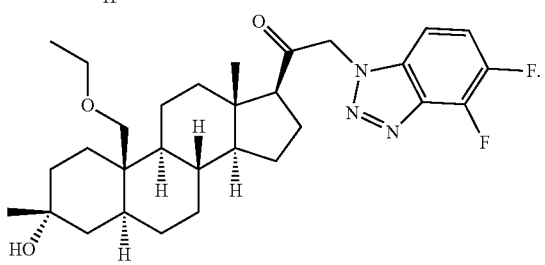

In one aspect, provided is a pharmaceutical composition comprising a compound of any one of the preceding claims and a pharmaceutically acceptable excipient.

In one aspect, provided is a method of inducing sedation and/or anesthesia in a subject, comprising administering to the subject an effective amount of a compound of the Formula (I):

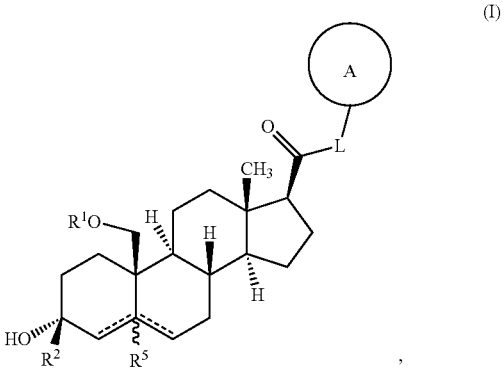

a pharmaceutically acceptable salt thereof, wherein: A is an optionally substituted nitrogen-containing heteroaryl or heterocyclyl; L is —C($R^3$)($R^3$)—, —O—, —S—, or —$NR^3$—; $R^1$ is hydrogen or $C_1$-$C_6$ alkyl, $C_1$-$C_6$ alkenyl, $C_1$-$C_6$ alkynyl, carbocyclyl, or heterocyclyl; $R^2$ is hydrogen, $C_1$-$C_6$ alkyl (e.g., $C_1$-$C_6$ haloalkyl) or $C_1$-$C_6$ alkoxy; each $R^3$ is independently hydrogen or $C_1$-$C_6$ alkyl; $R^5$ is absent or hydrogen; and ----- represents a single or double bond, wherein when one of ----- is a double bond, the other ----- is a single bond; and when one of the ----- is a double bond, $R^5$ is absent.

In one aspect, provided is a method of administering an effective amount of a compound, a pharmaceutically acceptable salt thereof, or pharmaceutical composition of a compound as described herein, e.g., a compound of the Formula (I), (Ia), (Ia-1), (Ia-2), (Ia-3), (Ia-4), (Ib), (Ib-1), (Ib-2), (Ib-3), or (Ib-4), to a subject in need thereof, wherein the subject experiences sedation and/or anesthesia within two hours of administration.

In some embodiments, the subject experiences sedation and/or anesthesia within one hour of administration.

In some embodiments, the subject experiences sedation and/or anesthesia instantaneously.

In some embodiments, the compound is administered by intravenous administration.

In some embodiments, the compound is administered chronically.

In some embodiments, the subject is a mammal. In some embodiments, the subject is a human.

In some embodiments, the compound is administered in combination with another therapeutic agent.

In one aspect, provided is a method for treating seizure in a subject, comprising administering to the subject an effective amount of a compound of the Formula (I):

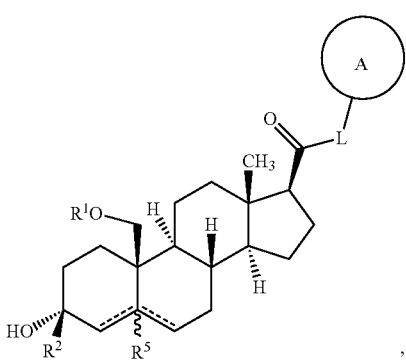

(I)

a pharmaceutically acceptable salt thereof, wherein: A is an optionally substituted nitrogen containing heteroaryl or heterocyclyl; L is —C($R^3$)($R^3$)—, —O—, —S—, or —N$R^3$—; $R^1$ is hydrogen or $C_1$-$C_6$ alkyl, $C_1$-$C_6$ alkenyl, $C_1$-$C_6$ alkynyl, carbocyclyl, or heterocyclyl; $R^2$ is hydrogen, $C_1$-$C_6$ alkyl (e.g., $C_1$-$C_6$ haloalkyl) or $C_1$-$C_6$ alkoxy; each $R^3$ is independently hydrogen or $C_1$-$C_6$ alkyl; $R^5$ is absent or hydrogen; and ----- represents a single or double bond, wherein when one of ----- is a double bond, the other ----- is a single bond; and when one of the ----- is a double bond, $R^5$ is absent.

In one aspect, provided is a method for treating epilepsy or status or status epilepticus in a subject, the method comprising administering to the subject an effective amount of a compound of the Formula (I):

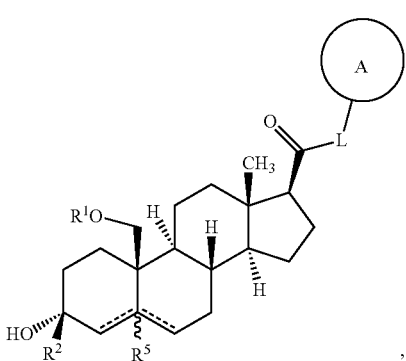

(I)

a pharmaceutically acceptable salt thereof, wherein: A is an optionally substituted nitrogen containing heteroaryl or heterocyclyl; L is —C($R^3$)($R^3$)—, —O—, —S—, or —N$R^3$—; $R^1$ is hydrogen or $C_1$-$C_6$ alkyl, $C_1$-$C_6$ alkenyl, $C_1$-$C_6$ alkynyl, carbocyclyl, or heterocyclyl; $R^2$ is hydrogen, $C_1$-$C_6$ alkyl (e.g., $C_1$-$C_6$ (haloalkyl) or $C_1$-$C_6$ alkoxy; each $R^3$ is independently hydrogen or $C_1$-$C_6$ alkyl; $R^5$ is absent or hydrogen; and ----- represents a single or double bond, wherein when one of ----- is a double bond, the other ----- is a single bond; and when one of the ----- is a double bond, $R^5$ is absent.

In one aspect, provided is a method for treating disorders related to GABA function in a subject in need thereof, the method comprising administering to the subject a therapeutically effective amount of a compound, a pharmaceutically acceptable salt thereof, or pharmaceutical composition of one of a compound as described herein, e.g., a compound of the Formula (I), (Ia), (Ia-1), (Ia-2), (Ia-3), (Ia-4), (Ib), (Ib-1), (Ib-2), (Ib-3), or (Ib-4).

In one aspect, provided is a method for treating a CNS-related disorder in a subject in need thereof, comprising administering to the subject an effective amount of a compound as described herein, e.g., a compound of the Formula (I), (Ia), (Ia-1), (Ia-2), (Ia-3), (Ia-4), (Ib), (Ib-1), (Ib-2), (Ib-3), or (Ib-4), or a pharmaceutically acceptable salt thereof. In some embodiments, the CNS-related disorder is a sleep disorder, a mood disorder, a schizophrenia spectrum disorder, a convulsive disorder, a disorder of memory and/or cognition, a movement disorder, a personality disorder, autism spectrum disorder, pain, traumatic brain injury, a vascular disease, a substance abuse disorder and/or withdrawal syndrome, or tinnitus. In some embodiments, the subject is a subject with Rett syndrome, Fragile X syndrome, or Angelman syndrome.

In one aspect, provided is a kit comprising a solid composition comprising a compound as described herein, e.g., a compound of the Formula (I), (Ia), (Ia-1), (Ia-2), (Ia-3), (Ia-4), (Ib), (Ib-1), (Ib-2), (Ib-3), or (Ib-4), and a sterile diluent.

Pharmaceutical Compositions

In one aspect, the invention provides a pharmaceutical composition comprising a compound of the present invention (also referred to as the "active ingredient") and a pharmaceutically acceptable excipient. In certain embodiments, the pharmaceutical composition comprises an effective amount of the active ingredient. In certain embodiments, the pharmaceutical composition comprises a therapeutically effective amount of the active ingredient. In certain embodiments, the pharmaceutical composition comprises a prophylactically effective amount of the active ingredient.

The pharmaceutical compositions provided herein can be administered by a variety of routes including, but not limited to, oral (enteral) administration, parenteral (by injection) administration, rectal administration, transdermal administration, intradermal administration, intrathecal administration, subcutaneous (SC) administration, intravenous (IV) administration, intramuscular (IM) administration, and intranasal administration.

Generally, the compounds provided herein are administered in an effective amount. The amount of the compound actually administered will typically be determined by a physician, in the light of the relevant circumstances, including the condition to be treated, the chosen route of administration, the actual compound administered, the age, weight, and response of the individual patient, the severity of the patient's symptoms, and the like.

When used to prevent the onset of a CNS-disorder, the compounds provided herein will be administered to a subject at risk for developing the condition, typically on the advice and under the supervision of a physician, at the dosage levels described above. Subjects at risk for developing a particular condition generally include those that have a family history of the condition, or those who have been identified by genetic testing or screening to be particularly susceptible to developing the condition.

The pharmaceutical compositions provided herein can also be administered chronically ("chronic administration"). Chronic administration refers to administration of a compound or pharmaceutical composition thereof over an extended period of time, e.g., for example, over 3 months, 6 months, 1 year, 2 years, 3 years, 5 years, etc., or may be continued indefinitely, for example, for the rest of the subject's life. In certain embodiments, the chronic administration is intended to provide a constant level of the compound in the blood, e.g., within the therapeutic window over the extended period of time.

The pharmaceutical compostions of the present invention may be further delivered using a variety of dosing methods. For example, in certain embodiments, the pharmaceutical composition may be given as a bolus, e.g., in order to raise the concentration of the compound in the blood to an effective level. The placement of the bolus dose depends on the systemic levels of the active ingredient desired throughout the body, e.g., an intramuscular or subcutaneous bolus dose allows a slow release of the active ingredient, while a bolus delivered directly to the veins (e.g., through an IV drip) allows a much faster delivery which quickly raises the concentration of the active ingredient in the blood to an effective level. In other embodiments, the pharmaceutical composition may be administered as a continuous infusion, e.g., by IV drip, to provide maintenance of a steady-state concentration of the active ingredient in the subject's body. Furthermore, in still yet other embodiments, the pharmaceutical composition may be administered as first as a bolus dose, followed by continuous infusion.

The compositions for oral administration can take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampules or syringes of the liquid compositions or pills, tablets, capsules or the like in the case of solid compositions. In such compositions, the compound is usually a minor component (from about 0.1 to about 50% by weight or preferably from about 1 to about 40% by weight) with the remainder being various vehicles or excipients and processing aids helpful for forming the desired dosing form.

With oral dosing, one to five and especially two to four and typically three oral doses per day are representative regimens. Using these dosing patterns, each dose provides from about 0.01 to about 20 mg/kg of the compound provided herein, with preferred doses each providing from about 0.1 to about 10 mg/kg, and especially about 1 to about 5 mg/kg.

Transdermal doses are generally selected to provide similar or lower blood levels than are achieved using injection doses, generally in an amount ranging from about 0.01 to about 20% by weight, preferably from about 0.1 to about 20% by weight, preferably from about 0.1 to about 10% by weight, and more preferably from about 0.5 to about 15% by weight.

Injection dose levels range from about 0.1 mg/kg/hour to at least 20 mg/kg/hour, all for from about 1 to about 120 hours and especially 24 to 96 hours. A preloading bolus of from about 0.1 mg/kg to about 10 mg/kg or more may also be administered to achieve adequate steady state levels. The maximum total dose is not expected to exceed about 5 g/day for a 40 to 80 kg human patient.

Liquid forms suitable for oral administration may include a suitable aqueous or nonaqueous vehicle with buffers, suspending and dispensing agents, colorants, flavors and the like. Solid forms may include, for example, any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavoring agent such as peppermint, methyl salicylate, or orange flavoring.

Injectable compositions are typically based upon injectable sterile saline or phosphate-buffered saline or other injectable excipients known in the art. As before, the active compound in such compositions is typically a minor component, often being from about 0.05 to 10% by weight with the remainder being the injectable excipient and the like.

Transdermal compositions are typically formulated as a topical ointment or cream containing the active ingredient(s). When formulated as a ointment, the active ingredients will typically be combined with either a paraffinic or a water-miscible ointment base. Alternatively, the active ingredients may be formulated in a cream with, for example an oil-in-water cream base. Such transdermal formulations are well-known in the art and generally include additional ingredients to enhance the dermal penetration of stability of the active ingredients or Formulation. All such known transdermal formulations and ingredients are included within the scope provided herein.

The compounds provided herein can also be administered by a transdermal device. Accordingly, transdermal administration can be accomplished using a patch either of the reservoir or porous membrane type, or of a solid matrix variety.

The above-described components for orally administrable, injectable or topically administrable compositions are merely representative. Other materials as well as processing techniques and the like are set forth in Part 8 of *Remington's Pharmaceutical Sciences,* 17th edition, 1985, Mack Publishing Company, Easton, Pennsylvania, which is incorporated herein by reference.

The compounds of the present invention can also be administered in sustained release forms or from sustained release drug delivery systems. A description of representative sustained release materials can be found in Remington's Pharmaceutical Sciences.

The present invention also relates to the pharmaceutically acceptable acid addition salt of a compound of the present invention. The acid which may be used to prepare the pharmaceutically acceptable salt is that which forms a non-toxic acid addition salt, i.e., a salt containing pharmacologically acceptable anions such as the hydrochloride, hydroiodide, hydrobromide, nitrate, sulfate, bisulfate, phosphate, acetate, lactate, citrate, tartrate, succinate, maleate, fumarate, benzoate, para-toluenesulfonate, and the like.

In another aspect, the invention provides a pharmaceutical composition comprising a compound of the present invention and a pharmaceutically acceptable excipient, e.g., a composition suitable for injection, such as for intravenous (IV) administration.

Pharmaceutically acceptable excipients include any and all diluents or other liquid vehicles, dispersion or suspension aids, surface active agents, isotonic agents, preservatives, lubricants and the like, as suited to the particular dosage form desired, e.g., injection. General considerations in the formulation and/or manufacture of pharmaceutical compositions agents can be found, for example, in *Remington's Pharmaceutical Sciences*, Sixteenth Edition, E. W. Martin (Mack Publishing Co., Easton, Pa., 1980), and *Remington: The Science and Practice of Pharmacy,* 21$^{st}$ Edition (Lippincott Williams & Wilkins, 2005).

For example, injectable preparations, such as sterile injectable aqueous suspensions, can be formulated according to the known art using suitable dispersing or wetting agents and suspending agents. Exemplary excipients that can be employed include, but are not limited to, water, sterile saline or phosphate-buffered saline, or Ringer's solution.

In certain embodiments, the pharmaceutical composition further comprises a cyclodextrin derivative. The most common cyclodextrins are α-, μ- and γ-cyclodextrins consisting of 6, 7 and 8 α-1,4-linked glucose units, respectively, optionally comprising one or more substituents on the linked sugar moieties, which include, but are not limited to, substituted or unsubstituted methylated, hydroxyalkylated, acylated, and sulfoalkylether substitution. In certain embodiments, the cyclodextrin is a sulfoalkyl ether β-cyclodextrin, e.g., for example, sulfobutyl ether β-cyclodextrin, also known as Captisol®. See, e.g., U.S. Pat. No. 5,376,645. In certain embodiments, the composition comprises hexapropyl-μ-cyclodextrin. In a more particular embodiment, the composition comprises hexapropyl-μ-cyclodextrin (10-50% in water).

The injectable composition can be sterilized, for example, by filtration through a bacterial-retaining filter, or by incorporating sterilizing agents in the form of sterile solid compositions which can be dissolved or dispersed in sterile water or other sterile injectable medium prior to use.

Generally, the compounds provided herein are administered in an effective amount. The amount of the compound actually administered will typically be determined by a physician, in the light of the relevant circumstances, including the condition to be treated, the chosen route of administration, the actual compound administered, the age, weight, response of the individual patient, the severity of the patient's symptoms, and the like.

The compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include pre-filled, pre-measured ampules or syringes of the liquid compositions. In such compositions, the compound is usually a minor component (from about 0.1% to about 50% by weight or preferably from about 1% to about 40% by weight) with the remainder being various vehicles or carriers and processing aids helpful for forming the desired dosing form.

The compounds provided herein can be administered as the sole active agent, or they can be administered in combination with other active agents. In one aspect, the present invention provides a combination of a compound of the present invention and another pharmacologically active agent. Administration in combination can proceed by any technique apparent to those of skill in the art including, for example, separate, sequential, concurrent, and alternating administration.

Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with ordinary experimentation. General considerations in the formulation and/or manufacture of pharmaceutical compositions can be found, for example, in *Remington: The Science and Practice of Pharmacy* 21$^{st}$ed., Lippincott Williams & Wilkins, 2005.

Methods of Use and Treatment

As generally described herein, the present invention is directed to C21-substituted neuroactive steroids designed, for example, to act as GABA modulators. In certain embodiments, such compounds are envisioned to be useful as therapeutic agents for the inducement of anesthesia and/or sedation in a subject. In some embodiments, such compounds are envisioned to be useful as therapeutic agents for treating a CNS-related disorder (e.g., sleep disorder, a mood disorder, a schizophrenia spectrum disorder, a convulsive disorder, a disorder of memory and/or cognition, a movement disorder, a personality disorder, autism spectrum disorder, pain, traumatic brain injury, a vascular disease, a substance abuse disorder and/or withdrawal syndrome, or tinnitus) in a subject in need (e.g., a subject with Rett syndrome, Fragile X syndrome, or Angelman syndrome).

Thus, in one aspect, the present invention provides a method of inducing sedation and/or anesthesia in a subject, comprising administering to the subject an effective amount of a compound of the present invention or a composition thereof. In certain embodiments, the compound is administered by intravenous administration.

Earlier studies (see, e.g., Gee et al., *European Journal of Pharmacology*, 136:419-423 (1987)) demonstrated that certain 3α-hydroxylated steroids are orders of magnitude more potent as modulators of the GABA receptor complex (GRC) than others had reported (see, e.g., Majewska et al., *Science* 232:1004-1007 (1986); Harrison et al., *J Pharmacol. Exp. Ther.* 241:346-353 (1987)). Majewska et al. and Harrison et al. taught that 3α-hydroxylated-5-reduced steroids are only capable of much lower levels of effectiveness. In vitro and in vivo experimental data have now demonstrated that the high potency of these steroids allows them to be therapeutically useful in the modulation of brain excitability via the GRC (see, e.g., Gee et al., *European Journal of Pharmacology*, 136:419-423 (1987); Wieland et al., *Psychopharmacology* 118(1):65-71 (1995)).

Various synthetic steroids have also been prepared as neuroactive steroids. See, for example, U.S. Pat. No. 5,232,917, which discloses neuroactive steroid compounds useful in treating stress, anxiety, insomnia, seizure disorders, and mood disorders, that are amenable to GRC-active agents, such as depression, in a therapeutically beneficial manner. Furthermore, it has been previously demonstrated that these steroids interact at a unique site on the GRC which is distinct from other known sites of interaction (e.g., barbiturates, benzodiazepines, and GABA) where therapeutically beneficial effects on stress, anxiety, sleep, mood disorders and seizure disorders have been previously elicited (see, e.g., Gee, K. W. and Yamamura, H. I., "Benzodiazepines and Barbiturates: Drugs for the Treatment of Anxiety, Insomnia and Seizure Disorders," in *Central Nervous System Disorders*, Horvell, ed., Marcel-Dekker, New York (1985), pp. 123-147; Lloyd, K. G. and Morselli, P. L., "Psychopharmacology of GABAergic Drugs," in *Psychopharmacology: The Third Generation of Progress*, H. Y. Meltzer, ed., Raven Press, N.Y. (1987), pp. 183-195; and Gee et al., *European Journal of Pharmacology*, 136:419-423 (1987). These compounds are desirable for their duration, potency, and oral activity (along with other forms of administration).

Compounds of the present invention, as described herein, are generally designed to modulate GABA function, and therefore to act as neuroactive steroids for the treatment and prevention of CNS-related conditions in a subject. Modulation, as used herein, refers to the inhibition or potentiation of GABA receptor function. Accordingly, the compounds and pharmaceutical compositions provided herein find use as therapeutics for preventing and/or treating CNS conditions in mammals including humans and non-human mammals. Thus, and as stated earlier, the present invention includes within its scope, and extends to, the recited methods of treatment, as well as to the compounds for such methods, and to the use of such compounds for the preparation of medicaments useful for such methods.

Exemplary CNS conditions related to GABA-modulation include, but are not limited to, sleep disorders [e.g., insomnia], mood disorders [e.g., depression, dysthymic disorder (e.g., mild depression), bipolar disorder (e.g., I and/or II), anxiety disorders (e.g., generalized anxiety disorder (GAD), social anxiety disorder), stress, post-traumatic stress disorder (PTSD), compulsive disorders (e.g., obsessive compulsive disorder (OCD))], schizophrenia spectrum disorders [e.g., schizophrenia, schizoaffective disorder], convulsive disorders [e.g., epilepsy (e.g., status epilepticus (SE)), seizures], disorders of memory and/or cognition [e.g., attention disorders (e.g., attention deficit hyperactivity disorder (ADHD)), dementia (e.g., Alzheimer's type dementia, Lewis body type dementia, vascular type dementia], movement disorders [e.g., Huntington's disease, Parkinson's disease], personality disorders [e.g., anti-social personality disorder, obsessive compulsive personality disorder], autism spectrum disorders (ASD) [e.g., autism, monogenetic causes of autism such as synaptophathy's, e.g., Rett syndrome, Fragile X syndrome, Angelman syndrome], pain [e.g., neuropathic pain, injury related pain syndromes, acute pain, chronic pain], traumatic brain injury (TBI), vascular diseases [e.g., stroke, ischemia, vascular malformations], substance abuse disorders and/or withdrawal syndromes [e.g., addition to opiates, cocaine, and/or alcohol], and tinnitus.

In yet another aspect, provided is a combination of a compound of the present invention and another pharmacologically active agent. The compounds provided herein can be administered as the sole active agent or they can be administered in combination with other agents. Administration in combination can proceed by any technique apparent to those of skill in the art including, for example, separate, sequential, concurrent and alternating administration.

In another aspect, provided is a method of treating or preventing brain excitability in a subject susceptible to or afflicted with a condition associated with brain excitability, comprising administering to the subject an effective amount of a compound of the present invention to the subject.

In yet another aspect, provided is a method of treating or preventing stress or anxiety in a subject, comprising administering to the subject in need of such treatment an effective amount of a compound of the present invention, or a composition thereof.

In yet another aspect, provided is a method of alleviating or preventing seizure activity in a subject, comprising administering to the subject in need of such treatment an effective amount of a compound of the present invention.

In yet another aspect, provided is a method of alleviating or preventing insomnia in a subject, comprising administering to the subject in need of such treatment an effective amount of a compound of the present invention, or a composition thereof.

In yet another aspect, provided is a method of inducing sleep and maintaining substantially the level of REM sleep that is found in normal sleep, wherein substantial rebound insomnia is not induced, comprising administering an effective amount of a compound of the present invention.

In yet another aspect, provided is a method of alleviating or preventing PMS or PND in a subject, comprising administering to the subject in need of such treatment an effective amount of a compound of the present invention.

In yet another aspect, provided is a method of treating or preventing mood disorders in a subject, comprising administering to the subject in need of such treatment an effective amount of a compound of the present invention. In certain embodiments the mood disorder is depression.

In yet another aspect, provided is a method of inducing anesthesia in a subject, comprising administering to the subject an effective amount of a compound of the present invention.

In yet another aspect, provided is a method of cognition enhancement or treating memory disorder by administering to the subject a therapeutically effective amount of a compound of the present invention. In certain embodiments, the disorder is Alzheimer's disease. In certain embodiments, the disorder is Rett syndrome.

In yet another aspect, provided is a method of treating attention disorders by administering to the subject a therapeutically effective amount of a compound of the present invention. In certain embodiments, the attention disorder is ADHD.

In certain embodiments, the compound is administered to the subject chronically. In certain embodiments, the compound is administered to the subject orally, subcutaneously, intramuscularly, or intravenously.

Anesthesia/Sedation

Anesthesia is a pharmacologically induced and reversible state of amnesia, analgesia, loss of responsiveness, loss of skeletal muscle reflexes, decreased stress response, or all of these simultaneously. These effects can be obtained from a single drug which alone provides the correct combination of effects, or occasionally with a combination of drugs (e.g., hypnotics, sedatives, paralytics, analgesics) to achieve very specific combinations of results. Anesthesia allows patients to undergo surgery and other procedures without the distress and pain they would otherwise experience.

Sedation is the reduction of irritability or agitation by administration of a pharmacological agent, generally to facilitate a medical procedure or diagnostic procedure.

Sedation and analgesia include a continuum of states of consciousness ranging from minimal sedation (anxiolysis) to general anesthesia.

Minimal sedation is also known as anxiolysis. Minimal sedation is a drug-induced state during which the patient responds normally to verbal commands. Cognitive function and coordination may be impaired. Ventilatory and cardiovascular functions are typically unaffected.

Moderate sedation/analgesia (conscious sedation) is a drug-induced depression of consciousness during which the patient responds purposefully to verbal command, either alone or accompanied by light tactile stimulation. No interventions are usually necessary to maintain a patent airway. Spontaneous ventilation is typically adequate. Cardiovascular function is usually maintained.

Deep sedation/analgesia is a drug-induced depression of consciousness during which the patient cannot be easily aroused, but responds purposefully (not a reflex withdrawal from a painful stimulus) following repeated or painful stimulation. Independent ventilatory function may be impaired and the patient may require assistance to maintain a patent airway. Spontaneous ventilation may be inadequate. Cardiovascular function is usually maintained.

General anesthesia is a drug-induced loss of consciousness during which the patient is not arousable, even to painful stimuli. The ability to maintain independent ventilatory function is often impaired and assistance is often required to maintain a patent airway. Positive pressure ventilation may be required due to depressed spontaneous ventilation or drug-induced depression of neuromuscular function. Cardiovascular function may be impaired.

Sedation in the intensive care unit (ICU) allows the depression of patients' awareness of the environment and reduction of their response to external stimulation. It can play a role in the care of the critically ill patient, and encompasses a wide spectrum of symptom control that will vary between patients, and among individuals throughout the course of their illnesses. Heavy sedation in critical care has been used to facilitate endotracheal tube tolerance and ventilator synchronization, often with neuromuscular blocking agents.

In some embodiments, sedation (e.g., long-term sedation, continuous sedation) is induced and maintained in the ICU for a prolonged period of time (e.g., 1 day, 2 days, 3 days, 5 days, 1 week, 2 week, 3 weeks, 1 month, 2 months). Long-term sedation agents may have long duration of action. Sedation agents in the ICU may have short elimination half-life.

Procedural sedation and analgesia, also referred to as conscious sedation, is a technique of administering sedatives or dissociative agents with or without analgesics to induce a state that allows a subject to tolerate unpleasant procedures while maintaining cardiorespiratory function.

Anxiety Disorders

Anxiety disorder is a blanket term covering several different forms of abnormal and pathological fear and anxiety. Current psychiatric diagnostic criteria recognize a wide variety of anxiety disorders.

Generalized anxiety disorder is a common chronic disorder characterized by long-lasting anxiety that is not focused on any one object or situation. Those suffering from generalized anxiety experience non-specific persistent fear and worry and become overly concerned with everyday matters. Generalized anxiety disorder is the most common anxiety disorder to affect older adults.

In panic disorder, a person suffers from brief attacks of intense terror and apprehension, often marked by trembling, shaking, confusion, dizziness, nausea, difficulty breathing. These panic attacks, defined by the APA as fear or discomfort that abruptly arises and peaks in less than ten minutes, can last for several hours and can be triggered by stress, fear, or even exercise; although the specific cause is not always apparent. In addition to recurrent unexpected panic attacks, a diagnosis of panic disorder also requires that said attacks have chronic consequences: either worry over the attacks' potential implications, persistent fear of future attacks, or significant changes in behavior related to the attacks. Accordingly, those suffering from panic disorder experience symptoms even outside of specific panic episodes. Often, normal changes in heartbeat are noticed by a panic sufferer, leading them to think something is wrong with their heart or they are about to have another panic attack. In some cases, a heightened awareness (hypervigilance) of body functioning occurs during panic attacks, wherein any perceived physiological change is interpreted as a possible life threatening illness (i.e. extreme hypochondriasis).

Obsessive compulsive disorder is a type of anxiety disorder primarily characterized by repetitive obsessions (distressing, persistent, and intrusive thoughts or images) and compulsions (urges to perform specific acts or rituals). The OCD thought pattern may be likened to superstitions insofar as it involves a belief in a causative relationship where, in reality, one does not exist. Often the process is entirely illogical; for example, the compulsion of walking in a certain pattern may be employed to alleviate the obsession of impending harm. And in many cases, the compulsion is entirely inexplicable, simply an urge to complete a ritual triggered by nervousness. In a minority of cases, sufferers of OCD may only experience obsessions, with no overt compulsions; a much smaller number of sufferers experience only compulsions.

The single largest category of anxiety disorders is that of Phobia, which includes all cases in which fear and anxiety is triggered by a specific stimulus or situation. Sufferers typically anticipate terrifying consequences from encountering the object of their fear, which can be anything from an animal to a location to a bodily fluid.

Post-traumatic stress disorder or PTSD is an anxiety disorder which results from a traumatic experience. Post-traumatic stress can result from an extreme situation, such as combat, rape, hostage situations, or even serious accident. It can also result from long term (chronic) exposure to a severe stressor, for example soldiers who endure individual battles but cannot cope with continuous combat. Common symptoms include flashbacks, avoidant behaviors, and depression.

Neurodegenerative Diseases and Disorders

The term "neurodegenerative disease" includes diseases and disorders that are associated with the progressive loss of structure or function of neurons, or death of neurons. Neurodegenerative diseases and disorders include, but are not limited to, Alzheimer's disease (including the associated symptoms of mild, moderate, or severe cognitive impairment); amyotrophic lateral sclerosis (ALS); anoxic and ischemic injuries; ataxia and convulsion (including for the treatment and prevention and prevention of seizures that are caused by schizoaffective disorder or by drugs used to treat schizophrenia); benign forgetfulness; brain edema; cerebellar ataxia including McLeod neuroacanthocytosis syndrome (MLS); closed head injury; coma; contusive injuries (e.g., spinal cord injury and head injury); dementias including multi-infarct dementia and senile dementia; disturbances of consciousness; Down syndrome; drug-induced or medication-induced Parkinsonism (such as neuroleptic-induced acute akathisia, acute dystonia, Parkinsonism, or tardive dyskinesia, neuroleptic malignant syndrome, or medication-induced postural tremor); epilepsy; fragile X syndrome; Gilles de la Tourette's syndrome; head trauma; hearing impairment and loss; Huntington's disease; Lennox syndrome; levodopa-induced dyskinesia; mental retardation; movement disorders including akinesias and akinetic (rigid) syndromes (including basal ganglia calcification, corticobasal degeneration, multiple system atrophy, Parkinsonism-ALS dementia complex, Parkinson's disease, postencephalitic parkinsonism, and progressively supranuclear palsy); muscular spasms and disorders associated with muscular spasticity or weakness including chorea (such as benign hereditary chorea, drug-induced chorea, hemiballism, Huntington's disease, neuroacanthocytosis, Sydenham's chorea, and symptomatic chorea), dyskinesia (including tics such as complex tics, simple tics, and symptomatic tics), myoclonus (including generalized myoclonus and focal cycloclonus), tremor (such as rest tremor, postural tremor, and intention tremor) and dystonia (including axial dystonia, dystonic writer's cramp, hemiplegic dystonia, paroxysmal dystonia, and focal dystonia such as blepharospasm, oromandibular dystonia, and spasmodic dysphonia and torticollis); neuronal damage including ocular damage, retinopathy or macular degeneration of the eye; neurotoxic injury which follows cerebral stroke, thromboembolic stroke, hemorrhagic stroke, cerebral ischemia, cerebral vasospasm, hypoglycemia, amnesia, hypoxia, anoxia, perinatal asphyxia and cardiac arrest; Parkinson's disease; seizure; status epilecticus; stroke; tinnitus; tubular sclerosis, and viral infection induced neurodegeneration (e.g., caused by acquired immunodeficiency syndrome (AIDS) and encephalopathies). Neurodegenerative diseases also include, but are not limited to, neurotoxic injury which follows cerebral stroke, thromboembolic stroke, hemorrhagic stroke, cerebral ischemia, cerebral vasospasm, hypoglycemia, amnesia, hypoxia, anoxia, perinatal asphyxia and cardiac arrest. Methods of treating or preventing a neurodegenerative disease also include treating or preventing loss of neuronal function characteristic of neurodegenerative disorder.

Epilepsy

Epilepsy is a brain disorder characterized by repeated seizures over time. Types of epilepsy can include, but are not limited to generalized epilepsy, e.g., childhood absence epilepsy, juvenile nyoclonic epilepsy, epilepsy with grand-mal seizures on awakening, West syndrome, Lennox-Gastaut syndrome, partial epilepsy, e.g., temporal lobe epilepsy, frontal lobe epilepsy, benign focal epilepsy of childhood.

Status Epilepticus (SE)

Status epilepticus (SE) can include, e.g., convulsive status epilepticus, e.g., early status epilepticus, established status epilepticus, refractory status epilepticus, super-refractory status epilepticus; non-convulsive status epilepticus, e.g., generalized status epilepticus, complex partial status epilepticus; generalized periodic epileptiform discharges; and periodic lateralized epileptiform discharges. Convulsive status epilepticus is characterized by the presence of convulsive status epileptic seizures, and can include early status epilepticus, established status epilepticus, refractory status epilepticus, super-refractory status epilepticus. Early status epilepticus is treated with a first line therapy. Established status epilepticus is characterized by status epileptic seizures which persist despite treatment with a first line therapy, and a second line therapy is administered. Refractory status epilepticus is characterized by status epileptic seizures which persist despite treatment with a first line and a second line therapy, and a general anesthetic is generally administered. Super refractory status epilepticus is characterized by status epileptic seizures which persist despite treatment with a first line therapy, a second line therapy, and a general anesthetic for 24 hours or more.

Non-convulsive status epilepticus can include, e.g., focal non-convulsive status epilepticus, e.g., complex partial non-convulsive status epilepticus, simple partial non-convulsive status epilepticus, subtle non-convulsive status epilepticus; generalized non-convulsive status epilepticus, e.g., late onset absence non-convulsive status epilepticus, atypical absence non-convulsive status epilepticus, or typical absence non-convulsive status epilepticus.

Compositions described herein can also be administered as a prophylactic to a subject having a CNS disorder e.g., a traumatic brain injury, status epilepticus, e.g., convulsive status epilepticus, e.g., early status epilepticus, established status epilepticus, refractory status epilepticus, super-refractory status epilepticus; non-convulsive status epilepticus, e.g., generalized status epilepticus, complex partial status epilepticus; generalized periodic epileptiform discharges; and periodic lateralized epileptiform discharges; prior to the onset of a seizure.

Seizure

A seizure is the physical findings or changes in behavior that occur after an episode of abnormal electrical activity in the brain. The term "seizure" is often used interchangeably with "convulsion." Convulsions are when a person's body shakes rapidly and uncontrollably. During convulsions, the person's muscles contract and relax repeatedly.

Based on the type of behavior and brain activity, seizures are divided into two broad categories: generalized and partial (also called local or focal). Classifying the type of seizure helps doctors diagnose whether or not a patient has epilepsy.

Generalized seizures are produced by electrical impulses from throughout the entire brain, whereas partial seizures are produced (at least initially) by electrical impulses in a relatively small part of the brain. The part of the brain generating the seizures is sometimes called the focus.

There are six types of generalized seizures. The most common and dramatic, and therefore the most well known, is the generalized convulsion, also called the grand-mal seizure. In this type of seizure, the patient loses consciousness and usually collapses. The loss of consciousness is followed by generalized body stiffening (called the "tonic" phase of the seizure) for 30 to 60 seconds, then by violent jerking (the "clonic" phase) for 30 to 60 seconds, after which the patient goes into a deep sleep (the "postictal" or after-seizure phase). During grand-mal seizures, injuries and accidents may occur, such as tongue biting and urinary incontinence.

Absence seizures cause a short loss of consciousness (just a few seconds) with few or no symptoms. The patient, most often a child, typically interrupts an activity and stares blankly. These seizures begin and end abruptly and may occur several times a day. Patients are usually not aware that they are having a seizure, except that they may be aware of "losing time."

Myoclonic seizures consist of sporadic jerks, usually on both sides of the body. Patients sometimes describe the jerks as brief electrical shocks. When violent, these seizures may result in dropping or involuntarily throwing objects.

Clonic seizures are repetitive, rhythmic jerks that involve both sides of the body at the same time.

Tonic seizures are characterized by stiffening of the muscles.

Atonic seizures consist of a sudden and general loss of muscle tone, particularly in the arms and legs, which often results in a fall.

Seizures described herein can include epileptic seizures; acute repetitive seizures; cluster seizures; continuous seizures; unremitting seizures; prolonged seizures; recurrent seizures; status epilepticus seizures, e.g., refractory convulsive status epilepticus, non-convulsive status epilepticus seizures; refractory seizures; myoclonic seizures; tonic seizures; tonic-clonic seizures; simple partial seizures; complex partial seizures; secondarily generalized seizures; atypical absence seizures; absence seizures; atonic seizures; benign Rolandic seizures; febrile seizures; emotional seizures; focal seizures; gelastic seizures; generalized onset seizures; infantile spasms; Jacksonian seizures; massive bilateral myoclonus seizures; multifocal seizures; neonatal onset seizures; nocturnal seizures; occipital lobe seizures; post traumatic seizures; subtle seizures; Sylvan seizures; visual reflex seizures; or withdrawal seizures.

Equivalents and Scope

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verha herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

EXAMPLES

In order that the invention described herein may be more fully understood, the following examples are set forth. The synthetic and biological examples described in this application are offered to illustrate the compounds, pharmaceutical compositions and methods provided herein and are not to be construed in any way as limiting their scope.

Materials and Methods

The compounds provided herein can be prepared from readily available starting materials using the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization.

Additionally, as will be apparent to those skilled in the art, conventional protecting groups may be necessary to prevent certain functional groups from undergoing undesired reactions. The choice of a suitable protecting group for a particular functional group as well as suitable conditions for protection and deprotection are well known in the art. For example, numerous protecting groups, and their introduction and removal, are described in T. W. Greene and P. G. M. Wuts, *Protecting Groups in Organic Synthesis*, Second Edition, Wiley, New York, 1991, and references cited therein.

The compounds provided herein may be isolated and purified by known standard procedures. Such procedures include (but are not limited to) recrystallization, column chromatography, HPLC, or supercritical fluid chromatography (SFC). The following schemes are presented with details as to the preparation of representative heteroaryls and heterocyclyls that have been listed herein. The compounds provided herein may be prepared from known or commercially available starting materials and reagents by one skilled in the art of organic synthesis. Exemplary chiral columns available for use in the separation/purification of the enantiomers/diastereomers provided herein include, but are not limited to, CHIRALPAK® AD-10, CHIRALCEL® OB, CHIRALCEL® OB-H, CHIRALCEL® OD, CHIRALCEL® OD-H, CHIRALCEL® OF, CHIRALCEL® OG, CHIRALCEL® OJ and CHIRALCEL® OK.

$^1$H-NMR reported herein (e.g., for intermediates) may be a partial representation of the full NMR spectrum of a compound, e.g., a compound described herein. For example, the reported $^1$H NMR may exclude the region between δ (ppm) of about 1 to about 2.5 ppm.

Exemplary general method for preparative HPLC: Column: Waters RBridge prep 10 □m C18, 19*250 mm. Mobile phase: aectonitrile, water (NH$_4$HCO$_3$) (30 L water, 24 g NH$_4$HCO$_3$, 30 mL NH$_3$·H$_2$O). Flow rate: 25 mL/min Exemplary general method for analytical HPLC: Mobile phase: A: water (10 mM NH$_4$HCO$_3$), B: acetonitrileGradient: 5%-95% B in 1.6 or 2 min Flow rate: 1.8 or 2 mL/min; Column: XBridge C18, 4.6*50 mm, 3.5 μm at 45 C.

Synthetic Methods

Example 1. General Procedure A: Preparation of A/B-Trans Scaffolds

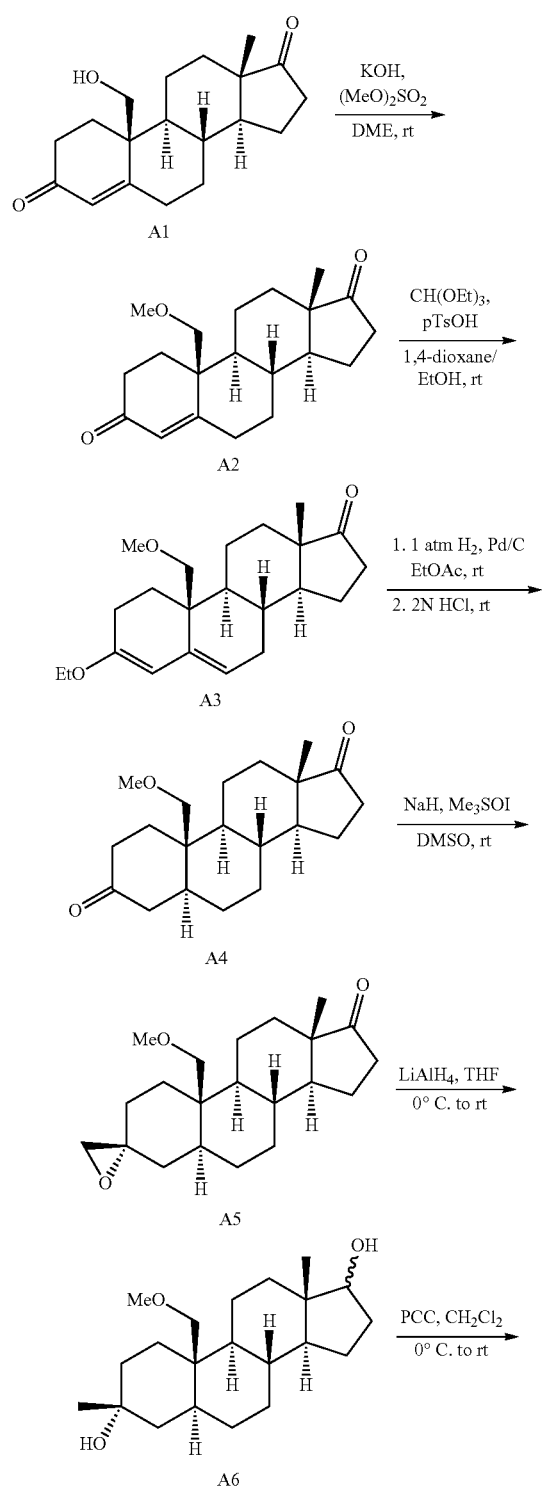

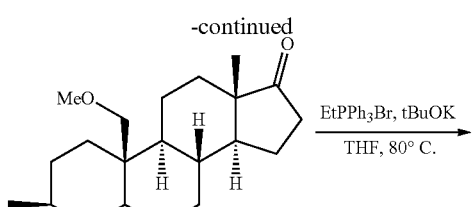

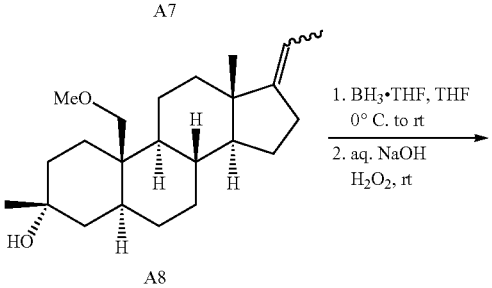

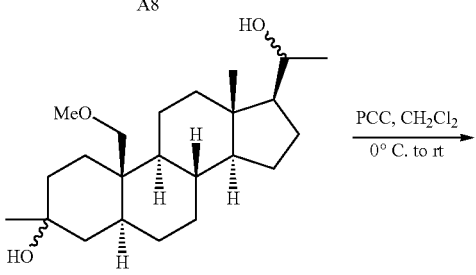

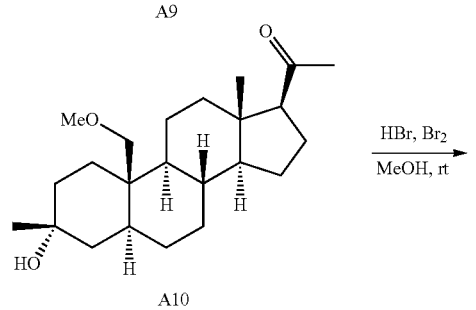

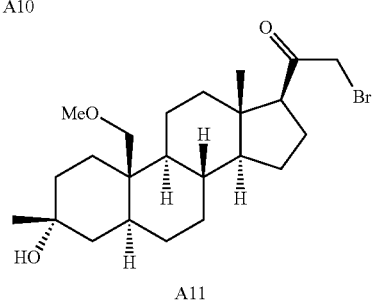

Step 1. Preparation of compound A2. Finely-ground potassium hydroxide (28.0 g, 165 mmol) was added to a solution of commercially available 19-hydroxyandrost-4-ene-3,17-dione (A1, 50.0 g, 165 mmol) in anhydrous 1,2-dimethoxyethane (500 mL) at 0° C. under nitrogen, after which methyl sulfate (43.7 g, 208 mmol) was added portionwise. The mixture was slowly warmed to room temperature, stirring for a total of 18 h, at which point TLC analysis of the mixture (7:3 hexanes/ethyl acetate) indicated completion of the reaction. The mixture was diluted with water (500 mL) and extracted with ethyl acetate (3×200 mL). The combined organic extracts were washed with saturated aqueous sodium chloride solution (100 mL), dried with anhydrous sodium sulfate and filtered. The solvents were removed under reduced pressure and the residue was purified by column chromatography on silica gel, eluting with heptane/ethyl acetate (2:1), to provide A2 as a yellow solid (26.8 g, 50%).

Step 2. Preparation of compound A3. Triethyl orthoformate (6.2 mL, 37 mmol) and p-toluenesulfonic acid (400 mg, 9.3 mmol) were added to a solution of compound A2 (9.9 g, 31.0 mmol) in anhydrous 1,4-dioxane (40 mL) and anhydrous ethanol (30 mL) at room temperature under nitrogen, and the mixture was stirred for 1.5 h, at which point TLC analysis of the mixture (7:3 hexanes/ethyl acetate) indicated completion of the reaction. The mixture was diluted with saturated aqueous sodium bicarbonate solution (100 mL), poured into water (300 mL) and extracted with ethyl acetate (3×100 mL). The combined organic extract solvents were removed under reduced pressure and the residue was purified by column chromatography on silica gel, eluting with heptane/ethyl acetate (2:1), to provide compound A3 as a white solid (7.0 g, 66%). Step 3. Preparation of compound A4. A mixture of compound A3 (7.0 g, 20.3) and palladium on carbon (3.0 g, 10 wt. %) in anhydrous ethyl acetate (200 mL) was shaken under an atmosphere of hydrogen (I atmosphere) at room temperature for 1 h, at which point TLC analysis of the mixture (2:1 hexanes/ethyl acetate) indicated completion of the reaction. The atmosphere was exchanged for nitrogen and the mixture was filtered through a pad of Celite under reduced pressure, washing the filter cake with ethyl acetate (50 mL). The filtrate solvents were treated with 10% aqueous hydrochloric acid solution (100 mL) and the biphasic mixture was stirred for 30 min. The mixture was extracted with ethyl acetate (2×100 mL) and the combined organic extracts were washed sequentially with saturated aqueous sodium bicarbonate and saturated aqueous sodium chloride solutions (50 mL each), dried with anhydrous sodium sulfate and filtered. The solvents were removed under reduced pressure and the residue was purified by column chromatography on silica gel, eluting with heptane/ethyl acetate (4:1), to provide compound A4 as a colorless oil (3.9 g, 60%).

Step 4. Preparation of compound A5. Sodium hydride (1.7 g, 45 mmol, 60% in mineral oil) was added portionwise to a solution of trimethylsulfoxonium iodide (9.1 g, 45 mmol) in anhydrous dimethyl sulfoxide (100 mL) at room temperature under nitrogen, and the mixture was stirred for 1 h, after which a solution of compound A4 (9.5 g, 29.8 mmol) in anhydrous dimethyl sulfoxide (100 mL) was added. The resulting mixture was stirred at room temperature for 12 h, at which point TLC analysis of the mixture (7:3 hexanes/ethyl acetate) indicated completion of the reaction. The mixture was diluted with water (500 mL) and extracted with methyl tert-butyl ether (2×300 mL). The combined organic extracts were washed with water (2×300 mL), dried with anhydrous magnesium sulfate and filtered. The solvents were removed under reduced pressure to provide compound A5 as a colorless oil that was used in the next step without further purification (7.5 g, 76%).

Step 5. Preparation of compound A6. Lithium aluminum hydride (67 mL, 67 mmol, 1 M solution in tetrahydrofuran) was added to a solution of crude compound A5 (7.5 g, 22.2 mmol) in anhydrous tetrahydrofuran (5 mL) at 0° C. under nitrogen, after which the mixture was slowly warmed to room temperature, stirring for a total of 2 h, at which point TLC analysis of the mixture (7:3 hexanes/ethyl acetate) indicated completion of the reaction. The mixture was carefully treated with water (10 mL) followed by saturated aqueous sodium chloride solution (30 mL) and extracted with ethyl acetate (3×50 mL). The combined organic extracts were dried with anhydrous magnesium sulfate, filtered and the solvents were removed under reduced pressure to provide compound A6 as a colorless oil that was used in the next step without further purification (5.5 g, 74%): LCMS m/z 319 [M+H−H$_2$O]$^+$.

Step 6. Preparation of compound A7. Pyridinium chlorochromate (4.0 g, 19 mmol) was added in one portion to a solution of crude compound A6 (4.2 g, 12.5 mmol) in anhydrous dichloromethane (100 mL) at 0° C. under nitrogen. The mixture was slowly warmed to room temperature, stirring for a total of 3 h, at which point TLC analysis of the mixture (7:3 hexanes/ethyl acetate) indicated completion of the reaction. The solids were removed by filtration and the filtrate solvents were removed under reduced pressure. The residue was purified by column chromatography on silica gel, eluting with heptane/ethyl acetate (7:3), to provide compound A7 as a light yellow solid (2.1 g, 50%): LCMS m/z 317 [M+H−H$_2$O]$^+$.

Step 7. Preparation of compound A8. Potassium tert-butoxide (4.3 g, 38 mmol) was added to a mixture of ethyltriphenylphosphonium bromide (14.2 g, 38 mmol) in anhydrous tetrahydrofuran (30 mL) at room temperature under nitrogen, after which the mixture was heated to 80° C. and stirred for 1 h. A solution of compound A7 (3.1 g, 9.3 mmol) in anhydrous tetrahydrofuran (10 mL) was added, after which stirring at 80° C. was continued for 2 h, at which point TLC analysis of the mixture (7:3 hexanes/ethyl acetate) indicated completion of the reaction. The cooled mixture was diluted with water (30 mL) and saturated aqueous sodium chloride solution (20 mL) and extracted with ethyl acetate (2×100 mL). The combined organic extract solvents were removed under reduced pressure and the residue was purified by column chromatography on silica gel, eluting with heptane/ethyl acetate (7:3), to provide compound A8 as an off-white solid (2.0 g, 66%): LCMS m/z 329 [M+H−H$_2$O]$^+$.

Step 8. Preparation of compound A9. Borane-tetrahydrofuran complex (20.0 mL, 20 mmol, 1 M solution in tetrahydrofuran) was added to a solution of compound A8 (2.0 g, 5.8 mmol) in anhydrous tetrahydrofuran (15 mL) at 0° C. under nitrogen, after which the mixture was slowly warmed to room temperature, stirring for a total of 1 h. The mixture was cooled in an ice bath and 10% aqueous sodium hydroxide solution (12 mL) was slowly added, followed by 30% aqueous hydrogen peroxide solution (12 mL). The resulting mixture was warmed to room temperature and stirred for 1 h, at which point TLC analysis of the mixture (7:3 hexanes/ethyl acetate) indicated completion of the reaction. The mixture was extracted with dichloromethane (2×100 mL) and the combined organic extracts were washed with saturated aqueous sodium chloride solution (25 mL), dried with sodium sulfate and filtered. The solvents were removed under reduced pressure to provide crude compound A9 as a white solid that was used in the next step without further purification (2.5 g, >99%).

Step 9. Preparation of compound A10. Pyridinium chlorochromate (2.4 g, 11 mmol) was added in one portion to a solution of crude compound A9 (2.5 g, 6.9 mmol) in anhydrous dichloromethane (30 mL) at 0° C. under nitrogen. The mixture was slowly warmed to room temperature, stirring for a total of 2 h, at which point TLC analysis of the mixture (7:3 hexanes/ethyl acetate) indicated completion of the reaction. The solids were removed by filtration and the filtrate solvents were removed under reduced pressure. The residue was purified by column chromatography on silica gel, eluting with heptane/ethyl acetate (7:3), to provide A10 as an off-white solid (1.5 g, 61%).

Step 10. Preparation of compound A11. Hydrogen bromide (3 drops, 48% in water) was added to a solution of A10, 1.4 g, 3.9 mmol) in anhydrous methanol (150 mL) at room temperature in the dark under nitrogen, after which bromine (0.4 mL, 7.7 mmol) was added. The mixture was stirred for 1 h, at which point TLC analysis of the mixture (7:3 hexanes/ethyl acetate) indicated completion of the reaction. The mixture was poured into ice-water (100 mL), treated with saturated aqueous sodium bicarbonate solution (30 mL) and extracted with ethyl acetate (2×60 mL). The combined organic extracts were washed with saturated aqueous sodium bicarbonate solution (4×100 mL) and saturated aqueous sodium chloride solution (50 mL), dried with magnesium sulfate and filtered. The solvents were removed under reduced pressure and the residue was purified by column chromatography on silica gel, eluting with heptane/ethyl acetate (1:1), to provide compound A11 as a colorless semi-solid (1.2 g, 71%): LCMS m/z 441 [M+H]$^+$.

Example 2. General Procedure A: Preparation of A/B-Trans Scaffolds

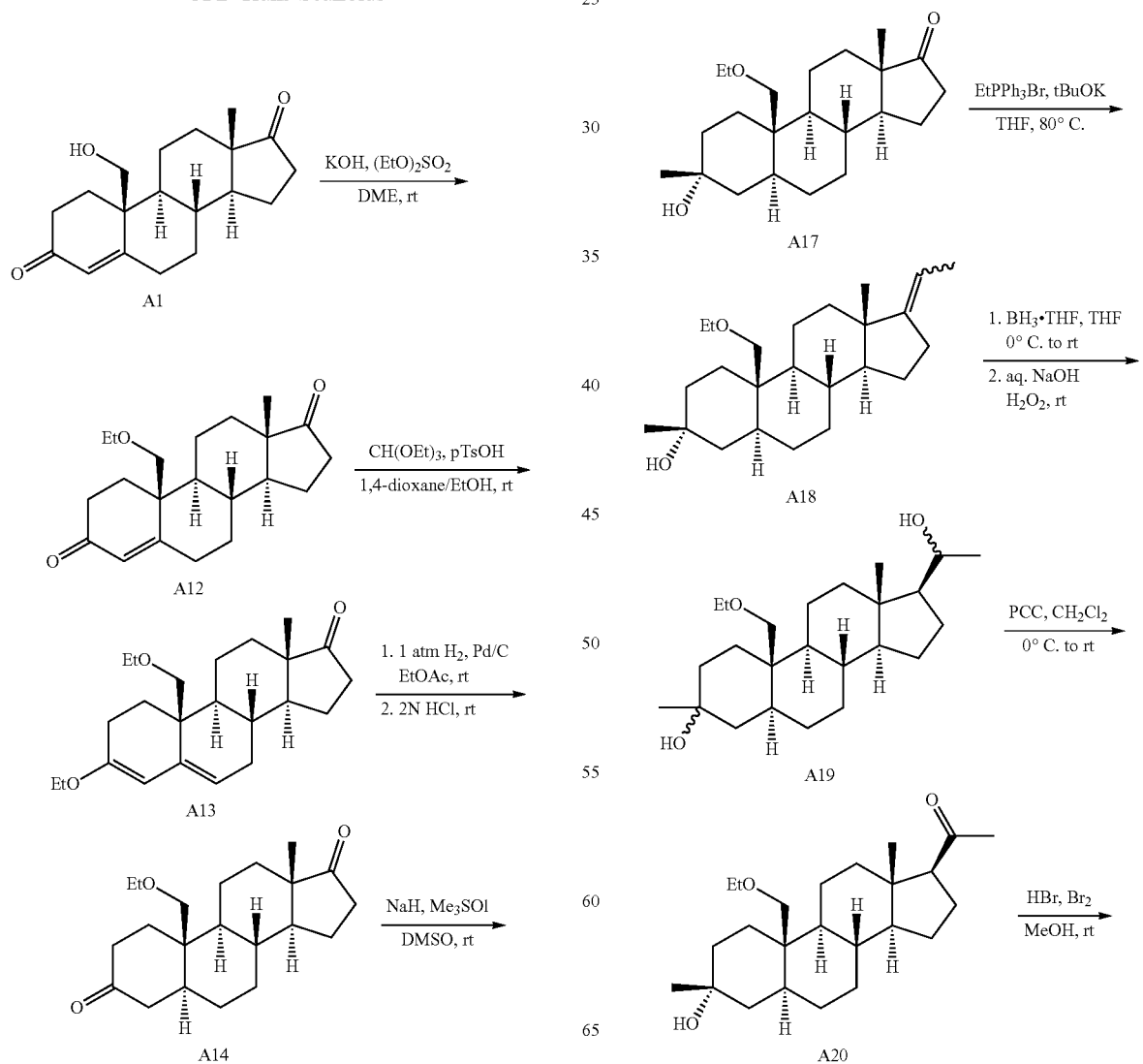

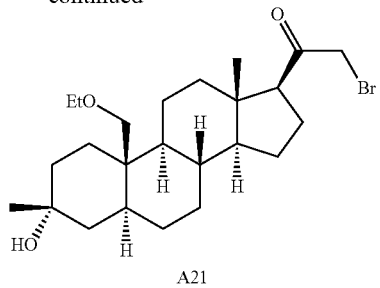

A21

Step 1. Preparation of compound A12. Prepared according General Procedure A, Step 1 from A1, 10.0 g, 33 mmol) and ethyl sulfate (17.3 mL, 132 mmol), with purification by column chromatography on silica gel to provide compound A12 as a yellow oil (4.6 g, 42%).

Step 2. Preparation of compound A13. Prepared according General Procedure A, Step 2 from compound A12 (4.6 g, 14 mmol) to provide crude compound A13 as a yellow oil that was used in the next step without further purification.

Step 3. Preparation of compound A14. Prepared according General Procedure A, Step 3 from crude compound A13, with purification by column chromatography on silica gel to provide compound A14 as a yellow oil (1.5 g, 31%).

Step 4. Preparation of compound A15. Prepared according General Procedure A, Step 4 from compound A14 (1.7 g, 5.1 mmol) to provide crude compound A15 as a yellow oil that was used in the next step without further purification.

Step 5. Preparation of compound A16. Prepared according General Procedure A, Step 5 from crude compound A15 to provide crude compound A16 as a yellow oil that was used in the next step without further purification.

Step 6. Preparation of compound A17. Prepared according General Procedure A, Step 6 from crude compound A16, with purification by column chromatography on silica gel to provide compound A17 as an off-white solid (751 mg, 40%).

Step 7. Preparation of compound A18. Prepared according General Procedure A, Step 7 from compound A17 (750 mg, 2.2 mmol), with purification by column chromatography on silica gel to provide compound A18 as a colorless oil (757 mg, 97%).

Step 8. Preparation of compound A19. Prepared according General Procedure A, Step 8 from compound A18 (757 mg, 2.1 mmol), to provide crude compound A19 as a yellow oil that was used in the next step without further purification.

Step 9. Preparation of A20. Prepared according General Procedure A, Step 9 from crude compound A19, with purification by column chromatography on silica gel to provide A20 as a white solid (515 mg, 65%): mp 106-107° C.; $^1$HNMR (500 MHz, CDCl$_3$) δ 3.51 (d, J=16.5 Hz, 1H), 3.43-3.36 (m, 3H), 2.53 (t, J=5.0 Hz, 1H), 2.18-1.96 (m, 6H), 1.74-0.92 (m, 25H), 0.84-0.82 (m, 1H), 0.62 (s, 3H) ppm; ESI MS m/z 359 [M+H–H$_2$O]$^+$.

Step 10. Preparation of A21. Hydrogen bromide (10 drops, 48% in water) was added to a solution of A20 (490 mg, 1.30 mmol) in anhydrous methanol (40 mL) at room temperature in the dark under nitrogen, after which bromine (235 mg, 13.0 mmol) was added. The mixture was stirred for 1 h, at which point TLC analysis of the mixture (7:3 hexanes/ethyl acetate) indicated completion of the reaction. The mixture was poured into ice-water (100 mL), treated with saturated aqueous sodium bicarbonate solution (30 mL) and extracted with ethyl acetate (2×60 mL). The combined organic extracts were washed with saturated aqueous sodium bicarbonate solution (4×100 mL) and saturated aqueous sodium chloride solution (50 mL), dried with magnesium sulfate and filtered. The solvents were removed under reduced pressure and the residue was purified by column chromatography on silica gel, eluting with heptane/ ethyl acetate (1:1), to provide compound A21 as a white solid (468 mg, 79%). LCMS m/z 437 [M+H–H$_2$O]$^+$.

Example 3. General Procedure B: Preparation of A/B-Trans Scaffold C-21 Analogs

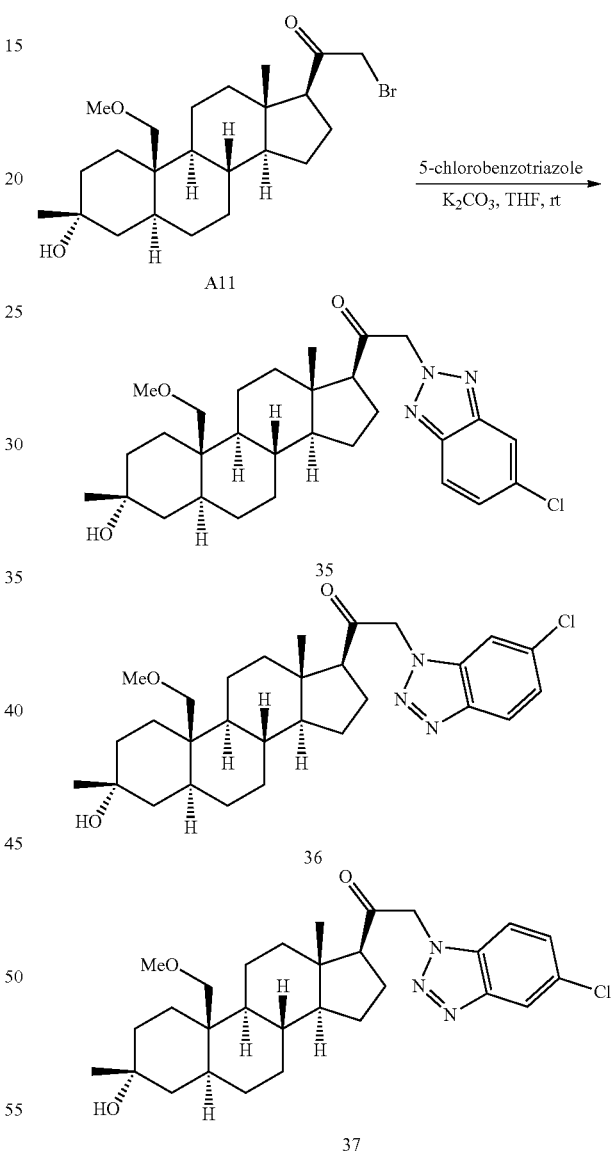

5-Chloro-1H-benzo[d][1,2,3]triazole (470 mg, 3.06 mmol) and potassium carbonate (704 mg, 5.1 mmol) were added to a solution of compound A11 (225 mg, 0.51 mmol) in anhydrous tetrahydrofuran (20 mL) at room temperature under nitrogen and the mixture was stirred for 16 h, at which point TLC analysis of the mixture (2:1 hexanes/ethyl acetate) indicated completion of the reaction. The mixture was diluted with water (120 mL) and extracted with ethyl acetate (3×100 mL). The combined organic extracts were washed with saturated aqueous sodium chloride solution (60 mL), dried with sodium sulfate and filtered. The solvents were removed under reduced pressure and the residue was semi-purified by column chromatography on silica gel, eluting with hexanes/ethyl acetate (3:1), to provide a mixture of the three regioisomers. The residue was further purified by reverse phase preparative HPLC to provide 35 as an off-white solid (150 mg, 29%): mp 205-207° C.; $^1$H NMR (300 MHz, CDCl$_3$) δ 7.87 (dd, J=1.8, 0.6 Hz, 1H), 7.81 (dd, J=9.0, 0.6 Hz, 1H), 7.34 (dd, J=9.0, 1.8 Hz, 1H), 5.55 (d, $J_{AB}$=17.1 Hz, 1H), 5.46 (d, $J_{AB}$=17.1 Hz, 1H), 3.48 (d, J=9.9 Hz, 1H), 3.38 (d, J=10.2 Hz, 1H), 3.30 (s, 3H), 2.66 (t, J=8.7 Hz, 1H), 2.30-2.18 (m, 1H), 2.18-2.09 (m, 1H), 2.09-2.00 (m, 1H), 1.82-1.38 (m, 11H), 1.38-1.06 (m, 10H), 1.06-0.92 (m, 1H), 0.92-0.80 (m, 1H), 0.76 (s, 3H) ppm; ESI MS m/z 514 [M+H]$^+$.

Further elution provided 36 as an off-white solid (86 mg, 17%): mp 97-101° C.; $^1$H NMR (300 MHz, CDCl$_3$) δ 8.03-7.97 (m, 1H), 7.36-7.31 (m, 2H), 5.42 (d, $J_{AB}$=18.3 Hz, 1H), 5.34 (d, $J_{AB}$=18.0 Hz, 1H), 3.49 (d, J=9.9 Hz, 1H), 3.38 (d, J=9.9 Hz, 1H), 3.31 (s, 3H), 2.72 (t, J=8.7 Hz, 1H), 2.30-2.10 (m, 2H), 2.10-2.00 (m, 1H), 1.85-1.40 (m, 11H), 1.39-0.80 (m, 12H), 0.75 (s, 3H) ppm; ESI MS m/z 5140 [M+H]$^+$.

Further elution provided 37 as an off-white solid (112 mg, 21%): mp 106-110° C.; $^1$H NMR (300 MHz, CDCl$_3$) δ 8.06 (d, J=1.2 Hz, 1H), 7.45 (dd, J=9.0, 1.5 Hz, 1H), 7.27 (d, J=8.7 Hz, 1H), 5.41 (s, 2H), 3.49 (d, J=9.9 Hz, 1H), 3.38 (d, J=10.2 Hz, 1H), 3.30 (s, 3H), 2.71 (t, J=8.7 Hz, 1H), 2.29-2.00 (m, 3H), 1.83-1.44 (m, 11H), 1.44-0.82 (m, 12H), 0.74 (s, 3H) ppm; ESI MS m/z 514 [M+H]$^+$.

Example 4. Preparation of Compound 8

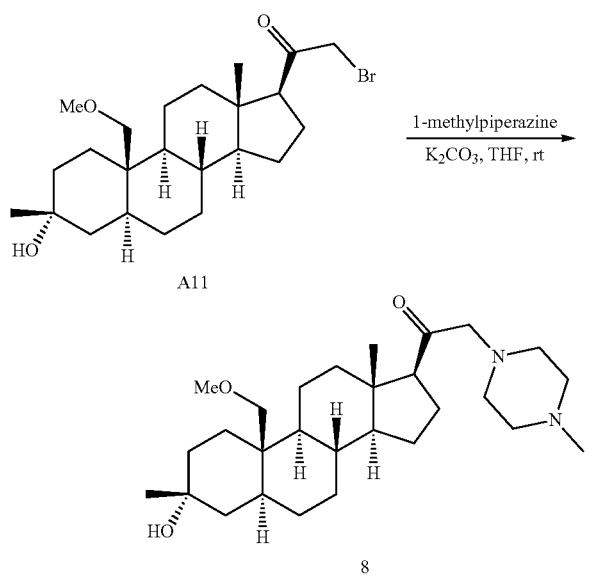

Prepared according General Procedure B from compound A11 (50 mg, 0.114 mmol) and N-methylpiperazine (227 mg, 2.27 mmol), with purification by reverse phase preparative HPLC to provide compound 8 as a white solid (36.6 mg, 70%): mp 136-137° C.; $^1$HNMR (500 MHz, CDCl$_3$) δ 3.46 (d, J=10.0 Hz, 1H), 3.36 (d, J=10.0 Hz, 1H), 3.28 (s, 3H), 3.17 (s, 2H), 2.60-2.51 (m, 8H), 2.30 (s, 3H), 2.18-2.14 (m, 1H), 2.02 (dt, J=13.0, 3.5 Hz, 1H), 1.88 (dt, J=12.0, 3.5 Hz, 1H), 1.71-1.46 (m, 10H), 1.34-1.72 (m, 11H), 0.98-0.84 (m, 1H), 0.84-0.80 (m, 1H), 0.64 (s, 3H) ppm; ESI MS m/z 461 [M+H]$^+$.

Example 5. Preparation of Compounds 3 and 1

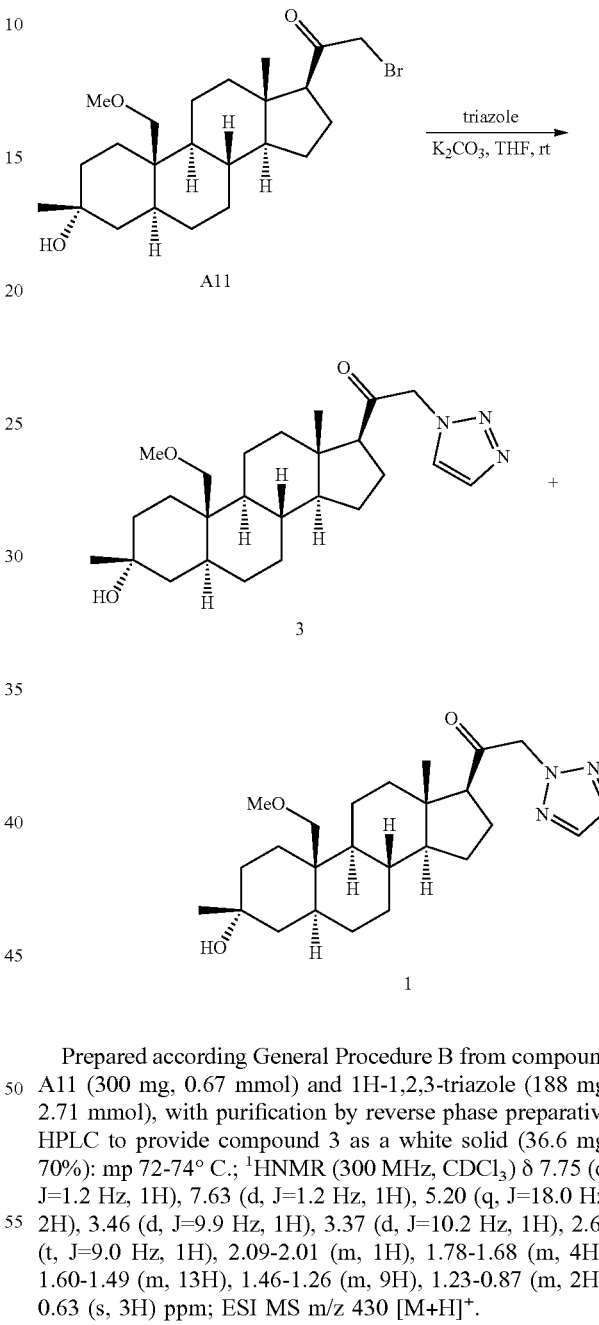

Prepared according General Procedure B from compound A11 (300 mg, 0.67 mmol) and 1H-1,2,3-triazole (188 mg, 2.71 mmol), with purification by reverse phase preparative HPLC to provide compound 3 as a white solid (36.6 mg, 70%): mp 72-74° C.; $^1$HNMR (300 MHz, CDCl$_3$) δ 7.75 (d, J=1.2 Hz, 1H), 7.63 (d, J=1.2 Hz, 1H), 5.20 (q, J=18.0 Hz, 2H), 3.46 (d, J=9.9 Hz, 1H), 3.37 (d, J=10.2 Hz, 1H), 2.65 (t, J=9.0 Hz, 1H), 2.09-2.01 (m, 1H), 1.78-1.68 (m, 4H), 1.60-1.49 (m, 13H), 1.46-1.26 (m, 9H), 1.23-0.87 (m, 2H), 0.63 (s, 3H) ppm; ESI MS m/z 430 [M+H]$^+$.

Further elution provided compound 1 as an off-white solid (110 mg, 38%): mp 157-150° C.; $^1$HNMR δ 7.67 (s, 2H), 5.23 (q, J=17.0 Hz, 2H), 3.47 (d, J=10.0 Hz, 1H), 3.37 (d, J=10.0 Hz, 1H), 3.28 (s, 3H), 2.57 (t, J=9.5 Hz, 1H), 2.24-2.17 (m, 1H), 2.09-2.01 (m, 2H), 1.75-1.67 (m, 4H), 1.62-1.47 (m, 10H), 1.38-1.23 (m, 3H), 1.23-1.08 (m, 4H), 1.02-0.92 (m, 1H), 0.86-0.81 (m, 1H), 0.73 (s, 3H) ppm; ESI MS m/z 430 [M+H]$^+$.

Example 6. Preparation of Compound 13

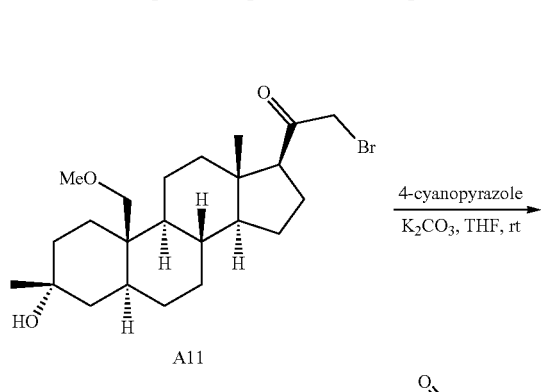

Prepared according General Procedure B from compound A11 (25 mg, 0.057 mmol) and 5-chlorotriazole (106 mg, 1.14 mmol), with purification by reverse phase preparative HPLC to provide compound 13 as a white solid (16.8 mg, 65%): mp 141-142° C.; $^1$HNMR (500 MHz, CDCl$_3$) δ 7.85 (s, 1H), 7.80 (s, 1H), 4.95 (dd, J=62.5, 17.5 Hz, 2H), 3.47 (dd, J=10.0 Hz, 1H), 3.37 (dd, J=10.0 Hz, 1H), 3.28 (s, 3H), 2.60 (t, J=9.0 Hz, 1H), 2.23-2.20 (m, 1H), 2.05-2.01 (m, 2H), 1.76-1.69 (m, 4H), 1.63-1.49 (m, 7H), 1.47-1.10 (m, 10H), 0.99-0.97 (m, 1H), 0.87-0.85 (m, 1H), 0.69 (s, 3H) ppm; ESI MS m/z 436 [M+H−H$_2$O]$^+$.

Example 7. Preparation of Compounds 14 and 15

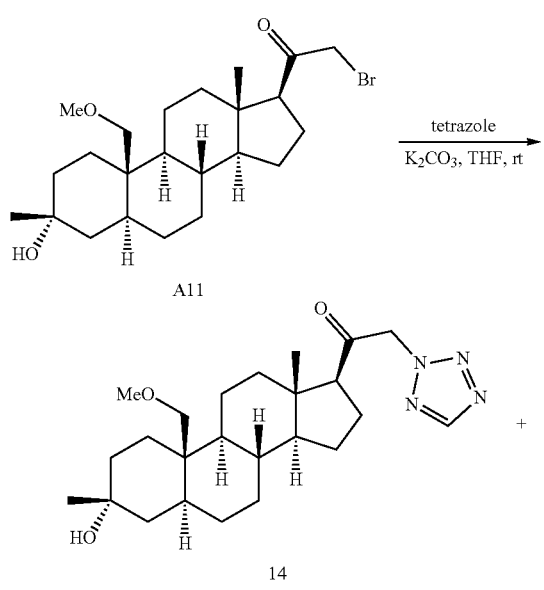

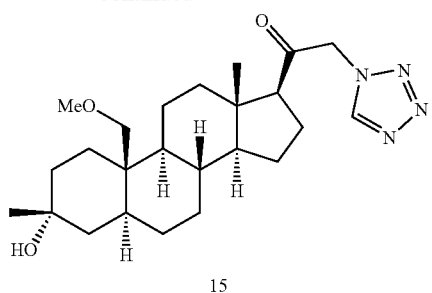

Prepared according General Procedure B from compound A11 (60 mg, 0.14 mmol) and tetrazole (57 mg, 0.81 mmol), with semi-purification by column chromatography on silica gel followed by reverse phase preparative HPLC to provide compound 15 as an off-white solid (6 mg, 10%): mp 88-91° C.; $^1$H NMR (500 MHz, CDCl$_3$) δ 8.73 (s, 1H), 5.30 (d, J$_{AB}$=18.5 Hz, 1H), 5.17 (d, J$_{AB}$=18.5 Hz, 1H), 3.47 (d, J=10.0 Hz, 1H), 3.37 (d, J=10.0 Hz, 1H), 3.29 (s, 3H), 2.66 (t, J=9.0 Hz, 1H), 2.28-2.20 (m, 1H), 2.07-2.00 (m, 2H), 1.82-1.69 (m, 4H), 1.65-1.40 (m, 7H), 1.35-1.09 (m, 10H), 1.04-0.95 (m, 1H), 0.92-0.83 (m, 1H), 0.69 (s, 3H) ppm; ESI MS m/z 431 [M+H]$^+$.

Further elution provided compound 14 as an off-white solid (7 mg, 12%): mp 72-75° C.; $^1$H NMR (500 MHz, CDCl$_3$) δ 8.56 (s, 1H), 5.47 (d, J$_{AB}$=17.0 Hz, 1H), 5.42 (d, J$_{AB}$=17.5 Hz, 1H), 3.47 (d, J=10.5 Hz, 1H), 3.38 (d, J=10.0 Hz, 1H), 3.29 (s, 3H), 2.64 (t, J=9.0 Hz, 1H), 2.27-2.19 (m, 1H), 2.18-2.00 (m, 2H), 1.80-1.68 (m, 4H), 1.66-1.46 (m, 6H), 1.44-1.37 (m, 1H), 1.35-1.08 (m, 10H), 1.04-0.94 (m, 1H), 0.90-0.83 (m, 1H), 0.74 (s, 3H) ppm; ESI MS m/z 431 [M+H]$^+$.

Example 8. Preparation of Compounds 16 and 17

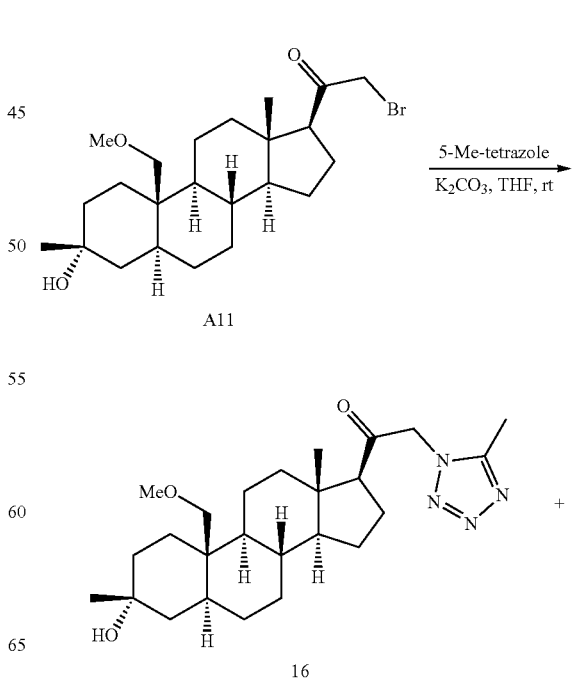

-continued

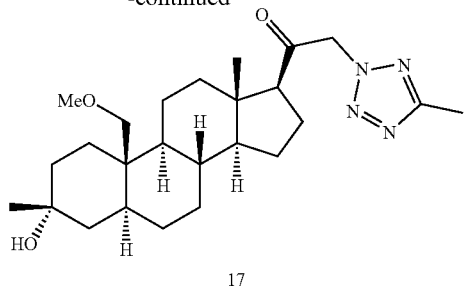

17

Hz, 1H), 3.46 (d, J=10.0 Hz, 1H), 3.37 (d, J=10.0 Hz, 1H), 3.28 (s, 3H), 3.13 (s, 3H), 2.57 (t, J=9.0 Hz, 1H), 2.26-2.16 (m, 1H), 2.07-1.98 (m, 2H), 1.76-1.67 (m, 4H), 1.63-1.46 (m, 6H), 1.41-1.07 (m, 11H), 1.03-0.92 (m, 1H), 0.91-0.80 (m, 1H), 0.69 (s, 3H) ppm; ESI MS m/z 463 [M+H]$^+$.

Example 10. Preparation of Compound 19

Prepared according General Procedure B from compound A11 (215 mg, 0.49 mmol) and 5-methyl-1H-tetrazole (253 mg, 2.92 mmol), with semi-purification by column chromatography on silica gel followed by reverse phase preparative HPLC to provide 16 as an off-white solid (56 mg, 26%): mp 88-91° C.; $^1$H NMR (300 MHz, CDCl$_3$) δ 5.13 (d, J$_{AB}$=18.0 Hz, 1H), 5.06 (d, J$_{AB}$=18.0 Hz, 1H), 3.48 (d, J=10.0 Hz, 1H), 3.37 (d, J=10.0 Hz, 1H), 3.29 (s, 3H), 2.66 (t, J=9.0 Hz, 1H), 2.47 (s, 3H), 2.27-2.15 (m, 1H), 2.08-1.98 (m, 2H), 1.85-1.38 (m, 11H), 1.37-0.95 (m, 11H), 0.91-0.83 (m, 1H), 0.70 (s, 3H) ppm; ESI MS m/z 445 [M+H]$^+$.

Further elution afforded 17 as an off-white solid (95 mg, 44%): mp 71-74° C.; $^1$H NMR (500 MHz, CDCl$_3$) δ 5.37 (d, J$_{AB}$=17.0 Hz, 1H), 5.32 (d, J$_{AB}$=17.5 Hz, 1H), 3.47 (d, J=10.0 Hz, 1H), 3.37 (d, J=10.0 Hz, 1H), 3.29 (s, 3H), 2.62 (t, J=9.0 Hz, 1H), 2.56 (s, 3H), 2.26-2.18 (m, 1H), 2.09-2.00 (m, 2H), 1.80-1.68 (m, 4H), 1.65-1.46 (m, 6H), 1.43-1.08 (m, 11H), 1.04-0.94 (m, 1H), 0.90-0.82 (m, 1H), 0.73 (s, 3H) ppm; ESI MS m/z 445 [M+H]$^+$.

Example 9. Preparation of Compound 18

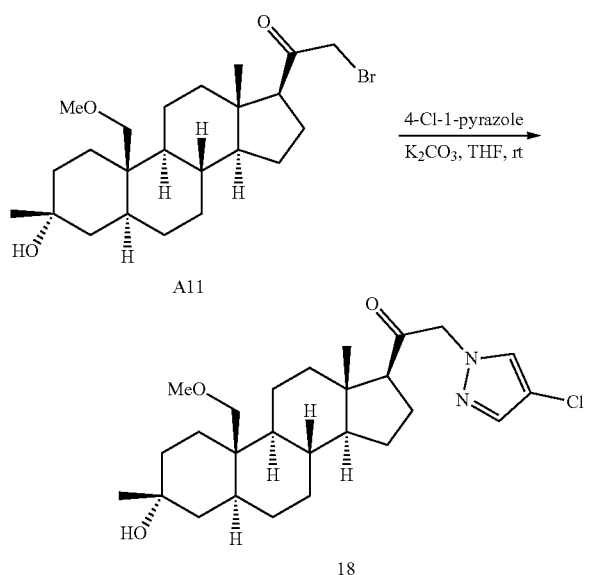

18

Prepared according General Procedure B from compound A11 (21 mg, 0.047 mmol) and 4-chloro-1H-pyrazole (29 mg, 0.28 mmol), with semi-purification by column chromatography on silica gel followed by reverse phase preparative HPLC to provide 18 as an off-white solid (10 mg, 46%): mp 100-104° C.; $^1$H NMR (500 MHz, CDCl$_3$) δ 7.45 (s, 1H), 7.40 (s, 1H), 4.90 (d, J$_{AB}$=17.5 Hz, 1H), 4.80 (d, J=17.5

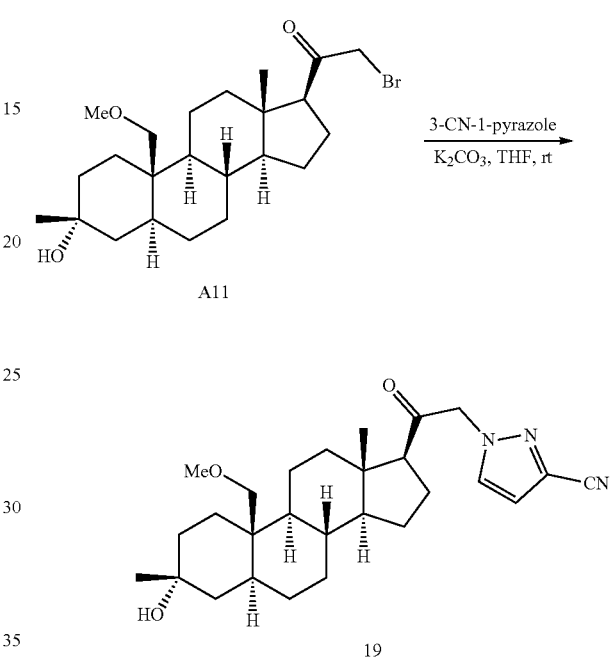

19

Prepared according General Procedure B from compound A11 (30 mg, 0.06 mmol) and 1H-pyrazole-3-carbonitrile (25 mg, 0.03 mmol), with semi-purification by column chromatography on silica gel followed by reverse phase preparative HPLC to provide 19 as an off-white solid (17 mg, 56%): mp 115-120° C.; $^1$HNMR (300 MHz, CDCl$_3$) δ 7.47 (d, J=2.4 Hz, 1H), 6.72 (d, J=2.4 Hz, 1H), 5.00 (q, J=18.0 Hz, 2H), 3.49 (d, J=9.9 Hz, 1H), 3.39 (d, J=10.2 Hz, 1H), 3.29 (s, 3H), 2.65 (t, J=9.0 Hz, 1H), 2.09-2.01 (m, 1H), 1.78-1.68 (m, 4H), 1.60-1.49 (m, 10H), 1.46-1.26 (m, 9H), 1.23-0.87 (m, 2H), 0.63 (s, 3H) ppm; ESI MS m/z 436 [M+H−H$_2$O]$^+$.

Example 11. Preparation of Compound 20

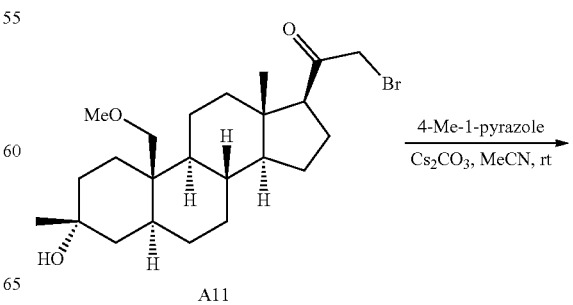

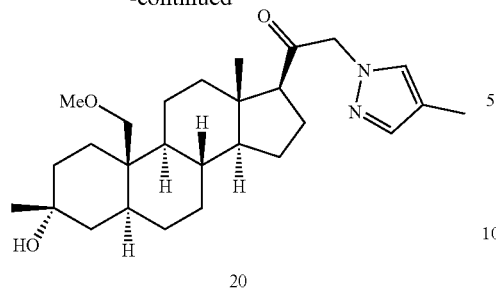

20

Prepared according General Procedure B from compound A11 (130 mg, 0.29 mmol) and 4-methyl-1H-pyrazole (247 mg, 3.01 mmol) with the substitution of cesium carbonate (480 mg, 1.5 mmol) in anhydrous acetonitrile (8 mL), with semi-purification by column chromatography on silica gel followed by reverse phase preparative HPLC to provide 20 as an off-white solid (15 mg, 11%): mp 67-71° C.; $^1$H NMR (500 MHz, CDCl$_3$) δ 7.33 (s, 1H), 7.16 (s, 1H), 4.87 (d, J$_{AB}$=18.0 Hz, 1H), 4.79 (d, J$_{AB}$=17.5 Hz, 1H), 3.46 (d, J=10.0 Hz, 1H), 3.37 (d, J=10.0 Hz, 1H), 3.28 (s, 3H), 3.13 (s, 3H), 2.56 (t, J=8.5 Hz, 1H), 2.23-2.15 (m, 1H), 2.09 (s, 3H), 2.07-2.00 (m, 2H), 1.75-1.65 (m, 4H), 1.62-1.45 (m, 6H), 1.40-1.08 (m, 11H), 1.02-0.94 (m, 1H), 0.89-0.82 (m, 1H), 0.69 (s, 3H) ppm; ESI MS m/z 443 [M+H]$^+$.

Example 12. Preparation of Compound 21

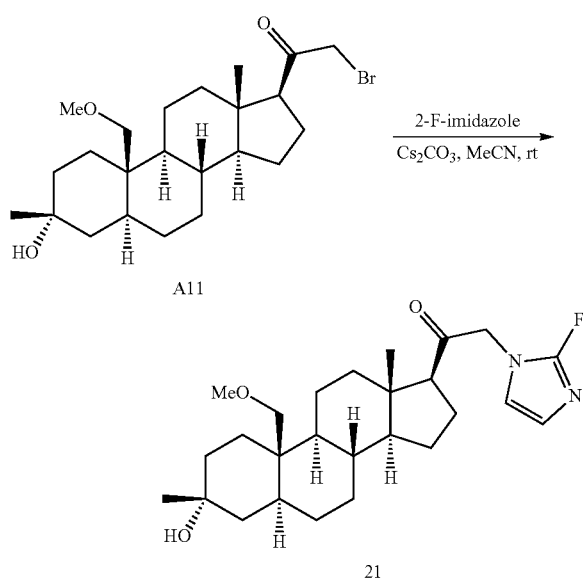

Prepared according General Procedure B from compound A11 (50 mg, 0.13 mmol) and 2-fluoroimidazole hydrochloride (75 mg, 0.61 mmol) with the substitution of cesium carbonate (200 mg, 0.62 mmol) in anhydrous acetonitrile (4 mL), with semi-purification by column chromatography on silica gel followed by reverse phase preparative HPLC to provide 21 as a yellow solid (35 mg, 69%): mp 78-81° C.; $^1$H NMR (300 MHz, CDCl$_3$) δ 6.91 (d, J=1.5 Hz, 1H), 6.64 (s, J=1.5 Hz, 1H), 5.54 (d, J$_{AB}$=18.3 Hz, 1H), 4.41 (d, J$_{AB}$=18.0 Hz, 1H), 3.48 (d, J=10.0 Hz, 1H), 3.37 (d, J=10.0 Hz, 1H), 3.30 (s, 3H), 2.54 (t, J=9.0 Hz, 1H), 2.28-2.14 (m, 1H), 2.09-1.98 (m, 2H), 1.80-1.64 (m, 4H), 1.64-1.46 (m, 6H), 1.44-0.80 (m, 13H), 0.69 (s, 3H) ppm; ESI MS m/z 470 [M+H]$^+$.

Example 13. Preparation of Compound 23

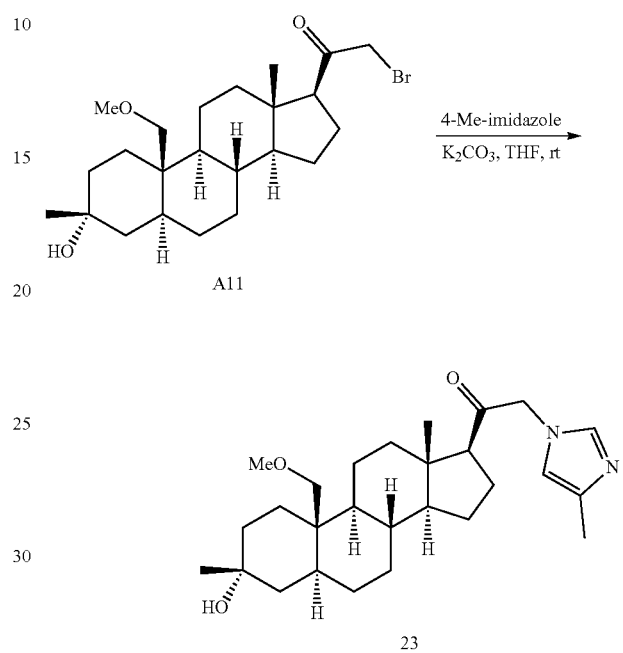

23

Prepared according General Procedure B from compound A11 (75 mg, 0.17 mmol) and 4-methylimidazole (279 mg, 3.4 mmol), with semi-purification by column chromatography on silica gel followed by reverse phase preparative HPLC to provide 23 as a white solid (18 mg, 24%): mp 87-89° C.; $^1$H NMR (500 MHz, CDCl$_3$) δ 7.40 (s, 1H), 6.56 (s, 1H), 4.63 (dd, J=18.0, 10.8 Hz, 2H), 3.47 (d, J=10.0 Hz, 1H), 3.37 (d, J=10.0 Hz, 1H), 3.29 (s, 3H), 2.60-2.54 (m, 1H), 2.24-2.17 (m, 3H), 2.08 (s, 1H), 2.04-2.01 (m, 1H), 1.96-1.93 (m, 1H), 1.76-1.68 (m, 4H), 1.63-1.46 (m, 6H), 1.42-1.09 (m, 11H), 1.02-0.93 (m, 1H), 0.87-0.82 (m, 1H), 0.68 (s, 3H) ppm; APCI MS m/z 443 [M+H]$^+$.

Example 14. Preparation of Compound 24

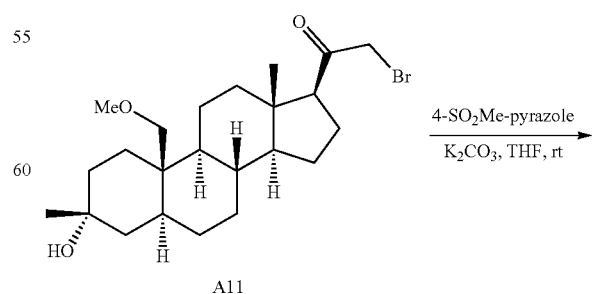

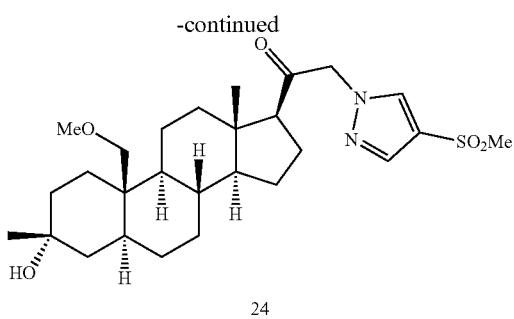

24

Prepared according General Procedure B from compound A11 (100 mg, 0.23 mmol) and 4-(methylsulfonyl)-1H-pyrazole (99 mg, 0.68 mmol), with semi-purification by column chromatography on silica gel followed by reverse phase preparative HPLC to provide 24 as a white solid (6 mg, 5%): mp 90-92° C.; $^1$H NMR (500 MHz, CDCl$_3$) δ 7.91 (s, 1H), 7.86 (s, 1H), 5.02 (d, $J_{AB}$=18.0 Hz, 1H), 4.90 (d, $J_{AB}$=17.5 Hz, 1H), 3.47 (d, J=10.0 Hz, 1H), 3.37 (d, J=10.0 Hz, 1H), 3.28 (s, 3H), 3.13 (s, 3H), 2.61 (t, J=9.0 Hz, 1H), 2.26-2.16 (m, 1H), 2.07-2.00 (m, 2H), 1.78-1.68 (m, 4H), 1.64-1.46 (m, 6H), 1.44-1.36 (m, 1H), 1.35-1.08 (m, 10H), 1.04-0.94 (m, 1H), 0.89-0.82 (m, 1H), 0.69 (s, 3H) ppm; APCI MS m/z 507 [M+H]$^+$.

Example 15. Preparation of Compounds 25 and 26

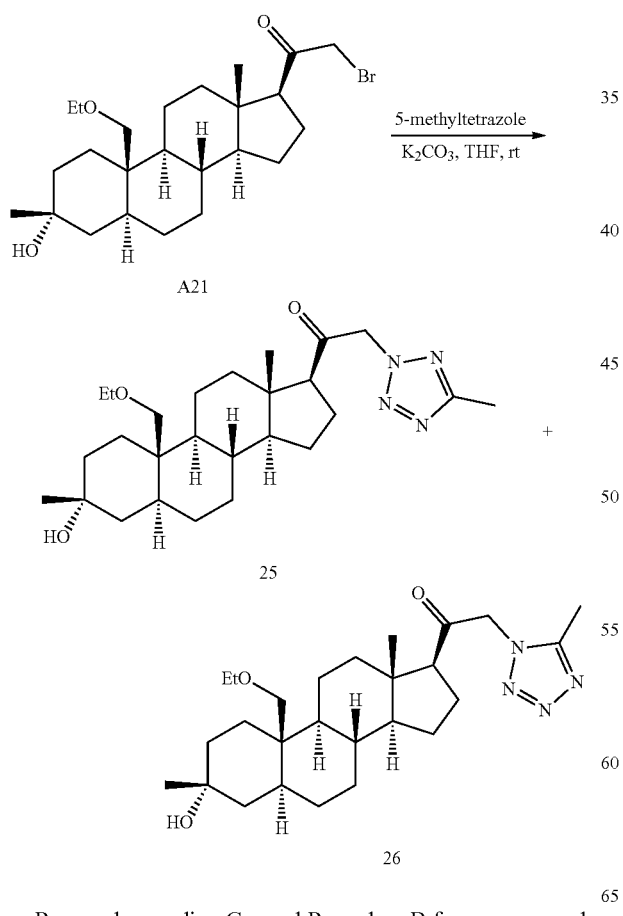

Prepared according General Procedure B from compound A21 (150 mg, 0.33 mmol) and 5-methyltetrazole (554 mg, 6.6 mmol), with purification by reverse phase preparative HPLC to provide 25 as a white solid (43.6 mg, 28%): mp 71-72° C.; $^1$HNMR (500 MHz, CDCl$_3$) δ 5.34 (dd, J=26.5, 17.5 Hz, 2H), 3.52 (d, J=10.0 Hz, 1H), 3.42-3.38 (m, 3H), 2.62 (t, J=9.0 Hz, 1H), 2.56 (s, 3H), 2.24-2.22 (m, 1H), 2.08-2.03 (m, 2H), 1.75-1.48 (m, 11H), 1.39-1.08 (m, 13H), 0.99-0.98 (m, 1H), 0.86-0.85 (m, 1H), 0.72 (s, 3H) ppm; ESI MS m/z 459 [M+H]$^+$.

Further elution provided 26 as a white solid (14.9 mg, 7%): mp 82-83° C.; $^1$HNMR (500 MHz, CDCl$_3$) δ 5.09 (dd, J=37.0, 18.0 Hz, 2H), 3.52 (d, J=10.0 Hz, 1H), 3.43-3.37 (m, 3H), 2.65 (t, J=9.0 Hz, 1H), 2.47 (s, 3H), 2.24-2.22 (m, 1H), 2.06-2.03 (m, 2H), 1.75-1.41 (m, 11H), 1.33-1.09 (m, 13H), 0.99-0.98 (m, 1H), 0.87-0.86 (m, 1H), 0.69 (s, 3H) ppm; ESI MS m/z 459 [M+H]$^+$.

Example 16. General Procedure C: Preparation of A/B-Cis Scaffolds

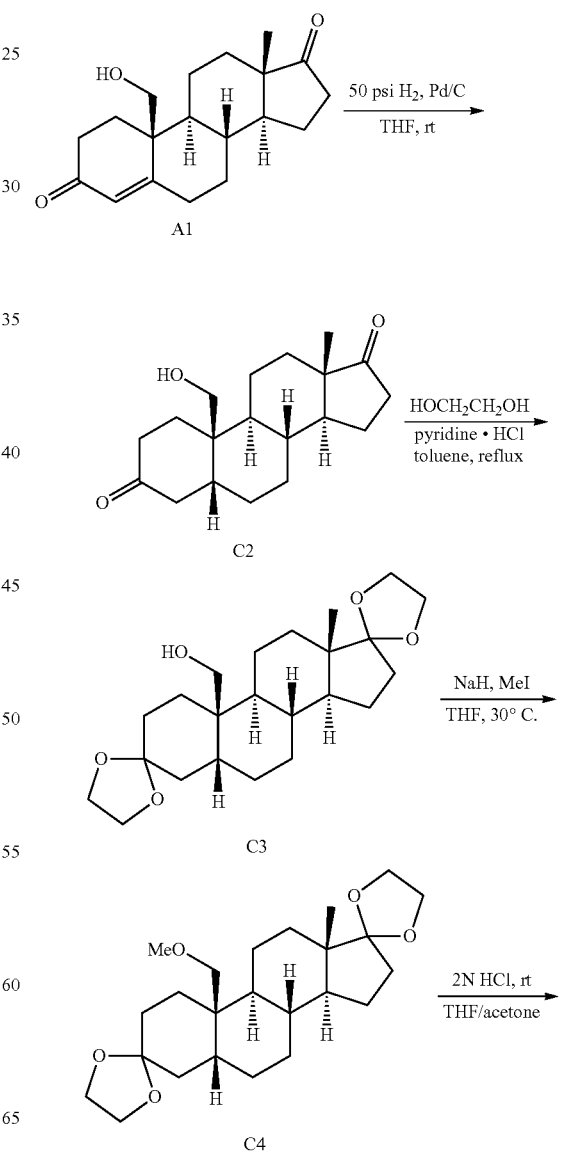

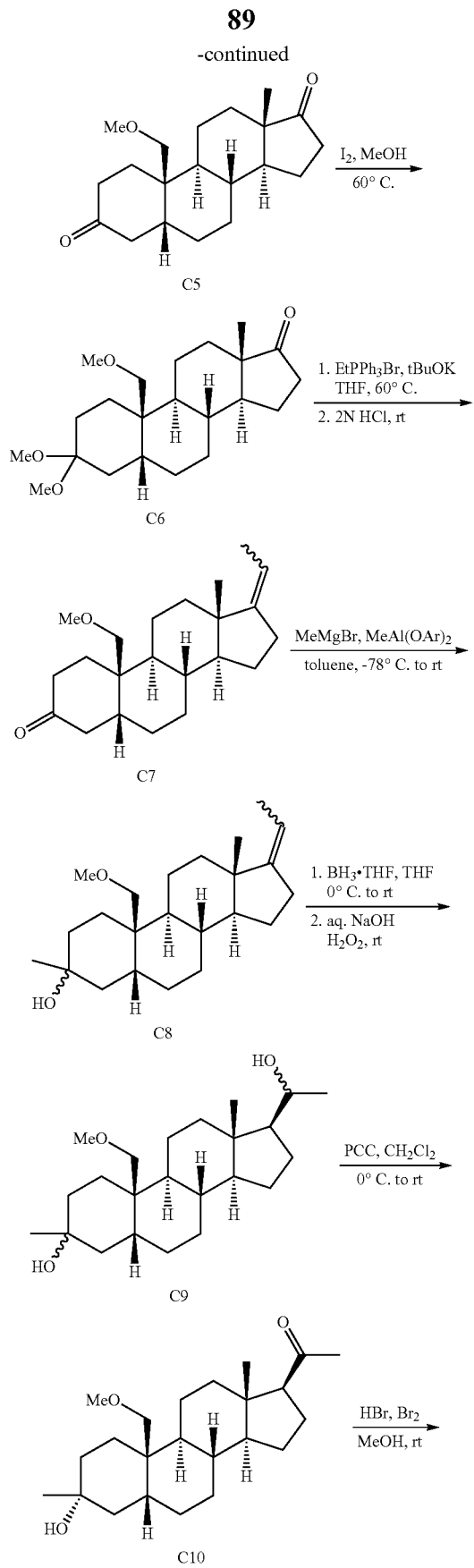

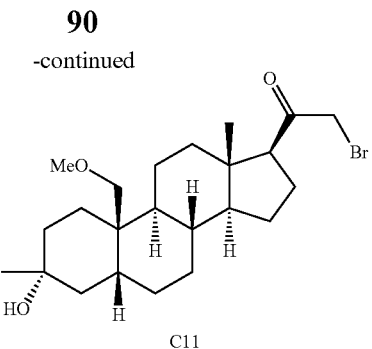

Step 1. Preparation of compound C2. A mixture of commercially available 19-hydroxyandrost-4-ene-3,17-dione (A1, 13.6 g, 45 mmol) and palladium on carbon (3.2 g, 10 wt. %) in anhydrous tetrahydrofuran (150 mL) was shaken under an atmosphere of hydrogen (50 psi) at room temperature for 12 h, at which point TLC analysis of the mixture (2:1 hexanes/ethyl acetate) indicated completion of the reaction. The atmosphere was exchanged for nitrogen and the mixture was filtered through a pad of Celite under reduced pressure, washing the filter cake with ethanol. The filtrate solvents were removed under reduced pressure to provide C2 as a white solid that was used in the next step without further purification (13.0 g, 95%): LCMS m/z 305 [M+H]$^+$.

Step 2. Preparation of compound C3. Pyridine hydrochloride (750 mg, 6.5 mmol) was added to a solution of crude compound C2 (15.0 g, 49 mmol) in ethylene glycol (65 mL) and anhydrous toluene (180 mL) at room temperature under nitrogen. The mixture was heated at reflux for 12 h with water removal by Dean-Stark apparatus, at which point TLC analysis of the mixture (2:1 hexanes/ethyl acetate) indicated completion of the reaction. The solvents were removed from the cooled mixture under reduced pressure and the residue was treated with saturated aqueous sodium chloride solution (50 mL) and extracted with ethyl acetate (3×50 mL). The combined organic extracts were washed with saturated aqueous sodium chloride solution (3×10 mL), dried with anhydrous sodium sulfate and filtered. The solvents were removed under reduced pressure to provide compound C3 as a colorless oil that was used in the next step without further purification (20.3 g, >99%): $^1$H NMR (300 MHz, CDCl$_3$) δ 4.11-3.81 (m, 8H), 3.60-3.54 (m, 1H), 2.05-1.92 (m, 3H), 1.81-163 (m, 4H), 1.59-1.35 (m, 12H), 1.28-1.12 (m, 5H), 0.8 (s, 3H) ppm; LCMS m/z 393 [M+H]$^+$.

Step 3. Preparation of compound C4. A solution of crude compound C3 (20.3 g, 49 mmol) in anhydrous tetrahydrofuran (120 mL) was added dropwise to a suspension of sodium hydride (7.9 g, 197 mmol, 60% in mineral oil) in anhydrous tetrahydrofuran (120 mL) at 0° C. under nitrogen, after which the mixture was stirred at 0° C. for 30 min. Iodomethane (15.3 mL, 246 mmol) was added dropwise, after which the mixture was heated to 35° C. and stirred for 3 h, at which point TLC analysis of the mixture (3:1 hexanes/ethyl acetate) indicated completion of the reaction. The cooled mixture was treated with saturated ammonium chloride solution (100 mL) and extracted with ethyl acetate (2×50 mL). The combined organic extracts were washed with saturated aqueous sodium chloride solution (2×20 mL), dried with anhydrous sodium sulfate and filtered. The solvents were removed under reduced pressure to provide crude compound C4 as a yellow oil that was used in the next step without further purification (25.6 g, >99%): LCMS m/z 407 [M+H]$^+$.

Step 4. Preparation of compound C5. A mixture of crude compound C4 (25.5 g, 49 mmol) in tetrahydrofuran (150 mL) and acetone (90 mL) at room temperature was treated with 2N HCl (123 mL) and the mixture was stirred for 16 h, at which point TLC analysis of the mixture (2:1 hexanes/ethyl acetate) indicated completion of the reaction. The reaction mixture was adjusted to pH 8 with slow addition of saturated aqueous sodium bicarbonate solution and extracted with ethyl acetate (3×125 mL). The combined organic extracts were washed with saturated aqueous sodium chloride solution (2×20 mL), dried with anhydrous sodium sulfate and filtered. The solvents were removed under reduced pressure and the residue was purified by column chromatography on silica gel, eluting with hexanes/ethyl acetate (2:1), to provide compound C5 as a white solid (10.6 g, 67%): $^1$H NMR (300 MHz, CDCl$_3$) δ 3.62-3.59 (m, 1H), 3.36-3.33 (m, 4H), 2.67-2.63 (m, 1H), 2.58-2.45 (m, 1H), 2.42-2.27 (m, 3H), 2.25-1.84 (m, 6H), 1.71-1.23 (m, 11H), 0.89 (s, 3H) ppm; LCMS m/z 319 [M+H]$^+$.

Step 5. Preparation of compound C6. Iodine (84 mg, 0.3 mmol) was added to a solution of compound C5 (10.6 g, 33 mmol) in anhydrous methanol (200 mL) at room temperature under nitrogen, after which the mixture was heated to 60° C. and stirred for 90 min, at which point TLC analysis of the mixture (2:1 hexanes/ethyl acetate) indicated completion of the reaction. The cooled mixture was treated with 1N sodium hydroxide solution (200 mL) and extracted with hexanes/ethyl acetate (3:1, 3×100 mL). The combined organic extracts were washed with saturated aqueous sodium chloride solution (2×25 mL), dried with anhydrous sodium sulfate and filtered. The solvents were removed under reduced pressure to provide compound C6 as a colorless oil that was used in the next step without further purification (13.8 g, >99%); LCMS m/z 365 [M+H]$^+$.

Step 6. Preparation of compound C7. Potassium tert-butoxide (11.2 g, 100 mmol) was added to a mixture of ethyltriphenylphosphonium bromide (36.9 g, 100 mmol) in anhydrous tetrahydrofuran (150 mL) at room temperature under nitrogen, after which the mixture was heated to 60° C. and stirred for 4 h. A solution of compound C6 (13.8 g, 33 mmol) in anhydrous tetrahydrofuran (100 mL) was added, after which stirring at 60° C. was continued for 18 h. The cooled mixture was diluted with water (200 mL) and hexanes (100 mL) and extracted with ethyl acetate (3×100 mL). The combined organic extracts were washed with saturated aqueous sodium chloride solution (2×25 mL), treated with 2N HCl (100 mL) and stirred at room temperature for 3 h. The resulting mixture was washed with saturated aqueous sodium bicarbonate and saturated aqueous sodium chloride solutions, dried with sodium sulfate and filtered. The solvents were removed under reduced pressure and the residue was purified by column chromatography on silica gel, eluting with hexanes/ethyl acetate (9:1), to provide compound C7 as a colorless oil (9.2 g, 84%): LCMS m/z 331 [M+H]$^+$.

Step 7. Preparation of compound C8. Bis(2,6-di-tert-butyl-4-methylphenoxide)methylaluminum (40.6 mL, 16 mmol, 0.4 M in toluene) was added in one portion to a solution of compound C7 (1.8 g, 5.4 mmol) in anhydrous toluene (20 mL) at −78° C. under nitrogen, after which the mixture was stirred for 10 min. Methylmagnesium bromide (11.6 mL, 16 mmol, 1.4 M in tetrahydrofuran/toluene) was added dropwise, after which the mixture was stirred at −78° C. for 1 h. The mixture was warmed to ice bath temperature and slowly treated with 2N HCl (60 mL), warmed to room temperature and extracted with ethyl acetate (3×50 mL). The combined organic extracts were washed with saturated aqueous sodium chloride solution (2×20 mL), dried with sodium sulfate and filtered. The solvents were removed under reduced pressure and the residue was purified by column chromatography on silica gel, eluting with hexanes/ethyl acetate (2:1), to provide crude compound C8 as a white semi-solid (1.5 g, 91%); LCMS m/z 347 [M+H]$^+$.

Step 8. Preparation of compound C9. Borane-tetrahydrofuran complex (27.6 mL, 27.6 mmol, 1.0 M solution in tetrahydrofuran) was added to a solution of compound C8 (2.4 g, 6.9 mmol) in anhydrous tetrahydrofuran (24 mL) at 0° C. under nitrogen, after which the mixture was slowly warmed to room temperature, stirring for a total of 4 h. The mixture was cooled in an ice bath and 10% aqueous sodium hydroxide solution (20 mL) was slowly added, followed by 30% aqueous hydrogen peroxide solution (20 mL). The resulting mixture was warmed to room temperature and stirred for 1 h and then treated with saturated aqueous sodium chloride solution (100 mL) and extracted with dichloromethane (3×100 mL). The combined organic extracts were washed with saturated aqueous sodium chloride solution (25 mL), dried with sodium sulfate and filtered. The solvents were removed under reduced pressure to provide crude compound C9 as a white solid that was used in the next step without further purification (2.7 g, >99%); LCMS m/z 365 [M+H]$^+$.

Step 9. Preparation of C10. Pyridinium chlorochromate (6.0 g, 28 mmol) was added in one portion to a solution of compound C9 (2.7 g, 6.9 mmol) in dichloromethane (100 mL) at 0° C. under nitrogen, after which the mixture was slowly warmed to room temperature, stirring for a total of 16 h. The solids were removed by filtration and the filtrate solvents were removed under reduced pressure. The residue was semi-purified by column chromatography on silica gel, eluting with hexanes/ethyl acetate (1:1), followed by further purification by reverse phase preparative HPLC to provide C10 as a white solid (2.15 g, 86%): mp 142-144° C.; $^1$HNMR (300 MHz, CDCl$_3$) δ 3.55 (d, J=9.0 Hz, 1H), 3.33 (s, 3H), 3.19 (d, J=9.0 Hz, 1H), 2.53 (t, J=9.0 Hz, 1H), 2.21-2.11 (m, 4H), 2.08-1.87 (m, 3H), 2.14-1.91 (m, 7H), 1.77-1.36 (m, 16H), 1.28 (s, 3H), 1.26-1.07 (m, 2H), 0.60 (s, 3H) ppm; LCMS m/z 345 [M+H−H$_2$O]$^+$.

Step 10. Preparation of compound C11. Hydrogen bromide (5 drops, 48% in water) was added to a solution of (C10, 2.15 g, 5.9 mmol) in anhydrous methanol (150 mL) at room temperature in the dark under nitrogen, after which bromine (0.6 mL, 12 mmol) was added and the mixture was stirred for 90 min. The mixture was poured into ice-water (250 mL) and treated with 2N sodium hydroxide solution (20 mL) followed by saturated aqueous sodium bicarbonate solution (100 mL). The solids were collected under reduced pressure and purified by column chromatography on silica gel, eluting with hexanes/ethyl acetate (1:1), to provide compound C11 as a white solid (1.4 g, 53%): LCMS m/z 442 [M+H]$^+$.

Example 17. Alternative Preparation of Intermediate C9

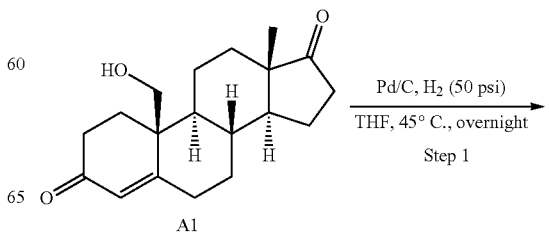

A1

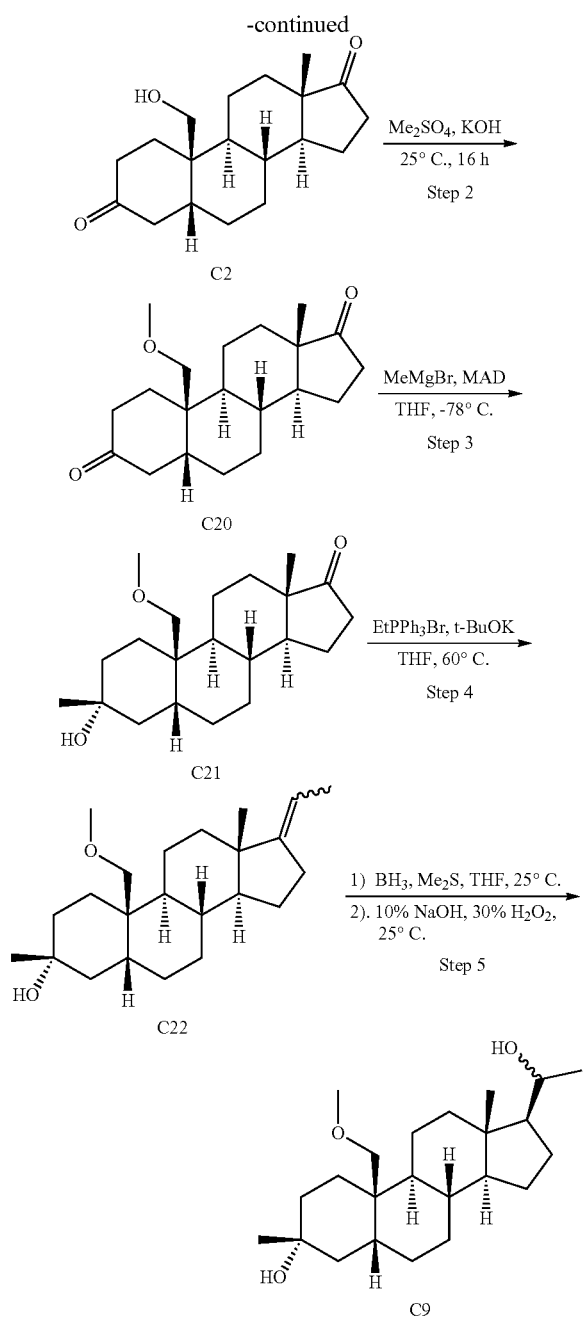

Step 1. Preparation of Compound C2. To a solution of Pd/C (1 g, 10% wet) in THF (10 mL) was added a solution of A1 (10 g, 33.07 mmol) in dry THF (140 mL) was added in the mixture. After TLC showed the starting material was consumed completely, the mixture was filtered with $CH_2Cl_2$ (300 mL) and concentrated. The residue was purified by column chromatograph on silica gel (PE:EA=8:1-4:1-2:1-1:1-EA) to give C2 (8.3 g, 82.43%) as a white solid. $^1$H NMR (400 MHz, CDCl3) δ (ppm)=3.96 (d, J=8.0 Hz, 1H), 3.69 (d, J=8.0 Hz, 1H), 2.69-2.65 (m, 1H), 2.45-2.29 (m, 4H), 2.12-1.69 (m, 8H), 1.63-1.23 (m, 7H), 0.88 (s, 3H)

Step 2. Preparation of Compound C20. To a solution of compound C2 (15 g, 49.3 mmol) in THF (150 mL) was added KOH (8.4 g, 149.7 mmol) and $Me_2SO_4$ (12.9 g, 100.67 mol) at 0° C. Then the mixture was warmed to 25° C. and stirred at the same temperature for 3 h. TLC (PE: EA=1:4) showed that the starting material was almost consumed. The mixture was quenched with the addition of 300 mL of water. The resulting solution was extracted with EtOAc (200 mL*3). The combined organic layers was washed with saturate aqueous NaCl (50 mL), dried over anhydrous $Na_2SO_4$ and evaporated in vacuum to give crude product, which was purified by column chromatography on silica gel (petroleum ether/ethyl acetate=4/1) to afford compound C20 (9.5 g, 60.5%) as a white solid.

Step 3. Preparation of Compound C21. To a solution of compound 2,6-di-tert-butyl-4-methylphenol (4.15 g, 18.84 mmol) in toluene (8 mL) was added $AlMe_3$ (4.7 mL, 9.42 mmol, 2 M in toluene) dropwise below 25° C. The solution was stirred at room temperature for 1 h. Then a solution of compound C20 (1 g, 3.14 mmol) in toluene (3 mL) was added dropwise at −78° C. After stirring at the same temperature for 1 h, MeMgBr (5.23 mL, 15.7 mmol, 3M in ethyl ether) was added dropwise at −78° C. The resulting solution was stirred at −78° C. to −50° C. for 3 h. TLC (PE/EtOAc=1/1) showed the reaction was complete. The reaction was quenched by saturated aqueous $NH_4Cl$ (200 mL) at −78° C. The resulting mixture was filtered through a celite pad and the pad was washed with EtOAc (100 mL). The combined organic layer was separated, washed with brine (100 mL×2) and concentrated in vacuum. The crude product was purified by a silica column chromatography (petroleum ether/ethyl acetate=4/1) to afford compound C21 (1 g, 95%) as a pale yellow oil.

Step 4. Preparation of Compound C22. To a solution of $PPh_3EtBr$ (42.17 g, 113.6 mmol) in THF (40 mL) was added a solution of t-BuOK (12.75 g, 113.6 mmol) in THF (40 mL) at 0° C. After stirring at 60° C. for 1 h, a solution of compound C21 (7.6 g, 22.72 mmol) in THF (40 mL) was added dropwise at 60° C. Then the reaction mixture was stirred at 60° C. for 8 h. TLC (PE/EtOAc=3/1) showed the starting material was also remained. To a solution of $PPh_3EtBr$ (42.17 g, 113.6 mmol) in THF (40 mL) was added a solution of t-BuOK (12.75 g, 113.6 mmol) in THF (40 mL) at 0° C. After stirring at 60° C. for 1 h. The solution was added to the reaction mixture. Then the reaction mixture was stirred at 60° C. for 8 h. TLC (PE/EA=3/1) showed the starting material was also remained and the reaction was nearly unchanged. The reaction mixture was filtered and the filtrate was concentrated in vacuum to remove most of the solvent. The residue was partitioned between EtOAc (300 mL) and water (100 mL×3). The organic layer was washed with brine (100 mL), dried over $Na_2SO_4$ and concentrated in vacuum. The crude product was purified by silica column (PE:EA=5:1) to give compound C22 (4.0 g, 50.8%) as a pale yellow oil. $^1$H NMR (400 MHz, $CDCl_3$) δ 5.15-5.09 (m, 1H), 3.58 (d, J=9.2 Hz, 1H), 3.49 (s, 1H), 3.33 (s, 3H), 3.20 (d, J=8.8 Hz, 1H), 2.40-1.10 (m, 28H), 0.85 (s, 3H).

Step 5. Preparation of Compound C9. To a solution of compound C22 (2.5 g, 7.21 mmol) in THF (30 mL) was added dropwise a solution of $BH_3$-$Me_2S$ (7.21 mL, 32.88 mmol) at 0° C. The solution was stirred at 25° C. for 3 h. TLC (PE/EtOAc=1/1) showed the reaction was complete. After cooling to 0° C., a solution of NaOH (27.5 mL, 3M) was added very slowly. After the addition was complete, $H_2O_2$ (15 mL, 30%) was added slowly and the inner temperature was maintained below 10° C. The resulting solution was stirred at room temperature for 2 h. The resulting solution was extracted with EtOAc (100 mL×3). The combined organic solution was washed with saturated aqueous $Na_2S_2O_3$ (100 mL), brine (100 mL), dried over $Na_2SO_4$ and concentrated in vacuum to give the crude product compound C23 (2.5 g, 95.15%) as a white solid. The crude product was used for the next step without further purification.

Example 18. General Procedure E: Preparation of A/B-Cis Scaffold C-21 Analogs

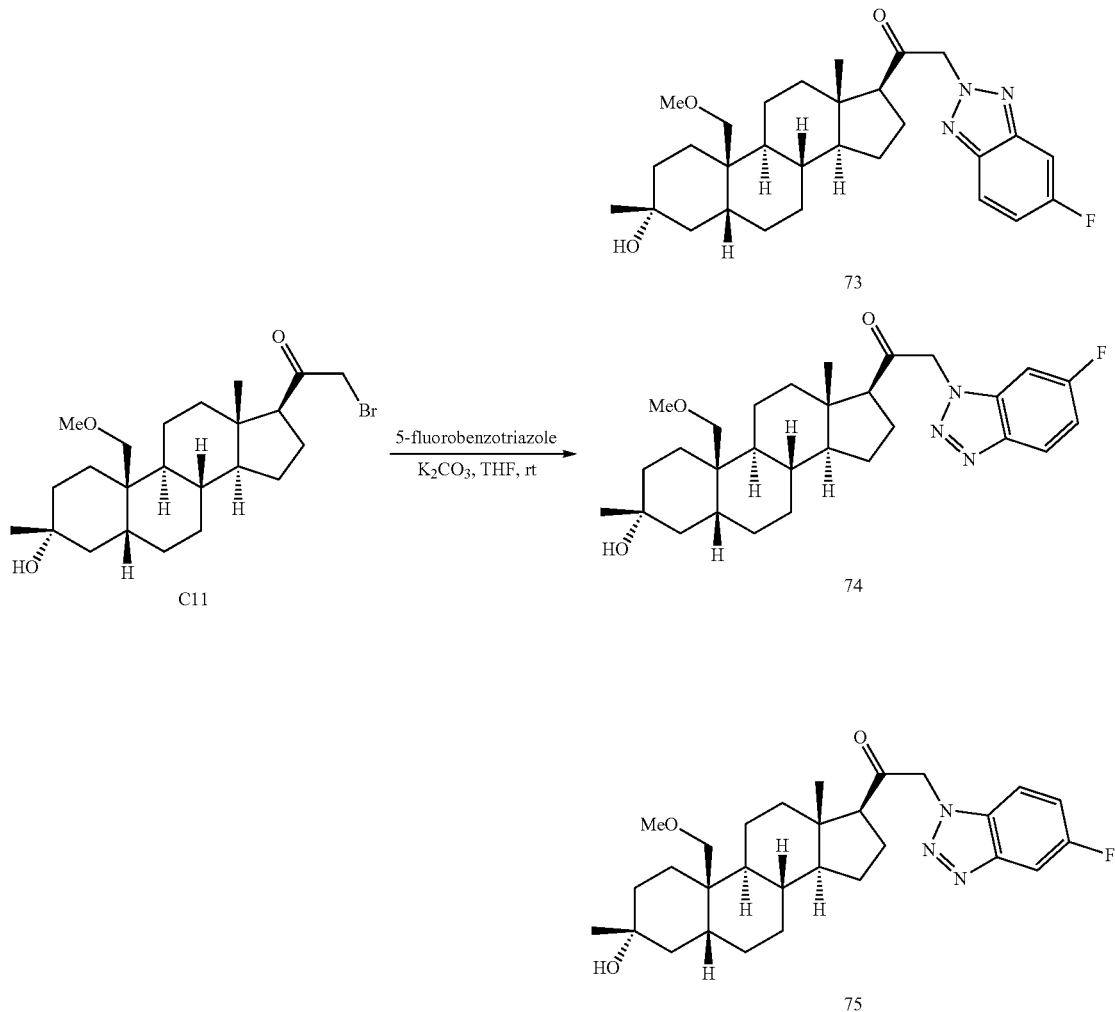

Preparation of compounds 73, 74, and 75. 5-Fluoro-1H-benzo[d][1,2,3]triazole (112 mg, 0.82 mmol) and potassium carbonate (373 mg, 2.7 mmol) were added to a solution of compound C11 (120 mg, 0.27 mmol) in anhydrous tetrahydrofuran (12 mL) at room temperature under nitrogen and the mixture was stirred for 16 h, at which point TLC analysis of the mixture (2:1 hexanes/ethyl acetate) indicated completion of the reaction. The mixture was diluted with water (80 mL) and extracted with ethyl acetate (3×80 mL). The combined organic extracts were washed with saturated aqueous sodium chloride solution (2×25 mL), dried with sodium sulfate and filtered. The solvents were removed under reduced pressure and the residue was semi-purified by column chromatography on silica gel, eluting with hexanes/ethyl acetate (3:1), to provide a mixture of the three regioisomers. The residue was further purified by reverse phase preparative HPLC to provide 73 as a white solid (44 mg, 33%): mp 82-84° C.; 1H NMR (500 MHz, CDCl$_3$) δ 7.86 (dd, J=9.0, 4.5 Hz, 1H), 7.46 (dd, J=9.0, 2.5 Hz, 1H), 7.20 (ddd, J=9.0, 9.0, 2.0 Hz, 1H), 5.50 (d, $J_{AB}$=17.5 Hz, 1H), 5.46 (d, $J_{AB}$=17.0 Hz, 1H), 3.54 (d, J=9.0 Hz, 1H), 3.34 (s, 3H), 3.21 (d, J=9.0 Hz, 1H), 2.64 (t, J=9.0 Hz, 1H), 2.27-2.18 (m, 1H), 2.18-2.11 (m, 1H), 1.96-1.88 (m, 2H), 1.83-1.40 (m, 12H), 1.39-1.10 (m, 10H), 0.73 (s, 3H) ppm; ESI MS m/z 496 [M−H].

Further elution provided 75 as a white solid (25 mg, 18%): mp 205-207° C.; $^1$H NMR (500 MHz, CDCl$_3$) δ 7.72-7.68 (m, 1H), 7.31-7.27 (m, 2H), 5.43 (d, $J_{AB}$=18.0 Hz, 1H), 5.36 (d, $J_{AB}$=18.0 Hz, 1H), 3.54 (d, J=9.0 Hz, 1H), 3.34 (s, 3H), 3.23 (d, J=9.0 Hz, 1H), 2.70 (t, J=9.0 Hz, 1H), 2.27-2.18 (m, 1H), 2.18-2.12 (m, 1H), 1.97-1.88 (m, 2H), 1.84-1.72 (m, 3H), 1.70-1.58 (m, 3H), 1.57-1.43 (m, 6H), 1.40-1.12 (m, 10H), 0.71 (s, 3H) ppm; ESI MS m/z 498 [M+H]$^+$.

Further elution provided 74 as an off-white solid (30 mg, 22%): mp 195-197° C.; $^1$H NMR (500 MHz, CDCl$_3$) δ 8.04 (dd, J=9.0, 4.5 Hz, 1H), 7.15 (dt, J=9.0, 2.5 Hz, 1H), 6.97 (dd, J=7.5, 2.0 Hz, 1H), 5.40 (d, $J_{AB}$=18.0 Hz, 1H), 5.33 (d, $J_{AB}$=18.0 Hz, 1H), 3.54 (d, J=9.0 Hz, 1H), 3.34 (s, 3H), 3.22 (d, J=9.0 Hz, 1H), 2.70 (t, J=9.0 Hz, 1H), 2.27-2.18 (m, 1H), 2.18-2.12 (m, 1H), 1.97-1.89 (m, 2H), 1.84-1.72 (m, 3H), 1.71-1.57 (m, 3H), 1.57-1.42 (m, 6H), 1.40-1.12 (m, 10H), 0.72 (s, 3H) ppm; ESI MS m/z 498 [M+H]$^+$.

Example 19. Preparation of Compound 27

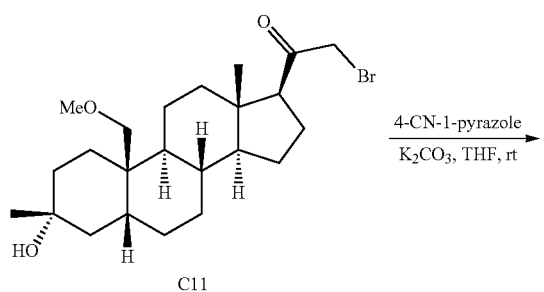

Prepared according General Procedure E, Step 2 from compound C11 (60 mg, 0.14 mmol) and 1H-pyrazole-4-carbonitrile (63 mg, 0.67 mmol), with purification by column chromatography on silica gel to provide compound 27 as an off-white solid (27.3 mg, 44%): mp 176-178° C.; $^1$HNMR (300 MHz, CDCl$_3$) δ 7.83 (d, J=12.3 Hz, 2H), 4.95 (q, J=18.3 Hz, 2H), 3.53 (d, J=9.0 Hz, 1H), 3.33 (s, 3H), 3.22 (d, J=9.0 Hz, 1H), 2.59 (t, J=9.3 Hz, 1H), 2.26-1.35 (m, 17H), 1.31-1.08 (m, 9H), 0.66 (s, 3H) ppm; ESI MS m/z 437 [M+H−H$_2$O]$^+$.

Example 20. Preparation of Compound 28

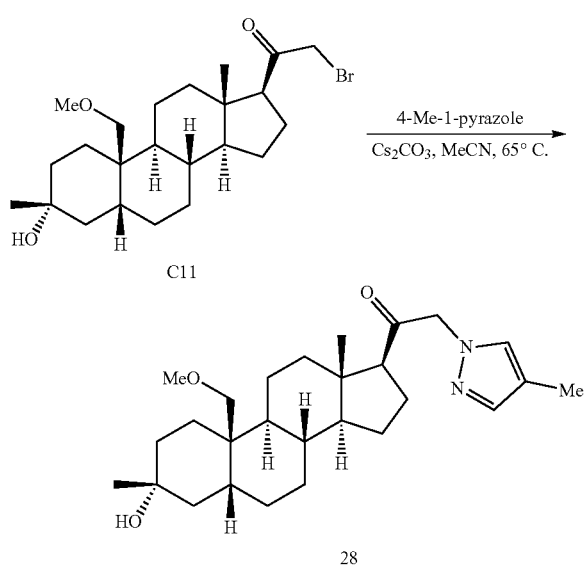

Prepared according General Procedure E, Step 2 from compound C11 (80 mg, 0.18 mmol) and 4-methyl-1H-pyrazole (45 mg, 0.54 mmol) with the substitution of cesium carbonate (177 mg, 0.54 mmol) in anhydrous acetonitrile (6 mL) at 65° C., with purification by column chromatography on silica gel to provide compound 28 as a white solid (58 mg, 73%): mp 158-160° C.; $^1$H NMR (500 MHz, CDCl$_3$) δ 7.34 (s, 1H), 7.16 (s, 1H), 4.86 (d, J$_{AB}$=17.5 Hz, 1H), 4.78 (d, J$_{AB}$=18.0 Hz, 1H), 3.54 (d, J=9.0 Hz, 1H), 3.32 (s, 3H), 3.19 (d, J=9.0 Hz, 1H), 2.54 (t, J=9.5 Hz, 1H), 2.23-2.13 (m, 1H), 2.09 (s, 3H), 2.07-2.02 (m, 1H), 1.97-1.87 (m, 2H), 1.80-1.35 (m, 12H), 1.33-1.10 (m, 10H), 0.66 (s, 3H) ppm; ESI MS m/z 443 [M+H]$^+$.

Example 21. Preparation of Compounds 29 and 30

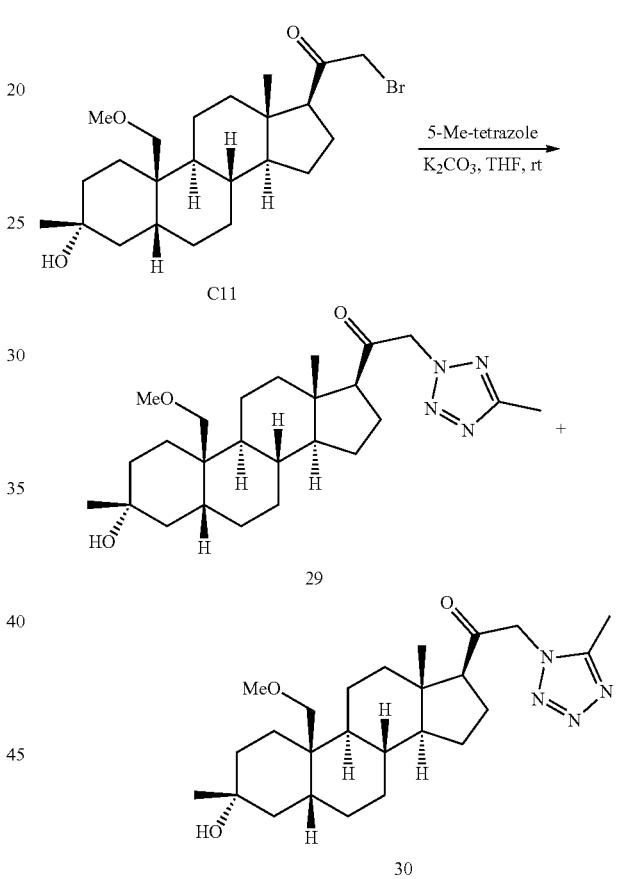

Prepared according General Procedure E, Step 2 from compound C11 (100 mg, 0.23 mmol) and 5-methyltetrazole (95 mg, 1.13 mmol), with semi-purification by column chromatography on silica gel followed by reverse phase preparative HPLC to provide 29 as an off-white solid (12.2 mg, 12%): mp 90-92° C.; $^1$HNMR (300 MHz, CDCl$_3$) δ 5.09 (q, J=18.0 Hz, 2H), 3.53 (d, J=9.0 Hz, 1H), 3.33 (s, 3H), 3.22 (d, J=9.0 Hz, 1H), 2.65 (t, J=9.0 Hz, 1H), 2.47 (s, 3H), 2.25-1.58 (m, 9H), 1.55-1.14 (m, 17H), 0.67 (s, 3H) ppm; ESI MS m/z 428 [M+H−H$_2$O]$^+$.

Further elution provided 30 as an off-white solid (13.4 mg, 13%): mp 70-72° C.; $^1$HNMR (300 MHz, CDCl$_3$) δ 5.34 (s, 2H), 3.54 (d, J=9.0 Hz, 1H), 3.33 (s, 3H), 3.20 (d, J=9.0 Hz, 1H), 2.64-2.57 (m, 4H), 2.43-1.91 (m, 6H), 1.81-1.10 (m, 20H), 0.70 (s, 3H) ppm; ESI MS m/z 428 [M+H−H$_2$O]$^+$.

Example 22. Preparation of Compounds 31 and 32

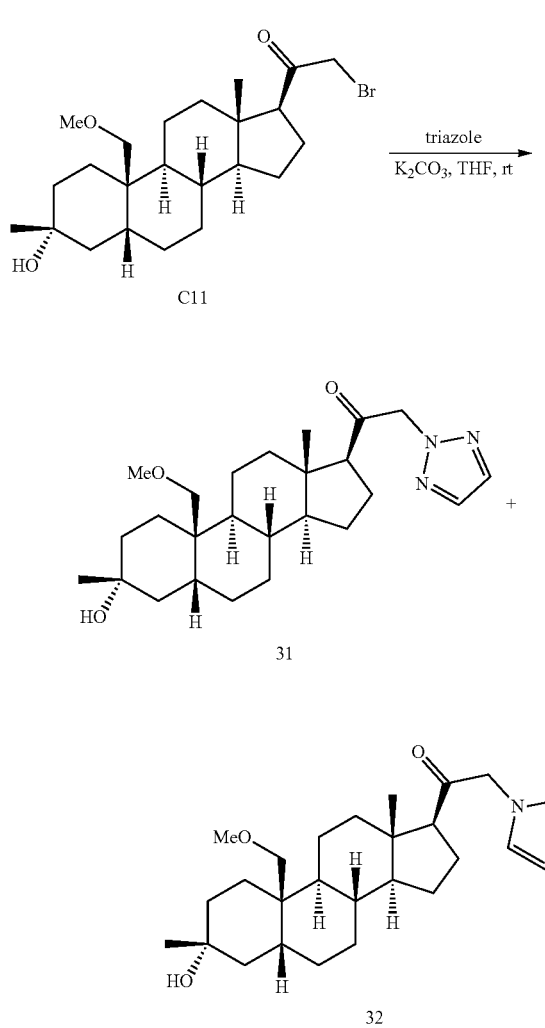

Prepared according General Procedure E, Step 2 from compound C11 (82 mg, 0.18 mmol) and 1H-1,2,3-triazole (75 mg, 1.08 mmol), with semi-purification by column chromatography on silica gel followed by reverse phase preparative HPLC to provide 32 as an off-white solid (17 mg, 22%): mp 80-83° C.; $^1$H NMR (500 MHz, CDCl$_3$) δ 7.79 (s, 1H), 7.66 (s, 1H), 5.26 (d, J$_{AB}$=18.0 Hz, 1H), 5.13 (d, J$_{AB}$=18.0 Hz, 1H), 3.53 (d, J=9.0 Hz, 1H), 3.33 (s, 3H), 3.20 (d, J=9.0 Hz, 1H), 2.64 (t, J=9.0 Hz, 1H), 2.26-2.16 (m, 1H), 2.12-2.06 (m, 1H), 1.96-1.70 (m, 6H), 1.66-1.42 (m, 6H), 1.35-1.10 (m, 11H), 0.90-0.83 (m, 1H), 0.66 (s, 3H) ppm; ESI MS m/z 430 [M+H]$^+$.

Further elution provided 31 as an off-white solid (12 mg, 16%): mp 71-74° C.; $^1$H NMR (500 MHz, CDCl$_3$) δ 7.68 (s, 2H), 5.24 (d, J$_{AB}$=17.5 Hz, 1H), 5.21 (d, J$_{AB}$=17.5 Hz, 1H), 3.54 (d, J=9.0 Hz, 1H), 3.33 (s, 3H), 3.19 (d, J=9.0 Hz, 1H), 2.56 (t, J=9.0 Hz, 1H), 2.24-2.15 (m, 1H), 2.11-2.05 (m, 1H), 1.96-1.88 (m, 2H), 1.82-1.68 (m, 3H), 1.66-1.40 (m, 6H), 1.40-1.09 (m, 11H), 0.90-0.83 (m, 1H), 0.70 (s, 3H) ppm; ESI MS m/z 430 [M+H]$^+$.

Example 23. Preparation of Compound 33

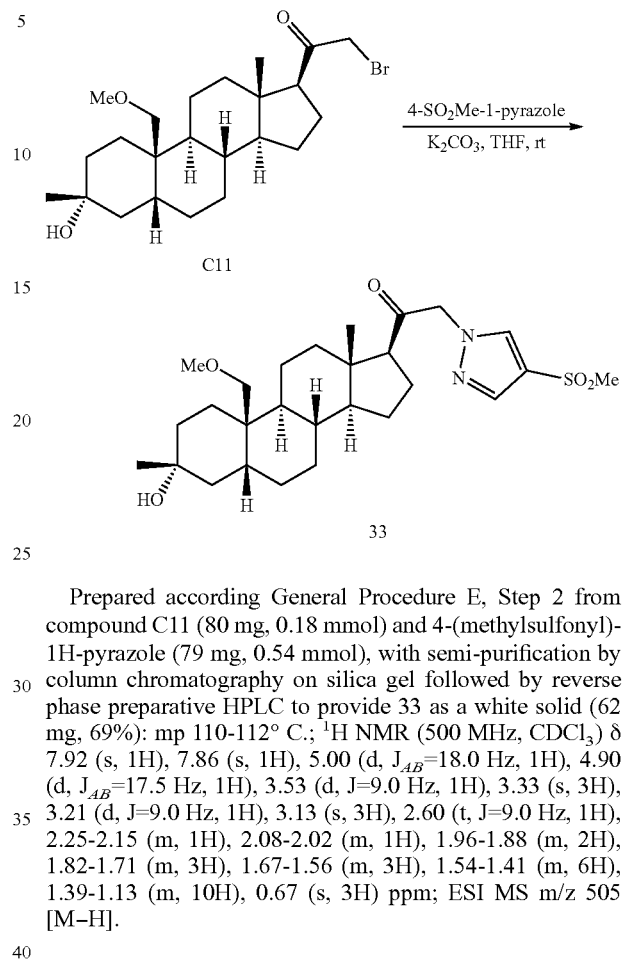

Prepared according General Procedure E, Step 2 from compound C11 (80 mg, 0.18 mmol) and 4-(methylsulfonyl)-1H-pyrazole (79 mg, 0.54 mmol), with semi-purification by column chromatography on silica gel followed by reverse phase preparative HPLC to provide 33 as a white solid (62 mg, 69%): mp 110-112° C.; $^1$H NMR (500 MHz, CDCl$_3$) δ 7.92 (s, 1H), 7.86 (s, 1H), 5.00 (d, J$_{AB}$=18.0 Hz, 1H), 4.90 (d, J$_{AB}$=17.5 Hz, 1H), 3.53 (d, J=9.0 Hz, 1H), 3.33 (s, 3H), 3.21 (d, J=9.0 Hz, 1H), 3.13 (s, 3H), 2.60 (t, J=9.0 Hz, 1H), 2.25-2.15 (m, 1H), 2.08-2.02 (m, 1H), 1.96-1.88 (m, 2H), 1.82-1.71 (m, 3H), 1.67-1.56 (m, 3H), 1.54-1.41 (m, 6H), 1.39-1.13 (m, 10H), 0.67 (s, 3H) ppm; ESI MS m/z 505 [M−H].

Example 24. Preparation of Compound 34

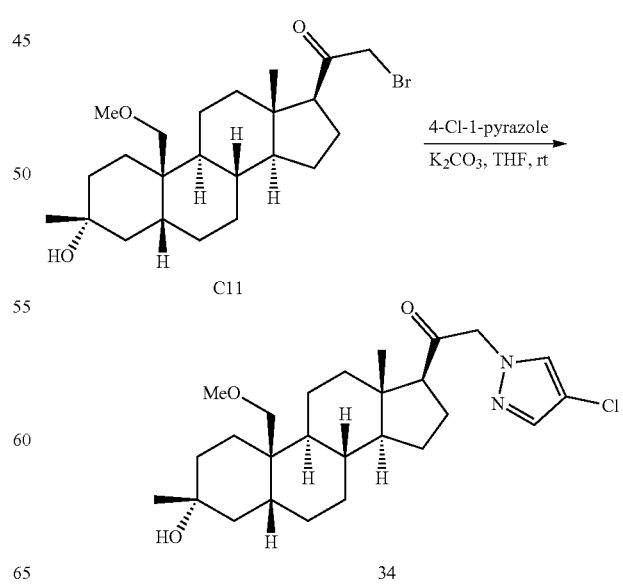

Prepared according General Procedure E, Step 2 from compound C11 (80 mg, 0.18 mmol) and 4-chloro-1H-pyrazole (45 mg, 0.54 mmol), with purification by column chromatography on silica gel to provide compound 34 as a white solid (58 mg, 70%): mp 163-165° C.; $^1$H NMR (500 MHz, CDCl$_3$) δ 7.45 (s, 1H), 7.41 (s, 1H), 4.99 (d, J$_{AB}$=17.5 Hz, 1H), 4.80 (d, J$_{AB}$=17.5 Hz, 1H), 3.53 (d, J=9.0 Hz, 1H), 3.33 (s, 3H), 3.21 (d, J=9.0 Hz, 1H), 2.56 (t, J=9.0 Hz, 1H), 2.24-2.14 (m, 1H), 2.07-2.01 (m, 1H), 1.96-1.88 (m, 2H), 1.80-1.69 (m, 3H), 1.66-1.35 (m, 9H), 1.34-1.10 (m, 10H), 0.66 (s, 3H) ppm; ESI MS m/z 463 [M+H]$^+$.

Example 25. Preparation of Compound 38

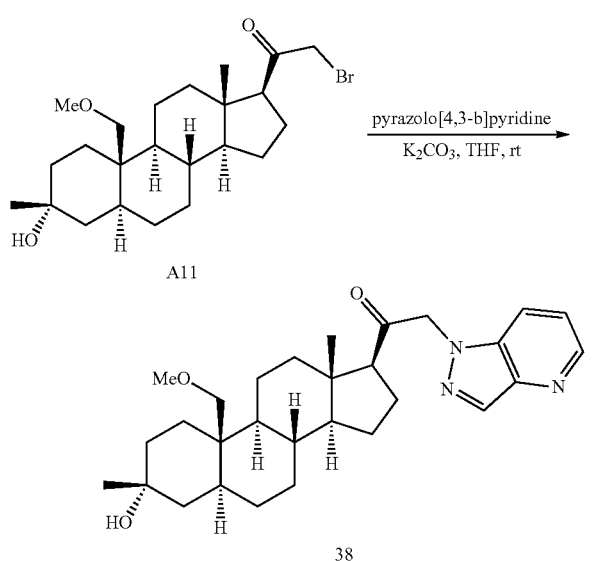

Prepared according General Procedure B from compound A11 (31 mg, 0.071 mmol) and 2H-pyrazolo[4,3-b]pyridine (168 mg, 1.41 mmol), with purification by reverse phase preparative HPLC to provide 38 as a white solid (8.7 mg, 25%): mp 153-154° C.; $^1$HNMR (500 MHz, CDCl$_3$) δ 8.60 (d, J=3.5 Hz, 1H), 8.28 (s, 1H), 7.59 (d, J=8.5 Hz, 1H), 7.29 (dd, J=8.5, 4.5 Hz, 1H), 5.16 (dd, J=29.0, 18.0 Hz, 2H), 3.48 (d, J=10.0 Hz, 1H), 3.38 (d, J=10.0 Hz, 1H), 3.30 (s, 3H), 2.66 (t, J=9.0 Hz, 1H), 2.22-2.00 (m, 1H), 2.13-2.11 (m, 1H), 2.10-2.08 (m, 1H), 1.79-1.40 (m, 11H), 1.33-1.11 (m, 10H), 0.99-0.97 (m, 1H), 0.88-0.86 (m, 1H), 0.73 (s, 3H) ppm; ESI MS m/z 480 [M+H]$^+$.

Example 26. Preparation of Compounds 39 and 40

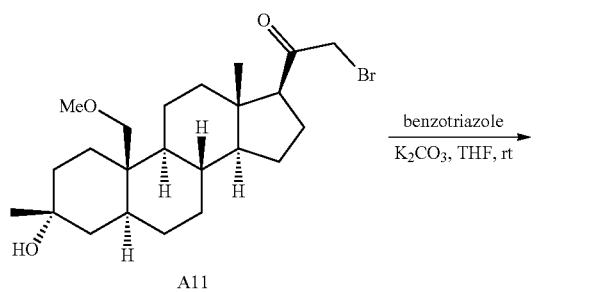

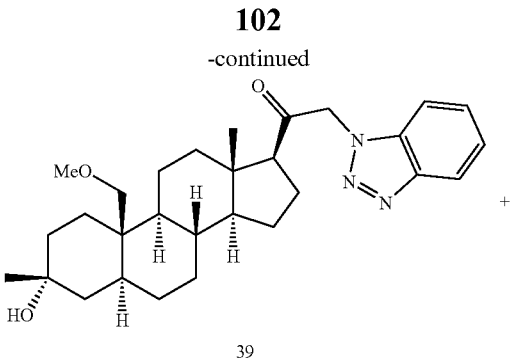

Prepared according General Procedure B from compound A11 (21 mg, 0.047 mmol) and 1H-benzotriazole (33 mg, 0.28 mmol), with semi-purification by column chromatography on silica gel followed by reverse phase preparative HPLC to provide 39 as an off-white solid (13 mg, 58%): mp 78-80° C.; $^1$H NMR (500 MHz, CDCl$_3$) δ 8.11-8.07 (m, 1H), 7.51-7.46 (m, 1H), 7.40-7.36 (m, 1H), 7.33 (d, J=7.5, 1H), 5.41 (s, 2H), 3.48 (d, J=10.0 Hz, 1H), 3.38 (d, J=10.0 Hz, 1H), 3.30 (s, 3H), 2.71 (t, J=9.0 Hz, 1H), 2.27-2.18 (m, 1H), 2.17-2.10 (m, 1H), 2.08-2.02 (m, 1H), 1.82-1.68 (m, 4H), 1.67-1.42 (m, 7H), 1.35-1.09 (m, 10H), 1.05-0.95 (m, 1H), 0.91-0.83 (m, 1H), 0.76 (s, 3H) ppm; ESI MS m/z 480 [M+H]$^+$.

Further elution provided 40 as an off-white solid (7 mg, 30%): mp 70-72° C.; $^1$H NMR (500 MHz, CDCl$_3$) δ 7.90-7.85 (m, 2H), 7.41-7.36 (m, 2H), 5.54 (d, J$_{AB}$=17.0 Hz, 1H), 5.48 (d, J$_{AB}$=17.0 Hz, 1H), 3.48 (d, J=10.0 Hz, 1H), 3.38 (d, J=10.0 Hz, 1H), 3.290 (s, 3H), 2.63 (t, J=9.0 Hz, 1H), 2.28-2.20 (m, 1H), 2.17-2.12 (m, 1H), 2.07-2.01 (m, 1H), 1.80-1.68 (m, 4H), 1.67-1.46 (m, 6H), 1.45-1.36 (m, 1H), 1.35-1.08 (m, 10H), 1.04-0.94 (m, 1H), 0.90-0.82 (m, 1H), 0.77 (s, 3H) ppm; ESI MS m/z 480 [M+H]$^+$.

Example 27. Preparation of Compounds 41, 42, and 43

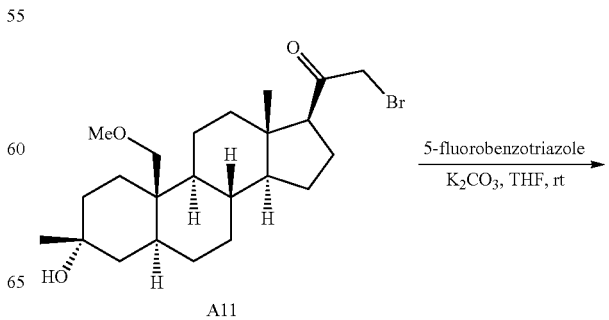

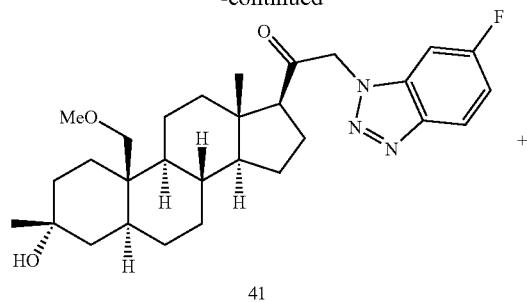

41

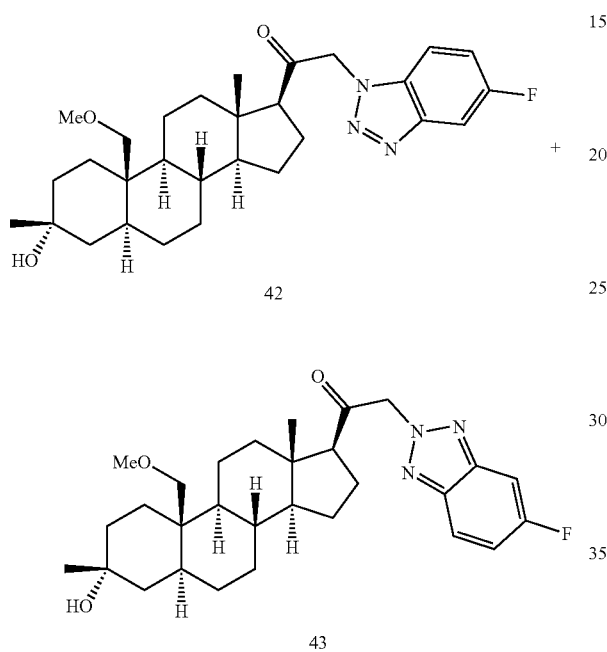

42

43

Prepared according General Procedure B from compound A11 (100 mg, 0.23 mmol) and 5-fluorobenzotriazole (124 mg, 0.91 mmol), with purification by reverse phase preparative HPLC to provide 43 as an off-white solid (39.2 mg, 40%): mp 55-60° C.; $^1$HNMR (300 MHz, CDCl$_3$) δ 7.86 (dd, J=4.8, 4.5 Hz, 1H), 7.46 (dd, J=9.0, 2.1 Hz, 1H), 7.23-7.16 (m, 1H), 5.49 (q, J=18.0 Hz, 2H), 3.48 (d, J=9.9 Hz, 1H), 3.38 (d, J=9.9 Hz, 1H), 3.37 (s, 3H), 2.66 (t, J=8.7 Hz, 1H), 2.29-2.01 (m, 3H), 1.79-1.50 (m, 15H), 1.45-1.05 (m, 6H), 1.01-0.82 (m, 2H), 0.76 (s, 3H) ppm; ESI MS m/z 498 [M+H]$^+$.

Further elution provided 41 as an off-white solid (21.2 mg, 34%): mp 65-70° C.; $^1$HNMR (300 MHz, CDCl$_3$) δ 8.03 (dd, J=9.0, 4.5 Hz, 1H), 7.18-7.12 (m, 1H), 6.99-6.58 (m, 1H), 5.37 (q, J=18.3 Hz, 2H), 3.47 (d, J=10.2 Hz, 1H), 3.38 (d, J=10.2 Hz, 1H), 3.31 (s, 3H), 2.72 (t, J=9.0 Hz, 1H), 2.28-2.02 (m, 3H), 1.79-1.33 (m, 13H), 1.29-0.84 (m, 10H), 0.75 (s, 3H) ppm; ESI MS ml: 498 [M+H]$^+$.

Further elution provided 42 as an off-white solid (21.2 mg, 34%): mp 60-65° C.; $^1$HNMR (300 MHz, CDCl$_3$) δ 7.73 (d, J=9.9 Hz, 1H), 7.35-7.21 (m, 2H), 5.40 (q, J=18.3 Hz, 2H), 3.49 (d, J=9.9 Hz, 1H), 3.37 (d, J=10.2 Hz, 1H), 3.30 (s, 3H), 2.72 (t, J=9.0 Hz, 1H), 2.28-2.03 (m, 3H), 1.82-1.46 (m, 9H), 1.37-1.16 (m, 12H), 1.06-0.84 (m, 2H), 0.74 (s, 3H) ppm; ESI MS m/z 498 [M+H]$^+$.

Example 28. Preparation of Compounds 44 and 45

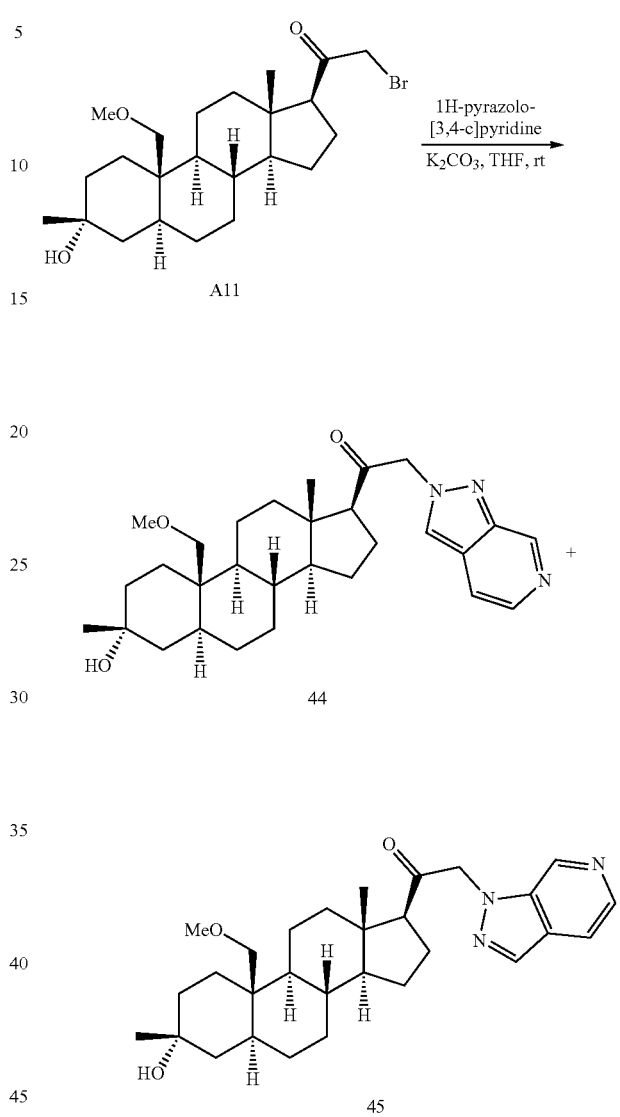

Prepared according General Procedure B from compound A11 (50 mg, 0.11 mmol) and 1H-pyrazolo[3,4-c]pyridine (67 mg, 0.57 mmol), with purification by reverse phase preparative HPLC to provide 44 as an off-white solid (7.5 mg, 14%): mp 160-162° C.; $^1$HNMR (300 MHz, CDCl$_3$) δ 9.26 (s, 1H), 8.17 (d, J=6.0 Hz, 1H), 7.97 (d, J=0.9 Hz, 1H), 7.53 (dd, J=6.0, 1.2 Hz, 1H), 5.27 (q, J=18.0 Hz, 2H), 3.46 (d, J=9.9 Hz, 2H), 3.37 (d, J=10.2 Hz, 2H), 2.68 (t, J=9.3 Hz, 1H), 2.30-2.19 (m, 1H), 1.18-2.01 (m, 3H), 1.79-1.64 (m, 5H), 1.61-1.45 (m, 7H), 1.39-1.08 (m, 8H), 1.05-0.84 (m, 3H), 0.74 (s, 3H) ppm; ESI MS m/z 480 [M+H]$^+$.

Further elution provided 45 as an off-white solid (14.2 mg, 26%): mp 92-94° C.; $^1$H NMR (300 MHz, CDCl$_3$) δ 8.80 (s, 1H), 8.34 (d, J=5.4 Hz, 1H), 8.09 (d, J=0.6 Hz, 1H), 7.64 (dd, J=5.7, 1.2 Hz, 1H), 5.25 (q, J=18.0 Hz, 2H), 3.48 (d, J=9.9 Hz, 2H), 3.38 (d, J=9.9 Hz, 2H), 3.31 (s, 3H), 2.70 (t, J=8.7 Hz, 1H), 2.27-1.98 (m, 3H), 1.81-1.44 (m, 10H), 1.34-1.12 (m, 9H), 1.10-0.81 (m, 2H), 0.74 (s, 3H) ppm; ESI MS m/z 480 [M+H]$^+$.

Example 29. Preparation of Compound 46

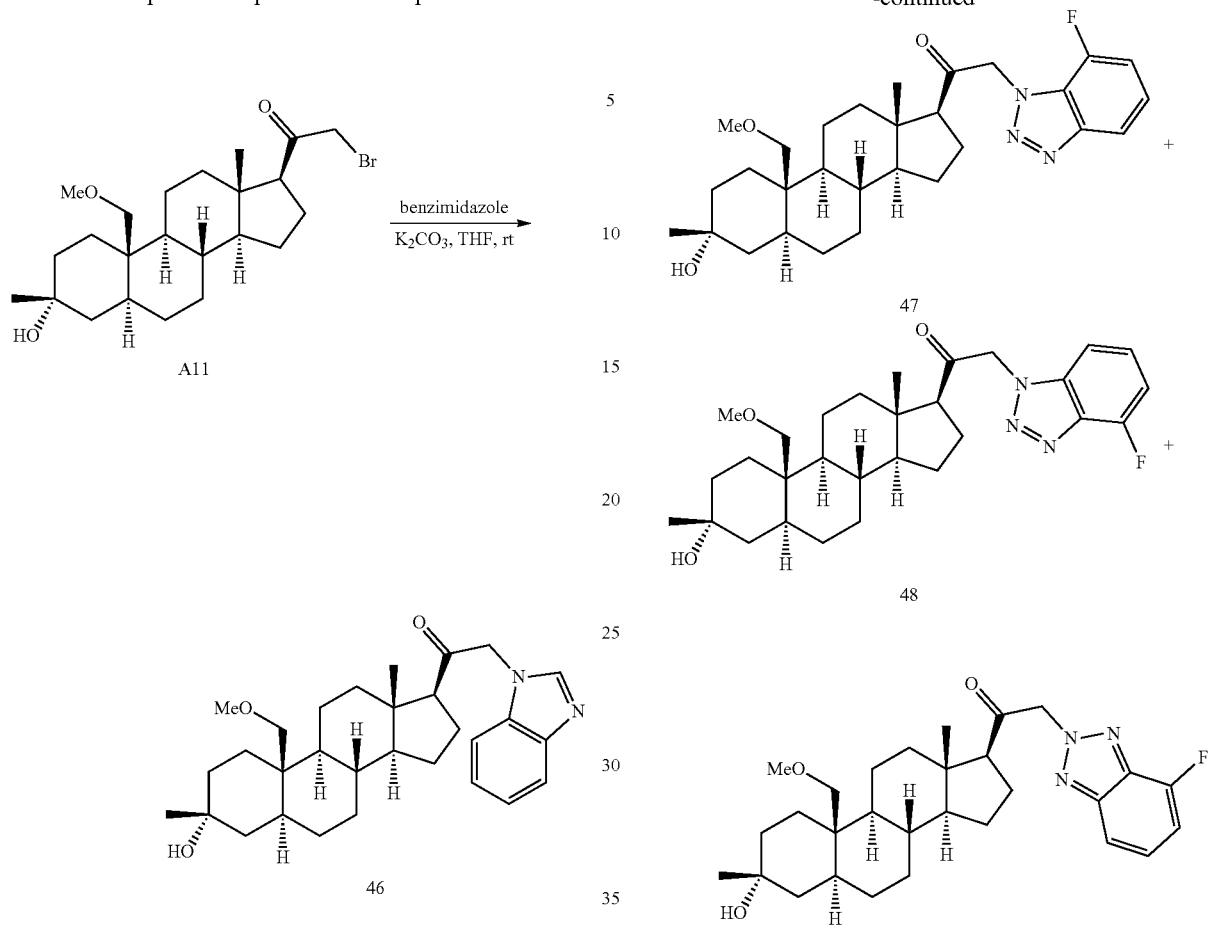

Prepared according General Procedure B from compound A11 (50 mg, 0.114 mmol) and benzimidazole (268 mg, 2.3 mmol), with purification by reverse phase preparative HPLC to provide 46 as a white solid (36.5 mg, 67%): mp 104-105° C.; $^1$HNMR (500 MHz, CDCl$_3$) δ 7.99 (s, 1H), 7.86-7.82 (m, 1H), 7.33-7.29 (m, 2H), 7.20-7.18 (m, 1H), 4.93 (dd, J=24.0, 18.5 Hz, 2H), 3.49 (d, J=10.0 Hz, 1H), 3.38 (d, J=10.0 Hz, 1H), 3.30 (s, 3H), 2.66 (t, J=9.0 Hz, 1H), 2.24-2.22 (m, 1H), 2.07-2.05 (m, 1H), 1.80-1.42 (m, 11H), 1.34-1.11 (m, 11H), 0.99-0.98 (m, 1H), 0.88-0.86 (m, 1H), 0.73 (s, 3H) ppm; ESI MS m/z 479 [M+H]$^+$.

Example 30. Preparation of Compounds 47, 48, and 49

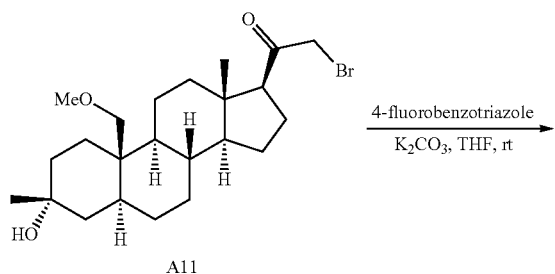

Prepared according General Procedure B from compound A11 (100 mg, 0.227 mmol) and 4-fluorobenzotriazole (311 mg, 2.27 mmol), with purification by reverse phase preparative HPLC to provide 49 as a white solid (22.5 mg, 20%): mp 125-126° C.; $^1$HNMR (500 MHz, CDCl$_3$) δ 7.67 (d, J=8.5 Hz, 1H), 7.32-7.30 (m, 1H), 7.03 (dd, J=10.5, 7.5 Hz, 1H), 5.54 (dd, J=28.0, 17.0 Hz, 2H), 3.48 (d, J=10.0 Hz, 1H), 3.38 (d, J=10.0 Hz, 1H), 3.30 (s, 3H), 2.67 (t, J=9.0 Hz, 1H), 2.24-2.22 (m, 1H), 2.15-2.13 (m, 1H), 2.05-2.03 (m, 1H), 1.78-1.50 (m, 9H), 1.42-1.40 (m, 1H), 1.34-1.12 (m, 11H), 0.99-0.98 (m, 1H), 0.87-0.86 (m, 1H), 0.77 (s, 3H) ppm; ESI MS m/z 498 [M+H]$^+$.

Further elution provided 47 as a white solid (7.3 mg, 6%): mp 83-84° C.; $^1$HNMR (500 MHz, CDCl$_3$) δ 7.86 (d, J=8.0 Hz, 1H), 7.29-7.27 (m, 1H), 7.13 (dd, J=10.5, 7.5 Hz, 1H), 5.54 (s, 2H), 3.49 (d, J=10.0 Hz, 1H), 3.38 (d, J=10.0 Hz, 1H), 3.30 (s, 3H), 2.70 (t, J=9.0 Hz, 1H), 2.24-2.22 (m, 1H), 2.15-2.13 (m, 1H), 2.06-2.04 (m, 1H), 1.79-1.73 (m, 4H), 1.63-1.43 (m, 7H), 1.34-1.13 (m, 10H), 1.02-1.00 (m, 1H), 0.89-0.87 (m, 1H), 0.75 (s, 3H) ppm; ESI MS m/z 498 [M+H]$^+$.

Further elution provided 48 as a white solid (26.3 mg, 23%): mp 129-130° C.; $^1$HNMR (500 MHz, CDCl$_3$) δ 7.42 (td, J=8.0, 4.5 Hz, 1H), 7.10 (d, J=8.5 Hz, 1H), 7.04 (dd, J=10.0, 7.5 Hz, 1H), 5.42 (s, 2H), 3.49 (d, J=10.0 Hz, 1H), 3.38 (d, J=10.0 Hz, 1H), 3.30 (s, 3H), 2.70 (t, J=9.0 Hz, 1H), 2.23-2.21 (m, 1H), 2.15-2.13 (m, 1H), 2.06-2.04 (m, 1H), 1.78-1.46 (m, 10H), 1.34-1.12 (m, 11H), 1.01-0.99 (m, 1H), 0.89-0.88 (m, 1H), 0.74 (s, 3H) ppm; ESI MS m/z 498 [M+H]$^+$.

Example 31. Preparation of Compounds 50 and 51

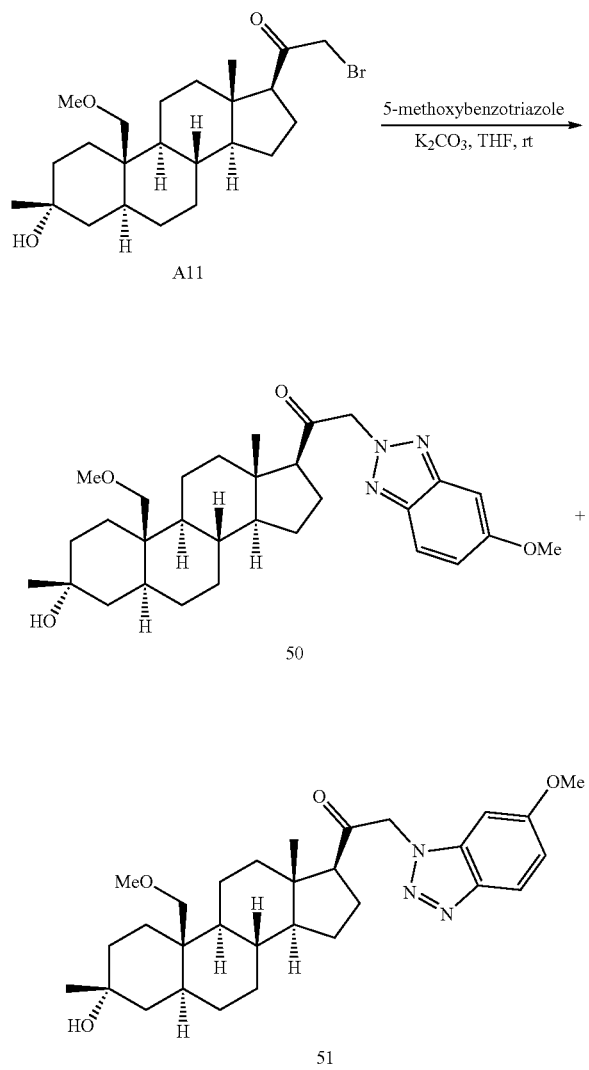

Prepared according General Procedure B from compound A11 (140 mg, 0.32 mmol) and 5-methoxybenzotriazole (132 mg, 0.89 mmol), with purification by reverse phase preparative HPLC to provide 50 as a white solid (12.9 mg, 8%): mp 165-166° C.; $^1$HNMR (500 MHz, CDCl$_3$) δ 7.72 (d, J=10.0 Hz, 1H), 7.07-7.05 (m, 2H), 5.43 (dd, J=29.5, 17.0 Hz, 2H), 3.87 (s, 3H), 3.47 (d, J=10.0 Hz, 1H), 3.38 (d, J=10.0 Hz, 1H), 3.29 (s, 3H), 2.63 (t, J=9.0 Hz, 1H), 2.24-2.22 (m, 1H), 2.14-2.12 (m, 1H), 2.05-2.04 (m, 1H), 1.77-1.69 (m, 4H), 1.62-1.10 (m, 17H), 0.99-0.98 (m, 1H), 0.86-0.84 (m, 1H), 0.76 (s, 3H) ppm; ESI MS m/z 510 [M+H]$^+$. Further elution provided 51 as a white solid (11.8 mg, 7%): mp 106-107° C.; $^1$HNMR (500 MHz, CDCl$_3$) δ 7.93 (d, J=9.0 Hz, 1H), 7.02 (dd, J=9.0, 2.0 Hz, 1H), 6.61 (d, J=2.0 Hz, 1H), 5.33 (d, J=3.5 Hz, 2H), 3.88-3.86 (m, 3H), 3.48 (d, J=10.0 Hz, 1H), 3.38 (d, J=10.0 Hz, 1H), 3.30 (s, 3H), 2.70 (t, J=9.0 Hz, 1H), 2.23-2.21 (m, 1H), 2.15-2.13 (m, 1H), 2.06-2.04 (m, 1H), 1.76-1.70 (m, 4H), 1.64-1.44 (m, 6H), 1.34-1.13 (m, 11H), 0.99-0.98 (m, 1H), 0.89-0.87 (m, 1H), 0.75 (s, 3H) ppm; ESI MS m/z 510 [M+H]$^+$.

Example 32. Preparation of Compounds 52, 53, and 54

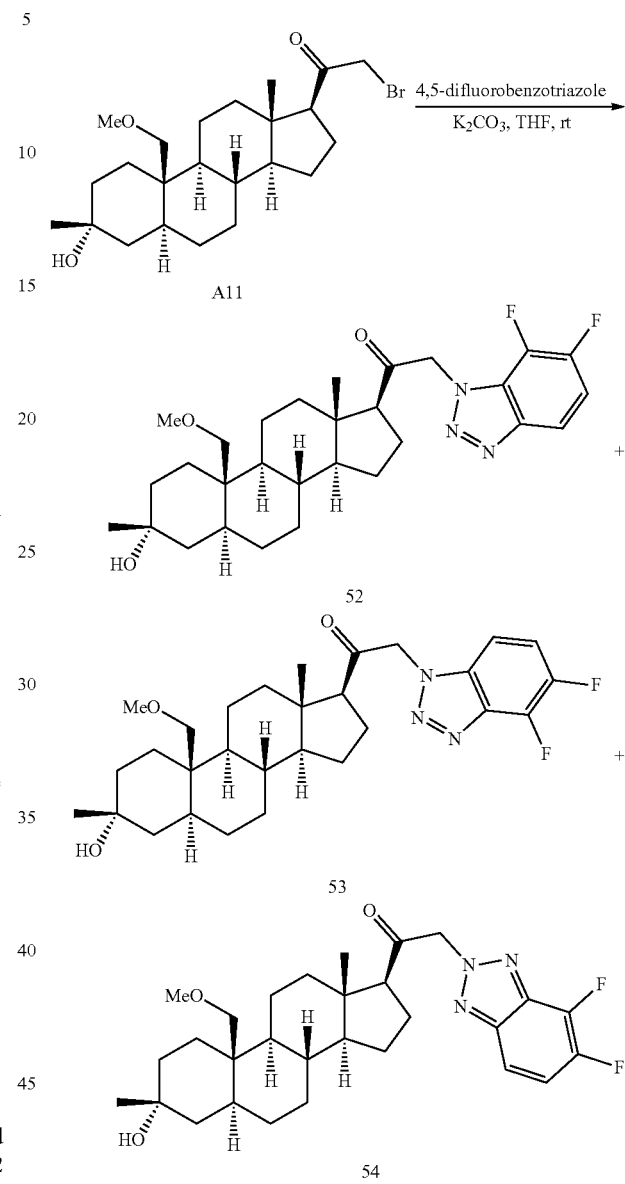

Prepared according General Procedure B from compound A11 (100 mg, 0.23 mmol) and 4,5-difluorobenzotriazole (352 mg, 2.3 mmol), with purification by reverse phase preparative HPLC to provide 54 as a white solid (46.0 mg, 32%): mp 86-87° C.; $^1$HNMR (500 MHz, CDCl$_3$) δ 7.63 (ddd, J=9.0, 3.5, 1.0 Hz, 1H), 7.30-7.28 (m, 1H), 5.53 (dd, J=31.5, 17.0 Hz, 2H), 3.48 (d, J=10.0 Hz, 1H), 3.38 (d, J=10.0 Hz, 1H), 3.30 (s, 3H), 2.65 (t, J=9.0 Hz, 1H), 2.24-2.22 (m, 1H), 2.14-2.12 (m, 1H), 2.06-2.04 (m, 1H), 1.78-1.73 (m, 4H), 1.63-1.41 (m, 7H), 1.34-1.12 (m, 10H), 1.03-1.00 (m, 1H), 0.88-0.86 (m, 1H), 0.77 (s, 3H) ppm; ESI MS m/z 498 [M+H–H$_2$O]$^+$.

Further elution provided 52 as a white solid (19.3 mg, 13%): mp 82-83° C.; $^1$HNMR (500 MHz, CDCl$_3$) δ 7.80 (ddd, J=9.0, 3.5, 1.0 Hz, 1H), 7.23-7.21 (m, 1H), 5.52 (s, 2H), 3.49 (d, J=10.0 Hz, 1H), 3.38 (d, J=10.0 Hz, 1H), 3.30 (s, 3H), 2.70 (t, J=9.0 Hz, 1H), 2.23-2.21 (m, 1H), 2.14-2.12

(m, 1H), 2.07-2.05 (m, 1H), 1.79-1.72 (m, 4H), 1.64-1.44 (m, 7H), 1.35-1.13 (m, 10H), 1.02-1.01 (m, 1H), 0.89-0.88 (m, 1H), 0.75 (s, 3H) ppm; ESI MS m/z 516 [M+H]+.

Further elution provided 53 as a white solid (34.3 mg, 24%): mp 144-145° C.; ¹HNMR (500 MHz, CDCl₃) δ 7.38-7.37 (m, 1H), 7.04 (ddd, J=9.0, 3.0, 1.0 Hz, 1H), 5.41 (dd, J=22.5, 18.0 Hz, 2H), 3.49 (d, J=10.0 Hz, 1H), 3.38 (d, J=10.0 Hz, 1H), 3.30 (s, 3H), 2.71 (t, J=9.0 Hz, 1H), 2.24-7.22 (m, 1H), 2.12.14-2.12 (m, 1H), 2.07-2.05 (m, 1H), 1.78-1.71 (m, 4H), 1.64-1.47 (m, 7H), 1.34-1.13 (m, 10H), 1.02-1.01 (m, 1H), 0.89-0.88 (m, 1H), 0.74 (s, 3H) ppm; ESI MS m/z 516 [M+H]+.

Example 33. Preparation of Compounds 55 and 56

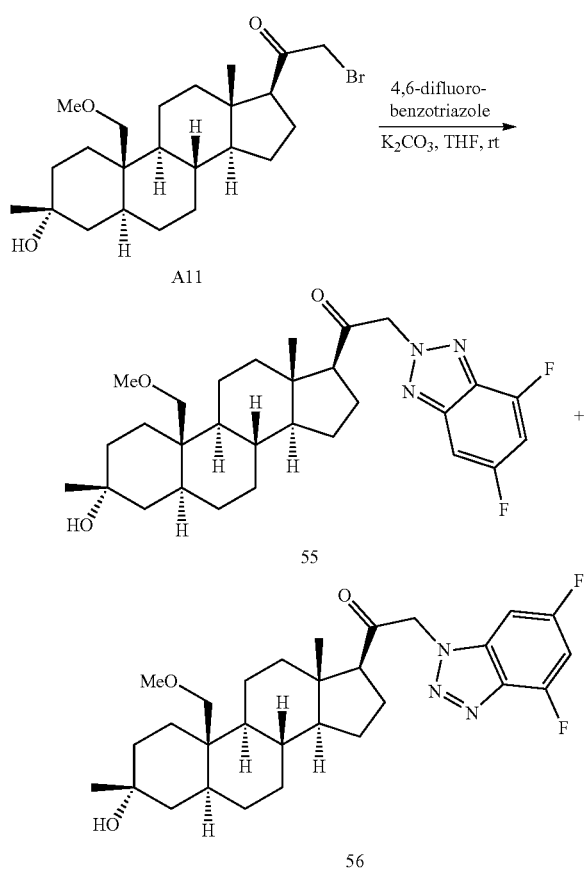

Prepared according General Procedure B from compound A11 (125 mg, 0.28 mmol) and 4,6-difluoro-1H-benzo[d][1,2,3]triazole (219 mg, 1.60 mmol), with semi-purification by column chromatography on silica gel followed by reverse phase preparative HPLC to provide 55 as an off-white solid (28 mg, 19%): mp 182-186° C.; ¹H NMR (300 MHz, CDCl₃) δ 7.30 (dd, J=8.1, 1.5 Hz, 1H), 6.90 (ddd, J=9.9, 9.9, 2.1 Hz, 1H), 5.55 (d, $J_{AB}$=17.1 Hz, 1H), 5.47 (d, $J_{AB}$=17.1 Hz, 1H), 3.48 (d, J=9.9 Hz, 1H), 3.37 (d, J=10.2 Hz, 1H), 3.30 (s, 3H), 2.67 (t, J=8.7 Hz, 1H), 2.30-2.17 (m, 1H), 2.17-2.09 (m, 1H), 2.09-1.99 (m, 1H), 1.83-1.66 (m, 4H), 1.66-1.40 (m, 7H), 1.40-0.81 (m, 12H), 0.76 (s, 3H) ppm; ESI MS m/z 516 [M+H]+.

Further elution provided 56 as an off-white solid (19 mg, 13%): mp 96-100° C.; ¹H NMR (300 MHz, CDCl₃) δ 6.87 (ddd, J=9.6, 9.6, 1.8 Hz, 1H), 6.79 (ddd, J=7.5, 2.1, 0.6 Hz, 1H), 5.41 (d, $J_{AB}$=18.0 Hz, 1H), 5.34 (d, $J_{AB}$=18.3 Hz, 1H), 3.49 (d, J=9.9 Hz, 1H), 3.38 (d, J=9.9 Hz, 1H), 3.31 (s, 3H), 2.72 (t, J=8.7 Hz, 1H), 2.30-2.00 (m, 3H), 1.85-1.41 (m, 11H), 1.38-0.82 (m, 12H), 0.74 (s, 3H) ppm; SI MS m/z 516 [M+H]+.

Example 34. Preparation of Compounds 57 and 58

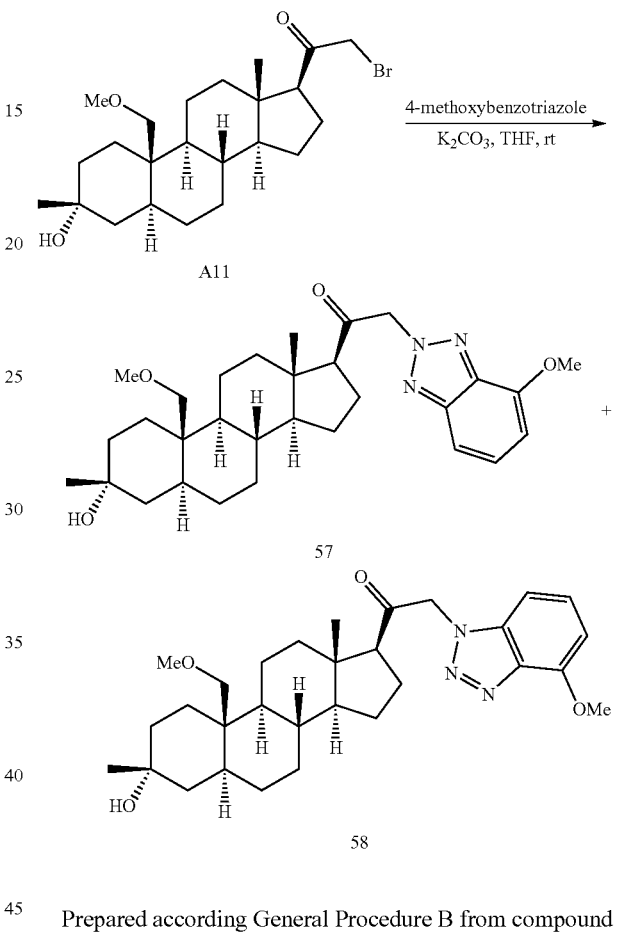

Prepared according General Procedure B from compound A11 (100 mg, 0.23 mmol) and 4-methoxybenzotriazole (675 mg, 4.5 mmol), with purification by reverse phase preparative HPLC to provide 58 as a light brown solid (27 mg, 23%): mp 78-80° C.; ¹H NMR (500 MHz, CDCl₃) δ 7.39 (t, J=8.0 Hz, 1H), 6.86 (d, J=8.1 Hz, 1H), 6.70 (d, J=7.8 Hz, 1H), 5.37 (dd, J=18.0, 2.7 Hz, 2H), 4.12 (s, 3H), 3.48 (d, J=10.0 Hz, 1H), 3.38 (d, J=10.1 Hz, 1H), 3.30 (s, 3H), 2.68 (t, J=9.0 Hz, 1H), 2.24-2.18 (m, 11H), 2.14-2.09 (m, 1H), 2.06-2.02 (m, 1H), 1.76-1.69 (m, 4H), 1.64-1.55 (m, 3H), 1.54-1.37 (m, 4H), 1.36-1.19 (m, 10H), 1.18-1.08 (m, 2H), 1.04-0.93 (m, 1H), 0.90-0.84 (m, 2H), 0.75 (s, 3H) ppm; APCI MS m/z 510 [M+H]+.

Further elution afforded 57 as an off-white solid (33 mg, 29%): mp 200-202° C.; H NMR (500 MHz, CDCl₃) δ 7.63 (d, J=8.4 Hz, 1H), 7.24 (d, J=8.3 Hz, 1H), 6.76 (d, J=7.7 Hz, 1H), 5.58 (dd, J=17.9, 9.3 Hz, 2H), 3.89 (s, 3H), 3.49 (d, J=10.0 Hz, 1H), 3.39 (d, J=10.0 Hz, 1H), 3.30 (s, 3H, 2.67 (t, J=8.9 Hz, 1H), 2.25-2.18 (m, 1H), 2.06-2.02 (m, 1H), 1.73-1.67 (m, 3H), 1.65-1.47 (m, 7H), 1.42-1.11 (m, 12H), 1.04-0.95 (m, 1H), 0.89-10.84 (m, 1H), 0.75 (s, 3H) ppm; APCI MS m/z 510 [M+H]+.

Example 35. Preparation of Compounds 59, 60, and 61

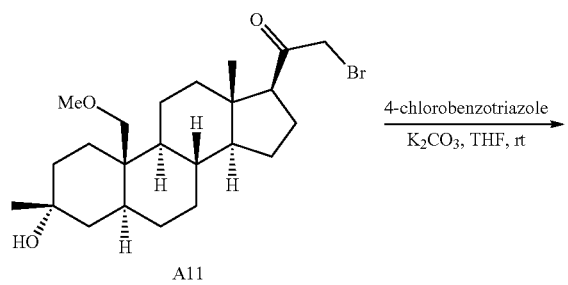

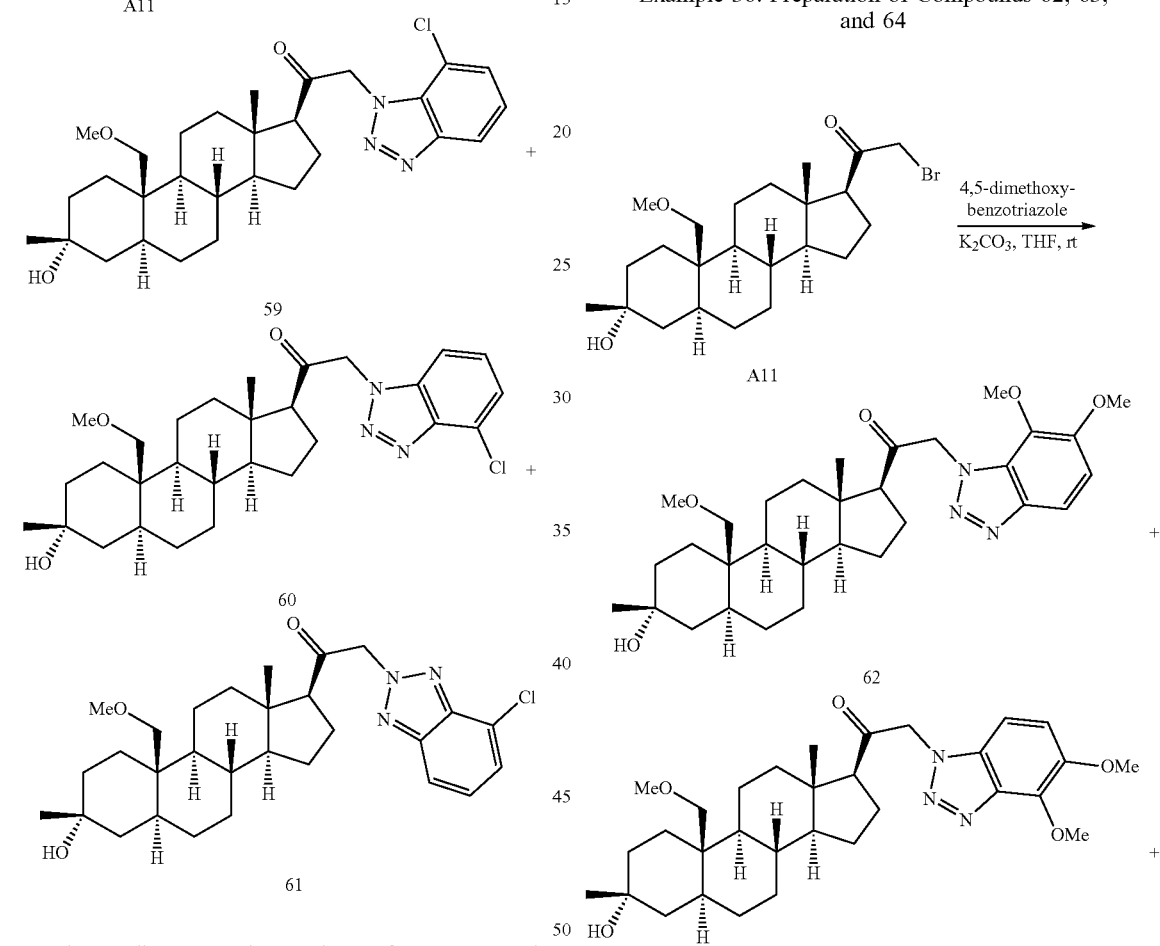

Prepared according General Procedure B from compound A11 (150 mg, 0.34 mmol) and 4-chlorobenzotriazole (156 mg, 1.02 mmol), with semi-purification by column chromatography on silica gel followed by reverse phase preparative HPLC to provide 61 as a light brown solid (64 mg, 37%): mp 170-172° C.; $^1$H NMR (500 MHz, CDCl$_3$) δ 7.79 (dd, J=8.5, 0.5 Hz, 1H), 7.40 (dd, J=7.0, 0.5 Hz, 1H), 7.32 (dd, J=8.5, 7.5 Hz, 1H), 5.57 (d, J$_{AB}$=17.0 Hz, 1H), 5.53 (d, J$_{AB}$=17.0 Hz, 1H), 3.48 (d, J=10.0 Hz, 1H), 3.38 (d, J=10.0 Hz, 1H), 3.30 (s, 3H), 2.66 (t, J=9.0 Hz, 1H), 2.28-2.18 (m, 1H), 2.17-2.10 (m, 1H), 2.07-2.01 (m, 1H), 1.81-1.68 (m, 4H), 1.66-1.46 (m, 6H), 1.44-1.36 (m, 1H), 1.35-1.08 (m, 10H), 1.04-0.94 (m, 1H), 0.90-0.83 (m, 1H), 0.77 (s, 3H) ppm; ESI MS m/z 514 [M+H]$^+$.

Further elution afforded 59 as a light brown solid (8 mg, 4%): mp 162-164° C.; $^1$H NMR (500 MHz, CDCl$_3$) δ 7.99 (d, J=8.5 Hz, 1H), 7.43 (d, J=7.5 Hz, 1H), 7.29 (t, J=7.5 Hz, 1H), 5.71 (s, 2H), 3.48 (d, J=10.0 Hz, 1H), 3.38 (d, J=10.0 Hz, 1H), 3.30 (s, 3H), 2.72 (t, J=9.0 Hz, 1H), 2.27-2.10 (m, 2H), 2.08-2.02 (m, 1H), 1.85-1.37 (m, 11H), 1.35-1.09 (m, 10H), 1.05-0.95 (m, 1H), 0.91-0.83 (m, 1H), 0.76 (s, 3H) ppm; APCI MS m/z 514 [M+H]$^+$.

Further elution provided 60 as a light brown solid (32 mg, 18%): mp 105-107° C.; $^1$H NMR (500 MHz, CDCl$_3$) δ 7.43-7.36 (m, 2H), 7.23 (dd, J=7.5, 1.5 Hz, 1H), 5.42 (s, 2H), 3.49 (d, J=10.0 Hz, 1H), 3.38 (d, J=10.0 Hz, 1H), 3.30 (s, 3H), 2.71 (t, J=9.0 Hz, 1H), 2.27-2.18 (m, 1H), 2.18-2.10 (m, 1H), 2.08-2.01 (m, 1H), 1.82-1.68 (m, 4H), 1.67-1.42 (m, 7H), 1.35-1.09 (m, 10H), 1.05-0.95 (m, 1H), 0.91-0.84 (m, 1H), 0.75 (s, 3H) ppm; ESI MS m/z 514 [M+H]$^+$.

Example 36. Preparation of Compounds 62, 63, and 64

Prepared according General Procedure B from compound A11 (100 mg, 0.23 mmol) and 4,5-dimethoxy-1H-benzo[d][1,2,3]triazole (101 mg, 0.57 mmol), with semi-purification by column chromatography on silica gel followed by reverse phase preparative HPLC to provide 64 as a light yellow solid (32 mg, 26%): mp 188-190° C.; $^1$H NMR (500 MHz, CDCl$_3$) δ 7.50 (d, J=9.0 Hz, 1H), 7.22 (d, J=9.5 Hz, 1H), 5.49 (d, J$_{AB}$=17.0 Hz, 1H), 5.43 (d, J$_{AB}$=17.0 Hz, 1H), 4.27 (s, 3H), 3.95 (s, 3H), 3.48 (d, J=10.0 Hz, 1H), 3.38 (d, J=10.0 Hz, 1H), 3.29 (s, 3H), 2.63 (t, J=8.5 Hz, 1H), 2.27-2.17 (m, 1H), 2.16-2.10 (m, 1H), 2.07-2.01 (m, 1H), 1.79-1.68 (m, 4H), 1.65-1.46 (m, 7H), 1.42-1.08 (m, 10H), 1.03-0.93 (m, 1H), 0.89-0.81 (m, 1H), 0.76 (s, 3H) ppm; APCI MS m/z 540 [M+H]$^+$.

Further elution provided 63 as a white solid (19 mg, 15%): mp 88-90° C.; $^1$H NMR (500 MHz, CDCl$_3$) δ 7.24 (d, J=9.0 Hz, 1H), 6.82 (d, J=9.0 Hz, 1H), 5.36 (d, J$_{AB}$=18.0 Hz, 1H), 5.32 (d, J$_{AB}$=18.0 Hz, 1H), 4.57 (s, 3H), 3.93 (s, 3H), 3.49 (d, J=10.0 Hz, 1H), 3.38 (d, J=10.0 Hz, 1H), 3.30 (s, 3H), 2.69 (t, J=9.0 Hz, 1H), 2.26-2.17 (m, 1H), 2.16-2.10 (m, 1H), 2.08-2.01 (m, 1H), 1.80-1.68 (m, 4H), 1.66-1.41 (m, 7H), 1.36-1.09 (m, 10H), 1.04-0.94 (m, 1H), 0.90-0.83 (m, 1H), 0.74 (s, 3H) ppm; APCI MS m/z 540 [M+H]$^+$.

Further elution provided 62 as a white solid (13 mg, 11%): mp 110-112° C.; $^1$H NMR (500 MHz, CDCl$_3$) δ 7.75 (br s, 1H), 7.11 (d, J=7.5 Hz, 1H), 5.54 (d, J$_{AB}$=18.0 Hz, 1H), 5.50 (d, J$_{AB}$=18.0 Hz, 1H), 3.96 (s, 3H), 3.90 (s, 3H), 3.48 (d, J=10.0 Hz, 1H), 3.38 (d, J=10.0 Hz, 1H), 3.30 (s, 3H), 2.69 (t, J=8.5 Hz, 1H), 2.28-2.01 (m, 3H), 1.83-1.68 (m, 4H), 1.65-1.47 (m, 6H), 1.44-1.37 (m, 1H), 1.36-1.08 (m, 10H), 1.04-0.94 (m, 1H), 0.90-0.83 (m, 1H), 0.76 (s, 3H) ppm; APCI MS m/z 540 [M+H]$^+$.

Example 37. Preparation of Compounds 65 and 66

Prepared according General Procedure B from compound A11 (125 mg, 0.28 mmol) and 4,6-dimethoxy-1H-benzo[d][1,2,3]triazole (127 mg, 0.71 mmol), with purification by column chromatography on silica gel to provide 65 as a light yellow solid (42 mg, 28%): mp 106-108° C.; $^1$H NMR (500 MHz, CDCl$_3$) δ 6.67 (d, J=2.0 Hz, 1H), 6.33 (d, J=2.0 Hz, 1H), 5.43 (d, J$_{AB}$=17.0 Hz, 1H), 5.38 (d, J$_{AB}$=17.0 Hz, 1H), 3.98 (s, 3H), 3.96 (s, 3H), 3.47 (d, J=10.0 Hz, 1H), 3.38 (d, J=10.0 Hz, 1H), 3.29 (s, 3H), 2.61 (t, J=9.0 Hz, 1H), 2.26-2.16 (m, 1H), 2.13-2.07 (m, 1H), 2.07-2.00 (m, 1H), 1.77-1.67 (m, 4H), 1.63-1.46 (m, 7H), 1.39-1.08 (m, 10H), 1.02-0.93 (m, 1H), 0.88-0.80 (m, 1H), 0.75 (s, 3H) ppm; APCI MS m/z 540 [M+H]$^+$.

Further elution provided 66 as an off-white solid (52 mg, 34%): mp 110-112° C.; $^1$H NMR (500 MHz, CDCl$_3$) δ 6.34 (d, J=2.0 Hz, 1H), 6.16 (d, J=2.0 Hz, 1H), 5.28 (s, 2H), 4.06 (s, 3H), 3.84 (s, 3H), 3.48 (d, J=10.0 Hz, 1H), 3.38 (d, J=10.0 Hz, 1H), 3.29 (s, 3H), 2.66 (t, J=9.0 Hz, 1H), 2.25-2.16 (m, 1H), 2.13-2.08 (m, 1H), 2.07-2.01 (m, 1H), 1.79-1.67 (m, 4H), 1.64-1.46 (m, 6H), 1.45-1.37 (m, 1H), 1.35-1.08 (m, 10H), 1.03-0.93 (m, 1H), 0.89-0.82 (m, 1H), 0.74 (s, 3H) ppm; APCI MS m/z 540 [M+H]$^+$.

Example 38. Preparation of Compound 67

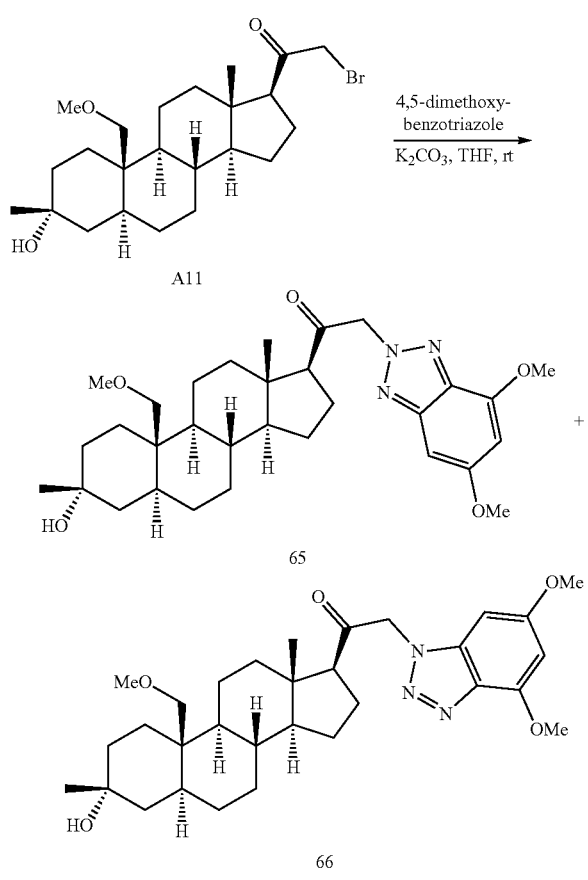

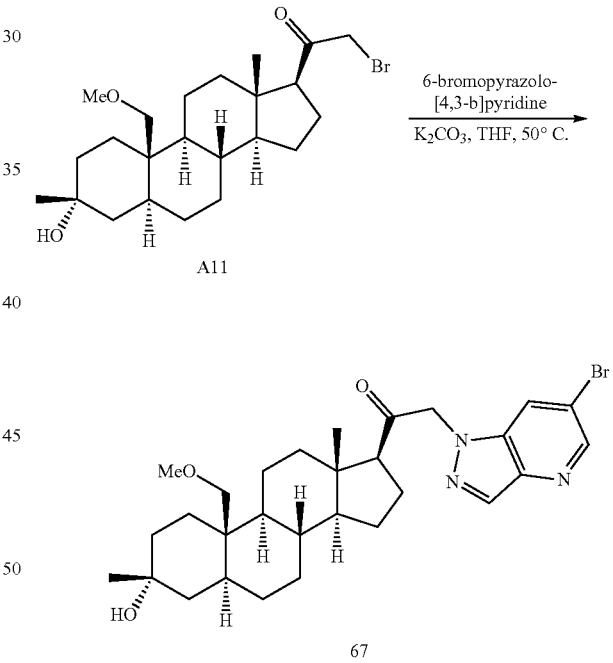

Prepared according General Procedure B from compound A11 (200 mg, 0.45 mmol) and 6-bromo-1H-pyrazolo[4,3-b]pyridine (450 mg, 2.27 mmol), with semi-purification by column chromatography on silica gel followed by reverse phase preparative HPLC to provide 67 as an off-white solid (43 mg, 17%): mp 102-105° C.; $^1$H NMR (300 MHz, CDCl3) δ 8.60 (d, J=1.5 Hz, 1H), 8.23 (s, 1H), 7.75 (s, 1H), 5.16 (d, J$_{AB}$=18.0 Hz, 1H), 5.06 (d, J$_{AB}$=18.0 Hz, 1H), 3.48 (d, J=10.0 Hz, 1H), 3.38 (d, J=10.0 Hz, 1H), 3.30 (s, 3H), 2.68 (t, J=9.3 Hz, 1H), 2.30-1.93 (m, 3H), 1.92-1.38 (m, 11H), 1.37-0.80 (m, 12H), 0.73 (s, 3H) ppm; ESI MS m/z 558 [M+H]$^+$.

Example 39. Preparation of Compounds 68 and 69

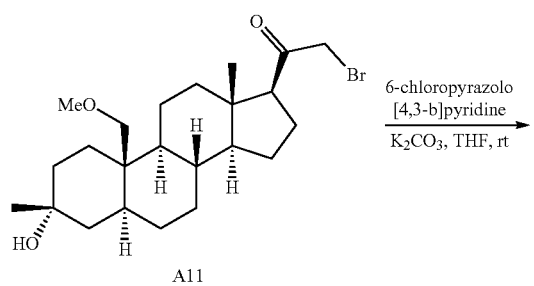

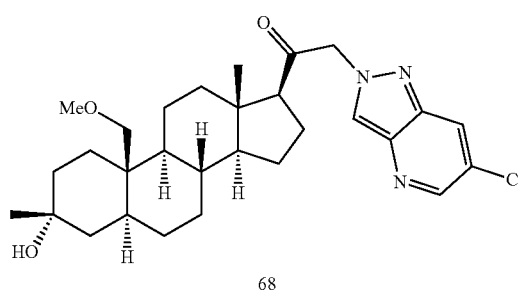

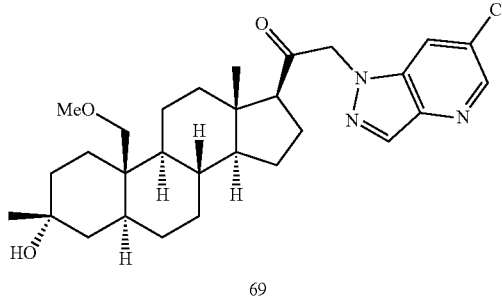

Prepared according General Procedure B from compound A11 (86 mg, 0.19 mmol) and 6-chloro-1H-pyrazolo[4,3-b]pyridine (570 mg, 3.7 mmol), with purification by reverse phase preparative HPLC to provide 68 as a white solid (12 mg, 12%): mp 88-90° C.; $^1$H NMR (500 MHz, CDCl$_3$) δ 8.59 (s, 1H), 8.51 (s, 1H), 8.34 (s, 1H), 5.40-5.22 (m, 2H), 3.48 (d, J=10.0 Hz, 1H), 3.38 (d, J=10.0 Hz, 1H), 3.30 (s, 3H), 2.67 (t, J=8.6 Hz, 1H), 2.27-2.21 (m, 1H), 2.11-1.86 (m, 2H), 1.85-1.41 (m, 11H), 1.34-1.09 (m, 11H), 1.04-0.93 (m, 1H), 0.91-0.81 (m, 1H), 0.73 (s, 3H) ppm; APCI MS m/z 514 [M+H]$^+$.

Further elution provided 69 as a white solid (40 mg, 40%): mp 115-117° C.; $^1$H NMR (500 MHz, CDCl$_3$) δ 8.58 (s, 1H), 8.40 (s, 1H), 7.77 (s, 1H), 5.18 (dd, J=18.0, 32.1 Hz, 2H), 3.49 (d, J=10.0 Hz, 1H), 3.38 (d, J=10.0 Hz, 1H), 3.30 (s, 3H), 2.69 (t, J=8.9 Hz, 1H), 2.24-2.18 (m, 1H), 2.14-2.10 (m, 1H), 2.07-2.03 (m, 1H), 1.80-1.68 (m, 4H), 1.67-1.56 (m, 3H), 1.55-1.42 (m, 4H), 1.39-1.11 (m, 10H), 1.05-0.98 (m, 1H), 0.91-0.85 (m, 1H), 0.73 (s, 3H) ppm; APCI MS m/z 514 [M+H]$^+$.

Example 40. Preparation of Compounds 70, 71, and 72

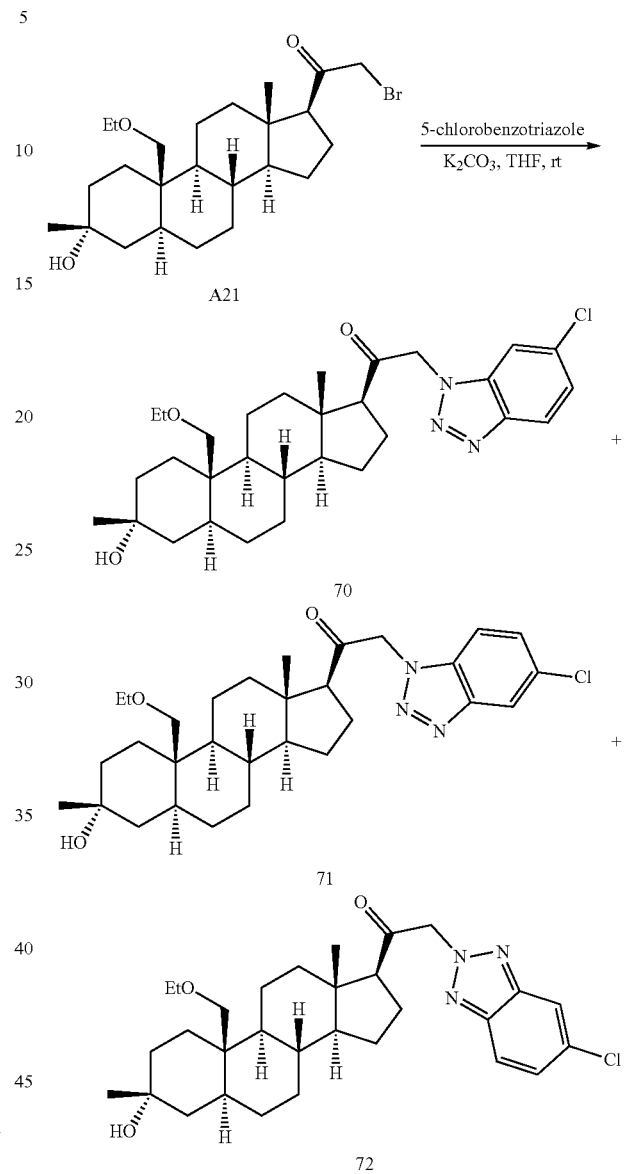

Prepared according General Procedure B from compound A21 (200 mg, 0.44 mmol) and 5-chlorobenzotriazole (1.35 g, 8.8 mmol), with purification by reverse phase preparative HPLC to provide 72 as a white solid (12.6 mg, 5%): mp 76-77° C.; $^1$HNMR (500 MHz, CDCl$_3$) δ 7.87 (d, J=1.5 Hz, 1H), 7.81 (d, J=9.0 Hz, 1H), 7.34 (dd, J=9.0, 1.5 Hz, 1H), 5.50 (dd, J=32.5, 17.0 Hz, 2H), 3.52 (d, J=9.5 Hz, 1H), 3.43-3.38 (m, 3H), 2.65 (t, J=9.0 Hz, 1H), 2.25-2.23 (m, 1H), 2.14-2.13 (m, 1H), 2.06-2.04 (m, 1H), 1.77-1.48 (m, 10H), 1.41-1.38 (m, 1H), 1.33-1.11 (m, 13H), 1.02-1.00 (m, 1H), 0.88-0.86 (m, 1H), 0.75 (s, 3H) ppm; ESI MS m/z 528 [M+H]$^+$.

Further elution provided 70 as a white solid (17.1 mg, 7%): mp 69-70° C.; $^1$HNMR (500 MHz, CDCl$_3$) δ 8.00 (d, J=9.0 Hz, 1H), 7.35-7.33 (m, 2H), 5.37 (dd, J=40.5, 18.0 Hz, 2H), 3.53 (d, J=9.5 Hz, 1H), 3.43-3.40 (m, 3H), 2.72 (t, J=9.0 Hz, 1H), 2.24-2.23 (m, 1H), 2.16-2.14 (m, 1H), 2.08-2.06 (m, 1H), 1.79-1.42 (m, 11H), 1.37-1.13 (m, 11H), 1.01-0.99 (m, 1H), 0.88 (t, J=7.0 Hz, 3H), 0.74 (s, 3H) ppm; ESI MS m/z 528 [M+H]⁺.

Further elution provided 71 as a white solid (23.6 mg, 10%): mp 82-83° C.; ¹HNMR (500 MHz, CDCl₃) δ 8.06 (d, J=1.5 Hz, 1H), 7.45 (dd, J=9.0, 1.5 Hz, 1H), 7.28 (d, J=9.0 Hz, 1H), 5.40 (dd, J=29.5, 18.0 Hz, 2H), 3.53 (d, J=10.0 Hz, 1H), 3.42-3.39 (m, 3H), 2.71 (t, J=9.0 Hz, 1H), 2.24-2.23 (m, 1H), 2.16-2.14 (m, 1H), 2.08-2.05 (m, 1H), 1.77-1.48 (m, 11H), 1.33-1.13 (m, 11H), 1.02-0.99 (m, 1H), 0.88 (t, J=7.0 Hz, 3H), 0.74 (s, 3H) ppm; ESI MS m/z 528 [M+H]⁺.

Example 41. Preparation of Compound 76

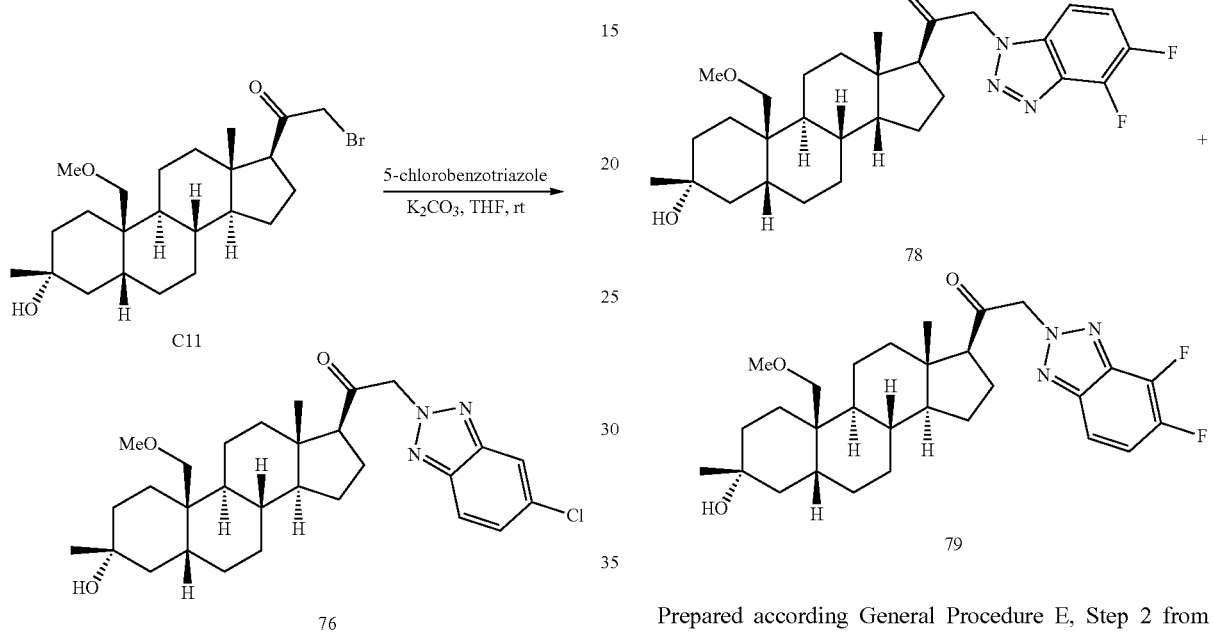

76

Prepared according General Procedure E, Step 2 from compound C11 (120 mg, 0.27 mmol) and 5-chlorobenzimidazole (125 mg, 0.82 mmol), with semi-purification by column chromatography on silica gel followed by reverse phase preparative HPLC to provide 76 as a white solid (19 mg, 14%): mp 85-87° C.; ¹H NMR (300 MHz, CDCl₃) δ 7.88-7.80 (m, 2H), 7.35 (d, J=9.1 Hz, 1H), 5.49 (s, 2H), 3.55 (d, J=9.0 Hz, 1H), 3.34 (s, 3H), 3.22 (d, J=9.0 Hz, 1H), 2.64 (t, J=8.5 Hz, 1H), 2.27-2.12 (m, 2H), 1.94-1.85 (m, 2H), 1.84-1.36 (m, 15H), 1.35-1.14 (m, 10H), 0.73 (s, 3H) ppm; APCI MS m/z 514 [M+H]⁺.

Example 42. Preparation of Compounds 77, 78, and 79

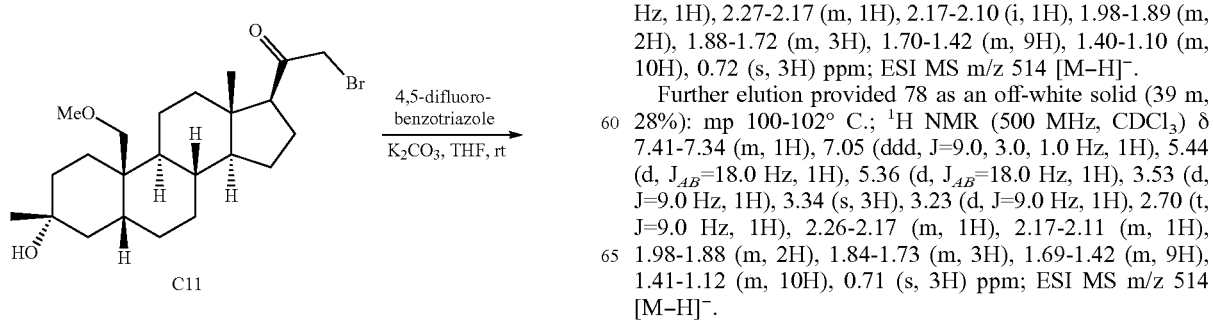

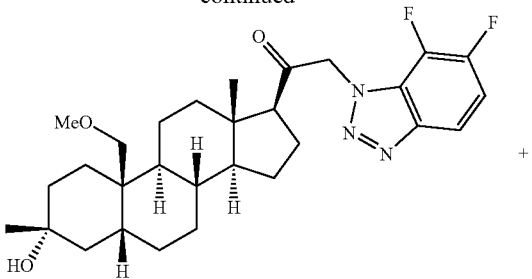

77

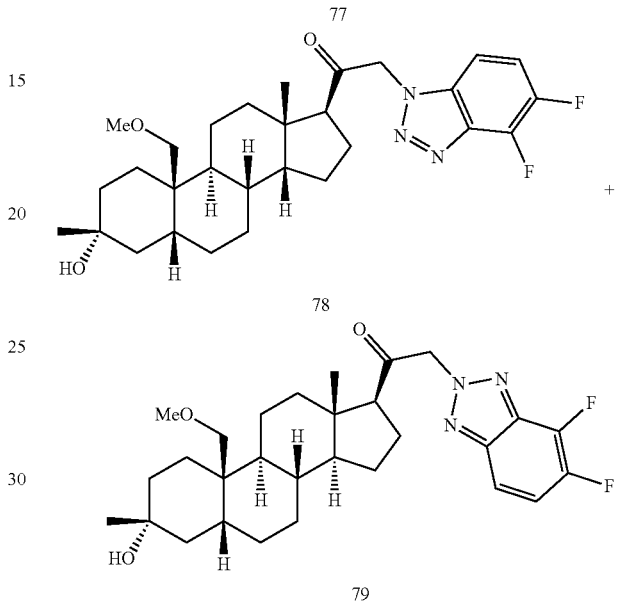

78

79

Prepared according General Procedure E, Step 2 from compound C11 (120 mg, 0.27 mol) and 4,5-difluoro-1H-benzo[d][1,2,3]triazole (126 mg, 0.82 mmol), with semi-purification by column chromatography on silica gel followed by reverse phase preparative HPLC to provide 79 as a white solid (62 mg, 44%): mp 103-105° C.; ¹H NMR (500 MHz, CDCl₃) δ 7.64 (ddd, J=9.0, 3.5, 1.0 Hz, 1H), 7.32-7.26 (m, 1H), 5.54 (d, J$_{AB}$=17.0 Hz, 1H), 5.49 (d, J$_{AB}$=17.0 Hz, 1H), 3.54 (d, J=9.0 Hz, 1H), 3.34 (s, 3H), 3.22 (d, J=9.0 Hz, 1H), 2.65 (t, J=9.0 Hz, 1H), 2.27-2.18 (m, 1H), 2.17-2.11 (i, 1H), 1.97-1.88 (2, 2H), 1.84-1.73 (m, 3H), 1.68-1.40 (m, 9H), 1.40-1.11 (m, 10H), 0.74 (s, 3H) ppm; ESI MS m/z 514 [M−H]⁻.

Further elution provided 77 as a white solid (20 mg, 14%): mp 98-100° C.; ¹H NMR (500 MHz, CDCl₃) δ 7.81 (ddd, J=9.0, 4.0, 1.0 Hz, 1H), 7.24-7.19 (m, 1H), 5.54 (d, J$_{AB}$=18.5 Hz, 1H), 5.50 (d, J$_{AB}$=18.5 Hz, 1H), 3.55 (d, J=9.0 Hz, H), 3.34 (s, 3H), 3.22 (d, J=9.0 Hz, 1H), 2.71 (t, J=9.0 Hz, 1H), 2.27-2.17 (m, 1H), 2.17-2.10 (i, 1H), 1.98-1.89 (m, 2H), 1.88-1.72 (m, 3H), 1.70-1.42 (m, 9H), 1.40-1.10 (m, 10H), 0.72 (s, 3H) ppm; ESI MS m/z 514 [M−H]⁻.

Further elution provided 78 as an off-white solid (39 m, 28%): mp 100-102° C.; ¹H NMR (500 MHz, CDCl₃) δ 7.41-7.34 (m, 1H), 7.05 (ddd, J=9.0, 3.0, 1.0 Hz, 1H), 5.44 (d, J$_{AB}$=18.0 Hz, 1H), 5.36 (d, J$_{AB}$=18.0 Hz, 1H), 3.53 (d, J=9.0 Hz, 1H), 3.34 (s, 3H), 3.23 (d, J=9.0 Hz, 1H), 2.70 (t, J=9.0 Hz, 1H), 2.26-2.17 (m, 1H), 2.17-2.11 (m, 1H), 1.98-1.88 (m, 2H), 1.84-1.73 (m, 3H), 1.69-1.42 (m, 9H), 1.41-1.12 (m, 10H), 0.71 (s, 3H) ppm; ESI MS m/z 514 [M−H]⁻.

Example 43. Preparation of Compound 80

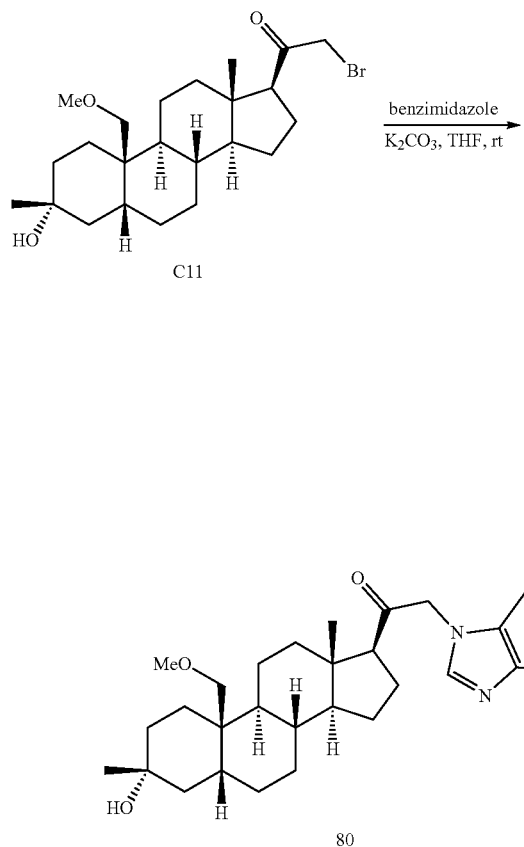

Prepared according General Procedure E, Step 2 from compound C11 (100 mg, 0.23 mmol) and benzimidazole (80 mg, 0.68 mmol), with purification by reverse phase preparative HPLC to provide 80 as a white solid (68 mg, 63%): mp 130-132° C.; $^1$H NMR (300 MHz, CDCl$_3$) δ 8.74 (b s, 1H), 7.91-7.87 (m, 1H), 7.41-7.38 (m, 2H), 7.25-7.22 (m, 1H), 5.16 (dd, J=18.3, 5.8 Hz, 2H), 3.54 (d, J=9.1 Hz, 1H), 3.34 (s, 3H), 3.23 (d, J=9.1 Hz, 1H), 2.71 (t, J=8.9 Hz, 1H), 2.29-2.08 (m, 2H), 1.94-1.09 (m, 26H), 0.72 (s, 3H) ppm; APCI MS m/z 479 [M+H]$^+$.

Example 44. Preparation of Compounds 81, 82, and 83

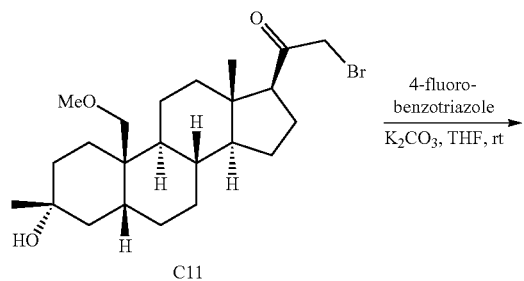

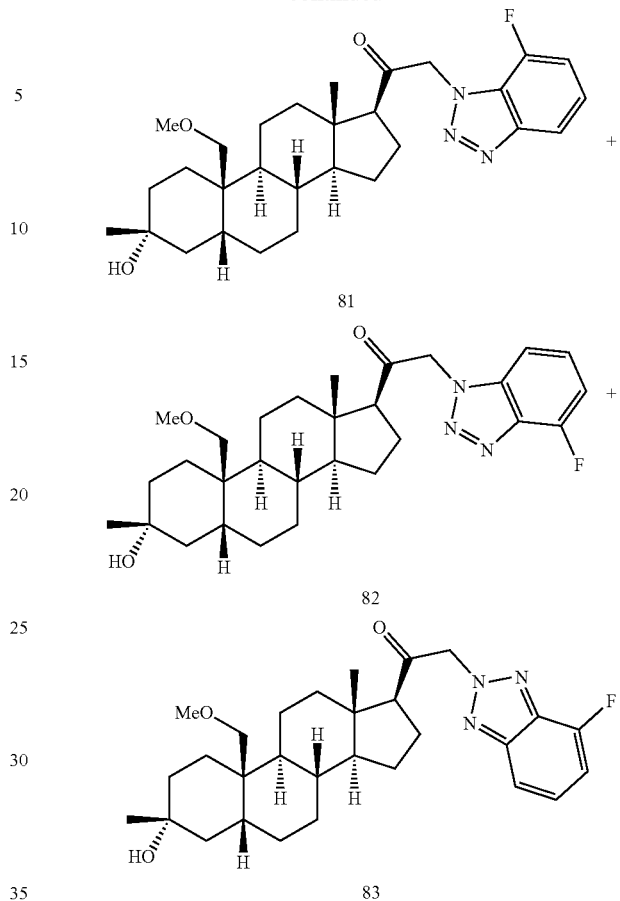

Prepared according General Procedure E, Step 2 from compound C11 (120 mg, 0.27 mmol) and 4-fluoro-1H-benzo[d][1,2,3]triazole (112 mg, 0.82 mmol), with purification by reverse phase preparative HPLC to provide 82 as an off-white solid (40 mg, 30%): mp 199-201° C.; $^1$H NMR (500 MHz, CDCl$_3$) δ 7.45-7.40 (m, 1H), 7.11 (d, J=8.3 Hz, 1H), 7.06-7.02 (m, 1H), 5.41 (dd, J=18.0, 9.2 Hz, 2H), 3.54 (d, J=9.0 Hz, 1H), 3.34 (s, 3H), 3.23 (d, J=9.0 Hz, 1H), 2.70 (t, J=8.9 Hz, 1H), 2.27-2.13 (m, 2H), 1.97-1.89 (m, 2H), 1.83-1.68 (m, 5H), 1.67-1.43 (m, 9H), 1.41-1.12 (m, 9H), 0.72 (s, 3H) ppm; APCI MS m/z 498 [M+H]$^-$ Further elution provided 81 as a white solid (20 mg, 15%): mp 98-100° C.; $^1$H NMR (500 MHz, CDCl$_3$) δ 7.86 (d, J=8.4 Hz, 1H), 7.31-7.26 (m, 1H), 7.15-7.11 (m, 1H), 5.43 (dd, J=18.2, 0.95 Hz, 2H), 3.55 (d, J=9.0 Hz, 1H), 3.34 (s, 3H), 3.22 (d, J=9.0 Hz, 1H), 2.70 (t, J=9.0 Hz, 1H), 2.25-2.12 (m, 2H), 1.97-1.75 (m, 6H), 1.70-1.44 (m, 9H), 1.39-1.13 (m, 10H), 0.72 (s, 3H) ppm; APCI MS m/z 498 [M+H]$^+$.

Further elution provided 83 as an off-white solid (48 mg, 36%): mp 172-174° C.; $^1$H NMR (500 MHz, CDCl$_3$) δ 7.67 (d, J=8.6 Hz, 1H), 7.35-7.30 (m, 1H), 7.06-7.02 (m, 1H), 5.53 (dd, J=17.0, 2.6 Hz, 2H), 3.55 (d, J=9.0 Hz, 1H), 3.34 (s, 3H), 3.21 (d, J=9.0 Hz, 1H), 2.65 (t, J=9.0 Hz, 1H), 2.26-2.13 (m, 3H), 1.96-1.89 (m, 2H), 1.83-1.71 (m, 3H), 1.67-1.40 (m, 9H), 1.37-1.11 (m, 9H), 0.74 (s, 3H) ppm; APCI MS m/z 498 [M+H]$^+$.

Example 45. Preparation of Compound 4

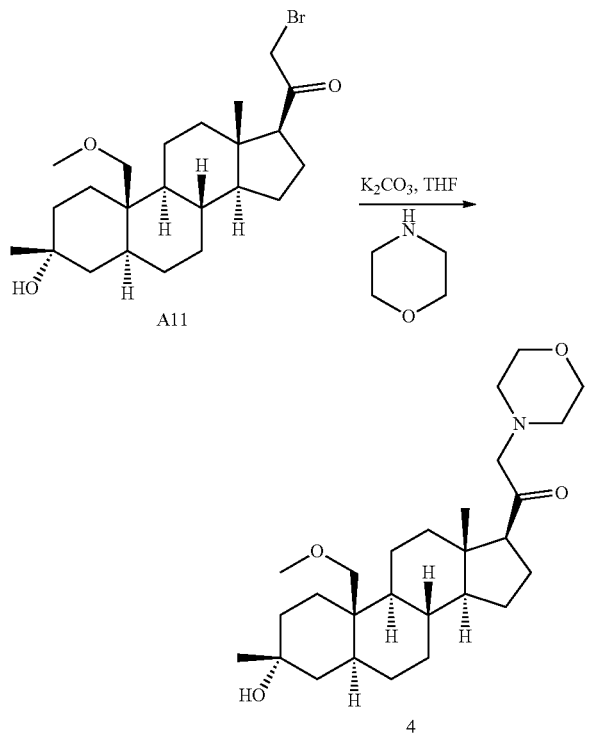

To a solution of compound A11 (40 mg, 0.09 mmol) in THF (2 mL) was added morpholine (390 mg, 4.5 mmol) and K$_2$CO$_3$ (120 mg, 0.9 mmol). The resulting solution was stirred at room temperature overnight. Then LCMS showed the reaction was complete. The reaction was diluted with EtOAc (40 mL), and washed with brine (15 mL×2). The organic layer was dried over Na$_2$SO$_4$, filtered and concentrated. The residue was purified by prep-HPLC to give compound 4 (18 mg, 45%) as a white solid. Compound 4: $^1$H NMR: (500 MHz, CDCl$_3$), δ (ppm), 3.79-3.77 (m, 4H), 3.48 (AB, 1H, J=10 Hz), 3.38 (AB, 1H, J=10 Hz), 3.30 (s, 3H), 3.22 (s, 2H), 2.58 (t, 1H, J=9.3 Hz), 2.5 (s, 4H), 1.25 (s, 3H), 0.66 (s, 3H).

Example 46. Preparation of Compound 2

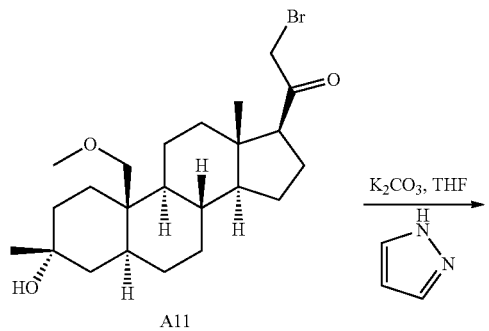

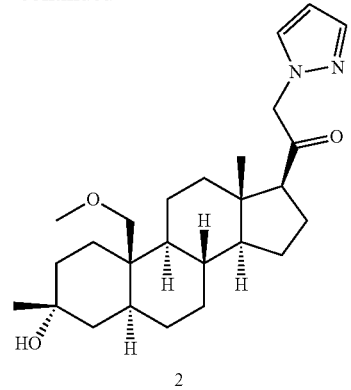

To a solution of compound A11 (40 mg, 0.09 mmol) in THF (2 mL) was added 1H-pyrazole (300 mg, 4.5 mmol) and K$_2$CO$_3$ (120 mg, 0.9 mmol). The resulting solution was stirred at room temperature overnight. Then LCMS showed the reaction was complete. The reaction was diluted with EtOAc (40 mL), and washed with brine (15 mL×3). The organic layer was dried over Na$_2$SO$_4$, filtered and concentrated. The residue was purified by prep-HPLC to give 2 (16 mg, 40%) as a white solid. Compound 2: $^1$H NMR: (500 MHz, CDCl$_3$), δ (ppm), 7.57 (d, 1H, J=1 Hz), 7.43 (d, 1H, J=1.5 Hz), 6.35 (s, 1H), 4.98 (AB, 1H, J=17.5 Hz), 4.90 (AB, 1H, J=18 Hz), 3.48 (AB, 1H, J=10.5 Hz), 3.39 (AB, 1H, J=9.5 Hz), 3.31 (s, 3H), 2.60 (t, 1H, J=8.8 Hz), 1.25 (s, 3H), 0.72 (s, 3H).

Example 47. Preparation of Compound 5

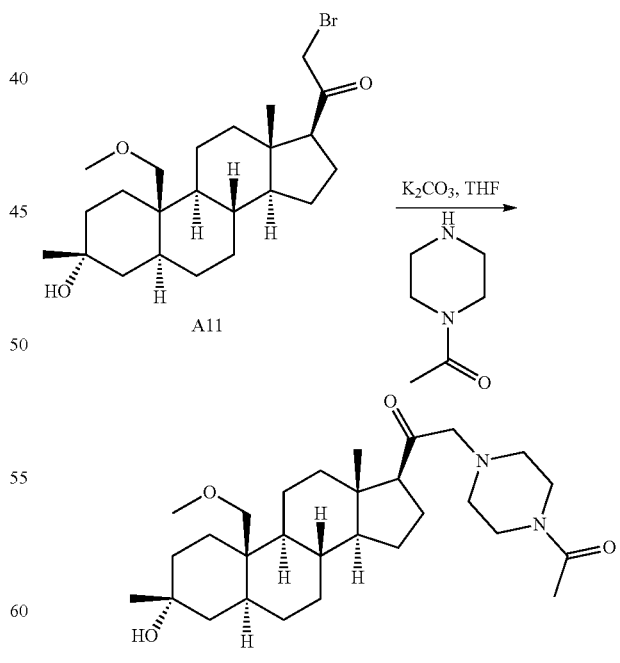

Compound A11 (30 mg, 0.07 mmol), K$_2$CO$_3$ (50 mg) and 1-(piperazin-1-yl)ethanone (200 mg) were dissolved in THF (3 mL) and stirred at room temperature overnight. The solvent was removed in vacuo and the residue was purified by prep-HPLC to give compound 5 (6 mg, 20%) as a white solid. Compound 5: $^1$H NMR: (400 MHz, CDCl$_3$), S (ppm), 3.68-3.66 (m, 2H), 3.51 (t, 2H, J=5 Hz), 3.45 (AB, 1H, J=10 Hz), 3.37 (AB, 1H, J=10 Hz), 3.28 (s, 3H), 3.21 (s, 2H), 2.52-2.44 (m, 5H), 2.08 (s, 3H), 1.23 (s, 3H), 0.64 (s, 3H).

Example 48. Preparation of Compound B11

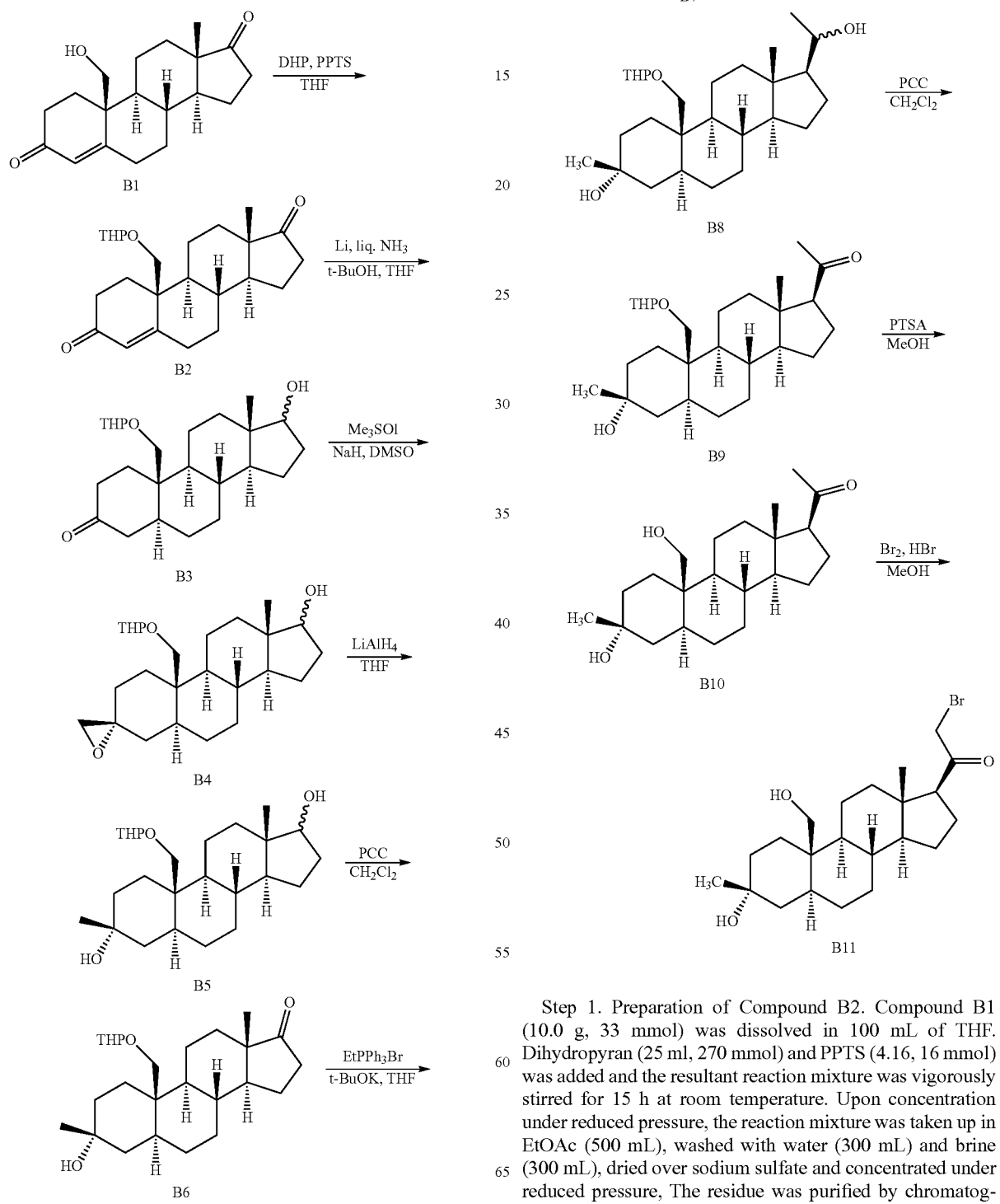

Step 1. Preparation of Compound B2. Compound B1 (10.0 g, 33 mmol) was dissolved in 100 mL of THF. Dihydropyran (25 ml, 270 mmol) and PPTS (4.16, 16 mmol) was added and the resultant reaction mixture was vigorously stirred for 15 h at room temperature. Upon concentration under reduced pressure, the reaction mixture was taken up in EtOAc (500 mL), washed with water (300 mL) and brine (300 mL), dried over sodium sulfate and concentrated under reduced pressure, The residue was purified by chromatography on silica gel (eluant: petroleum ether/EtOAc=10/1~3/

1) to afford compound B2 12.52 g (97.65%). Compound B2: LC-MS: m/z=409.0 [M+Na]+

Step 2. Preparation of Compound B3. Lithium metal (3.0 g, 0.4 mmol) were added to condensed ammonia (500 ml) in a three neck flask at −70° C. Then a solution of Compound B2 (5.0 g, 13 mmol) and tert-BuOH (0.95 g, 13 mmol) in anhydrous tetrahydrofuran (100 mL) was added dropwise and stirred for 0.8 hours. Ammonium chloride (30.0 g) was added to quench the reaction and the ammonia was left to evaporate overnight. The residue was extracted with EtOAc (300 mL). The organic layers were washed with saturated NaCl solution (2×200 mL), dried over $Na_2SO_4$ and concentrated under reduced pressure, The residue was purified by chromatography on silica gel (eluant: petroleum ether/EtOAc=10/1~2/1) to afford 2.0 g of compound 3 (39.60%). Compound B3: LC-MS: m/z=413.3 [M+Na]+

Step 3. Preparation of Compound B4. $Me_3SOI$ (16.9 g, 76.80 mmol) was dissolved in 80 mL of DMSO and NaH (1.84 g, 76.80 mmol) was added. The mixture was stirred at room temperature for 1 hour, then compound B3 (6.0 g, 15.36 mmol) dissolved in 60 mL of DMSO was added. The solution was stirred at room temperature overnight. Water (10 mL) was then added to the reaction mixture. The aqueous reaction mixture was extracted with EtOAc (300 mL×3). The extracts were dried over $Na_2SO_4$, filtered, concentrated. The crude compound B4 was directly used in the next step without further purification.

Step 4. Preparation of Compound B5. The crude compound B4 was slowly added into a suspension of $LiAlH_4$ (1.75 g, 51 mmol) in 100 ml of dry THF at 0° C. The mixture was stirred at room temperature for 2 h, then 2.1 g of 15% aq NaOH was slowly added to quench the reaction. The reaction mixture extracted with EtOAc (200 mL×3). The organic layers were dried over $MgSO_4$, filtered, and concentrated. The crude compound B5 was directly used in the next step without further purification.

Step 5. Preparation of Compound B6. The crude compound B5 was dissolved in 100 ml of dry $CH_2Cl_2$, and 4.0 g of PCC was added at 0° C. Then the mixture was stirred at room temp for 6 h. The reaction mixture was then filtered, concentrated, and purified by flash chromatography on silica gel using 10/1~3/1 petroleum ether:ethyl acetate=10/1-3/1 elution to give compound B6, 3.10 g (50.89%, three-step yield).

Step 6. Preparation of Compound B7. To a suspension of Ethyltriphenylphosphonium bromide (14.20 g, 38.3 mmol) in dry THF (40 mL) was added KOtBu (4.30 g, 38.3 mmol) under $N_2$ atmosphere. The mixture was heated at reflux for 1 hour, during which time the mixture turned bright orange. Then compound B6 (3.1 g, 7.66 mmol) in dry THF (25 mL) was added to the above refluxing solution and stirred at reflux overnight. After cooling to room temperature, the solution was poured into brine (100 mL). The aqueous solution was extracted with ethyl acetate (100 mL×3). The extracts were washed with brine (30 mL×2), dried over $Na_2SO_4$, filtered, concentrated and purified by column chromatography on silica gel (petroleum ether/EtOAC from 10/1 to 4/1) to give compound B7 2.2 g (68.97%) as white solid. Furthermore, the C-3 isomer (0.30 g, 9.63%) was also obtained.

Step 7. Preparation of Compound B8. To a solution of compound B7 (3 g, 7.2 mmol) in dry THF (20 mL) was added borane-tetrahydrofuran complex (29 mL of 1.0 M solution in THF) and the reaction mixture was stirred at ambient temperature for 1 hour. 10% aqueous NaOH (20 mL) was slowly added. The mixture was cooled in ice and 30% aqueous solution of $H_2O_2$(20 mL) was slowly added. The mixture was stirred at ambient temperature for 1 hour and then extracted with $CH_2Cl_2$ (3×100 mL). The combined $CH_2Cl_2$ extracts were washed with 10% aqueous $Na_2S_2O_3$ (50 mL), which was directly used in the next step without further purification.

Step 8. Preparation of Compound B9. The combined $CH_2Cl_2$ extracts of the compound B8 of last step was used without further purification. 3.5 g of PCC was added at 0° C. Then the mixture was stirred at room temperature for 6 h, The mixture was filtered, concentrated, and purified by flash chromatography on silica gel using 12/1~7/1 (petroleum ether:ethyl acetate) elution to give 1.28 g of compound B9 (41.23% two steps). Compound B9: LC-MS: m/z=455.3 [M+Na]+. 1H NMR (500 MHz, CDCl3) δ (ppm): 4.57&4.53 (1H, t, J=3.5 Hz), 3.96&3.87 (1H, AB, J=11.0 Hz), 3.82 (1H, t, J=9.5 Hz), 3.56-3.53 (1H, m), 3.44&3.27 (1H, AB, J=10.5 Hz), 2.53 (1H, t, J=9.0 Hz), 2.12&2.11 (3H, s), 1.22&1.21 (3H, s), 0.64&0.61 (1H, s).

Step 9. Preparation of Compound B10. Compound B9 (1.28 g, 2.96 mmol) was dissolved in 50 mL of dry MeOH and 100 mg of PTSA was added. The reaction mixture was stirred at room temperature overnight. The reaction mixture was then concentrated under reduced pressure. This product mixture was separated by flash chromatography on silica gel using 8/1-2/1 (petroleum ether:EtOAc) elution to give 674 mg of compound B10 (65.32%). Compound B10: LC-MS: m/z=331.3[M−H2O+H]+, m/z=349.2[M+H]+ 1H NMR (500 MHz, CDCl3) δ (ppm): 3.89 (1H, AB, J=12.0 Hz), 3.72 (1H, AB, J=12.0 Hz), 2.53 (1H, t, J=9.0 Hz), 2.11 (3H, s), 1.22 (3H, s), 0.64 (3H, s). 13C NMR (125.77 MHz, CDCl3) δ (ppm): 209.78, 69.68, 63.80, 60.12, 57.07, 54.39, 44.36, 42.04, 41.18, 39.62, 39.31, 36.05, 35.39, 31.85, 31.68, 31.54, 28.04, 27.91, 24.39, 22.86, 22.75, 13.72.

Step 10. Preparation of Compound B11. Compound B10 (50 mg, 0.14 mmol) was dissolved in 5 mL of dry MeOH and 3 drops of $Br_2$ and 2 drops of HBr aq. was added. The reaction mixture was stirred at room temperature for 3 h, then the reaction mixture was treated with triethylamine at 0° C., concentrated under reduced pressure and was directly used in the next step without further purification. Compound B11: LC-MS: m/z=410.1&411.2[M−H2O+H]+.

Example 49. Preparation of Compound 9

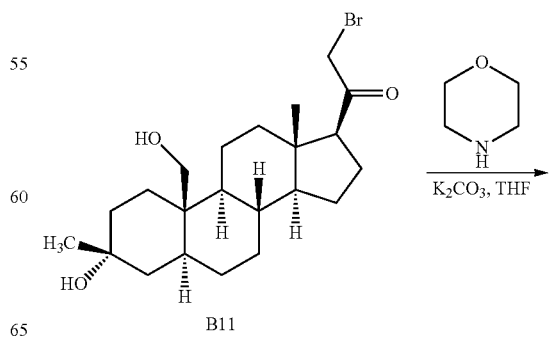

127

-continued

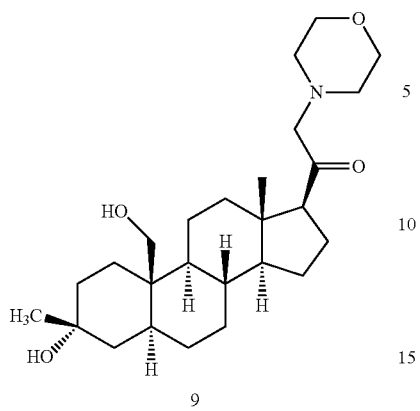

9

Crude compound B11 was directly used, 8 mL THF and 100 mg of K₂CO₃, 0.5 ml of morpholine was added. The reaction mixture was stirred at room temperature overnight. The solution was diluted with ethyl acetate (100 mL). The resulting solution was washed with brine (100 mL), dried over sodium sulfate and concentrated in vacuo. The residue was purified with reverse phase prep-HPLC to give 25 mg (41.18%, two steps from 50 mg of compound B10) product 9 as white solid. Compound 9: ¹H NMR (500 MHz, CDCl3) δ (ppm): 3.89 (1H, dd, J=4.0 Hz, J=11.5 Hz), 3.76 (4H, t, J=4.5 Hz), 3.72 (1H, dd, J=3.0 Hz, J=11.0 Hz), 3.19 (2H, s), 2.58 (1H, t, J=9.5 Hz), 2.45-2.55 (4H, m), 2.20~2.15 (1H, m), 2.07~2.04 (1H, m), 1.92~1.89 (1H, m), 1.23 (3H, s), 0.67 (3H, s).

Example 50. Preparation of Compounds 12 & 10

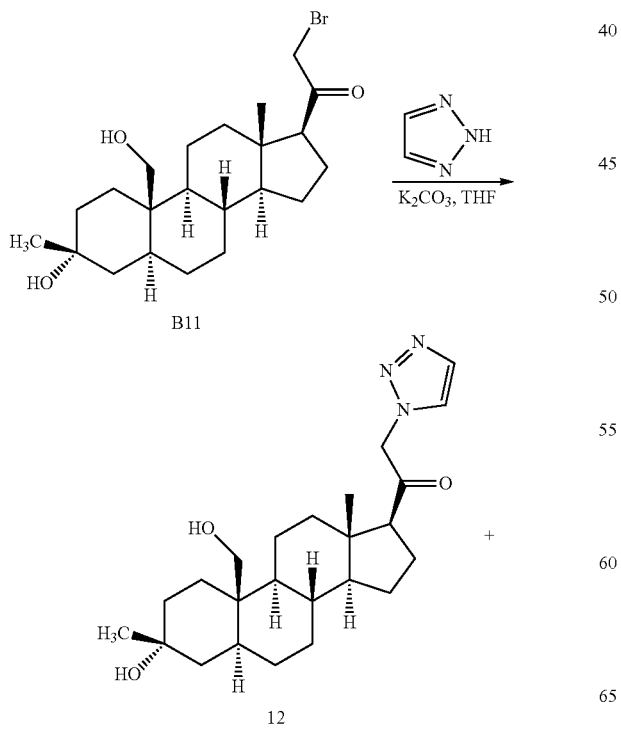

128

-continued

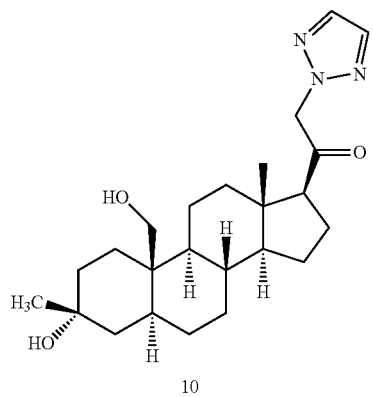

10

Crude compound B11 was directly used, and 8 mL of dry THF and 100 mg of K₂CO₃, 0.5 ml of 1H-1,2,3-triazole was added. The reaction mixture was stirred at room temperature overnight. The solution was diluted with EtOAc (100 mL). The resulting solution was washed with brine (100 mL), dried over sodium sulfate and concentrated in vacuo. The residue was purified with reverse phase prep-HPLC to give 10 mg of Compound 12 and 19 mg of Compound 10 as white solid.

Compound 12: 1H NMR (500 MHz, CDCl3) δ (ppm): 7.76 (1H, s), 7.64 (1H, s), 5.24 (1H, AB, J=17.5 Hz), 5.16 (1H, AB, J=18.0 Hz), 3.89 (1H, AB, J=11.5 Hz), 3.73 (1H, AB, J=11.5 Hz), 2.65 (1H, t, J=9.0 Hz), 2.25~2.19 (1H, m), 2.10~2.05 (2H, m), 1.23 (3H, s), 0.71 (3H, s). Compound 10: ¹H NMR (500 MHz, CDCl3) δ (ppm): 7.68 (2H, s), 5.25 (1H, AB, J=17.5 Hz), 5.22 (1H, AB, J=17.5 Hz) 3.89 (1H, AB, J=11.5 Hz), 3.73 (1H, AB, J=11.5 Hz), 2.58 (1H, t, J=8.5 Hz), 2.24~2.20 (1H, m), 2.11~2.04 (21H, m), 1.23 (3H, s), 0.75 (3H, s).

Example 51. Preparation of Compound 11

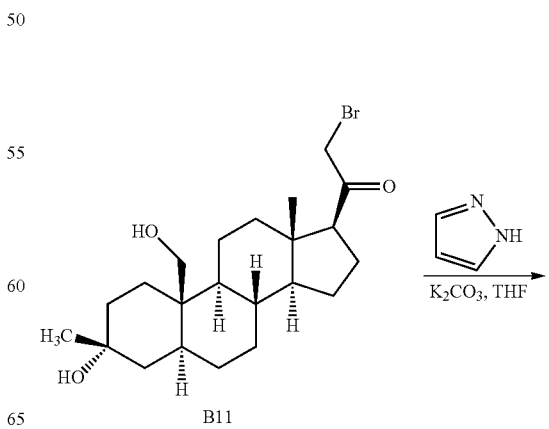

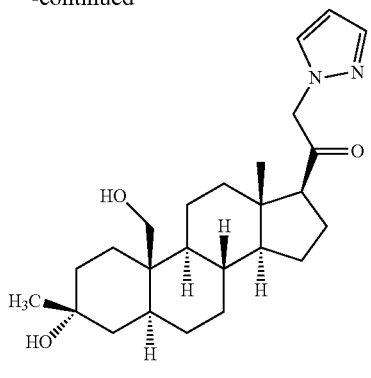

11

Crude compound B11 was directly used, 8 mL of dry THF and 100 mg of K$_2$CO$_3$, 0.5 ml of pyrazole was added. The reaction mixture was stirred at room temperature overnight. The solution was diluted with ethyl acetate (100 mL). The resulting solution was washed with brine (100 mL), dried over sodium sulfate and concentrated in vacuo. The residue was purified with reverse phase prep-HPLC to give 30 mg of Compound 11 white solid. Compound 11: $^1$H NMR (500 MHz, CDCl3) δ (ppm): 7.54 (1H, d, J=1.0 Hz), 7.40 (1H, dt, J=2.0 Hz), 6.33 (1H, t, J=1.5 Hz), 4.94 (1H, AB, J=17.5 Hz), 4.90 (1H, AB, J=17.0 Hz), 3.88 (1H, AB, J=11.5 Hz), 3.73 (1H, AB, J=12.0 Hz), 2.58 (1H, t, J=8.5 Hz) 2.23~2.17 (1H, m), 2.07~2.05 (2H, m), 1.23 (3H, s), 0.72 (3H, s).

Example 52. Preparation of Compound 6

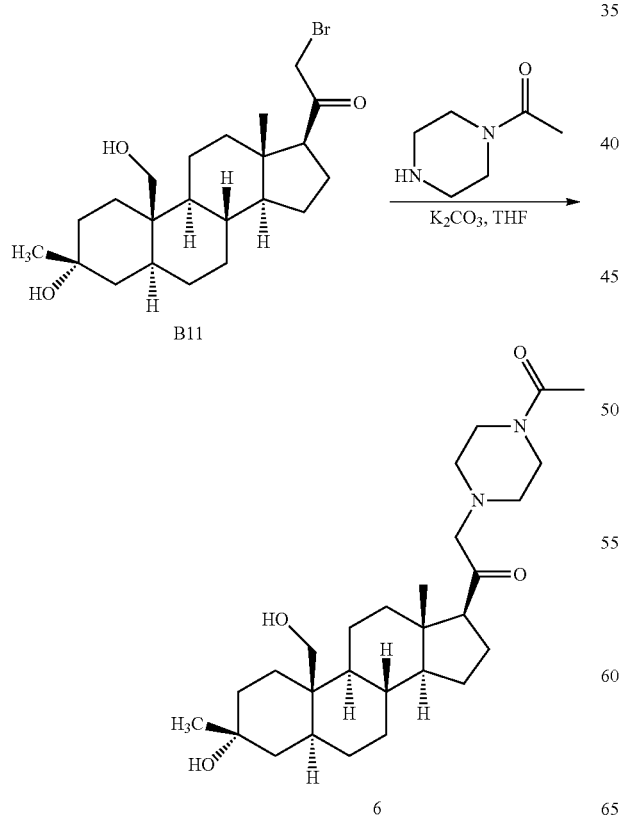

Crude compound B11 was directly used, 8 mL of dry THF and 100 mg of K$_2$CO$_3$, 0.5 ml of 1-(piperazin-1-yl)ethanone was added. The reaction mixture was stirred at room temperature overnight. The solution was then diluted with ethyl acetate (100 mL). The resulting solution was washed with brine (100 mL), dried over sodium sulfate and concentrated in vacuo. The residue was purified with reverse phase prep-HPLC to give 29 mg (43.64%, two steps from 50 mg of compound B10) Compound 6 as white solid. Compound 6: $^1$H NMR (500 MHz, CDCl3) δ (ppm): 3.89 (1H, AB, J=11.5 Hz), 3.72 (1H, AB, J=11.5 Hz), 3.68~3.65 (2H, m), 3.51 (2H, t, J=5.0 Hz) 3.21 (3H, s), 2.55 (1H, t, J=9.5 Hz), 2.45 (3H, t, J=5.0 Hz), 1.23 (3H, s), 0.67 (3H, s)

Example 53. Preparation of Compound 7

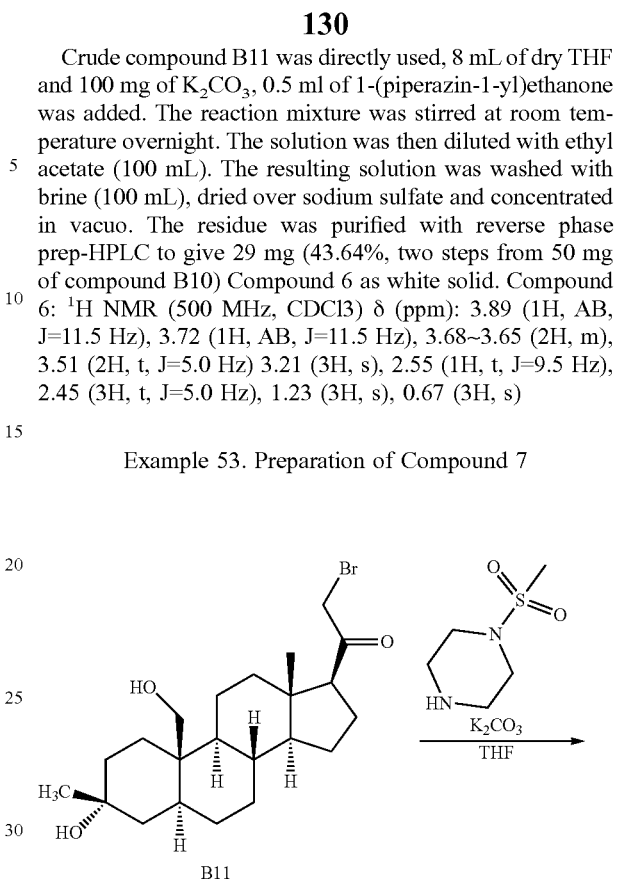

59 mg (0.12 mmol) of crude Compound B11 was dissolved in 8 mL THF and 100 mg (0.77 mmol) of K$_2$CO$_3$, 100 mg (0.61 mmol) of 1-(Methylsulfonyl)piperazine was added. The reaction mixture was stirred at room temperature overnight. The solution was diluted with ethyl acetate (100 mL). The resulting solution was washed with brine (100 mL), dried over sodium sulfate and concentrated in vacuo. The residue was purified with reverse phase prep-HPLC to give 8 mg (0.02 mmol, 10.9%) product 7 as white solid. Compound 7: $^1$H NMR (500 MHz, CDCl3) δ (ppm): 3.89 (1H, AB, J=11.5 Hz), 3.72 (1H, AB, J=12 Hz), 3.30 (4H, t, J=5.0 Hz), 3.25 (2H, s), 2.78 (3H, s) 2.61 (4H, t, J=5.0 Hz), 2.52 (1H, t, J=8.5 Hz), 2.13~2.01 (1H, m), 1.23 (3H, s), 0.67 (3H, s).

Example 54. Preparation of Compound E15
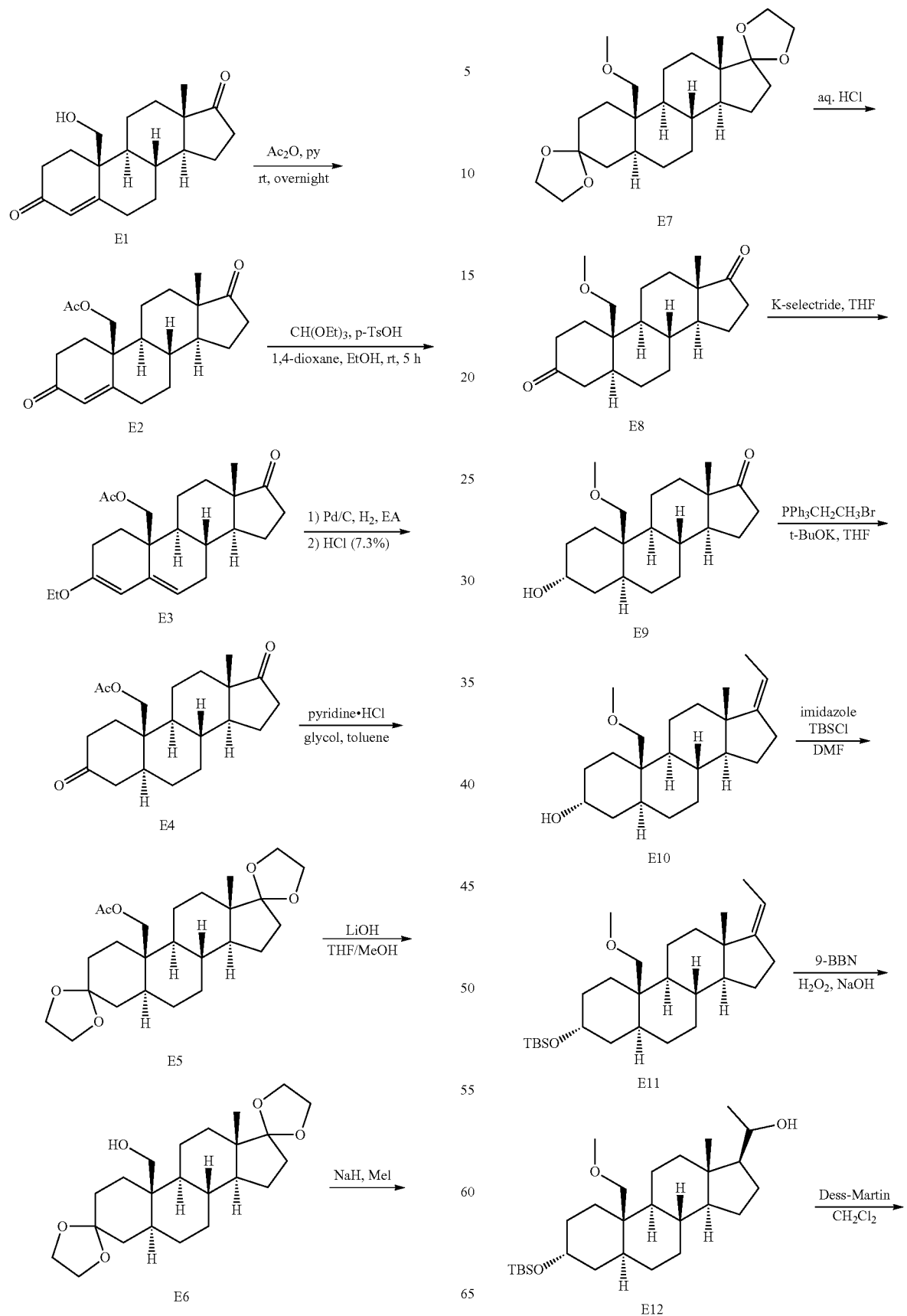

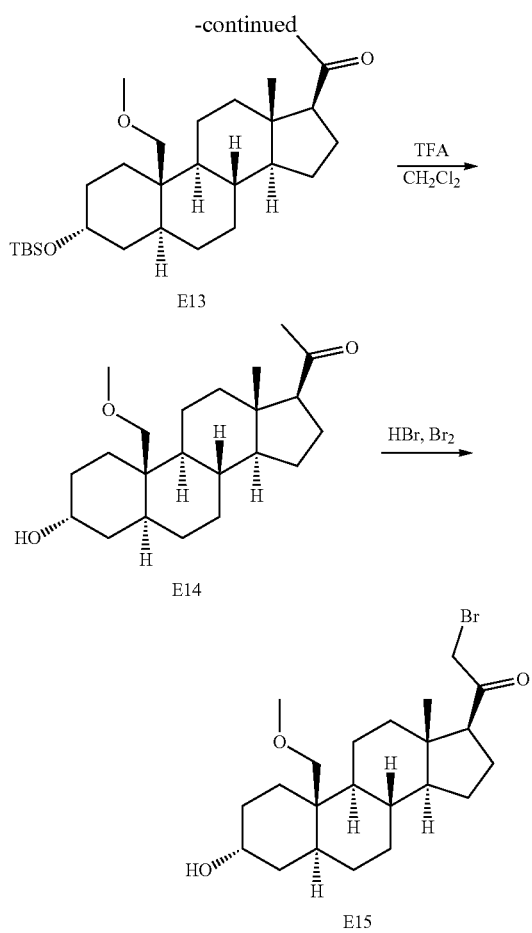

Step 1. Preparation of E2. To a solution of E1 (250.0 g, 0.83 mol) in pyridine (1 L) was added Ac₂O (168.8 g, 1.65 mol) dropwise at 19° C. After the addition was completed, the reaction mixture was stirred at 19° C. overnight. TLC (petroleum ether:ethyl acetate=1:1) showed that the reaction was completed. Then the reaction mixture was concentrated in vacuum, the residue was poured to water and extracted with dichloromethane (3×500 mL), the organic layers were washed with 2 N HCl (200 mL), saturated NaHCO₃(300 mL), brine and dried over anhydrous sodium sulfate, filtered, concentrated to give the crude target product E2 (283.7 g, 99.7%) as brown oil.

¹H NMR (E2): (400 MHz, CDCl3) δ 5.95-5.90 (m, 1H), 4.70-4.64 (m, 1H), 4.20-4.13 (m, 1H), 2.68-2.55 (m, 1H), 2.54-2.30 (m, 5H), 2.15-1.90 (m, 6H), 1.90-1.75 (m, 4H), 1.63-1.38 (m, 2H), 1.33-1.07 (m, 4H), 0.90 (s, 3H).

Step 2. Preparation of E3. To a solution of E2 (250.0 g, 0.73 mol) in 1,4-dioxane (700 mL) and EtOH (467 mL) was added CH(OEt)₃ (227.2 g, 1.53 mol) and p-TsOH (2.8 g, 14.60 mmol) at 29° C. After the addition was completed, the reaction mixture was stirred for 1 hr at 29° C. TLC (petroleum ether:ethyl acetate=3:1) showed that the reaction was completed. Then the reaction mixture was quenched with saturated NaHCO₃ (300 mL) and poured to water, extracted with EtOAc (3×500 mL), the organic layers were washed with brine and dried over anhydrous sodium sulfate, filtered, concentrated, recrystallized from petroleum ether:ethyl acetate=10:1 to give the target product E3 (155.8 g, 57.6%) as a white solid. ¹H NMR (E3): (400 MHz, CDCl3) δ 5.42-5.38 (m, 1H), 5.15-5.10 (m, 1H), 4.46-4.50 (m, 1H), 4.32-4.25 (m, 1H), 4.05-3.98 (m, 1H), 3.85-3.70 (m, 2H), 2.53-2.42 (m, 1H), 2.37-2.20 (m, 3H), 2.18-1.91 (m, 7H), 1.90-1.72 (m, 3H), 1.62-1.48 (m, 2H), 1.40-1.20 (m, 6H), 1.20-1.12 (m, 1H), 0.90 (s, 3H).

Step 3. Preparation of E4. To a solution of E3 (30.0 g, 80.54 mmol) in EtOAc (400 mL) was added Pd/C (1.5 g, 50% water) under N₂. The reaction mixture was degassed under vacuum and purged with H₂ several times. Then the reaction mixture was stirred for 1 hr at 15° C. under H₂ atmosphere. Then it was filtered and the filtrate was stirred at 15° C., 10% HCl (100 mL) was added and the reaction mixture was stirred for 1 hr at 15° C. TLC (petroleum ether:ethyl acetate=3:1) showed that the reaction was completed. The reaction mixture was poured to water and extracted with EtOAc (3×200 mL), the organic layers were washed with saturated NaHCO₃, brine and dried over anhydrous sodium sulfate, filtered, concentrated and purified by silica gel column (petroleum ether:ethyl acetate=10:1-3:1) to give the product E4 (33.0 g, yield: 59.1%) as colorless oil. ¹H NMR (E4): (400 MHz, CDCl3) δ 4.75-4.50 (m, 1H), 4.45-4.38 (m, 1H), 2.55-2.35 (m, 5H), 2.31-2.20 (m, 1H), 2.15-2.05 (m, 4H), 2.05-1.65 (m, 6H), 1.60-1.15 (m, 7H), 1.15-1.00 (m, 1H), 0.95-0.85 (m, 4H).

Step 4. Preparation of E5. To a solution of E4 (31.0 g, 89.48 mmol) and ethane-1,2-diol (50 mL) in toluene (200 mL) was added cat. amount of pyridine·HCl (0.3 g, 2.60 mmol) at 16° C. After the addition was completed, the reaction mixture was heated to reflux and removed water by Dean-Stark trap for 18 hr. TLC (petroleum ether:ethyl acetate=3:1) showed that the reaction was completed. Then the reaction mixture was cooled to 16° C., poured to water, and extracted with EtOAc (3×100 mL), the organic layers were washed with brine and dried over anhydrous sodium sulfate, filtered, concentrated to give the crude product E5 (36.9 g, yield: 94.8%) as a white solid, which was used for next step. ¹H NMR (E5): (400 MHz, CDCl3) δ 4.40-4.30 (m, 2H), 4.20-4.10 (m, 2H), 4.00-3.80 (m, 8H), 2.20-1.90 (m, 5H), 1.85-1.05 (m, 20H), 1.05-0.75 (m, 5H).

Step 5. Preparation of E6. To a solution of E5 (55.0 g, 126.56 mmol) in THF (200 mL) and MeOH (50 mL) was added 4 N LiOH (94.9 mL, 379.69 mmol) at 20° C. After the addition was completed, the reaction mixture was stirred for 18 hr at 20° C. TLC (petroleum ether:ethyl acetate=3:1) showed that the reaction was completed. Then the reaction mixture was poured to water, and extracted with EtOAc (3×200 mL), the organic layers were washed with brine and dried over anhydrous sodium sulfate, filtered, concentrated to give the crude product E6 (46.3 g, yield: 93.1%) as a white solid. ¹H NMR (E6): (400 MHz, CDCl3) δ 4.00-3.75 (m, 10H), 2.25-2.15 (m, 1H), 2.05-1.90 (m, 1H), 1.85-1.60 (m, 8H), 1.60-1.40 (m, 7H), 1.35-1.00 (m, 5H), 1.00-0.75 (m, 5H).

Step 6. Preparation of E7. To a suspension of 60% NaH (9.6 g, 0.24 mol) in dry THF (100 mL) was added dropwise a solution of compound E6 (46.3 g, 0.12 mol) in dry THF (200 mL) at 25° C. under N₂. The mixture was stirred at for 30 min, then MeI (51.1 g, 0.36 mol) was added dropwise at 25° C. After the addition was completed, the reaction mixture was stirred for 4 hr at 45° C. TLC (petroleum ether:ethyl acetate=3:1) showed that the reaction was completed. The reaction was cooled to room temperature, quenched with saturated NH₄Cl (200 mL), poured to water, extracted with EtOAc (3×200 mL), the organic layers were washed with brine and dried over anhydrous sodium sulfate, filtered, concentrated to give the crude product E7 (50.0 g, crude) as yellow solid. ¹H NMR (E7): (400 MHz, CDCl3) δ 3.95-3.80 (m, 8H), 3.55-3.40 (m, 2H), 3.28 (s, 3H), 2.18-2.10 (m, 1H), 2.01-1.95 (m, 1H), 1.81-1.57 (m, 8H), 1.46-1.37 (m, 8H), 1.29-1.18 (m, 4H), 1.02-0.85 (m, 7H).

Step 7. Preparation of E8. To a solution of compound E7 (50.0 g, 0.12 mol) in THF (200 mL) and acetone (40 mL) was added aqueous 2 N HCl (40 mL). After the addition was completed, the reaction mixture was stirred for 18 hr at 25° C. TLC (petroleum ether:ethyl acetate=3:1) indicated the reaction was completed. Then the reaction mixture was poured to water, extracted with EtOAc (3×200 mL), the organic layers were washed with saturated $NaHCO_3$, brine and dried over anhydrous sodium sulfate, filtered, concentrated to give the crude product E8 (41.0 g, crude) as a yellow solid which was used to the next step directly. $^1H$ NMR (E8): (400 MHz, CDCl3) δ 3.73-3.58 (m, 2H), 3.34 (s, 3H), 2.55-2.40 (m, 3H), 2.42-2.30 (m, 1H), 2.20-1.65 (m, 8H), 1.60-1.20 (m, 10H), 1.10-0.75 (m, 7H).

Step 8. Preparation of E9. To a solution of E8 (40.0 g, 125.7 mmol) in dry THF (500 mL) was added dropwise K-selectride (151 mL, 150.8 mmol, 1 M in THF) at −78° C. under $N_2$. After the addition was completed, the reaction mixture was stirred for 3 hr at −78° C. TLC (petroleum ether:ethyl acetate=3:1) indicated the reaction was completed. The reaction mixture was slowly quenched with 30% $H_2O_2$ (17.1 g, 150.5 mmol) at −78° C., then reaction mixture was poured to saturate $NH_4Cl$, extracted with EtOAc (3×100 mL). The organic phase was washed with saturated $Na_2S_2O_3$, brine, dried over sodium sulfate and evaporated to give the crude product. The crude product was purified by washing with PE:EtOAc=10:1 to give the target product E9 (23.5 g, 58%) as a white solid. $^1H$ NMR (E9): (400 MHz, CDCl3) 54.10 (m, 1H), 3.52 (d, 1H), 3.42 (d, 1H), 3.30 (s, 3H), 2.50-2.40 (m, 1H), 2.16-2.03 (m, 1H), 1.98-1.90 (m, 2H), 1.86-1.64 (m, 10H), 1.55-1.47 (m, 3H), 1.32-1.17 (m, 6H), 1.12-0.95 (m, 1H), 0.88-0.81 (m, 4H).

Step 9. Preparation of E10. To a suspension of $Ph_3PEtBr$ (25.97 g, 70 mmol) in dry THF (100 mL) was added dropwise a solution of t-BuOK (7.70 g, 70 mmol) in dry THF (50 mL) under $N_2$ at 0° C. The mixture was stirred at room temperature for 1.5 h. Then a solution of E9 (2.8 g, 8.75 mmol) in THF (30 mL) was added dropwise and the resulting mixture was stirred at 60° C. for 12 h. TLC (petroleum ether:ethyl acetate=3:1) indicated that the starting material was consumed completely. The reaction was quenched with saturated aqueous $NH_4Cl$ solution (100 mL) and extracted with EtOAc (50 mL×2). The combined organic phases were dried over $Na_2SO_4$ and concentrated in vacuum. The residue was purified by column chromatography on silica gel (eluent: petroleum ether:ethyl acetate=40:1) to give E10 (1.8 g, 62%) as white powder. $^1H$ NMR (E10): (400 MHz, CDCl3) δ 5.15-5.05 (m, 1H), 4.13-4.05 (m, 1H), 3.55-3.35 (m, 2H), 3.30 (s, 3H), 2.45-1.90 (m, 4H), 1.80-1.35 (m, 13H), 1.30-0.95 (m, 8H), 0.90 (s, 3H), 0.85-0.70 (m, 1H).

Step 10. Preparation of E11. To a solution of E10 (1.8 g, 5.41 mmol) in DMF (20 mL) was added imidazole (737 mg, 10.82 mmol) and TBSCl (1.22 g, 8.12 mmol). The mixture was stirred overnight at room temperature. TLC (petroleum ether:ethyl acetate=3:1) showed the starting material was consumed completely. The reaction was diluted with EtOAc (20 mL) and washed with brine (20 mL). The organic layer was dried over anhydrous sodium sulfate and concentrated under vacuum. The crude product was purified by silica gel chromatography on silica gel eluted with petroleum ether to give E11 (2.33 g, 96%) as white solid. $^1H$ NMR (E11): (400 MHz, CDCl3) δ 5.11-5.09 (m, 1H), 4.01-4.00 (m, 1H), 3.50-3.39 (m, 2H), 3.29 (s, 3H), 2.40-2.30 (m, 1H), 2.25-2.10 (m, 2H), 1.90-1.82 (m, 1H), 1.53-1.40 (m, 5H), 1.30-0.95 (m, 8H), 0.89-0.88 (m, 9H), 0.86-0.75 (m, 2H), 0.02-0.01 (m, 6H).

Step 11. Preparation of E12. To a solution of 9-BBN (81 mL, 40.84 mmol) was added E11 (2.33 g, 5.06 mmol) in THF (20 mL). The mixture was stirred at 60° C. for 16 h. Then the mixture was cooled to room temperature and added 10% NaOH aqueous (40 mL) and $H_2O_2$ (20 mL) dropwise. After stirred for 1 h, the mixture was quenched with aqueous $Na_2S_2O_3$ and extracted with EtOAc (100 mL). The organic layers combined and dried over anhydrous sodium sulfate. The organic phase was concentrated under vacuum. The crude product was purified by column chromatography on silica gel (eluent: petroleum ether:ethyl acetate=40:1) to give E12 (2.3 g, 90%) as white solid. $^1H$ NMR (E12): (400 MHz, CDCl3) δ 4.00-3.99 (m, 1H), 3.71-3.65 (m, 1H), 3.49-3.38 (m, 2H), 3.28 (s, 3H), 2.42-2.39 (m, 1H), 1.89-1.82 (m, 5H), 1.75-1.46 (m, 17H), 1.38-1.00 (m, 14H), 0.89 (s, 9H), 0.68 (s, 3H), 0.00 (m, 6H).

Step 12. Preparation of E13. To a solution of E12 (2.1 g, 4.52 mmol) in $CH_2Cl_2$ (20 mL) was added Dess-Martin (3.8 g, 9.04 mmol). The mixture was stirred at 12° C. for 5 h. TLC (petroleum ether:ethyl acetate=3:1) showed the starting material was consumed completely. The mixture was quenched with a mixture solution of $Na_2S_2O_3/NaHCO_3$ (3:1, 12 g) in water (50 mL). The mixture was extracted with EtOAc (200 mL). The organic layers was dried over anhydrous sodium sulfate. The organic phase was concentrated under vacuum to afford E13 as white solid (2.3 g, crude). $^1H$ NMR (E13): (400 MHz, CDCl3) 4.00-3.99 (m, 1H), 3.49-3.38 (m, 2H), 3.27 (s, 3H), 2.41-2.39 (m, 2H), 2.20-2.12 (m, 1H), 2.11 (s, 3H), 2.00-1.95 (m, 1H), 1.89-1.84 (m, 3H), 1.75-1.45 (m, 14H), 1.42-0.92 (m, 11H), 0.89 (s, 9H), 0.87-0.82 (m, 1H), 0.62 (s, 3H), 0.00 (m, 6H).

Step 13. Preparation of E14. To a solution of E13 (230 mg, 0.48 mmol) in $CH_2Cl_2$ (6 mL) was added TFA (1 mL). The mixture was stirred at 15° C. for 30 min. TLC (petroleum ether:ethyl acetate=3:1) showed the starting material was consumed completely. The reaction was quenched with aqueous $NaHCO_3$ (10 mL) and extracted with EtOAc (30 mL×2). The organic layer was dried over anhydrous sodium sulfate. The organic phase was concentrated under vacuum. The crude product was purified by column chromatography on silica gel (eluent: petroleum ether:ethyl acetate=10:1) to give E14 (166 mg, 95%) as white solid. $^1H$ NMR (E14): (400 MHz, CDCl3) 4.12-4.11 (m, 1H), 3.52-3.42 (m, 2H), 3.30 (s, 3H), 2.58-2.53 (m, 1H), 2.20-2.16 (m, 1H), 2.13 (s, 3H), 2.06-1.97 (m, 2H), 1.75-1.60 (m, 8H), 1.59-1.10 (m, 11H), 1.03-0.92 (m, 1H), 0.90-0.82 (m, 1H), 0.63 (s, 3H).

Step 14. Preparation of E15. To a solution of E14 (2 g, 5.21 mmol) in MeOH (25 mL) was added HBr (5 drops) and $Br_2$ (8 mL). The mixture was stirred at room temperature for 4 h. LC-MS showed the starting material was consumed. The reaction was diluted with $H_2O$ (20 mL) and extracted with EtOAc (50 mL). The organic layer was dried over anhydrous sodium sulfate. The organic phase was concentrated under vacuum. The crude product was purified by column chromatography on silica gel (eluent: petroleum ether:ethyl acetate=10:1) give E15 (1 g, 41%) as white solid. $^1H$-NMR showed there was 70% of E15 and 30% of E14. $^1H$ NMR (E15): (400 MHz, CDCl3) 4.11-4.10 (m, 1H), 3.94-3.88 (m, 2H), 3.49-3.39 (m, 2H), 3.28 (s, 3H), 2.84-2.79 (m, 1H), 2.20-2.15 (m, 1H), 2.04-1.87 (m, 2H), 1.74-1.60 (m, 8H), 1.57-1.16 (m, 12H), 1.03-0.76 (m, 2H), 0.64 (s, 3H).

Example 55. Preparation of Compounds 90 & 91

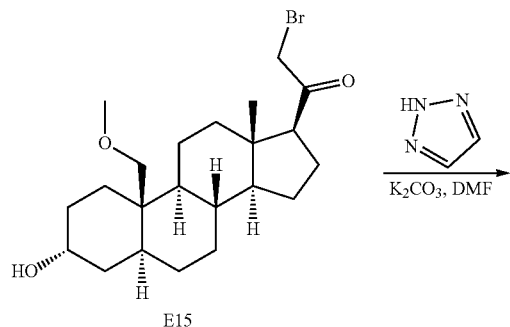

To a solution of K$_2$CO$_3$ (952 mg, 6.9 mmol) in DMF (20 mL) was added 2H-1,2,3-triazole (969 mg, 13.8 mmol). The mixture was stirred at room temperature for 30 min, and then was added a solution of E15 (1 g, 2.3 mmol) in DMF (20 mL). The mixture was stirred at room temperature overnight. TLC (petroleum ether:ethyl acetate=1:1) showed the starting material was consumed completely. The reaction was diluted with EtOAc (50 mL) and washed with brine (50 mL). The organic layer was dried over anhydrous sodium sulfate. The organic phase was concentrated under vacuum. The crude product was purified by column chromatography on silica gel (eluent: petroleum ether:ethyl acetate=5:1) give 90 (204 mg, 21%) as white powder and 91 (437 mg, 45%) as white powder. $^1$H NMR (90): (400 MHz, CDCl3) 7.70 (s, 2H), 5.31-5.20 (m, 2H), 4.13-4.12 (m, 1H), 3.52-3.43 (m, 2H), 3.31 (s, 3H), 2.63-2.58 (m, 1H), 2.24-2.22 (m, 1H), 2.12-1.97 (m, 2H), 1.78-1.62 (m, 9H), 1.54-1.10 (m, 10H), 1.09-0.96 (m, 1H), 0.91-0.84 (m, 1H), 0.75 (s, 3H). $^1$H NMR (91): (400 MHz, CDCl3) 7.75 (s, 1H), 7.63 (s, 1H), 5.27-5.11 (m, 2H), 4.13-4.10 (m, 1H), 3.50-3.40 (m, 2H), 3.28 (s, 3H), 2.67-2.64 (m, 1H), 2.26-2.18 (m, 1H), 2.08-1.92 (m, 2H), 1.74-1.25 (m, 15H), 1.19-0.87 (m, 8H), 0.69 (s, 3H).

Example 56. Preparation of Compound 92

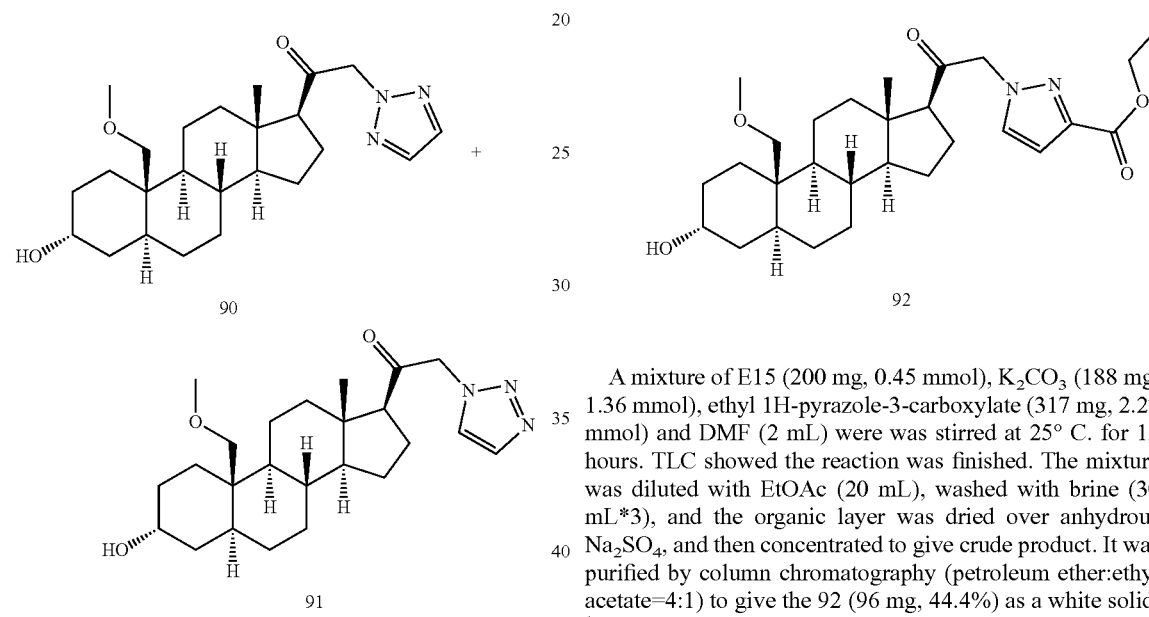

A mixture of E15 (200 mg, 0.45 mmol), K$_2$CO$_3$ (188 mg, 1.36 mmol), ethyl 1H-pyrazole-3-carboxylate (317 mg, 2.27 mmol) and DMF (2 mL) were was stirred at 25° C. for 12 hours. TLC showed the reaction was finished. The mixture was diluted with EtOAc (20 mL), washed with brine (30 mL*3), and the organic layer was dried over anhydrous Na$_2$SO$_4$, and then concentrated to give crude product. It was purified by column chromatography (petroleum ether:ethyl acetate=4:1) to give the 92 (96 mg, 44.4%) as a white solid. $^1$H NMR (92): (400 MHz, CDCl3) δ 7.42 (d, J=2.4 Hz, 1H), 6.86 (d, J=2.4 Hz, 1H), 5.05-4.95 (m, 2H), 4.39 (q, J=7.2 Hz, 2H), 4.20-4.10 (m, 1H), 3.49-3.39 (m, 2H), 3.28 (s, 3H), 2.60-2.55 (m, 1H), 2.22-1.91 (m, 3H), 1.75-1.50 (m, 6H), 1.45-1.10 (m, 15H), 1.05-0.92 (m, 1H), 0.90-0.84 (m, 1H), 0.70 (s, 3H)

Example 57. Preparation of Compound 93

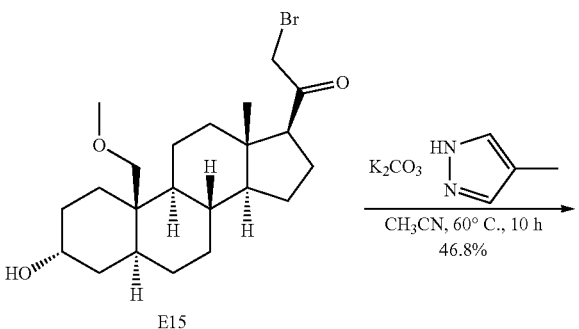

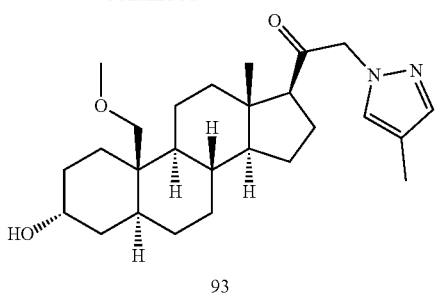

93

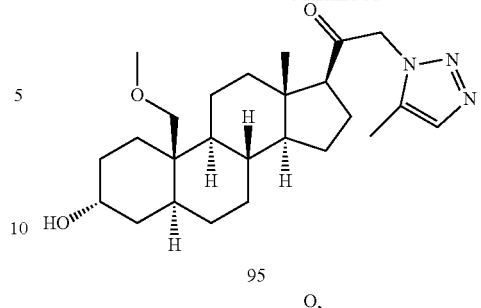

95

To a solution of E15 (200 mg, 0.47 mmol) in CH₃CN (15 mL) at 29° C., then K₂CO₃ (194.01 g, 1.4 mmol) and 4-methyl-1H-pyrazole (192.09 mg, 2.34 mmol) was added in the mixture at 29° C. The solution was stirred at 60° C. for 10 h. After the TLC showed that the starting material was consumed completely, then the mixture was concentrated. The mixture was extracted with CH₂Cl₂ (30 mL) and NaCl (aq) (20 mL*2). The combined organic layers were dried over Na₂SO₄ and concentrated to give crude product. The product was purified by column chromatograph on silica gel eluted with (petroleum ether/ethyl acetate=10:1 to 6:1) to give 93 (94.4 mg, yield: 46.81%). ¹H NMR (93): (400 MHz, CDCl3) δ 7.36 (s, 1H), 7.18 (s, 1H), 4.85 (dd, J=34 Hz, J=17.6 Hz, 2H), 4.15-4.10 (m, 1H), 3.47 (dd, J=28.8 Hz, J=10 Hz, 2H), 3.31 (s, 3H), 2.62-2.55 (m, 1H), 2.28-2.18 (m, 1H), 2.13-1.97 (m, 5H), 1.78-1.64 (m, 8H), 1.48-1.13 (m, 10H), 1.04-0.84 (m, 2H), 0.71 (s, 3H)

Example 58. Preparation of Compounds 94, 95 & 96

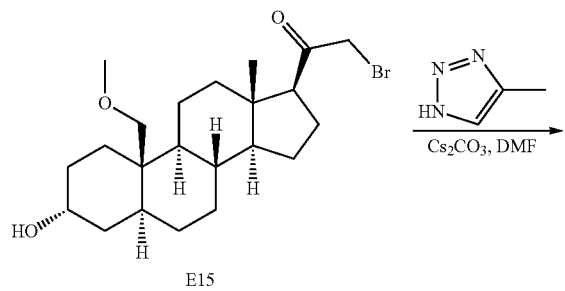

96

To a solution of E15 (150 mg, 0.35 mmol) in DMF (6 mL) was added Cs₂CO₃ (343 mg, 1.05 mmol) and 4-methyl-1, 2, 3-triazole (145 mg, 1.75 mmol) at 28° C. The reaction mixture was stirred at the same temperature for 6 h. TLC showed that the starting material was consumed completely. The mixture was poured into water (20 mL), and extracted with EtOAc (10 mL*2). The combined organic layers were dried over Na₂SO₄ and concentrated to give crude product. The crude product was purified by pre-HPLC to give pure 94 (35.8 mg) and a mixture of 95 and 96 (20 mg). Then the mixture was purified by SFC to give 95 (3.9 mg) and 96 (5.6 mg). Total yield: 23.7%. The structure of the three targets was confirmed by NOE.

¹H NMR (94): (400 MHz, CDCl3) δ 7.42 (s, 1H), 5.19-5.08 (m, 2H), 4.13-4.09 (m, 1H), 3.53-3.38 (m, 2H), 3.29 (s, 3H), 2.61-2.54 (m, 1H), 2.33 (s, 3H), 2.26-2.15 (m, 1H), 2.11-1.95 (m, 2H), 1.78-1.61 (m, 9H), 1.52-1.06 (m, 9H), 1.04-0.81 (m, 2H), 0.72 (s, 3H).

¹H NMR (95): (400 MHz, CDCl3) δ 7.50 (s, 1H), 5.23-5.05 (m, 2H), 4.15-4.06 (m, 1H), 3.58-3.42 (m, 2H), 3.31 (s, 3H), 2.71-2.61 (m, 1H), 2.33-2.14 (m, 6H), 2.12-1.96 (m, 4H), 1.34-1.18 (m, 10H), 1.06-0.83 (m, 6H), 0.70 (s, 3H).

¹H NMR (96): (400 MHz, CDCl3) δ 7.35 (s, 1H), 5.22-5.02 (m, 2H), 4.15-4.10 (m, 1H), 3.56-3.39 (m, 2H), 3.31 (s, 3H), 2.67-2.61 (m, 1H), 2.39 (s, 3H), 2.29-1.88 (m, 10H), 1.33-1.22 (m, 10H), 1.02-0.97 (m, 1H), 0.92-0.84 (m, 2H), 0.70 (s, 3H).

Example 59. Preparation of 97 and 98

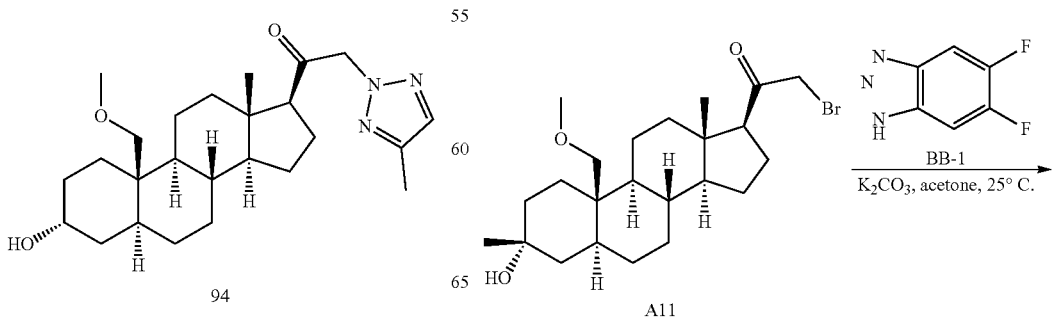

-continued

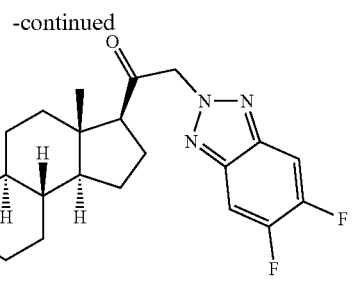

97

98

To a solution of A11 (360 mg, 0.82 mmol) in acetone (2.5 mL) was added 5,6-difluoro-2H-benzo[d] [1,2,3]triazole (BB-1) (190 mg, 1.23 mmol) and $K_2CO_3$ (230 mg, 1.64 mmol). The mixture was stirred at 30° C. for 3 hours. TLC showed the reaction was compeleted. To the mixture was added water (2 mL), extracted with EtOAc (5 mL*2). The combined organic layer was concentrated in vacuum, purified by prep-HPLC to give 97 (25 mg, 6%) and 98 (141 mg, 33%) as a white solid.

$^1$H NMR (97): (400 MHz, CDCl$_3$) δ 7.59 (t, J=8.4 Hz, 2H), 5.53-5.42 (m, 2H), 3.48-3.36 (m, 2H), 3.29 (s, 3H), 2.65 (t, J=8.4 Hz, 1H), 2.27-2.02 (m, 3H), 1.80-0.85 (m, 23H), 0.75 (s, 3H). LCMS (97): $t_R$=1.366 min in 2 min chromatography, 10-80 AB, purity 96.3%, MS ESI calcd. for $C_{29}H_{40}F_2N_3O_3$ [M+H]$^+$ 516, found 498 ([M+H−18]$^+$).

$^1$H NMR (98): (400 MHz, CDCl$_3$) δ 7.83 (t, J=8.0 Hz, 1H), 7.12 (t, J=7.6 Hz, 1H), 5.43-5.32 (m, 2H), 3.50-3.37 (m, 2H), 3.30 (s, 3H), 2.80-2.68 (m, 1H), 2.30-2.02 (m, 3H), 1.80-0.85 (m, 23H), 0.75 (s, 3H). LCMS (98): $t_R$=1.317 min in 2 min chromatography, 10-80 AB, purity 99.6%, MS ESI calcd. for $C_{29}H_{40}F_2N_3O_3$ [M+H]$^+$ 516, found 516.

SCHEME A

General Procedure for the Preparation of Compounds 99-146

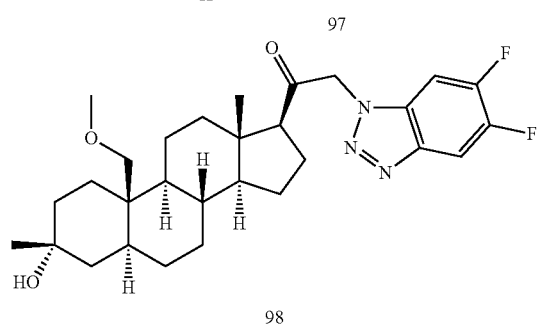

A11

| Example | Structure of BB-n | Product(s) | NMR/LC-MS |
|---|---|---|---|
| 60 | 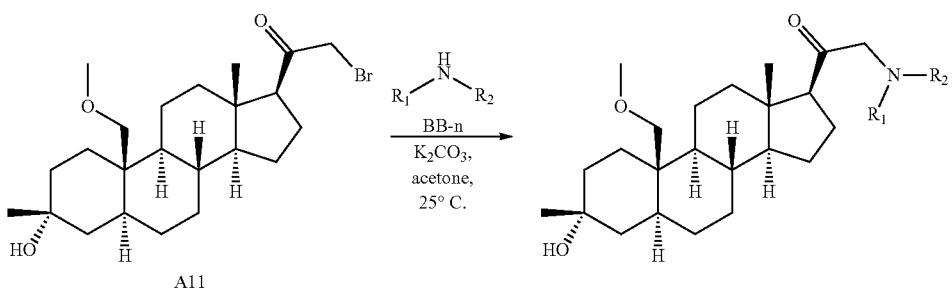 BB-16 | 99 | $^1$H NMR (400 MHz, CDCl$_3$) δ 8.74 (d, J = 2.4 Hz, 1H), 8.23 (d, J = 2.4 Hz, 1H), 5.60-5.49 (m, 2H), 3.49-3.37 (m, 2H), 3.30 (s, 3H), 2.68 (t, J = 8 Hz, 1H), 2.23-2.03 (m, 3H), 1.79-0.88 (m, 23H), 0.77 (s, 3H). LCMS $t_R$ = 1.486 min in 2 min chromatography, 10-80AB, purity 100.0%, MS ESI calcd. for C28H40ClN4O3 [M + H]$^+$ 515, found 515. |
|  |  | 100 | $^1$H NMR (400 MHz, CDCl$_3$) δ 8.59 (d, J = 2.0 Hz, 1H), 8.37 (d, J = 2.0 Hz, 1H), 5.56-5.45 (m, 2H), 3.51-348 (m, 1H), 3.40-3.37 (m, 1H), 3.31 (s, 3H), 2.27 (t, J = 8.8 Hz, 1H), 2.25-2.22 (m, 2H), 2.10-1.95 (m, 1H), 1.78-1.28 (m, 12H), 1.28-0.80 (m, 11H), 0.79-0.72 (s, 3H). LCMS $t_R$ = 1.495 min in 2 min chromatography, 10-80AB, purity 99.7%, MS ESI calcd. for C28H40ClN4O3 [M + H]$^+$ 515, found 515. |

SCHEME A-continued

General Procedure for the Preparation of Compounds 99-146

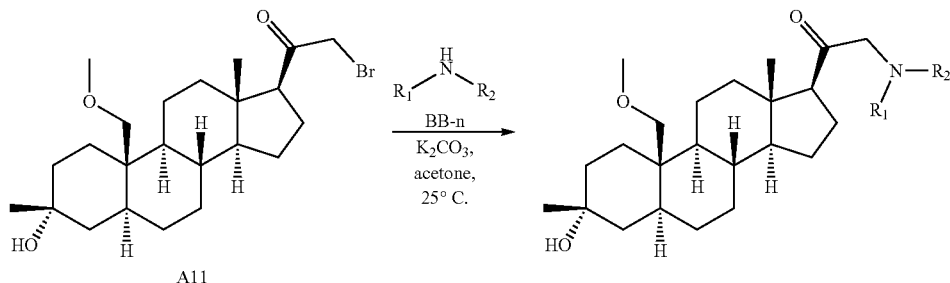

| Example | Structure of BB-n | Product(s) | NMR/LC-MS |
|---|---|---|---|
|  |  | 101 | ¹H NMR (400 MHz, CDCl₃) δ 8.68 (s, 1H), 7.77 (s, 1H), 5.50-5.36 (m, 2H), 3.49-3.47 (m, 1H), 3.39-3.37 (m, 1H), 3.30 (s, 3H), 2.60-2.80 (m, 1H), 2.22-2.03 (m, 3H), 1.90-1.38 (m, 13H), 1.34-1.18 (m, 8H), 1.15-0.73 (m, 5H). LCMS $t_R$ = 1.446 min in 2 min chromatography, 10-80AB, purity 98.9%, MS ESI calcd. for C28H40ClN4O3 [M + H]⁺ 515, found 515. |
| 61 | BB-19 | 102 | ¹H NMR (400 MHz, CDCl₃) δ 8.59 (d, J = 2.4 Hz, 1H), 8.46 (d, J = 2.4 Hz, 1H), 8.35 (s, 1H), 5.38-5.24 (m, 2H), 3.50-3.48 (m, 1H), 3.40-3.37 (m, 1H), 3.31 (s, 3H), 2.74-2.71 (m, 1H), 2.25-2.22 (m, 3H), 1.80-0.88 (m, 23H), 0.78-0.65 (m, 3H) LCMS $t_R$ = 1.376 min in 2 min chromatography, 10-80AB, purity 92.9%, MS ESI calcd. for C28H41N4O3 [M + H]⁺ 481, found 481. |
|  |  | 103 | ¹H NMR (400 MHz, CDCl₃) δ 8.64 (d, J = 1.6 Hz, 1H), 8.56 (d, J = 1.6 Hz, 1H), 8.26 (s, 1H), 5.37-5.21 (m, 2H), 3.49-3.46 (m, 1H), 3.39-3.37 (m, 1H), 3.33 (s, 3H), 2.75-2.65 (m, 1H), 2.17-2.01 (m, 3H), 1.76-0.80 (m, 23H) 0.74 (s, 3H) LCMS $t_R$ = 1.281 min in 2 min chromatography, 10-80AB, purity 99.1%, MS ESI calcd. for C28H41N4O3 [M + H]⁺ 481, found 481. |
| 62 | BB-4 | 104 | ¹H NMR (400 MHz, CDCl₃) δ 7.90 (d, J = 2.0 Hz, 1H), 7.72 (s, 1H), 7.28-7.26 (m, 1H), 5.58-5.48 (m, 2H), 3.49-3.47 (m, 1H), 3.49-3.47 (m, 1H), 3.29 (s, 3H), 2.67 (t, J = 8.4 Hz, 1H), 2.25-1.80 (m, 3H), 1.75-0.81 (m, 23H), 0.77 (s, 3H). LCMS $t_R$ = 1.618 min in 2 min chromatography, 10-80AB, purity 98.7%, MS ESI calcd. for C30H41F3N3O4 [M + H]⁺ 564, found 564. |

SCHEME A-continued

General Procedure for the Preparation of Compounds 99-146

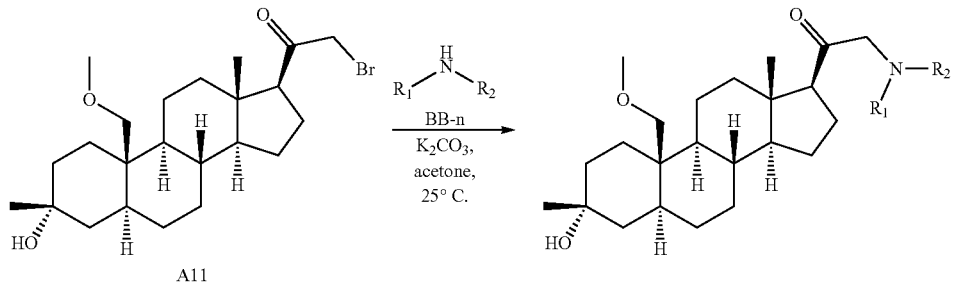

A11 → (product with BB-n, K₂CO₃, acetone, 25° C.)

| Example | Structure of BB-n | Product(s) | NMR/LC-MS |
|---|---|---|---|
|  |  | 144 | $^1$H NMR (400 MHz, CDCl3) δ 8.10 (d, J = 9.2 Hz, 1H), 7.27-7.25 (m, 1H), 7.19 (s, 1H), 5.54-5.35 (m, 2H), 3.50-3.48 (m, 1H), 3.40-3.37 (m, 1H), 3.30 (s, 3H), 2.75-2.73 (m, 1H), 2.27-2.01 (m, 3H), 1.80-0.80 (m, 23H), 0.74 (s, 3H). LCMS $t_R$ = 1.002 min in 1.5 min chromatography, 5-95AB, purity 96.4%, MS ESI calcd. for C30H41F3N3O4 [M + H]⁺ 564, found 564. |
|  |  | 146 | $^1$H NMR (400 MHz, CDCl3) δ 7.94 (s, 1H), 7.40-7.34 (m, 2H), 5.49-5.38 (m, 2H), 3.50-3.48 (m, 1H), 3.40-3.37 (m, 1H), 3.31 (s, 3H), 2.76-2.73 (m, 1H), 2.27-2.01 (m, 3H), 1.80-0.80 (m, 23H), 0.75 (s, 3H). LCMS $t_R$ = 0.998 min in 1.5 min chromatography, 5-95AB, purity 94.7%, MS ESI calcd. for C30H41F3N3O4 [M + H]+ 564, found 564. |
| 63 | BB-21 | 105 | $^1$H NMR (400 MHz, CDCl$_3$) δ 7.98 (s, 1H), 7.72 (d, J = 1.6 Hz, 1H), 7.34-7.31 (m, 1H), 7.14 (d, J = 8.8 Hz, 1H), 5.17-5.07 (m, 2H), 3.50-3.47 (m, 1H), 3.39-3.37 (m, 1H), 3.30 (s, 3H), 2.64 (t, J = 8.4 Hz, 1H), 2.12-2.01 (m, 3H), 1.74-0.80 (m, 23H), 0.74 (s, 3H). LCMS $t_R$ = 1.547 min in 2 min chromatography, 10-80AB, purity 100.0%, MS ESI calcd. for C30H42ClN2O3 [M + H]⁺ 513, found 513. |
|  |  | 106 | $^1$H NMR (400 MHz, CDCl$_3$) δ 7.88 (s, 1H), 7.64-7.62 (m, 2H), 7.23-7.20 (m, 1H), 5.24-5.12 (m, 2H), 3.49-3.46 (m, 1H), 3.39-3.47 (m, 1H), 3.29 (s, 3H), 2.70-2.60 (m, 1H), 2.18-0.79 (m, 26H), 0.73 (s, 3H). LCMS $t_R$ = 1.506 min in 2 min chromatography, 10-80AB, purity 99.8%, MS ESI calcd. for C30H42ClN2O3 [M + H]⁺ 513, found 513. |

SCHEME A-continued

General Procedure for the Preparation of Compounds 99-146

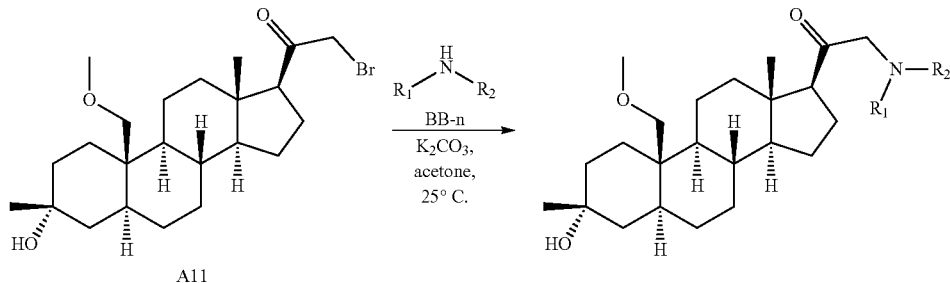

| Example | Structure of BB-n | Product(s) | NMR/LC-MS |
|---|---|---|---|
| 64 | BB-23 | 107 | ¹H NMR (400 MHz, CDCl₃) δ 8.00 (s, 1H), 7.38-7.35 (m, 1H), 7.17-7.14 (m, 2H), 5.18-5.09 (m, 2H), 3.50-3.47 (m, 1H), 3.39-3.37 (m, 1H), 3.30 (s, 3H), 2.64 (t, J = 8.4 Hz, 1H), 2.21-2.03 (m, 3H), 1.75-0.80 (m, 23H), 0.74 (s, 3H). LCMS $t_R$ = 1.479 min in 2 min chromatography, 10-80AB, purity 99.5%, MS ESI calcd. for C30H42FN2O3 [M + H]⁺ 497, found 497. |
|  |  | 108 | ¹H NMR (400 MHz, CDCl3) δ 7.89 (s, 1H), 7.68 (dd, J = 4.4 Hz, J =8.6 Hz, 1H), 7.23-7.20 (m, 1H), 7.10-7.08 (m, 1H), 5.25-5.15 (m, 2H), 3.49-3.46 (m, 1H), 3.39-3.37 (m, 1H), 3.30 (s, 3H), 2.65 (t, J = 8.4 Hz, 1H), 2.30-2.08 (m, 3H), 1.75-0.80 (m, 23H), 0.74 (s, 3H). LCMS $t_R$ = 1.455 min in 2 min chromatography, 10-80AB, purity 96.5%, MS ESI calcd. for C30H42FN2O3 [M + H]⁺ 497, found 497. |
| 65 | BB-8 | 109 | ¹H NMR (400 MHz, CDCl₃) δ 7.63 (d, J = 8.6 Hz, 1H), 7.36 (dd, J = 6.4 Hz, J = 8.6 Hz, 1H), 5.54-5.52 (m, 2H), 3.49-3.47 (m, 1H), 3.30 (s, 3H), 3.40-3.37 (m, 1H), 2.70-2.60 (m, 1H), 2.30-1.90 (m, 3H), 1.80-0.80 (m, 23H), 0.77 (s, 3H). LCMS $t_R$ = 1.434 min in 2 min chromatography, 10-80AB, purity 99.2%, MS ESI calcd. for C29H40ClFN3O3 [M + H]⁺ 532, found 514 [M + H − H₂O]⁺. |
|  |  | 138 | ¹H NMR (400 MHz, CDCl₃) δ 7.48 (dd, J = 6.0 Hz, J = 8.8 Hz, 1H), 7.07 (d, J = 7.6 Hz, 1H), 5.46-5.36 (m, 2H), 3.50-3.48 (m, 1H), 3.40-3.37 (m, 1H), 3.30 (s, 3H), 2.72 (t, J = 8.6 Hz, 1H). 2.30-0.80 (m, 26H), 0.74 (s, 3H). LCMS $t_R$ = 1.374 min in 2 min chromatography, 10-80AB, purity 99.8%, MS ESI calcd. for C29H40ClFN3O3 [M + H]⁺ 532, found 532. |

SCHEME A-continued

General Procedure for the Preparation of Compounds 99-146

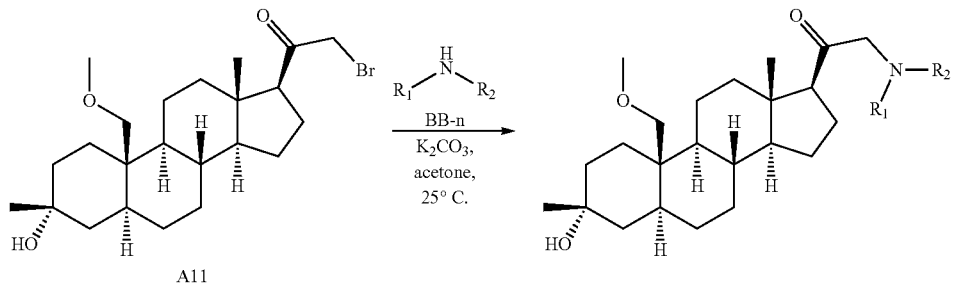

| Example | Structure of BB-n | Product(s) | NMR/LC-MS |
|---|---|---|---|
| 66 | BB-22 | 110 | ¹H NMR (400 MHz, CDCl₃) δ 8.01 (s, 1H), 7.68 (dd, J = 5.2 Hz, J = 8.4 Hz, 1H), 6.96-6.84 (m, 2H), 5.14-5.04 (m, 2H), 3.66-3.47 (m, 1H), 3.39-3.37 (m, 1H), 3.29 (s, 3H), 2.65 (t, J = 8.4 Hz, 1H), 2.09-2.03 (m. 3H), 1.80-0.80 (m, 23H), 0.74 (s, 3H). LCMS $t_R$ = 1.480 min in 2 min chromatography, 10-80AB, purity 100.0%, MS ESI calcd. for C30H42FN2O3 [M + H]⁺ 497, found 497. |
|  |  | 111 | ¹H NMR (400 MHz, CDCl₃) δ 7.93 (s, 1H), 7.64 (dd, J = 5.4 Hz, J = 8.8 Hz, 1H), 7.30-7.20 (m, 1H), 6.92-6.87 (m, 1H), 5.23-5.11 (m, 2H), 3.49-3.46 (m, 1H), 3.39-3.37 (m, 1H), 3.29 (s, 3H), 2.65 (t, J = 8.4 Hz, 1H), 2.08-1.90 (m, 3H), 1.80-0.80 (m, 23H) 0.73 (s 3H). LCMS $t_R$ = 1.446 min in 2 min chromatography, 10-80AB, purity 96.7%, MS ESI calcd. for C30H42FN2O3 [M + H]⁺ 497, found 497. |
| 79 | BB-20 | 112 | ¹H NMR (400 MHz, CDCl₃) δ 8.01 (s, 1H), 7.66 (d, J = 8.4 Hz, 1H), 7.20 (s, 1H), 7.13 (d, J = 8.6, 1H), 5.15-5.05 (m, 2H), 3.50-3.47 (m, 1H), 3.40-3.37 (m, 1H), 3.30 (s, 3H), 2.66 (t, J = 8.4, 1H), 2.20-2.05 (m, 4H), 1.80-0.80 (m, 22H), 0.74 (s, 3H). LCMS $t_R$ = 1.548 min in 2 min chromatography, 10-80AB, purity 100.0%, MS ESI calcd. for C30H42ClN2O3 [M + H]⁺ 513, found 513. |
|  |  | 113 | ¹H NMR (400 MHz, CDCl₃) δ 7.93 (s, 1H), 7.70 (s, 1H), 7.61 (d, J = 8.6 Hz, 1H), 7.07-7.04 (m, 1H), 5.30-5.20 (m, 2H), 3.49-3.46 (m, 1H), 3.39-3.37 (m, 1H), 3.29 (s, 3H), 2.65 (t, J = 8.4 Hz, 1H), 2.10-0.80 (m, 26H), 0.72 (s, 3H). LCMS $t_R$ = 1.517 min in 2 min chromatography, 10-80AB, purity 99.7%, MS ESI calcd. for C30H42ClN2O3 [M + H]⁺ 513, found 513. |

SCHEME A-continued

General Procedure for the Preparation of Compounds 99-146

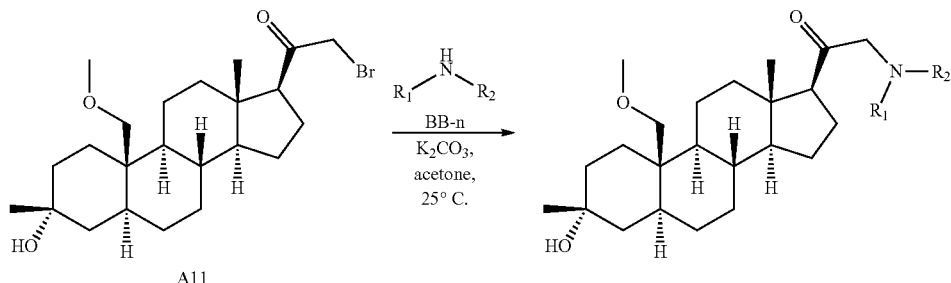

| Example | Structure of BB-n | Product(s) | NMR/LC-MS |
|---|---|---|---|
| 68 | BB-1 | 114 | ¹HNMR (400 MHz, CDCl3) δ 7.39-7.36 (m, 1H), 7.06-7.03 (m, 1H), 5.54-5.35 (m, 2H), 3.50-3.48 (m, 1H), 3.40-3.37 (m, 1H), 3.30 (s, 3H), 2.74-2.70 (m, 1H), 2.27-2.01 (m, 3H), 1.80-0.80 (m, 23H), 0.74 (s, 3H). LCMS $t_R$ = 0.967 min in 1.5 min chromatography, 5-95AB, purity 100.0%, MS ESI calcd. for C29H40F2N3O3 [M + H]⁺ 516, found 516. |
|  |  | 115 | ¹HNMR (400 MHz, CDCl₃) δ 7.82-7.79 (m, 1H), 7.24-7.21 (m, 1H), 5.54-5.35 (m, 2H), 3.50-3.48 (m, 1H), 3.40-3.37 (m, 2.27-2.01 (m, 3H), 1.80-0.80 (m, 23H), 0.75 (s, 3H). LCMS $t_R$ = 0.986 min 1.5 min chromatography, 5-95AB, purity 96.8%, MS ESI calcd. for C29H40F2N3O3 [M + H]⁺ 516, found 516. |
|  |  | 128 | ¹HNMR (400 MHz, CDCl3) δ 7.65-7.62 (m, 1H), 7.29-7.27 (m, 1H), 5.54-5.35 (m, 2H), 3.50-3.48 (m, 1H), 3.40-3.37 (m, 1H), 3.29 (s, 3H), 2.74-2.70 (m, 1H), 2.27-2.01 (m, 3H), 1.80-0.80 (m, 23H), LCMS $t_R$ = 1.012 min in 1.5 min chromatography, 5-95AB, purity 95.6%, MS ESI calcd. for C29H40F2N3O3 [M + H]⁺ 516, found 498 [M + H − H2O]⁺. |
| 69 |  | 116 | ¹H NMR (400 MHz, CDCl₃) δ 5.39-5.29 (m, 2H), 3.47-3.45 (m, 1H), 3.38-3.35 (m, 1H), 3.28 (s, 3H), 2.74-2.60 (m, 1H), 2.55 (s, 3H), 2.27-2.01 (m, 3H), 1.80-0.80 (m, 23H), 0.72 (s, 3H). LCMS $t_R$ = 0.909 min 1.5 min chromatography, 5-95AB, purity 100.0%, MS ESI calcd. for $C_{25}H_{41}N_4O_3$ [M + H]⁺ 445, found 445. |
|  |  | 117 | ¹H NMR (400 MHz, CDCl₃) δ 5.14-5.04 (m, 2H), 3.48-3.45 (m, 1H), 3.38-3.35 (m, 1H), 3.28 (s, 3H), 2.74-2.60 (m, 1H), 2.46 (s, 3H), 2.27-2.01 (m, 3H), 1.80-0.80 (m, 23H), 0.69 (s, 3H). LCMS $t_R$ = 0.882 min in 1.5 min chromatography, 5-95AB, purity 94.3% MS ESI calcd. for $C_{25}H_{41}N_4O_3$ [M + H]⁺ 445, found 427 [M + H − 18]⁺. |

SCHEME A-continued

General Procedure for the Preparation of Compounds 99-146

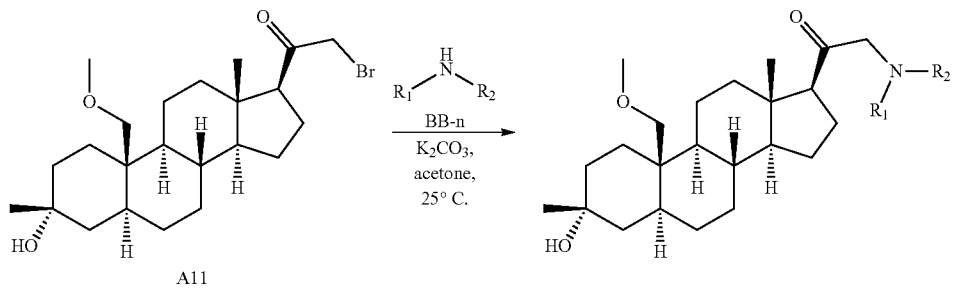

| Example | Structure of BB-n | Product(s) | NMR/LC-MS |
|---|---|---|---|
| 70 | (3-cyano-1H-pyrazole) | 118 | $^1$H NMR (400 MHz, CDCl$_3$) δ 7.47 (d, J = 2.4 Hz, 1H), 6.72 (d, J = 2.0 Hz, 1H), 5.04-4.89 (m, 2H), 3.47-3.45 (m, 1H), 3.38-3.35 (m, 1H), 3.28 (s, 3H), 2.59 (t, J = 8.4 Hz, 1H), 2.27-2.01 (m, 3H), 1.80-0.80 (m, 23H), 0.68 (s, 3H). LCMS t$_R$ = 1.347 min in 2 min chromatography, 10-80AB, purity 100.0%, MS ESI calcd. for C$_{27}$H$_{40}$N$_3$O$_3$ [M + H]$^+$ 454, found 436 [M + H − 18]$^+$. |
| 71 | (5-chloro-1H-benzotriazole) | 119 | $^1$H NMR (400 MHz, CDCl$_3$) δ 7.99 (dd, J = 2.4 Hz, J = 6.4 Hz, 1H), 7.34-7.32 (m, 2H), 5.42-5.31 (m, 2H), 3.49-3.47 (m, 1H), 3.39-3.36 (m, 1H), 3.30 (s, 3H), 2.73-2.60 (m, 1H), 2.30-1.90 (m, 3H), 1.80-0.80 (m, 23H), 0.74 (s, 3H). LCMS t$_R$ = 1.430 min in 2 min chromatography, 10-80AB, purity 99.5%, MS ESI calcd. for C$_{29}$H$_{41}$ClN$_3$O$_3$ [M + H]$^+$ 514, found 514. |
| | | 120 | $^1$H NMR (400 MHz, CDCl$_3$) δ 7.87 (s, 1H), 7.82 (d, J = 8.6 Hz, 2H), 7.36-7.33 (m, 1H), 5.56-5.45 (m, 2H), 3.49-3.47 (m, 1H), 3.40-3.37 (m, 1H), 3.30 (s, 3H), 2.73-2.60 (m, 1H), 2.30-1.90 (m, 3H), 1.80-0.80 (m, 23H), 0.76 (s, 3H). LCMS t$_R$ = 1.473 min in 2 min chromatography, 10-80AB, purity 98.2%, MS ESI calcd. for C$_{29}$H$_{41}$ClN$_3$O$_3$ [M + H]$^+$ 514, found 496 [M + H − 18]$^+$. |
| | | 121 | $^1$H NMR (400 MHz, CDCl$_3$) δ 8.05 (s, 1H), 7.44 (dd, J = 1.6 Hz, J = 8.8 Hz, 1H), 7.26 (d, J = 8.4 Hz, 1H), 5.49-5.38 (m, 2H), 3.49-3.46 (m, 1H), 3.38-3.36 (m, 1H), 3.29 (s, 3H), 2.80-2.60 (m, 1H), 2.27-2.01 (m, 3H), 1.80-0.80 (m, 23H), 0.72 (s, 3H). LCMS t$_R$ = 1.409 min in 2 min chromatography, 10-80AB, purity 100.0%, MS ESI calcd. for C$_{29}$H$_{41}$ClN$_3$O$_3$ [M + H]$^+$ 514, found 514. |

SCHEME A-continued

General Procedure for the Preparation of Compounds 99-146

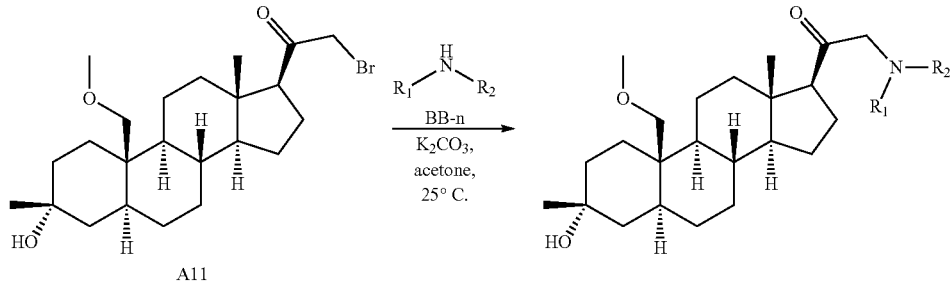

A11

| Example | Structure of BB-n | Product(s) | NMR/LC-MS |
|---|---|---|---|
| 72 | (4,5-difluoro benzotriazole) | 122 | $^1$H NMR (400 MHz, CDCl$_3$) δ 6.89-6.86 (m, 1H), 6.79 (dd, J = 1.6 Hz, J = 7.2 Hz, 1H), 5.52-5.32 (m, 2H), 3.49-3.47 (m, 1H), 3.39-3.36 (m, 1H), 3.29 (s, 3H), 2.71 (t, J = 8.8 Hz, 1H), 2.27-2.01 (m, 3H), 1.80-0.80 (m, 23H), 0.74 (s, 3H). LCMS $t_R$ = 0.982 min in 1.5 min chromatography, 5-95AB, purity 100.0%, MS ESI calcd. for C$_{29}$H$_{40}$F$_2$N$_3$O$_3$ [M + H]$^+$ 516, found 516. |
|  |  | 123 | $^1$H NMR (400 MHz, CDCl$_3$) δ 7.31 (dd, J = 1.6 Hz, J = 8.4 Hz, 1H), 6.94-6.88 (m, 1H), 5.57-5.46 (m, 2H), 3.49-3.47 (m, 1H), 3.40-3.37 (m, 1H), 3.30 (s, 3H), 2.74-2.70 (m, 1H), 2.27-2.01 (m, 3H), 1.80-0.80 (m, 23H), 0.76 (s, 3H). LCMS $t_R$ = 1.015 min in 1.5 min chromatography, 5-95AB, purity 99.0%. MS ESI calcd. for C$_{29}$H$_{40}$F$_2$N$_3$O$_3$ [M + H]$^+$ 516, found 498 [M + H − 18]$^+$. |
|  |  | 124 | $^1$H NMR (400 MHz, CDCl$_3$) δ 7.52 (dd, J = 1.6 Hz, J = 8.0 Hz, 1H), 7.01-6.95 (m, 1H), 5.54-5.35 (m, 2H), 3.49-3.47 (m, 1H), 3.38-3.36 (m, 1H), 3.29 (s, 3H), 2.74-2.70 (m, 1H), 2.27-2.01 (m, 3H), 1.80-0.80 (m, 23H), 0.72 (s, 3H). LCMS $t_R$ = 0.985 min in 1.5 min chromatography, 5-95AB, purity 95.7%, MS ESI calcd. for C$_{29}$H$_{40}$F$_2$N$_3$O$_3$ [M + H]$^+$ 516, found 498 [M + H − 18]$^+$. |
| 73 | (3-trifluoromethyl pyrazole) | 125 | $^1$H NMR (400 MHz, CDCl$_3$) δ 7.45 (d, J = 1.2 Hz, 1H), 6.58 (d, J = 2.0 Hz, 1H), 5.01-4.91 (m, 2H), 3.47-3.45 (m, 1H), 3.38-3.35 (m, 1H), 3.28 (s, 3H), 2.58 (t, J = 8.8 Hz, 1H), 2.27-2.01 (m, 3H), 1.80-0.80 (m, 23H), 0.69 (s, 3H). LCMS $t_R$ = 1.389 min in 2 min chromatography, 10-80AB, purity 99.3%, MS ESI calcd. for C$_{27}$H$_{40}$F$_3$N$_2$O$_3$ [M + H]$^+$ 497, found 479 [M + H − 18]$^+$. |

SCHEME A-continued

General Procedure for the Preparation of Compounds 99-146

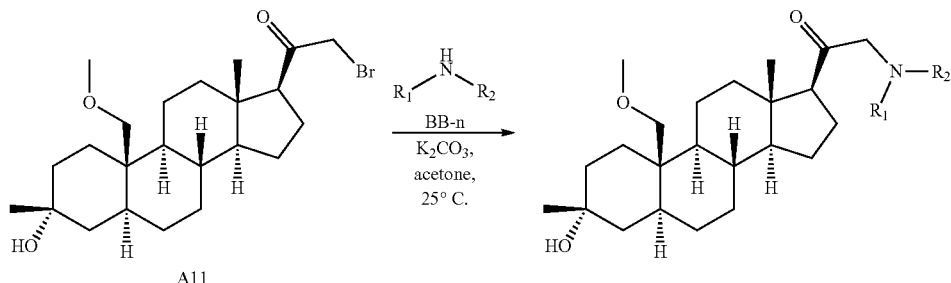

| Example | Structure of BB-n | Product(s) | NMR/LC-MS |
|---|---|---|---|
| 74 | BB-n structure with benzotriazole-OCF3 | 126 | $^1$H NMR (400 MHz, CDCl$_3$) δ 7.48 (t, J = 8.0 Hz, 1H), 7.27-7.22 (m, 2H), 5.50-5.40 (m, 2H), 3.50-3.49 (m, 1H), 3.39-3.37 (m, 1H), 3.30 (s, 3H), 2.75-2.65 (m, 1H), 2.27-2.01 (m, 3H), 1.80-0.80 (m, 23H), 0.75 (s, 3H).<br>LCMS $t_R$ = 1.459 min in 2 min chromatography, 10-80AB, purity 100.0%, MS ESI calcd. for C$_{30}$H$_{41}$F$_3$N$_3$O$_4$ [M + H]$^+$ 564, found 564. |
| 75 | BB-27 (pyrazole-CN) | 127 | $^1$HNMR (400 MHz, CDCl3) δ 7.85 (s, 1H), 7.81 (s, 1H), 5.04-4.87 (m, 2H), 3.49-3.45 (m, 1H), 3.38-3.36 (m, 1H), 3.28 (s, 3H), 2.60 (t, J = 8.8 Hz, 1H), 2.17-2.01 (m, 3H), 1.80-0.80 (m, 23H), 0.68 (s, 3H).<br>LCMS $t_R$ = 1.304 min in 1.5 min chromatography, 10-80AB, purity 98.5%, MS ESI calcd. for C$_{27}$H$_{40}$N$_3$O$_3$ [M + H]$^+$ 454, found 436 [M + H − 18]$^+$. |

Example 76. Preparation of Compounds 154 and 155

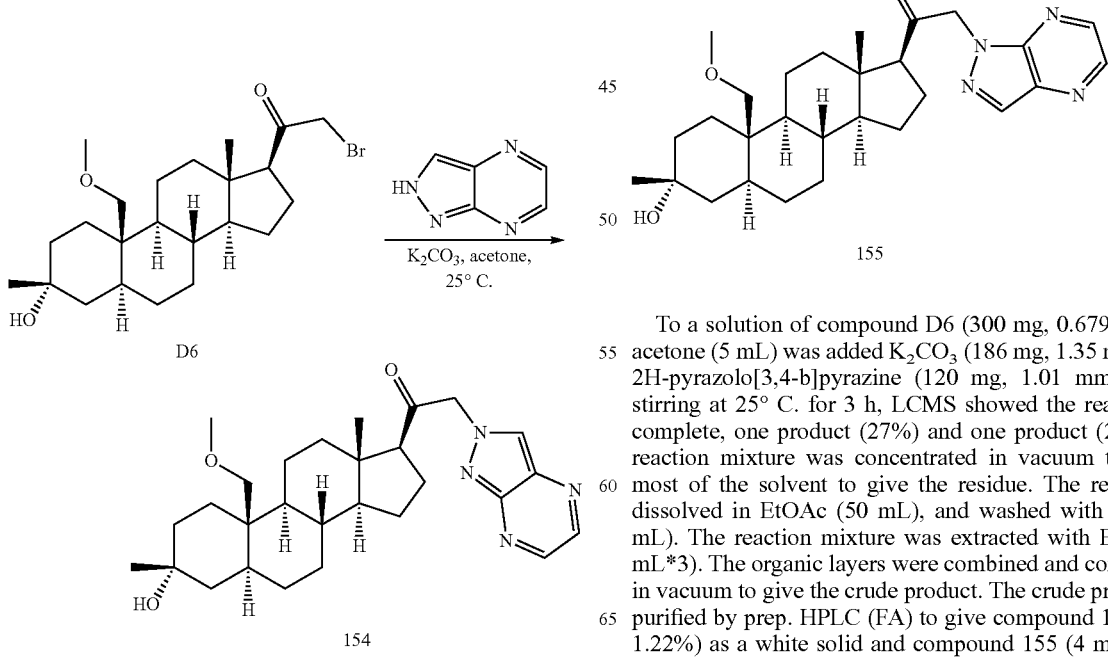

To a solution of compound D6 (300 mg, 0.679 mmol) in acetone (5 mL) was added K$_2$CO$_3$ (186 mg, 1.35 mmol) and 2H-pyrazolo[3,4-b]pyrazine (120 mg, 1.01 mmol). After stirring at 25° C. for 3 h, LCMS showed the reaction was complete, one product (27%) and one product (21%). The reaction mixture was concentrated in vacuum to remove most of the solvent to give the residue. The residue was dissolved in EtOAc (50 mL), and washed with water (50 mL). The reaction mixture was extracted with EtOAc (50 mL*3). The organic layers were combined and concentrated in vacuum to give the crude product. The crude product was purified by prep. HPLC (FA) to give compound 154 (4 mg, 1.22%) as a white solid and compound 155 (4 mg, 1.22%) as white solid.

¹H NMR (154) (yield 1.2%): (400 MHz, CDCl₃) δ 8.64 (d, J=2.0 Hz, 1H), 8.56 (d, J=2.0 Hz, 1H), 8.26 (s, 1H), 5.40-5.19 (m, 2H), 3.54 (d, J=8.4 Hz, 1H), 3.33 (s, 3H), 3.20 (d, J=9.2 Hz, 1H), 2.68 (t, J=8.8 Hz, 1H), 2.30-1.20 (m, 26H), 0.72 (d, J=13.2 Hz, 3H). LCMS $t_R$=1.155 min in 2 min chromatography, 10-80 AB, purity 96.2%, MS ESI calcd. for $C_{28}H_{41}N_4O_3$ [M+H]⁺ 481, found 481.

¹H NMR (155) (yield 1.2%): (400 MHz, CDCl₃) δ 8.59 (d, J=2.4 Hz, 1H), 8.44 (d, J=2.0 Hz, 1H), 8.34 (s, 1H), 5.36-5.24 (m, 2H), 3.55 (d, J=9.2 Hz, 1H), 3.34 (s, 3H), 3.22 (d, J=9.2 Hz, 1H), 2.68 (t, J=8.8 Hz, 1H), 2.30-1.20 (m, 26H), 0.71 (s, 3H). LCMS $t_R$=0.854 min in 1.5 min chromatography, 10-80 AB, purity 96.8%, MS ESI calcd. for $C_{28}H_{41}N_4O_3$ [M+H]⁺ 481, found 463[M+H−18]⁺.

Example 77. Preparation of Compound 156

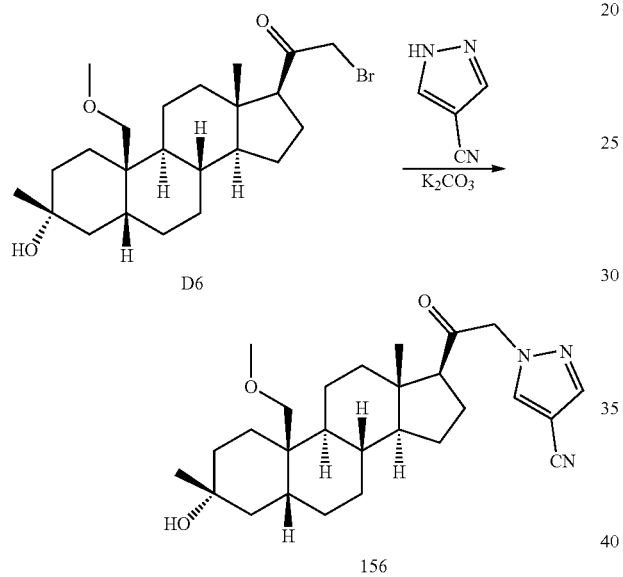

156

¹H NMR (156) (yield 41%): (400 MHz, CDCl₃) δ 7.88 (s, 1H), 7.83 (s, 1H), 5.07-4.87 (m, 2H), 3.55 (d, J=9.0 Hz, 1H), 3.35 (s, 3H), 3.22 (d, J=9.0 Hz, 1H), 2.65-2.58 (m, 1H), 2.28-2.15 (m, 1H), 2.10-2.01 (m, 1H), 1.97-1.91 (m, 2H), 1.82-1.40 (m, 14H), 1.35-1.09 (m, 8H), 0.68 (s, 3H). LCMS $t_R$=2.744 min in 4 min chromatography, 10-80 AB, purity 100.0%, MS ESI calcd. for $C_{27}H_{39}N_3O_3Na$ [M+Na]⁺477, found 477.

Example 78. Preparation of Compound 147

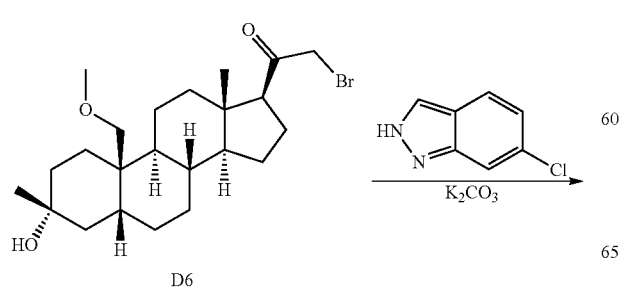

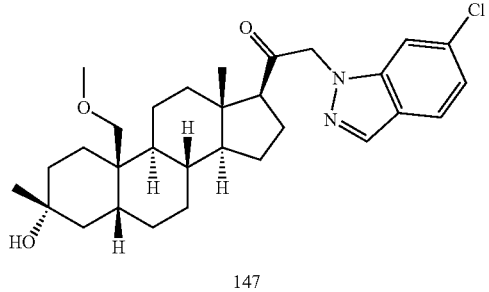

147

¹H NMR (147) (yield 4%): (400 MHz, CDCl₃) δ 8.03 (s, 1H), 7.68 (d, J=8.5 Hz, 1H), 7.22 (s, 1H), 7.15 (d, J=8.5 Hz, 1H), 5.20-5.03 (m, 2H), 3.57 (d, J=9.0 Hz, 1H), 3.36 (s, 3H), 3.23 (d, J=9.0 Hz, 1H), 2.65 (t, J=8.7 Hz, 1H), 2.30-2.09 (m, 2H), 1.99-1.91 (m, 2H), 1.77-1.45 (m, 14H), 1.34-1.14 (m, 8H), 0.73 (s, 3H). LCMS $t_R$=3.185 min in 4 min chromatography, 10-80 AB, purity 100.0%, MS ESI calcd. for $C_{30}H_{42}ClN_2O_3$[M+H]⁺513, found 513.

Example 79. Preparation of Compound 157

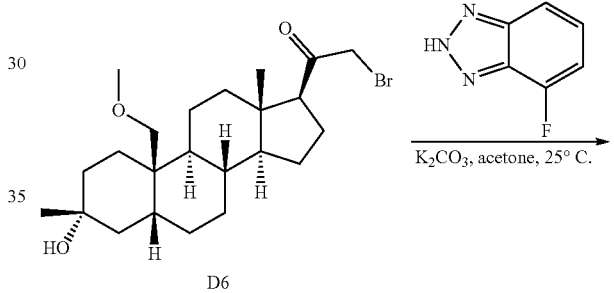

157

¹H NMR (157) (yield 3.5%): (400 MHz, CDCl₃) δ 7.47-7.43 (m, 1H), 7.14-7.06 (m, 2H), 5.49-5.38 (m, 2H), 3.55 (t, J=9.2 Hz, 1H), 3.36 (d, J=4.0 Hz, 3H), 3.25 (d, J=8.8 Hz, 1H), 2.73 (s, 1H), 2.30-1.20 (m, 26H), 0.74 (s, 3H). LCMS $t_R$=0.931 min in 1.5 min chromatography, 5-95 AB, purity 96.8%, MS ESI calcd. for $C_{29}H_{41}FN_3O_3$[M+H]⁺498, found 520[M+Na]⁺.

Example 80. Preparation of Compound 158

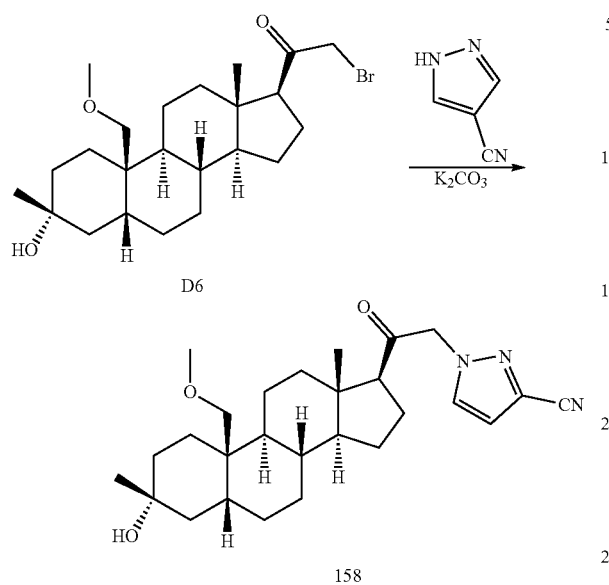

¹H NMR (158) (yield 18%): (400 MHz, CDCl₃) δ 7.50 (d, J=2.5 Hz, 1H), 6.75 (d, J=2.5 Hz, 1H), 5.08-4.90 (m, 2H), 3.55 (d, J=9.0 Hz, 1H), 3.37-3.31 (m, 3H), 3.22 (d, J=9.0 Hz, 1H), 2.64-2.57 (m, 1H), 2.28-01 (m, 2H), 1.99-1.91 (m, 2H), 1.84-1.40 (m, 14H), 1.39-1.08 (m, 8H), 0.67 (s, 3H). LCMS $t_R$=2.821 min in 4 min chromatography, 10-80 AB, purity 100.0%, MS ESI calcd. for $C_{27}H_{39}N_3O_3Na$ $[M+Na]^+$ 476, found 476.

Example 81. Preparation of Compound 159

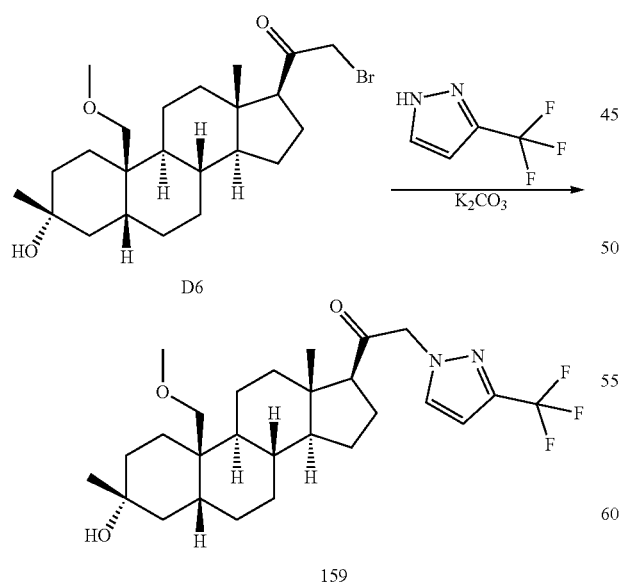

1H NMR (159) (yield:13%): (400 MHz, CDCl₃) δ 7.48 (s, 1H), 6.60 (d, J=2.0 Hz, 1H), 5.07-4.88 (m, 2H), 3.56 (d, J=9.0 Hz, 1H), 3.35 (s, 3H), 3.22 (d, J=9.0 Hz, 1H), 2.65-2.54 (m, 1H), 2.28-2.15 (m, 1H), 2.10-2.02 (m, 1H), 1.99-1.90 (m, 2H), 1.84-1.37 (m, 14H), 1.36-1.07 (m, 8H), 0.68 (s, 3H). LCMS $t_R$=3.049 min in 4 min chromatography, 10-80 AB, purity 100.0%, MS ESI calcd. for $C_{27}H_{40}F_3N_2O_3$ $[M+H]^+$ 497, found 479 $[M+H-H2O]^+$.

Example 82. Preparation of Compound 160

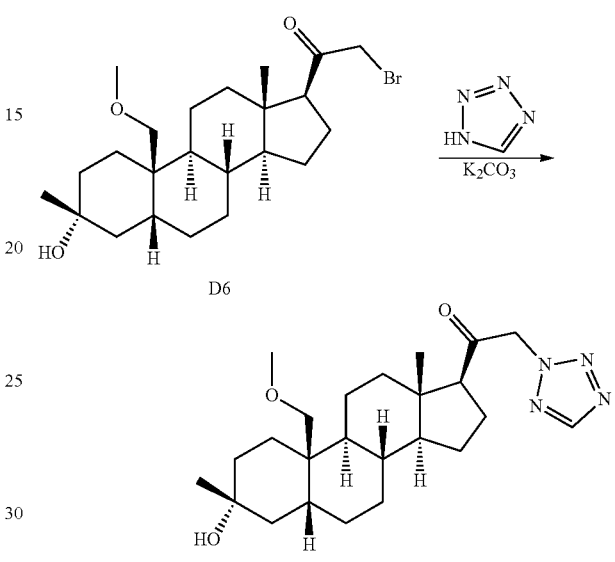

1H NMR (160) (yield 11%): (400 MHz, CDCl₃) δ 8.59 (s, 1H), 5.47 (s, 2H), 3.56 (d, J=9.0 Hz, 1H), 3.35 (s, 3H), 3.23 (d, J=9.0 Hz, 1H), 2.66 (t, J=8.8 Hz, 1H), 2.30-2.16 (m, 1H), 2.15-2.05 (m, 1H), 1.98-1.89 (m, 2H), 1.84-1.41 (m, 14H), 1.40-1.11 (m, 9H), 0.72 (s, 3H). LCMS $t_R$=2.667 min in 4 min chromatography, 10-80 AB, purity 100.0%, MS ESI calcd. for $C_{24}H_{39}N_4O_3$ $[M+H]^+$ 431, found 413 $[M+H-18]^+$.

Example 83. Preparation of Compound F5

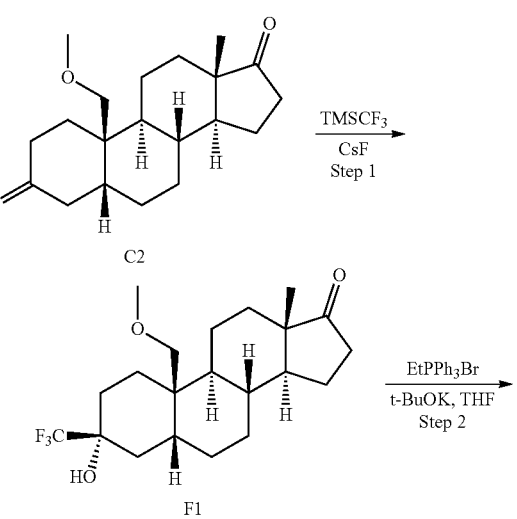

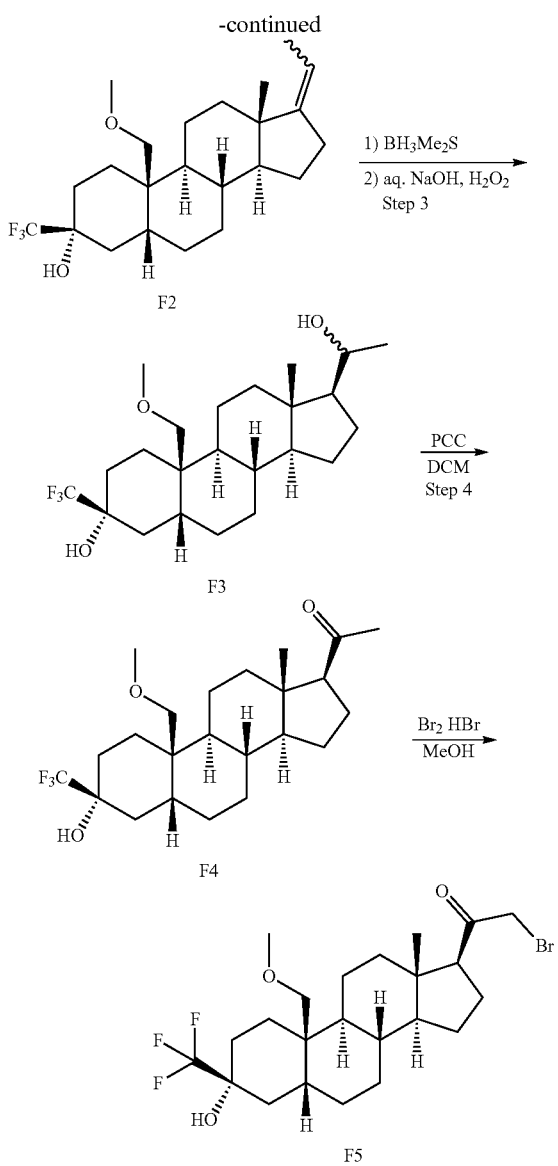

Step 1. Preparation of Compound F1. To a solution of C2 (2 g, 6.28 mmol) in THF (30 mL) in a flask was added CsF (953 mg, 6.28 mmol) at 0° C., then TMSCF$_3$ (1.33 g, 9.42 mmol) was added dropwise. The reaction was allowed to warm to 25° C. and stirred for 2 h. TLC(PE:EtOAc=3:1) showed the starting material was consumed completely. Then the reaction mixture was treated with 2M aq·HCl (10 mL) and stirred for 6 h. The reaction was then diluted with H$_2$O (30 mL) and extracted with EtOAc (30 mL×2). The combined organic layer was washed with brine (20 mL), dried over Na$_2$SO$_4$ and concentrated to get the crude product which was purified by silica gel column (PE:EtOAc=50:1 to 10:1) to afford product F1 (1.1 g, 45.0% yield) as a yellow oil. $^1$H NMR (400 MHz, CDCl$_3$) δ 3.49 (d, J=8.0 Hz, 1H), 3.32-3.22 (m, 4H), 2.46-2.39 (m, 1H), 2.10-1.71 (m, 8H), 1.68-1.10 (m, 14H), 0.85 (s, 3H).

Step 2. Preparation of Compound F2. To a solution of ethyltriphenylphosphonium bromide (5.19 g, 14.0 mmol) in THF (30 mL), was added t-BuOK (1.57 g, 14.0 mmol). The reaction mixture was heated to 60° C. for 1 h and F1 (1.1 g, 2.83 mmol) was added to the mixture which was stirred at 60° C. for an additional 8 h. TLC (PE:EtOAc=3:1) showed the reaction was complete. The reaction mixture was cooled, then diluted with H$_2$O (30 mL) and extracted with EtOAc (30 mL×2). The combined organic layer was washed with brine (20 mL), dried over Na$_2$SO$_4$ and concentrated. The residue was purified by silica gel column (PE:EtOAc=100:1 to 15:1) to afford product F2 (1 g, 88.6% yield) as a yellow oil. $^1$H NMR (400 MHz, CDCl$_3$) δ 5.15-5.02 (m, 1H), 3.56 (d, J=8.0 Hz, 1H), 2.46-2.39 (m, 1H), 3.34 (s, 3H), 3.29 (d, J=8.0 Hz, 1H), 2.43-1.80 (m, 7H), 1.58-1.10 (m, 19H), 0.90 (s, 3H).

Step 3. Preparation of Compound F3. To a solution of F2 (1 g, 2.49 mmol) in THF (15 mL) under N$_2$ protection was added dropwise a solution of BH$_3$-Me$_2$S (2.48 mL, 10 M) at 0° C. The solution was stirred at 25° C. for 4 h. TLC (PE/EtOAc=3/1) showed the reaction was complete. After cooling to 0° C., a solution of NaOH (9.93 mL, 3M) was added very slowly, a large amount of gas released. After the addition was complete, H$_2$O$_2$ (4.53 mL, 33%) was added slowly and the inner temperature was maintained below 10° C. The resulting solution was stirred at 25° C. for 1 h. The resulting solution was extract with EtOAc (20 mL×3). The combined organic solution was washed with saturated aqueous Na$_2$S$_2$O$_3$ (20 mL×3), brine (20 mL), dried over Na$_2$SO$_4$ and concentrated in vacuum to give the crude product (1 g) as yellow oil. The crude product was used for the next step without further purification.

Step 4. Preparation of Compound F$_4$. A mixture of F$_3$ (1.0 g, 2.38 mmol), PCC (0.767 g, 3.56 mmol) and silica gel (0.843 g, w/w=1/1.1) in DCM (15 mL) was stirred at 25° C. for 2 h, the reaction mixture color became brown. TLC (PE/EtOAc=3/1) showed the reaction was complete. The solution was filtered and the filter cake was washed with DCM (20 mL). The combined filtrate was concentrated in vacuum. The residue was purified by silica gel column eluted with PE:EtOAc=15:1 to 8:1 to give F5 (800 mg, 80.6%) as a white solid. MS ESI calcd. for C$_{24}$H$_{41}$O$_4$[M+H]$^+$ 417, found 399 ([M+H−18]$^+$). $^1$H NMR (400 MHz, CDCl$_3$) δ 3.52 (d, J=8.0 Hz, 1H), 3.33 (s, 3H), 3.28 (d, J=8.0 Hz, 1H), 2.58-2.52 (m, 1H), 2.20-1.60 (m, 15H), 1.53-1.10 (m, 11H), 0.62 (s, 3H).

Step 5. Preparation of Compound F5. To a solution of F4 (0.5 g, 1.20 mmol) and a catalytic amount of concentrated HBr (12.1 mg, 40% in water) in MeOH (15 mL) was added dropwise dibromine (230 mg, 1.44 mmol) at 0° C. The reaction mixture was stirred at 25° C. for 1 h. TLC (PE:EtOAc=3:1) showed the reaction was complete. The reaction was quenched by saturated aqueous NaHCO$_3$ and the pH was adjusted to 7-8. The reaction mixture was extracted with DCM (20 mL×2). The combined organic layer was washed with brine (20 mL), dried over Na$_2$SO$_4$ and concentrated to get the crude product F$_5$ (500 mg) as a yellow oil.

Example 84. Preparation of Compounds 161 and 162

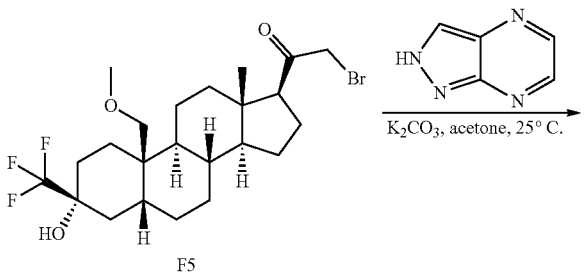

-continued

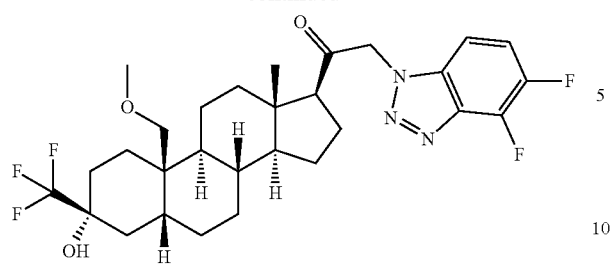

161

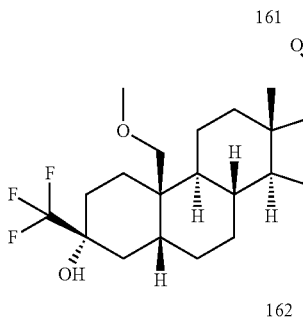

162

To a solution of compound F5 (150 mg, 0.302 mmol) in acetone (5 mL) was added K$_2$CO$_3$ (62.6 mg, 0.453 mmol) and 4,5-difluoro-2H-benzo[d][1,2,3]triazole (70.2 mg, 0.453 mmol). After stirring at 25° C. for 3 h, TLC (PE:EA=3:1) showed the reaction was complete. The reaction mixture was filtered, and the filtrate was concentrated in vacuum to give the crude product (150 mg). The crude product was purified by prep. HPLC (HCl) to give compound 162 (18 mg, 10.4%) as a white solid and compound 161 (31 mg, 18%) as a white solid.

$^1$H NMR (161) (yield 10.4%): (400 MHz, CDCl$_3$) δ 7.42-7.36 (m, 1H), 7.09-7.06 (m, 1H), 5.53-5.35 (m, 2H), 3.50 (t, J=9.2 Hz, 1H), 3.34-3.29 (m, 4H), 2.71 (d, J=8.8 Hz, 1H), 2.20-1.00 (m, 23H), 0.74 (s, 3H). LCMS t$_R$=1.350 min in 2 min chromatography, 10-80 AB, purity 100%, MS ESI calcd. for C$_{29}$H$_{37}$F$_5$N$_3$O$_3$[M+H]$^+$ 570, found 570.

$^1$H NMR (162) (yield 18%): (400 MHz, CDCl$_3$) δ 7.68-7.64 (m, 1H), 7.37-7.29 (m, 1H), 5.59-5.49 (m, 2H), 3.51 (t, J=7.6 Hz, 1H), 3.34-3.29 (m, 4H), 2.69 (d, J=8.8 Hz, 1H), 2.24-1.14 (m, 23H), 0.77 (s, 3H). LCMS t$_R$=1.398 min in 2 min chromatography, 10-80 AB, purity 100%, MS ESI calcd. for C$_{29}$H$_{37}$F$_5$N$_3$O$_3$[M+H]$^+$ 570, found 570.

Example 85. Preparation of Compounds 163, 164, and 165

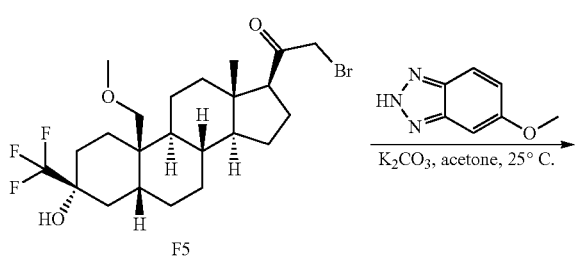

-continued

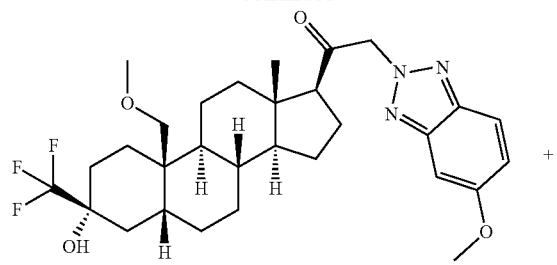

163

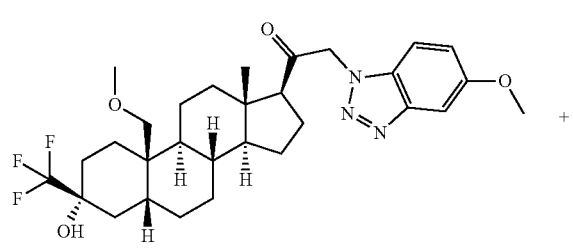

164

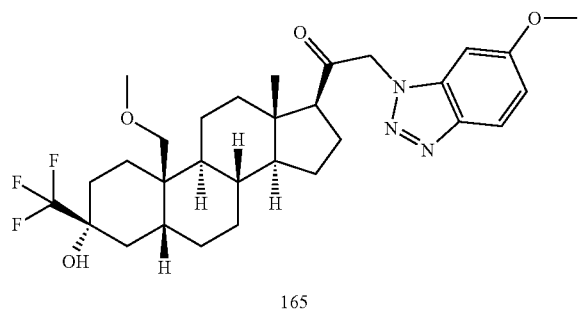

165

$^1$H NMR (163) (yield 11%): (400 MHz, CDCl$_3$) δ 7.73 (t, J=5.6 Hz, 1H), 7.09-7.06 (m, 2H), 5.48-5.38 (m, 2H), 3.88 (s, 3H), 3.50 (d, J=8.8 Hz, 1H), 3.31 (s, 3H), 3.28 (d, J=9.2 Hz, 1H), 2.62 (t, J=8.8 Hz, 1H), 2.17-1.11 (m, 23H), 0.74 (s, 3H). LCMS t$_R$=1.354 min in 2 min chromatography, 10-80 AB, purity 100%, MS ESI calcd. for C$_{30}$H$_{41}$F$_3$N$_3$O$_4$[M+H]$^+$ 564, found 564.

$^1$H NMR (164) (yield 11%): (400 MHz, CDCl$_3$) δ 7.38 (d, J=1.6 Hz, 1H), 7.21 (d, J=7.2 Hz, 1H), 7.15 (dd, J$_1$=7.2 Hz, J$_2$=1.6 Hz, 1H), 5.34 (s, 2H), 3.89 (s, 3H), 3.49 (d, J=6.8 Hz, 1H), 3.31 (s, 3H), 3.28 (d, J=6.8 Hz, 1H), 2.66 (t, J=7.2 Hz, 1H), 2.35-1.10 (m, 23H), 0.71 (s, 3H). LCMS t$_R$=0.964 min in 1.5 min chromatography, 5-95 AB, purity 95%, MS ESI calcd. for C$_{30}$H$_{41}$F$_3$N$_3$O$_4$[M+H]$^+$ 564, found 564.

$^1$H NMR (165) (yield 19%): (400 MHz, CDCl$_3$) δ 7.91 (d, J=9.2 Hz, 1H), 7.01 (dd, J$_1$=9.2 Hz, J$_2$=2.0 Hz, 1H), 6.59 (d, J=2.0 Hz, 1H), 5.38-5.27 (m, 2H), 3.85 (s, 3H), 3.49 (d, J=9.2 Hz, 1H), 3.31 (s, 3H), 3.28 (d, J=9.2 Hz, 1H), 2.67 (t, J=8.4 Hz, 1H), 2.43 (brs, 1H), 2.30-1.05 (m, 23H), 0.71 (s, 3H). LCMS t$_R$=1.354 min in 2 min chromatography, 10-80 AB, purity 100%, MS ESI calcd. for C$_{30}$H$_{41}$F$_3$N$_3$O$_4$[M+H]$^+$ 564, found 564.

167

Example 86. Preparation of Compound 166

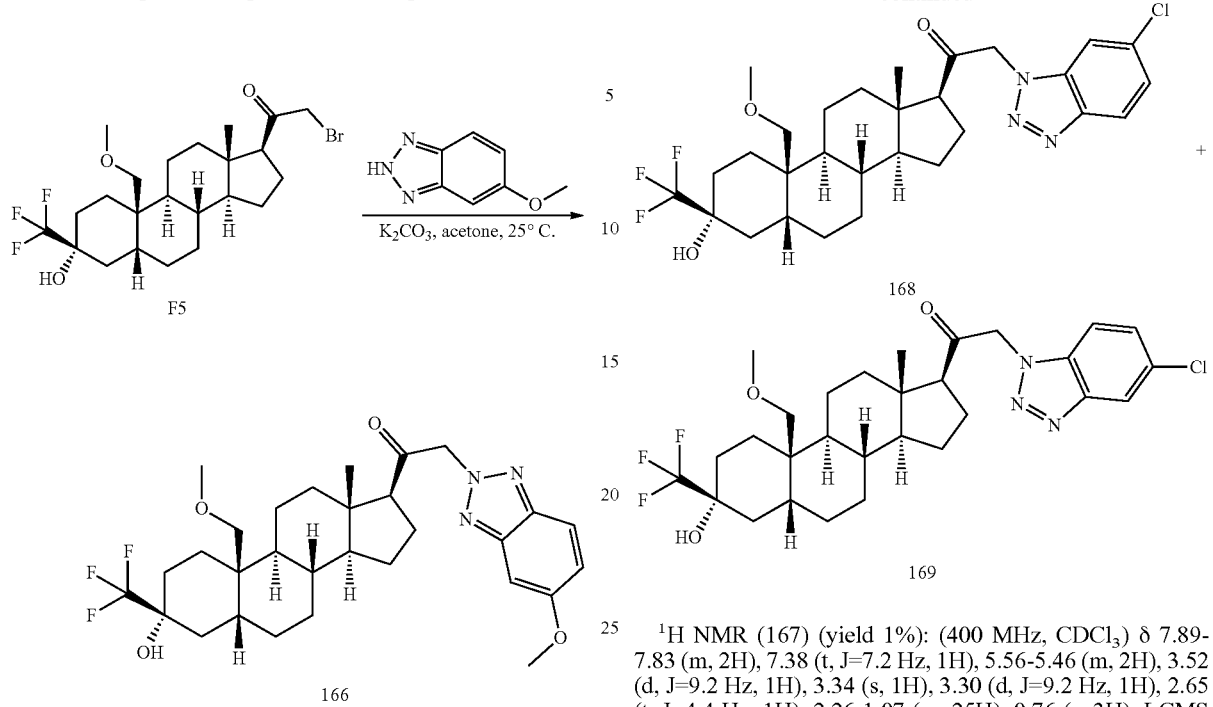

$^1$H NMR (166) (yield 10.5%): (400 MHz, CDCl$_3$) δ 7.73 (t, J=5.6 Hz, 1H), 7.09-7.06 (m, 2H), 5.48-5.38 (m, 2H), 3.88 (s, 3H), 3.50 (d, J=8.8 Hz, 1H), 3.31 (s, 3H), 3.28 (d, J=9.2 Hz, 1H), 2.62 (t, J=8.8 Hz, 1H), 2.17-1.11 (m, 22H), 0.74 (s, 3H). LCMS $t_R$=1.354 min in 2 min chromatography, 10-80 AB, purity 100%, MS ESI calcd. for C$_{30}$H$_{41}$F$_3$N$_3$O$_4$ [M+H]$^+$ 564, found 564.

Example 87. Preparation of Compounds 167, 168, and 169

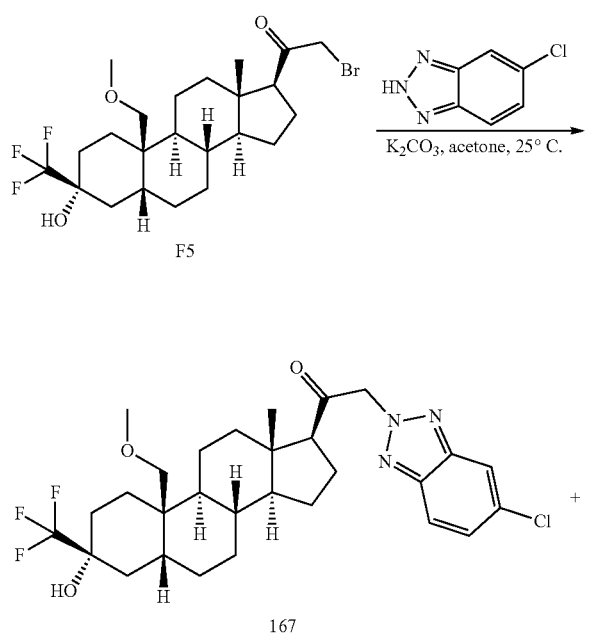

168

$^1$H NMR (167) (yield 1%): (400 MHz, CDCl$_3$) δ 7.89-7.83 (m, 2H), 7.38 (t, J=7.2 Hz, 1H), 5.56-5.46 (m, 2H), 3.52 (d, J=9.2 Hz, 1H), 3.34 (s, 1H), 3.30 (d, J=9.2 Hz, 1H), 2.65 (t, J=4.4 Hz, 1H), 2.26-1.07 (m, 25H), 0.76 (s, 3H). LCMS $t_R$=1.424 min in 2 min chromatography, 10-80 AB, purity 99%, MS ESI calcd. for C$_{29}$H$_{38}$ClF$_3$N$_3$O$_3$ [M+H]$^+$ 568, found 568.

$^1$H NMR (168) (yield 6%): (400 MHz, CDCl$_3$) δ 8.01-7.99 (m, 1H), 7.36-7.34 (m, 2H), 5.43-5.31 (m, 2H), 3.50 (d, J=8.8 Hz, 1H), 3.28-3.35 (m, 4H), 2.70 (t, J=8.8 Hz, 1H), 2.24-1.13 (m, 23H), 0.73 (s, 3H). LCMS $t_R$=1.009 min in 1.5 min chromatography, 5-95 AB, purity 97%, MS ESI calcd. for C$_{29}$H$_{38}$ClF$_3$N$_3$O$_3$ [M+H]$^+$ 568, found 568.

$^1$H NMR (169) (yield 8%): (400 MHz, CDCl3) δ 8.07 (s, 1H), 7.45 (t, J=7.2 Hz, 1H), 7.29 (s, 1H), 5.34-5.45 (m, 2H), 3.49 (d, J=8.8 Hz, 1H), 3.28-3.32 (m, 4H), 2.70 (t, J=9.2 Hz, 1H), 2.20-0.88 (m, 23H), 0.71 (s, 3H). LCMS $t_R$=0.995 min in 1.5 min chromatography, 5-95 AB, purity 99%, MS ESI calcd. for C$_{29}$H$_{38}$ClF$_3$N$_3$O$_3$ [M+H]$^+$ 568, found 568.

Example 88. Preparation of Compound C19

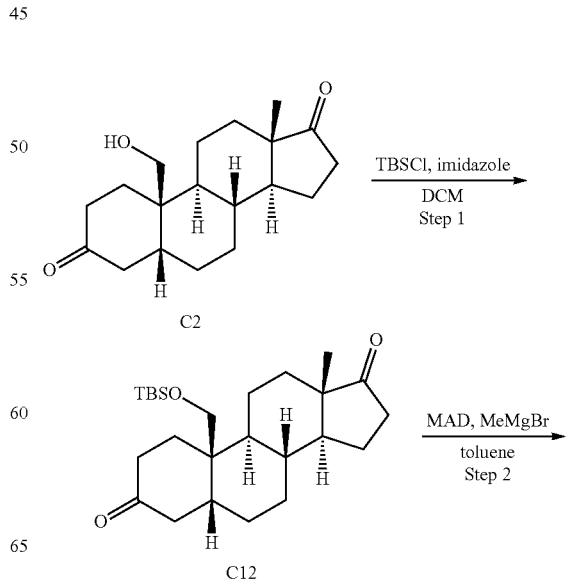

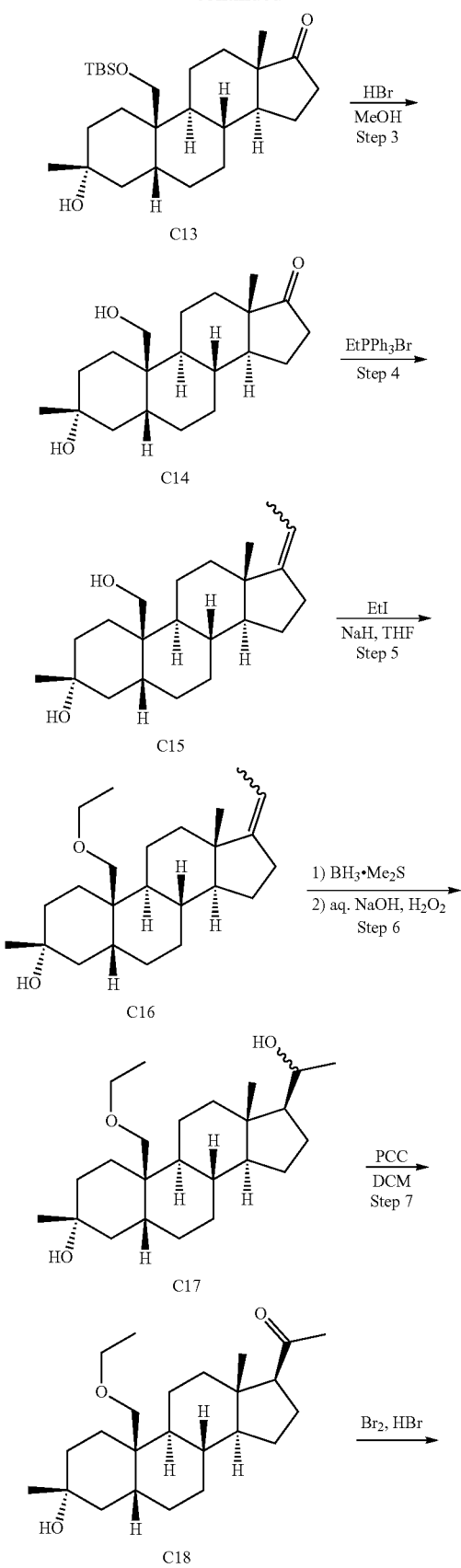

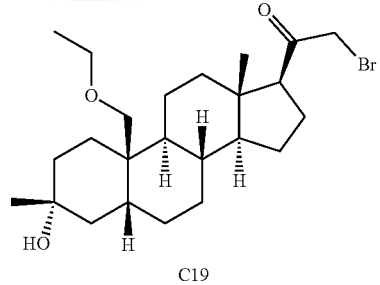

Step 1. Preparation of Compound C12. To a solution of C2 (4 g, 13.14 mmol) in 15 mL $CH_2Cl_2$ was added 1H-imidazole (2.68 g, 39.42 mmol) and tert-butylchlorodimethylsilane (2.97 g, 19.71 mmol) at 25° C., the reaction was stirred at 25° C. for 16 h. The reaction mixture was filtered with 50 mL $CH_2Cl_2$ and evaporated in vacuo. The residue was purified by column chromatography on silical gel (PE:EtOAc=50:1-30:1-20:1-15:1-10:1) to afford C12 (5 g, 90.87% yield) as a white solid. $^1$H NMR: (400 MHz, $CDCl_3$) δ 3.81 (d, J=8.0 Hz, 1H), 3.58 (d, J=8.0 Hz, 1H), 2.62-2.55 (m, 1H), 2.48-2.43 (m, 1H), 2.40-2.28 (m, 3H), 2.26-2.07 (m, 2H), 1.87-1.86 (m, 1H), 1.84-1.75 (m, 4H), 1.56-1.27 (m, 10H), 0.87 (s, 12H), 0.042 (s, 6H).

Step 2. Preparation of Compound C13. To a solution of C12 (15.79 g, 71.64 mmol) in 30 mL toluene was added a solution of $AlMe_3$ (17.91 mL, 3 eq) dropwise at 0° C. After 1 h, a solution of (5R,8R,9S,10R,13S,14S)-10-(((tert-butyldimethylsilyl)oxy)methyl)-13-methyldodecahydro-1H-cyclopenta[a]phenanthrene-3,17(2H,4H)-dione (5 g, 11.94 mmol) in toluene (40 mL) was added dropwise at −78° C., the reaction mixture was stirred at −78° C. for 1 h and then a solution of MeMgBr (11.94 mL, 3 eq) was added dropwise to the mixture at −78° C. which was stirred at −78° C. for another 2 h. After TLC (PE:EtOAc=3:1) showed the starting material was consumed completely, the reaction mixture was quenched with aq. $NH_4Cl$ (15 mL), filtered and washed with 500 mL EtOAc. The organic layer was extracted with 300 mL EtOAc, washed with brine and concentrated. The residue was purified by column chromatograph on silica gel (PE:EA=100-50:1-20:1-10:1-4:1) to give C13 (5 g, 96.3%) as a white solid. $^1$H NMR (400 MHz, $CDCl_3$), δ 3.76 (d, J=8.0 Hz, 1H), 3.40 (d, J=8.0 Hz, 1H), 2.44-2.39 (m, 1H), 2.09-1.70 (m, 6H), 1.61-1.18 (m, 19H), 0.89 (s, 12H), 0.04 (s, 6H).

Step 3. Preparation of Compound C14. To a solution of C13 (7 g, 16.1 mmol) in 70 mL MeOH was added a solution of HBr (6.5 g, 32.2 mmol, 40% in water). The reaction mixture was stirred at 25° C. for 0.7 h. After TLC (PE:EtOAc=3:1) showed the starting material was consumed completely, the reaction mixture was quenched with sat.aq·$NaHCO_3$ (200 mL) and extracted with 500 mL EtOAc, washed with brine (100 mL) and concentrated to give product C14 (5.6 g, crude) as a white solid.

Step 4. Preparation of Compound C15. To a solution of $PPh_3EtBr$ (51.8 g, 140 mmol) in THF (40 mL) was added a solution of t-BuOK (15.7 g, 140 mmol) in THF (40 mL) at 0° C. After stirring at 60° C. for 1 h, a solution of compound C14 (9 g, 28.0 mmol) in THF (40 mL) was added dropwise at 60° C. Then the reaction mixture was stirred at the same temperature for 8 h. TLC (PE/EtOAc=3/1) showed the reaction was completed, and a main product was found with lower polarity. The reaction mixture was extracted with EtOAc (300 mL) for three times. The organic layer was washed with brine (100 mL), dried over Na$_2$SO$_4$ and concentrated in vacuum to give the crude product. The crude product was purified by a silica gel column (PE:EA=5:1) to give compound C15 (5.0 g, 53.5%) as a pale yellow oil. $^1$H NMR (400 MHz, CDCl$_3$) δ 5.15-5.05 (m, 1H), 3.94 (d, J=10.8 Hz, 1H), 3.56 (d, J=10.8 Hz, 1H), 2.40-2.12 (m, 3H), 2.01-1.71 (m, 3H), 1.69-1.12 (m, 24H), 0.85 (s, 3H).

Step 5. Preparation of Compound C16. To a solution of C15 (500 mg, 1.50 mmol) in THF (15 mL) in a flask under N$_2$ protection was added NaH (171 mg, 4.5 mmol, 60% in oil) in portions. The reaction mixture was stirred for 10 min. Then iodoethane (701 mg, 4.5 mmol) was added. The reaction mixture was heated and stirred at 50° C. for another 2 h. TLC(PE:EA=3:1) showed the reaction was complete, and a main product was found with lower polarity. The reaction was quenched with aq. NH$_4$Cl (10 ml), extracted with EtOAc (20 mL×2). The combined organic layers were washed with aq. NaCl (20 mL) and dried over Na$_2$SO$_4$, then concentrated. The residue was purified by column chromatography on silica gel (PE:EtOAc=15:1 to 8:1) to afford the product C16 (500 mg, 91.9% yield) as a yellow oil. $^1$H NMR (400 MHz, CDCl$_3$) δ 5.12-5.09 (m, 1H), 3.60 (d, J=9.2 Hz, 1H), 3.48-3.42 (m, 2H), 3.23 (d, J=9.2 Hz, 1H), 2.38-2.12 (m, 3H), 1.95-1.72 (m, 3H), 1.65-1.10 (m, 26H), 0.85 (s, 3H).

Step 6. Preparation of Compound C17. To a solution of C16 (500 mg, 1.38 mmol) in THF (15 mL) was added dropwise a solution of BH$_3$-Me$_2$S (1.38 mL, 10 M) at 0° C. The solution was stirred at 25° C. for 4 h. TLC (PE:EtOAc=3:1) showed the reaction was almost complete, and a main product was found with higher polarity. After cooling to 0° C., a solution of NaOH (5.5 mL, 3M) was added very slowly. After the addition was complete, H$_2$O$_2$ (2.51 mL, 33%) was added slowly and the inner temperature was maintained below 10° C. The resulting solution was stirred at 25° C. for 2 h. The resulting solution was extract with EtOAc (20 mL×3). The combined organic solution was washed with saturated aqueous Na$_2$S$_2$O$_3$ (30 mL×3), brine (30 mL), dried over Na$_2$SO$_4$ and concentrated in vacuo to give the crude product (500 mg) as a yellow oil. The crude product was used for the next step without further purification.

Step 7. Preparation of Compound C18. A suspension of C$_{17}$ (500 mg, 1.32 mmol), PCC (426 mg, 1.98 mmol) and silica gel (469 mg, w/w=1/1.1) in DCM (15 mL) was stirred at 30° C. for 2 h, the reaction mixture color became brown. TLC (PE/EtOAc=3/1) showed the reaction was complete, and a main product was found with lower polarity. The solution was filtered and the filter cake was washed with DCM (20 mL). The combined filtrate was concentrated in vacuo. The residue was purified by column chromatography on silica gel eluted with PE/EtOAc=15/1 to 5/1 to give C18 (400 mg, 80.3%) as a white solid. MS ESI calcd. for C$_{24}$H$_{40}$O$_3$ [M+H]$^+$ 377, found 359 ([M+H−18]$^+$). $^1$H NMR (400 MHz, CDCl$_3$) δ 3.58 (d, J=9.2 Hz, 1H), 3.49-3.42 (m, 2H), 3.24 (d, J=9.2 Hz, 1H), 2.56-2.51 (m, 1H), 2.18-1.65 (m, 12H), 1.60-1.10 (m, 19H), 0.61 (s, 3H).

Step 8. Preparation of Compound C19. To a solution of C18 (400 mg, 1.06 mmol) and a catalytic amount of concentrated HBr (10.7 mg, 40% in water) in MeOH (15 mL) was added dropwise dibromine (254 mg, 1.59 mmol) at 0° C. The reaction mixture was stirred at 25° C. for 1 h. TLC (PE:EtOAc=3:1) showed the reaction was complete, and a main product was found with lower polarity. The reaction was quenched by saturated aqueous NaHCO$_3$ and the pH was adjusted to 7~8. The reaction mixture was extracted with DCM (20 mL×2). The combined organic layer was washed with brine (20 mL), dried over Na$_2$SO$_4$ and concentrated to get the crude product C19 (400 mg, 82.8% yield) as yellow oil.

Example 89. Preparation of Compound 170

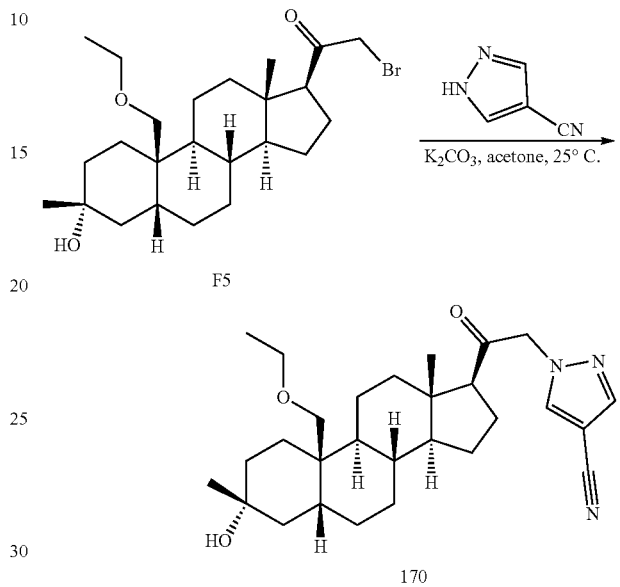

To a solution of compound F5 (150 mg, 0.329 mmol) in acetone (5 mL) was added K$_2$CO$_3$ (68.1 mg, 0.493 mmol) and 1H-pyrazole-4-carbonitrile (45.8 mg, 0.493 mmol). After stirring at 25° C. for 3 h, LCMS showed the reaction was complete. The reaction mixture was filtered, and the filtrate was concentrated in vacuum to give the crude product (150 mg). The crude product was purified by prep. HPLC (HCl) to give the desired product 170 (13 mg, 8.41%) as white solid.

$^1$H NMR (170) (yield 8.4%): (400 MHz, CDCl$_3$) δ 7.86 (s, 1H), 7.81 (s, 1H), 5.03-4.87 (m, 2H), 3.54 (d, J=9.2 Hz, 1H), 3.68-3.41 (m, 2H), 3.24 (d, J=9.2 Hz, 1H), 2.59 (t, J=9.2 Hz, 1H), 2.21-1.15 (m, 29H), 0.65 (s, 3H). LCMS t$_R$=0.949 min in 1.5 min chromatography, 5-95 AB, purity 98.6%, MS ESI calcd. for C$_{28}$H$_{42}$N$_3$O$_3$ [M+H]$^+$ 467, found 450[M+H−18]$^+$.

Example 90. Alternative Preparation of Compound A21

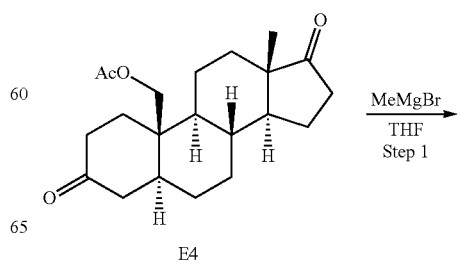

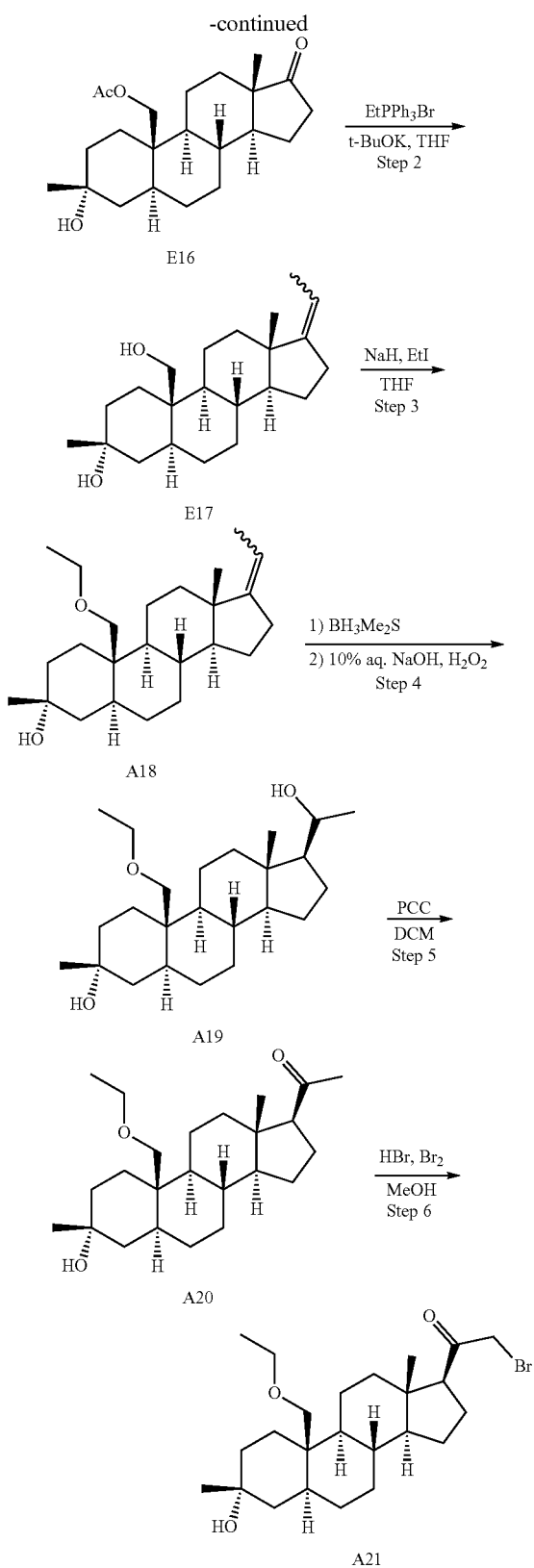

(15 mL, 3M in ether, 450 mmol) dropwise to control inner temperature below −70° C. The mixture was then stirred for 1 hour at −78° C. TLC showed the reaction was completed. To the mixture was added a solution of NH₄Cl (6 g) in water (30 mL) and inner temperature was raised to −20° C. The mixture was then warmed to 20° C. Organic layer was separated. The aqueous phase was extracted with EtOAc (50 mL). The combined organic layer was dried over Na2SO4, concentrated under vacuum and purified by column chromatography (PE:EtOAc=6:1 to 3:1) to give ((3R,5S,8R,9S,10R,13S,14S) -3-hydroxy-3,13-dimethyl-17-oxohexadecahydro-1H-cyclopenta[a]phenanthren-10-yl)methyl acetate (E16, 2.4 g, 46%) and ((3S,5S,8R,9S,10R,13S,14S)-3-hydroxy-3,13-dimethyl-17-oxohexadecahydro-1H-cyclopenta[a]phenanthren-10-yl)methyl acetate (1 g, 19%) as white solid.

¹H NMR (400 MHz, CDCl₃) δ 4.29 (d, J=12.1 Hz, 1H), 4.13 (d, J=12.1 Hz, 1H), 2.48-2.35 (m, 1H), 2.11-1.85 (m, 7H), 1.85-1.59 (m, 6H), 1.55-1.22 (m, 11H), 1.09-0.74 (m, 7H).

Step 2. Preparation of Compound E17. To a suspension of PPh3EtBr (4.61 g, 12.4 mmol) in THF (10 mL) was added a solution of t-BuOK (1.86 g, 16.6 mmol) in THF (20 mL) at 20° C. The color of the suspension was turned to dark red. After stirring at 60° C. for 1 h, a solution of ((3R,5S,8R,9S,10R,13S,14S) -3-hydroxy-3,13-dimethyl-17-oxohexadecahydro-1H-cyclopenta[a]phenanthren-10-yl)methyl acetate (E16, 1.5 g, 4.14 mmol) in THF (20 mL) was added dropwise at 60° C. Then the reaction mixture was stirred at 60° C. for 16 h. TLC showed the reaction was complete. To the reaction mixture was added NH₄Cl (50 mL, sat. aq.). The color of the mixture was turned to light yellow. The organic layer was separated. The aqueous phase was extracted with EtOAc (50 mL). The combined organic layer was concentrated under vacuum purified by column chromatography on silica gel (PE:EtOAc=10:1 to 4:1) to give (3R,5S,8S,9S,10R,13S,14S)-17-ethylidene-10-(hydroxymethyl)-3,13-dimethylhexadecahydro-1H-cyclopenta[a]phenanthren-3-ol (E17, 1.0 g, 72.6%) as white solid. ¹H NMR (400 MHz, CDCl₃) δ 5.19-5.08 (m, 1H), 3.93 (d, J=11.5 Hz, 1H), 3.74 (d, J=11.5 Hz, 1H), 2.44-2.33 (m, 1H), 2.32-2.13 (m, 2H), 2.12-2.04 (m, 1H), 1.87-1.71 (m, 2H), 1.69-1.43 (m, 12H), 1.38-1.08 (m, 11H), 1.07-0.74 (m, 6H)

Step 3. Preparation of Compound A18. To a solution of E17 (0.8 g, 2.4 mmol) in THF (10 mL) was added sodium hydride (475 mg, 11.9 mmol) in portions and iodoethane (1.85 g, 11.9 mmol). The mixture was stirred at 50° C. for 12 hours. The reaction mixture was quenched with water, extracted with EtOAc (10 mL*2). The combined organic layer was dried over anhydrous Na₂SO₄, filtered and concentrated. The residue was purified by column chromatography on silica gel (PE:EA=50:1) to give A18 (0.5 g, 57.5%) as colorless oil. ¹H NMR (400 MHz, CDCl₃) δ 5.13-5.08 (m, 1H), 3.52 (d, J=9.6 Hz, 1H), 3.43-3.38 (m, 3H), 2.38-2.32 (m, 1H), 2.25-2.12 (m, 2H), 2.06-2.01 (m, 1H), 1.74-1.57 (m, 2H), 1.56-1.39 (m, 6H), 1.31-1.27 (m, 2H), 1.24-1.16 (m, 11H), 1.14-1.07 (m, 2H), 1.05-0.91 (m, 2H), 0.88 (s, 3H), 0.87-0.74 (m, 3H).

Step 4. Preparation of Compound A19. To a solution of AN (0.5 g, 1.38 mmol) in THF (5 mL) at 0° C. was added BH₃-Me₂S (0.69 mL, 6.9 mmol) dropwise. The solution was stirred at 30° C. for 2 h. TLC (PE/EtOAc=5/1) showed the reaction was completed. After cooling to 0° C., an aqueous NaOH (5.51 g, 10% in water) was added very slowly. After the addition was completed, H₂O₂ (1.56 g, 30%) was added slowly and the inner temperature was maintained below 10° C. The resulting solution was stirred at room temperature for Step 1. Preparation of Compound E16. To a solution of ((5S,8R,9S,10R,13S,14S)-13-methyl-3,17-dioxohexadecahydro-1H-cyclopenta[a]phenanthren-10-yl)methyl acetate (E4, 5 g, 14.4 mmol) in THF (50 mL) was added MeMgBr 1 h. White solid was formed. To the mixture was added EtOAc (5 mL) and filtered. The filter cake was washed with EtOAc (5 mL). The combined organic layer was separated, washed with Na$_2$S$_2$O$_3$ (5 mL, 20%, aq.), dried over Na$_2$SO$_4$ and concentrated in vacuum to give A19 (0.4 g, purity: 78%, yield: 59.7%) as colorless oil which was used directly without further purification. LCMS t$_R$=1.085 min in 2 min chromatography, 30-90 AB, purity 77.6%, MS ESI calcd. for C$_{24}$H$_{42}$O$_3$[M+H]$^+$ 379, found 361 ([M+H−18]$^+$).

Step 5. Preparation of Compound A20. To a solution of A19 (0.4 g, 0.824 mmol, purity: 78%) in dichloromethane (5 mL) was added silica gel (1 g) and PCC (0.885 g, 4.11 mmol). The suspension was stirred at 30° C. for 16 hours. TLC (PE:EA=5:1) showed the reaction was consumed completely. The reaction mixture was filtered, and the filtrate was concentrated. The residue was purified by column chromatography on silica gel (PE:EA=10:1) to give A20 (0.2 g, 64.4%) as light yellow oil. $^1$H NMR (400 MHz, CDCl$_3$) U 3.50 (d, J=10.0 Hz, 1H), 3.42-3.37 (m, 3H), 2.53 (t, J=8.8 Hz, 1H), 2.20-2.15 (m, 1H), 2.11 (s, 3H), 2.07-1.97 (m, 2H), 1.73-1.64 (m, 4H), 1.50-1.47 (m, 2H), 1.37-1.25 (m, 6H), 1.21-1.14 (m, 9H), 1.12-0.75 (m, 5H), 0.61 (s, 3H). LCMS t$_R$=1.124 min in 2 min chromatography, 30-90 AB, purity 100%, MS ESI calcd. for C$_{24}$H$_{40}$O$_3$[M+H]$^+$377, found 359 ([M+H−18]).

Step 6. Preparation of Compound A21. To a solution of A20 (0.2 g, 0.531 mmol) in methanol (2 mL) was added HBr (8.93 mg, 0.053 mmol, 48% in water) and Br$_2$ (127 mg, 0.796 mmol). The mixture was stirred at 30° C. for 2 hours. The reaction mixture was quenched with aqueous NaHCO$_3$ to adjust the pH about 8. The mixture was poured to water (10 mL) and extracted with EtOAc (10 mL*2). The combined organic layers were dried over anhydrous sodium sulfate, filtered and concentrated to give A21 (0.2 g, 82.6%) as a light yellow solid which was used without further purification. LCMS t$_R$=1.184 min in 2 min chromatography, 30-90 AB, purity 100%, MS ESI calcd. for C$_{24}$H$_{39}$BrO$_3$ [M+H]$^+$ 455, found 437 ([M+H−18]).

Example 91. Preparation of Compound 171

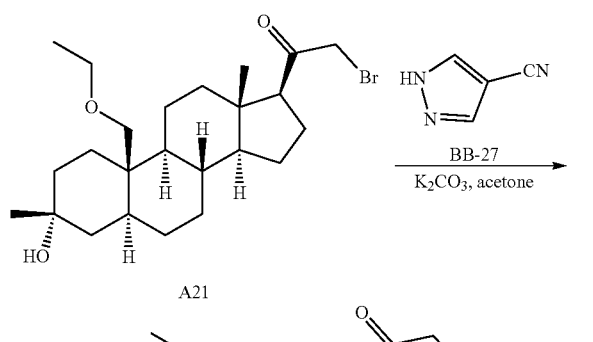

To a solution of A21 (90 mg, 0.197 mmol) in acetone (2 mL) was added potassium carbonate (67.9 mg, 0.492 mmol) and 1H-pyrazole-4-carbonitrile (27.4 mg, 0.295 mmol). The suspension was stirred at 40° C. for 12 hours. The reaction mixture was cooled and filtered, and the filtrate was concentrated. The residue was purified by prep. HPLC to give 171 (22 mg, 23.8%) as a white solid. $^1$H NMR (400 MHz, CDCl$_3$) δ 7.85 (s, 1H), 7.81 (s, 1H), 5.02 (d, J=18.0 Hz, 1H), 4.89 (m, J=18.0 Hz, 1H), 3.51 (d, J=9.2 Hz, 1H), 3.42-3.37 (m, 3H), 2.60 (t, J=9.2 Hz, 1H), 2.25-2.17 (m, 1H), 2.06-1.99 (m, 2H), 1.75-1.69 (m, 4H), 1.54-1.50 (m, 3H), 1.46-0.81 (m, 19H), 0.67 (s, 3H). LCMS t$_R$=1.109 min in 2 min chromatography, 30-90 AB, purity 100%, MS ESI calcd. for C$_{28}$H$_{41}$N$_3$O$_3$ [M+H]$^+$ 468, found 490 ([M+Na]).

Example 92. Preparation of Compounds 172 and 173

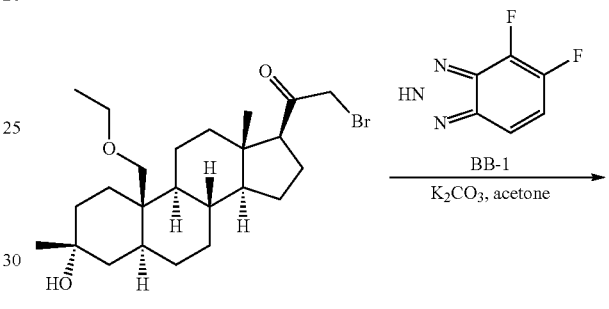

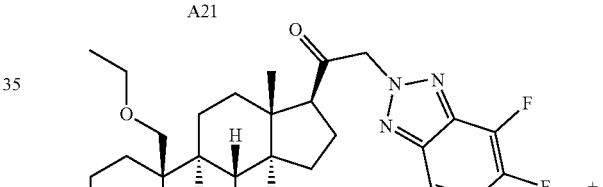

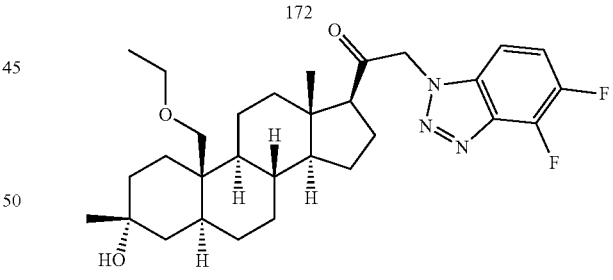

To a solution of 2-bromo-1-((3R,5S,8S,9S,10R,13S,14S,17S)-10-(ethoxymethyl)-3-hydroxy-3,13-dimethylhexadecahydro-1H-cyclopenta[a]phenanthren-17-yl)ethanone (90 mg, 0.197 mmol) in acetone (2 mL) was added potassium carbonate (67.9 mg, 0.492 mmol) and 4,5-difluoro-2H-benzo[d][1,2,3]triazole (45.7 mg, 0.295 mmol). The mixture was stirred at 50° C. for 16 hours. The mixture was cooled, filtered and concentrated. The residue was purified by prep-HPLC to give 2-(4,5-difluoro-2H-benzo[d][1,2,3]triazol-2-yl)-1-((3R,5S,8S,9S,10R,13S,14S,17S)-10-(ethoxymethyl)-3-hydroxy-3,13-dimethylhexadecahydro-1H-cyclopenta[a]phenanthren-17-yl)ethanone (172, 10 mg, 9.28%, purity: 97%) as light yellow solid and 2-(4,5-difluoro-1H-benzo[d][1,2,3]triazol-1-yl)-1-((3R,5S,8S,9S,10R,13S,14S,17S)-10-(ethoxymethyl)-3-hydroxy-3,13-dimethylhexadecahydro-1H-cyclopenta[a]phenanthren-17-yl)ethanone (173, 15 mg, 14.0%, purity: 98%) as light yellow solid.

$^1$H NMR (172): (400 MHz, CDCl$_3$) δ 7.63 (dd, J=3.2 Hz, 8.8 Hz, 1H), 7.31-7.24 (m, 2H), 5.57-5.46 (m, 2H), 3.53 (d, J=9.6 Hz, 1H), 3.43-3.40 (m, 3H), 2.66 (t, J=8.8 Hz, 1H), 2.27-2.03 (m, 3H), 1.79-1.69 (m, 4H), 1.65-1.57 (m, 4H), 1.32-1.26 (m, 6H), 1.22-1.12 (m, 8H), 1.09-0.82 (m, 4H), 0.76 (s, 3H). LCMS t$_R$=1.066 min in 1.5 min chromatography, 5-95 AB, purity 97%, MS ESI calcd. for C$_{30}$H$_{42}$F$_2$N$_3$O$_3$ [M+H]$^+$ 530, found 512 ([M+H−18]$^+$).

$^1$H NMR (173): (400 MHz, CDCl$_3$) δ 7.40-7.33 (m, 1H), 7.05 (d, J=7.2 Hz, 1H), 5.46-5.35 (m, 2H), 3.52 (d, J=10.0 Hz, 1H), 3.43-3.38 (m, 3H), 2.71 (t, J=8.4 Hz, 1H), 2.24-2.03 (m, 3H), 1.75-1.69 (m, 4H), 1.62-1.53 (m, 4H), 1.32-1.16 (m, 14H), 1.13-0.83 (m, 4H), 0.72 (s, 3H). LCMS t$_R$=1.037 min in 1.5 min chromatography, 5-95 AB, purity 98%, MS ESI calcd. for C$_{30}$H$_{42}$F$_2$N$_3$O$_3$[M+H]$^+$530, found 530 ([M+H]$^+$).

Assay Methods

Compounds provided herein can be evaluated using various assays; examples of which are described below.

Steroid Inhibition of TBPS Binding

TBPS binding assays using rat brain cortical membranes in the presence of 5 μM GABA has been described (Gee et al, *J. Pharmacol. Exp. Ther.* 1987, 241, 346-353; Hawkinson et al, *Mol. Pharmacol.* 1994, 46, 977-985; Lewin, A. H et al., *Mol. Pharmacol.* 1989, 35, 189-194).

Briefly, cortices are rapidly removed following decapitation of carbon dioxide-anesthetized Sprague-Dawley rats (200-250 g). The cortices are homogenized in 10 volumes of ice-cold 0.32 M sucrose using a glass/teflon homogenizer and centrifuged at 1500×g for 10 min at 4° C. The resultant supernatants are centrifuged at 10,000×g for 20 min at 4° C. to obtain the P2 pellets. The P2 pellets are resuspended in 200 mM NaCl/50 mM Na—K phosphate pH 7.4 buffer and centrifuged at 10,000×g for 10 min at 4° C. This washing procedure is repeated twice and the pellets are resuspended in 10 volumes of buffer. Aliquots (100 μL) of the membrane suspensions are incubated with 3 nM [$^{35}$S]-TBPS and 5 μL aliquots of test drug dissolved in dimethyl sulfoxide (DMSO) (final 0.5%) in the presence of 5 μM GABA. The incubation is brought to a final volume of 1.0 mL with buffer. Nonspecific binding is determined in the presence of 2 μM unlabeled TBPS and ranged from 15 to 25%. Following a 90 min incubation at room temp, the assays are terminated by filtration through glass fiber filters (Schleicher and Schuell No. 32) using a cell harvester (Brandel) and rinsed three times with ice-cold buffer. Filter bound radioactivity is measured by liquid scintillation spectrometry. Non-linear curve fitting of the overall data for each drug averaged for each concentration is done using Prism (GraphPad). The data are fit to a partial instead of a full inhibition model if the sum of squares is significantly lower by F-test. Similarly, the data are fit to a two component instead of a one component inhibition model if the sum of squares is significantly lower by F-test. The concentration of test compound producing 50% inhibition (IC$_{50}$) of specific binding and the maximal extent of inhibition (I$_{max}$) are determined for the individual experiments with the same model used for the overall data and then the mean±SEM.s of the individual experiments are calculated. Picrotoxin serves as the positive control for these studies as it has been demonstrated to robustly inhibit TBPS binding.

Various compounds are or can be screened to determine their potential as modulators of [$^{35}$S]-TBPS binding in vitro. These assays are or can be performed in accordance with the above discussed procedures.

For Table 1, "A" indicates an IC$_{50}$<10 nM, "B" indicates an IC$_{50}$ of 10 nM to 50 nM, "C" indicates an IC$_{50}$>50 nM to 100 nM, "D" indicates an IC$_{50}$>100 nM to 500 nM, and "E" indicates IC$_{50}$ 500 nM.

TABLE 1

| Compound | 35S-TBPS Radioligand Displacement (IC50) |
|---|---|
| 1 | B |
| 2 | E |
| 3 | E |
| 4 | E |
| 5 | E |
| 6 | E |
| 7 | E |
| 8 | E |
| 9 | E |
| 10 | E |
| 11 | E |
| 12 | E |
| 13 | C |
| 14 | B |
| 15 | D |
| 16 | B |
| 17 | E |
| 21 | D |
| 23 | D |
| 24 | D |
| 25 | B |
| 26 | C |
| 27 | A |
| 28 | C |
| 29 | D |
| 30 | A |
| 31 | B |
| 32 | C |
| 33 | B |
| 34 | A |
| 35 | B |
| 36 | B |
| 37 | B |
| 38 | C |
| 39 | B |
| 40 | B |
| 41 | B |
| 42 | B |
| 43 | A |
| 44 | B |
| 45 | C |
| 46 | C |
| 47 | B |
| 48 | B |
| 49 | B |
| 50 | B |
| 51 | B |
| 52 | B |
| 53 | C |
| 54 | B |
| 55 | C |
| 56 | C |
| 57 | C |
| 58 | A |
| 59 | B |
| 60 | B |
| 61 | A |
| 62 | B |
| 63 | B |
| 64 | B |
| 65 | A |
| 66 | B |
| 67 | B |
| 68 | B |

TABLE 1-continued

| Compound | 35S-TBPS Radioligand Displacement (IC50) |
|---|---|
| 69 | B |
| 70 | C |
| 71 | B |
| 72 | B |
| 73 | A |
| 74 | A |
| 75 | B |
| 76 | A |
| 77 | A |
| 78 | A |
| 79 | A |
| 80 | B |
| 81 | B |
| 82 | B |
| 83 | A |
| 90 | C |
| 91 | D |
| 92 | B |
| 93 | D |
| 97 | B |
| 98 | C |
| 99 | B |
| 100 | D |
| 101 | B |
| 102 | D |
| 103 | E |
| 104 | C |
| 105 | E |
| 106 | D |
| 107 | E |
| 108 | D |
| 109 | C |
| 110 | C |
| 111 | C |
| 112 | C |
| 113 | D |
| 114 | B |
| 115 | B |
| 127 | B |
| 128 | A |
| 138 | D |
| 144 | C |
| 146 | C |
| 154 | E |
| 155 | C |
| 157 | B |
| 161 | D |
| 162 | D |
| 171 | B |

Patch Clamp Electrophysiology of Recombinant $\alpha_1\beta_2\gamma_2$ and $\alpha_4\beta_3\delta$ GABA$_A$ Receptors Cellular electrophysiology is used to measure the pharmacological properties of our GABA$_A$ receptor modulators in heterologous cell systems. Each compound is tested for its ability to affect GABA mediated currents at a submaximal agonist dose (GABA $EC_{20}$=2 μM). LTK cells are stably transfected with the $\alpha_1\beta_2\gamma_2$ subunits of the GABA receptor and CHO cells are transiently transfected with the $\alpha_4\beta_3\delta$ subunits via the Lipofecatamine method. Cells were passaged at a confluence of about 50-80% and then seeded onto 35 mm sterile culture dishes containing 2 ml culture complete medium without antibiotics or antimycotics. Confluent clusters of cells are electrically coupled (Pritchett et al., Science, 1988, 242, 1306-1308.). Because responses in distant cells are not adequately voltage clamped and because of uncertainties about the extent of coupling (Verdoorn et al., Neuron 1990, 4, 919-928), cells were cultivated at a density that enables the recording of single cells (without visible connections to other cells).

Whole cell currents were measured with HEKA EPC-10 amplifiers using PatchMaster software or by using the high throughput QPatch platform (Sophion). Bath solution for all experiments contained (in mM): NaCl 137 mM, KCl 4 mM, CaCl$_2$ 1.8 mM, MgCl$_2$ 1 mM, HEPES 10 mM, D-Glucose 10 mM, pH (NaOH) 7.4. In some cases 0.005% cremophor was also added. Intracellular (pipette) solution contained: KCl 130 mM, MgCl$_2$ 1 mM, Mg-ATP 5 mM, HEPES 10 mM, EGTA 5 mM, pH 7.2. During experiments, cells and solutions were maintained at room temperature (19° C.-30° C.). For manual patch clamp recordings, cell culture dishes were placed on the dish holder of the microscope and continuously perfused (I ml/min) with bath solution. After formation of a Gigaohm seal between the patch electrodes and the cell (pipette resistance range: 2.5 MΩ-6.0 MΩ; seal resistance range:>1 GΩ) the cell membrane across the pipette tip was ruptured to assure electrical access to the cell interior (whole-cell patch-configuration). For experiments using the QPatch system, cells were transferred as suspension to the QPatch system in the bath solution and automated whole cell recordings were performed.

Cells were voltage clamped at a holding potential of −80 mV. For the analysis of test articles, GABA receptors were stimulated by 2 μM GABA after sequential pre-incubation of increasing concentrations of the test article. Pre-incubation duration was 30 s and the duration of the GABA stimulus was 2 s. Test articles were dissolved in DMSO to form stock solutions (10 mM). Test articles were diluted to 0.01, 0.1, 1, and 10 μM in bath solution. All concentrations of test articles were tested on each cell. The relative percentage potentiation was defined as the peak amplitude in response to GABA $EC_{20}$ in the presence of the test article divided by the peak amplitude in response to GABA $EC_{20}$ alone, multiplied by 100.

TABLE 2

Electrophysiological evaluation of the exemplary compounds at GABA$_A$-R.

| Name | GABA ($\alpha1\beta2\gamma2$) Qpatch in Ltk, % efficacy at 10 μM | GABA ($\alpha4\beta3\delta$) Manual patch in CHO, % efficacy at 10 μM |
|---|---|---|
| 1 | B | C |
| 14 | B | C |
| 15 | C | B |
| 16 | C | C |
| 19 | B | B |
| 30 | B | C |
| 35 | B | B |
| 36 | B | B |
| 37 | C | C |
| 43 | C | B |
| 52 | B | C |
| 54 | B | C |
| 55 | C | C |
| 76 | C | C |

For Table 2. GABAA receptors $\alpha1\beta2\gamma2$ and $\alpha_4\beta_3\delta$% efficacy: "A" 10-100, "B" >100-500, "C" >500; D indicates the data is not available or has not been determined.

GABA Receptor Potentiation

The Two Electrode Voltage Clamp (TEVC) technique was used to investigate the effects of compounds at a concentration of 10 μM on GABA$_A$ receptors composed of the $\alpha_1\beta_2\gamma_2$ or $\alpha_4\beta_3\delta$ subunits expressed in oocytes from the *Xenopus laevis*. GABA-evoked currents were recorded from oocytes that expressed the GABA receptors and the modulatory effects of the test items on these currents were investigated.

Ovaries were harvested from *Xenopus laevis* females that had been deeply anesthetized by cooling at 4° C. and immersion in Tricaine methanesulfonate (MS-222 at a concentration of 150 mg/L) in sodium bicarbonate (300 mg/L). Once anesthetized the animal was decapitated and pithed following the rules of animal rights from the Geneva canton. A small piece of ovary was isolated for immediate preparation while the remaining part was placed at 4° C. in a sterile Barth solution containing in mM NaCl 88, KCl 1, NaHCO$_3$ 2.4, HEPES 10, MgSO$_4$·7H$_2$O 0.82, Ca(NO$_3$)$_2$·4H$_2$O 0.33, CaCl$_2$·6H$_2$O 0.41, at pH 7.4, and supplemented with 20 µg/ml of kanamycin, 100 unit/ml penicillin and 100 µg/ml streptomycin. All recordings were performed at 18° C. and cells were super-fused with medium containing in mM: NaCl 82.5, KCl 2.5, HEPES 5, CaCl$_2$·2H$_2$O, ·6H$_2$O 1, pH 7.4.

Plasmids containing the RNAs of the human GABRA1/GABRB2/GABRG2 and GABRA4/GABRB3/GABRD genes were injected into oocytes using a proprietary automated injection device (Hogg el al., *J. Neurosci. Methods*, (2008) 169: 65-75). These genes encode for the $\alpha_1\beta_2\gamma_2$ and $\alpha_4\beta_3\delta$ GABA$_A$ subunits respectively. Receptor expression was assessed using electrophysiology at least two days later. The ratio of RNA injection for $\alpha_1\beta_2\gamma_2$ was 1:1:1 and for $\alpha_4\beta_3\delta$ was 5:1:5. Electrophysiological recordings were made using an automated process equipped with standard TEVC and data were captured and analyzed using a proprietary data acquisition and analysis software running under Matlab (Mathworks Inc.). The membrane potential of the oocytes was maintained at −80 mV throughout the experiments. To explore the effects of proprietary compounds, currents were evoked by applying 10 µM ($\alpha_1\beta_2\gamma_2$) or 3 µM ($\alpha_4\beta_3\delta$) GABA for 30 s. These concentrations approximated the EC$_{50}$ concentration of GABA at each receptor subtype. Oocytes were then re-exposed to GABA again for 30 s. 15 s after beginning the GABA application, test article was co-applied at a concentration of 10 µM for 15 s. Potentiation of the peak current was assessed. Data was filtered at 10 Hz, captured at 100 Hz and analyzed using proprietary data acquisition and analysis software running under Matlab (Mathworks Inc.). For statistical analysis values were computed either with Excel (Microsoft) or Matlab (mathworks Inc.). To obtain mean measurements with standard deviations, all experiments were carried out using at least three cells.

GABA was prepared as a concentrated stock solution (10$^{-1}$ (M) in water and then diluted in the recording medium to obtain the desired test concentration. Compounds were prepared as stock solution (10$^{-2}$ M) in DMSO and then diluted in the recording medium to obtain the desired test concentration. Residual DMSO did not exceed the concentration of 1% a concentration that has been shown to have no effects on *Xenopus* oocyte function.

TABLE 3

Electrophysiological evaluation of the exemplary compounds at GABA$_A$-R.

| Name | GABA ($\alpha1\beta2\gamma2$) % efficacy at 10 µM | GABA ($\alpha4\beta3\delta$) % efficacy at 10 µM |
|---|---|---|
| 13 | C | E |
| 17 | C | E |
| 18 | C | C |
| 20 | B | E |
| 21 | A | A |
| 23 | B | E |
| 24 | B | D |
| 25 | B | E |
| 26 | B | C |
| 27 | C | E |
| 28 | D | E |
| 29 | A | B |
| 31 | B | E |
| 32 | A | C |
| 33 | A | A |
| 34 | A | D |
| 38 | B | D |
| 39 | B | D |
| 40 | D | E |
| 41 | C | E |
| 42 | B | D |
| 44 | C | E |
| 45 | B | C |
| 46 | C | E |
| 47 | B | C |
| 48 | B | A |
| 49 | B | D |
| 50 | B | D |
| 51 | B | C |
| 53 | A | D |
| 56 | A | D |
| 57 | A | B |
| 58 | B | B |
| 59 | B | B |
| 60 | A | D |
| 61 | B | E |
| 62 | B | C |
| 63 | B | E |
| 64 | C | B |
| 65 | B | D |
| 66 | A | C |
| 67 | A | B |
| 68 | A | C |
| 69 | B | C |
| 70 | A | C |
| 71 | A | C |
| 72 | A | C |
| 73 | B | D |
| 74 | B | E |
| 75 | B | E |
| 77 | C | E |
| 78 | A | C |
| 79 | B | C |
| 80 | B | E |
| 81 | B | D |
| 82 | B | B |
| 83 | C | E |
| 97 | B | D |
| 98 | B | C |
| 99 | C | D |
| 100 | B | D |
| 101 | B | E |
| 102 | A | A |
| 103 | C | E |
| 104 | A | C |
| 105 | A | C |
| 106 | A | C |
| 107 | B | E |
| 108 | A | D |
| 109 | A | C |
| 110 | B | E |
| 111 | B | D |
| 112 | A | D |
| 113 | A | B |

For Table 3. GABAA receptors $\alpha1\beta2\gamma2$ and $\alpha4\beta3\delta$ % efficacy: "A" 50-500, "B" >500-1000, "C" >1000-1500, "D" >1500-2000; "E" >2000.

What is claimed is:

1. A compound of the Formula (Ib):

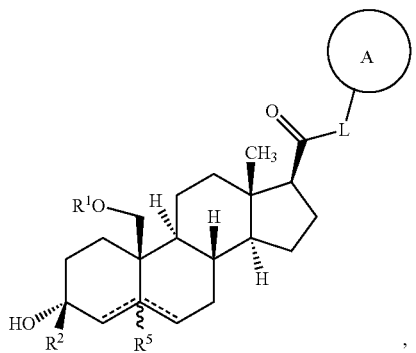

(Ib)

or a pharmaceutically acceptable salt thereof,
wherein:

A is an optionally substituted nitrogen-containing bicyclic heteroaryl or bicyclic heterocyclyl;

L is —C($R^3$)($R^3$)—, —O—, —S—, or —N$R^3$—;

$R^1$ is hydrogen, $C_1$-$C_6$ alkyl, $C_2$-$C_6$ alkenyl, $C_2$-$C_6$ alkynyl, carbocyclyl, or heterocyclyl;

$R^2$ is $C_1$-$C_6$ alkyl or $C_1$-$C_6$ alkoxy;

each $R^3$ is independently hydrogen;

$R^5$ is absent or hydrogen; and

====== is a single or double bond, wherein when one of ====== is a double bond, the other ====== is a single bond; and when one of the ====== is a double bond, $R^5$ is absent.

2. The compound or pharmaceutically acceptable salt of claim 1, wherein the compound of Formula (Ib) is a compound of Formula (Ib-3) or (Ib-4):

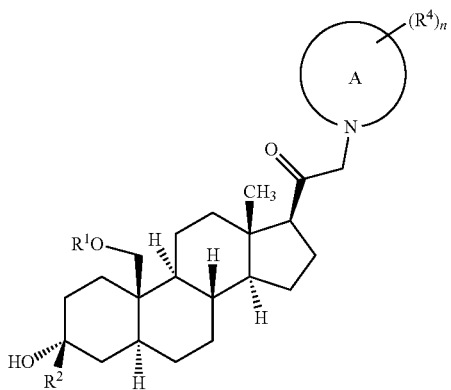

(Ib-3)

or

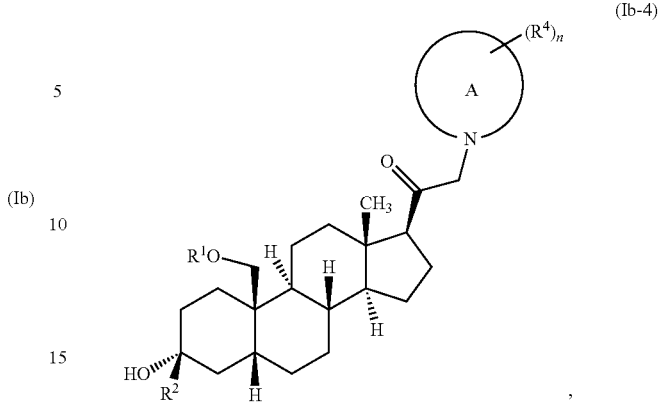

(Ib-4)

or a pharmaceutically acceptable salt thereof,
wherein:

$R^4$ is cyano, nitro, hydroxy, halo, $C_1$-$C_6$ alkyl, $C_1$-$C_6$ alkoxy, —C(O)$R^a$, —C(O)N($R^b$)($R^c$), —C(O)O$R^a$, —N($R^b$)($R^c$), —OC(O)N($R^b$)($R^c$), —OC(O)O$R^a$, —OC(O)$R^a$, —S(O)$_{0-2}$$R^a$, —S(O)$_{0-2}$O$R^a$, or —S(O)$_{0-2}$N($R^b$)($R^c$);

each $R^a$ is independently hydrogen or $C_1$-$C_6$ alkyl;

each $R^b$ and $R^c$ is independently hydrogen, $C_1$-$C_6$ alkyl, carbocyclyl, heterocyclyl, aryl, heteroaryl, or $R^b$ and $R^c$, together with the nitrogen atom to which they are bound to form a ring; and n is 0, 1, 2, or 3.

3. The compound or pharmaceutically acceptable salt of claim 2, wherein n is 0.

4. The compound or pharmaceutically acceptable salt of claim 2, wherein n is 1 or 2, and wherein each $R^4$ is independently cyano, halo, $C_1$-$C_6$ alkyl, $C_1$-$C_6$ alkoxy, —C(O)$R^a$, or —S(O)$_{0-2}$$R^a$.

5. The compound or pharmaceutically acceptable salt of claim 4, wherein each $R^a$ is independently $C_1$-$C_6$ alkyl.

6. The compound or pharmaceutically acceptable salt of claim 5, wherein each $R^a$ is methyl.

7. The compound or pharmaceutically acceptable salt of claim 4, wherein each $R^4$ is —S(O)$_2$$R^a$.

8. The compound or pharmaceutically acceptable salt of claim 7, wherein $R^a$ is methyl.

9. The compound or pharmaceutically acceptable salt of claim 2, wherein $R^1$ is $C_1$-$C_6$ alkyl and $R^4$ is —C(O)$R^a$.

10. The compound or pharmaceutically acceptable salt of claim 2, wherein n is 0 or 1, $R^1$ is hydrogen or $C_1$-$C_6$ alkyl; and $R^2$ is methyl.

11. The compound or pharmaceutically acceptable salt of claim 2, wherein each $R^4$ is independently $C_1$-$C_6$ alkyl, —C(O)$R^a$, or —S(O)$_{0-2}$$R^a$.

12. The compound of pharmaceutically acceptable salt of claim 1, wherein A is benzotriazole, azabenzotriazole, diazabenzotriazole, benzopyrazole, azabenzopyrazole, or diazabenzopyrazole.

13. The compound or pharmaceutically acceptable salt of claim 1, wherein $R^1$ is $C_1$-$C_6$ alkyl, $C_2$-$C_6$ alkenyl, $C_2$-$C_6$ alkynyl, carbocyclyl, or heterocyclyl.

14. The compound or pharmaceutically acceptable salt of claim 12, wherein $R^1$ is methyl, ethyl, or isopropyl.

15. The compound or pharmaceutically acceptable salt of claim 1, wherein $R^2$ is methyl.

16. A compound selected from
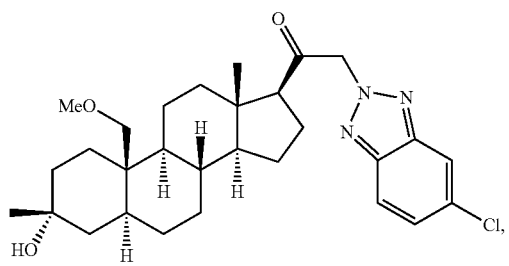
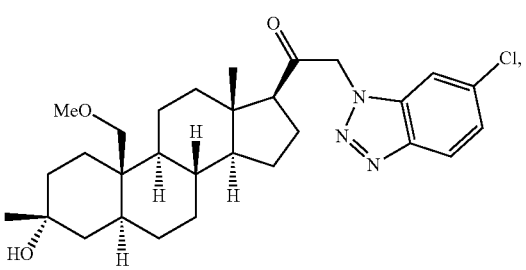
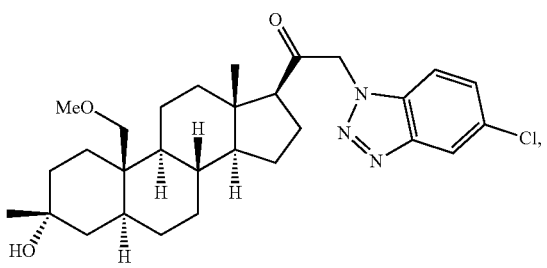
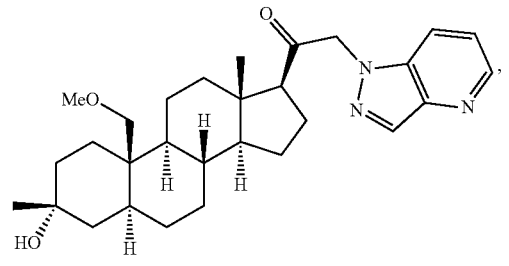
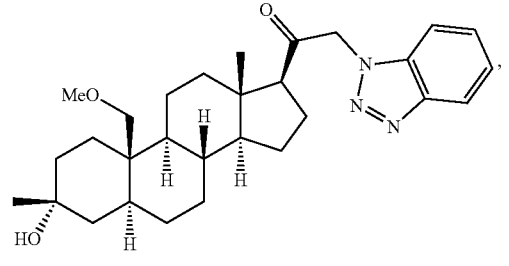
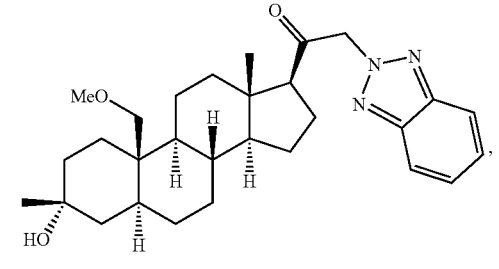
-continued
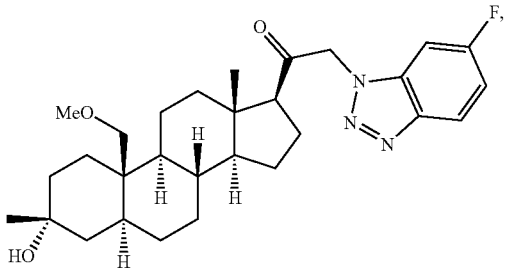
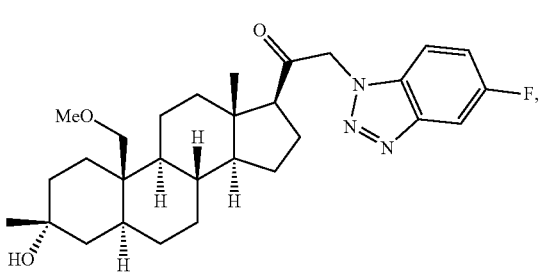
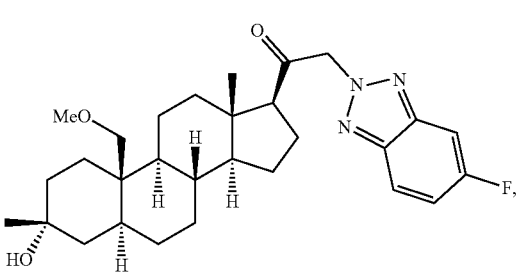
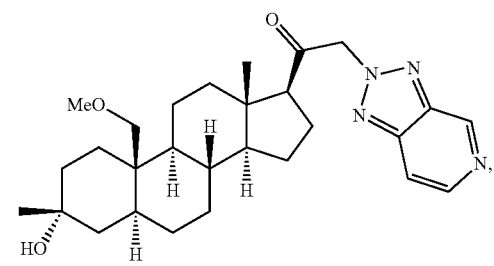
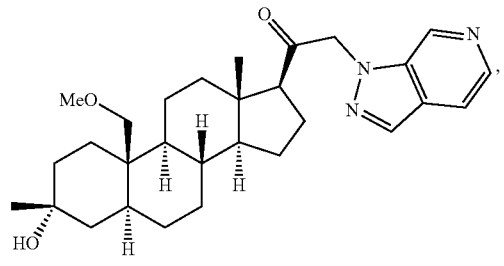
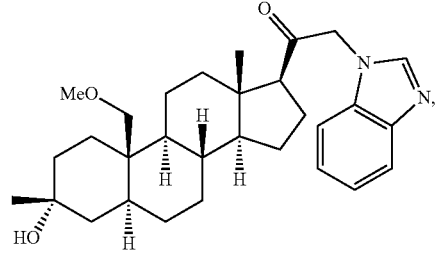

187
-continued
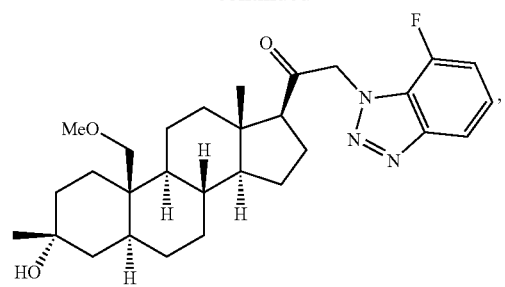
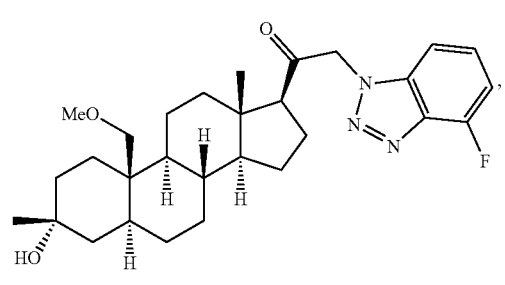
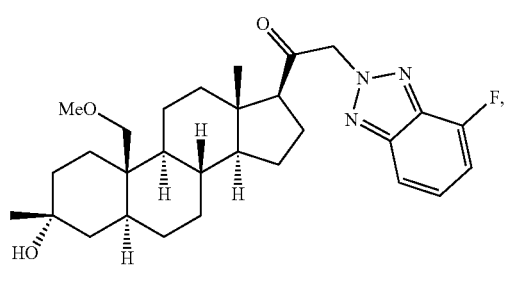
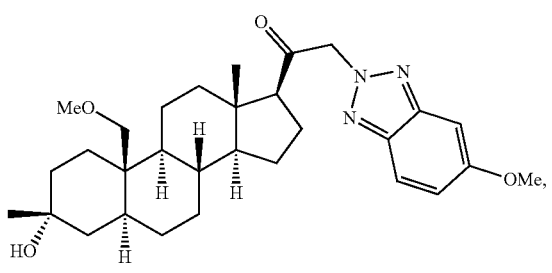
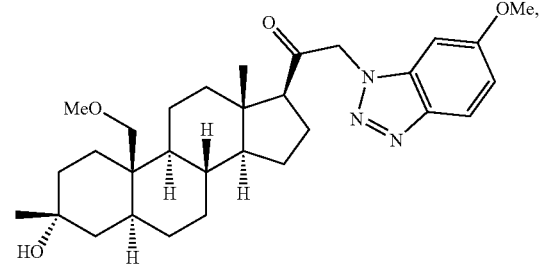
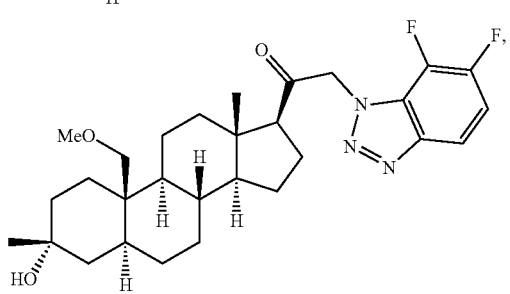
188
-continued
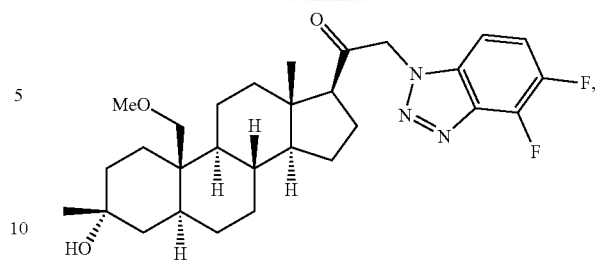
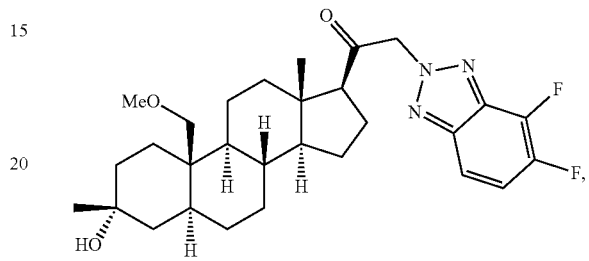
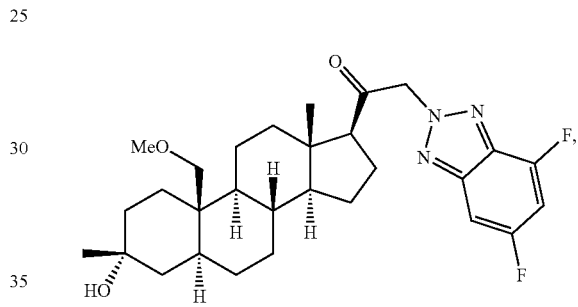
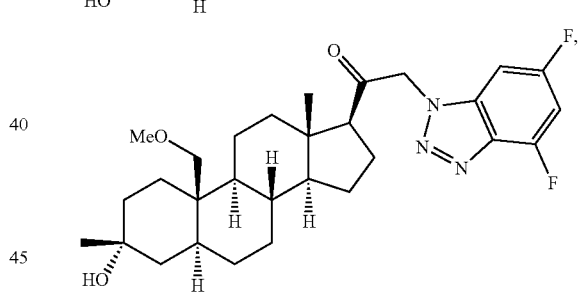
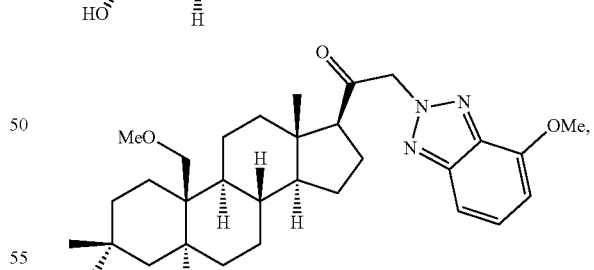
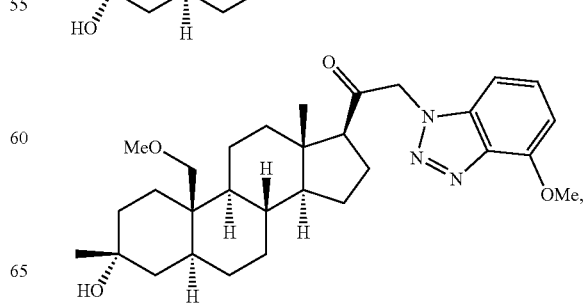

189
-continued
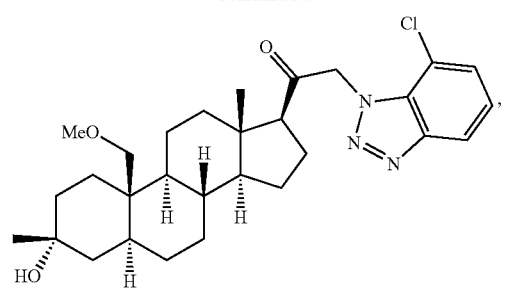
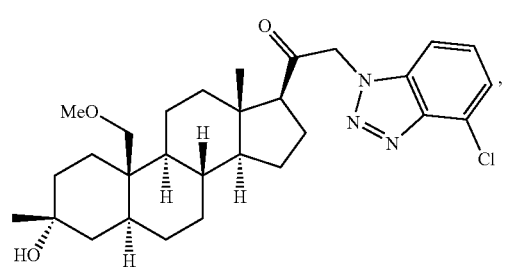
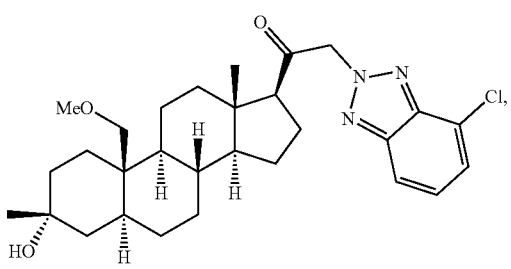
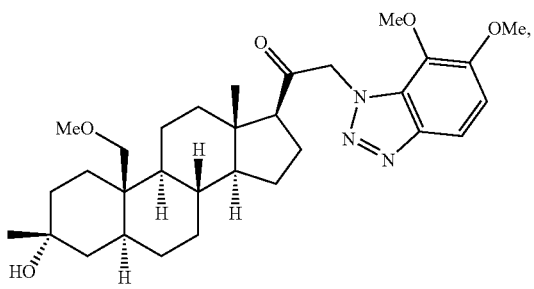
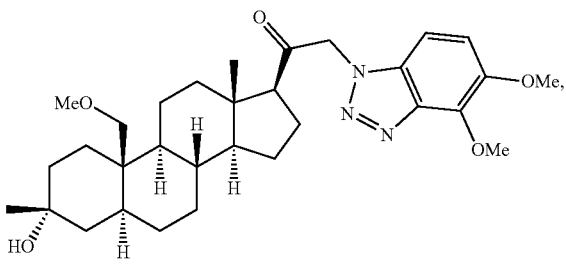
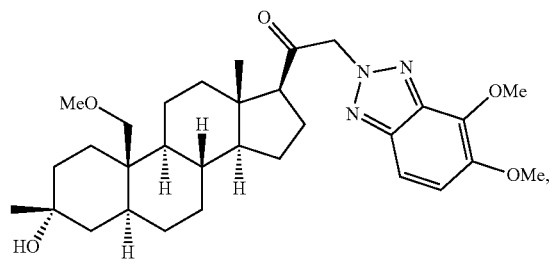
190
-continued
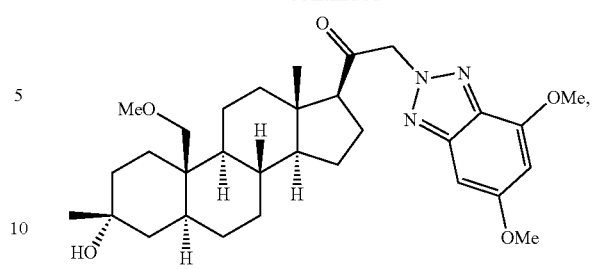
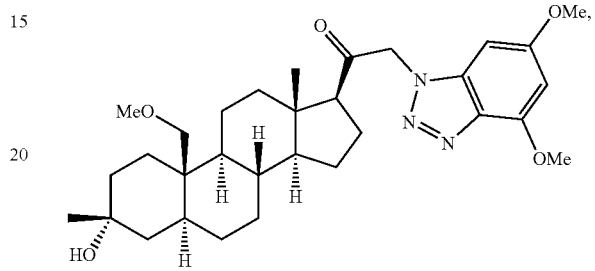
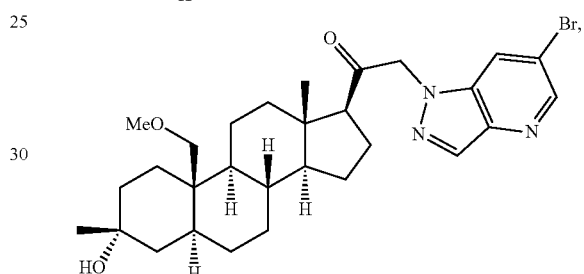
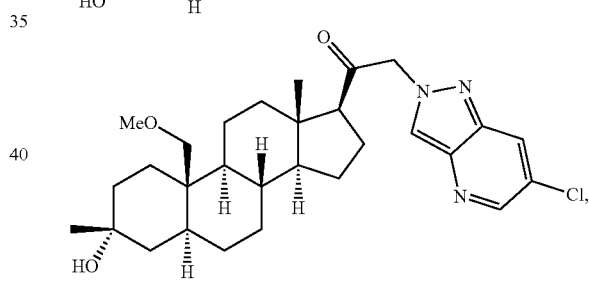
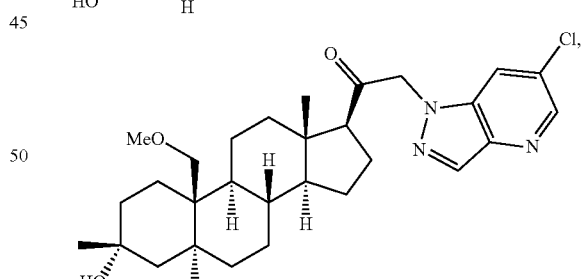
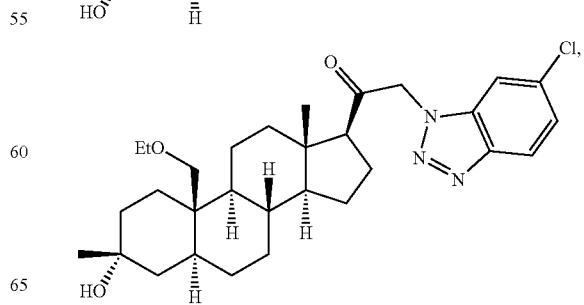

191
-continued
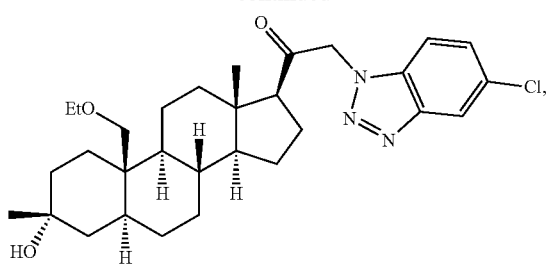
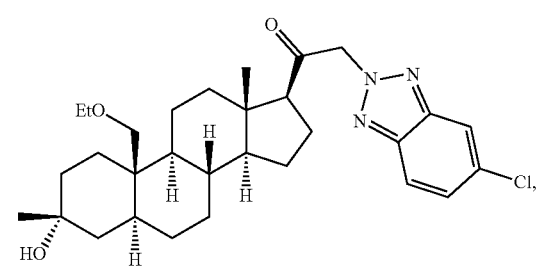
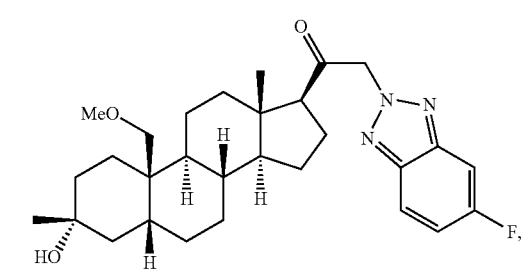
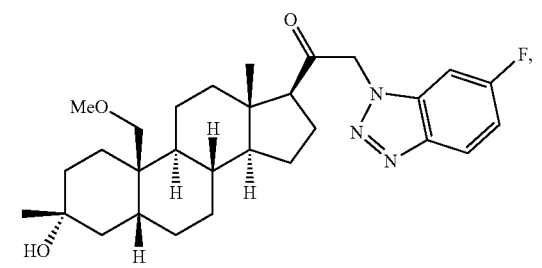
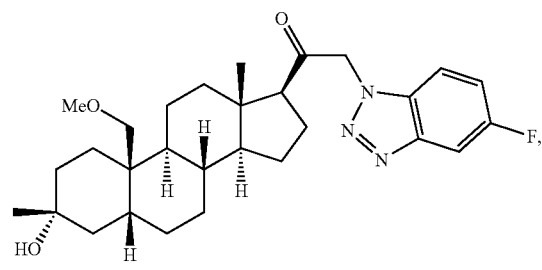
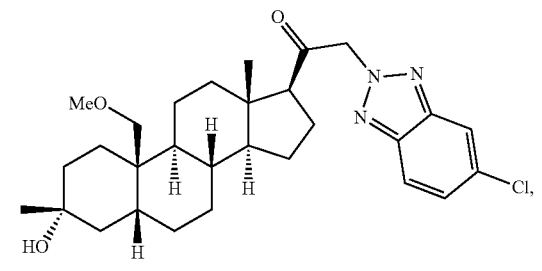
192
-continued
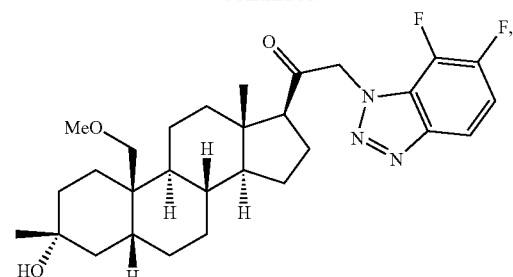
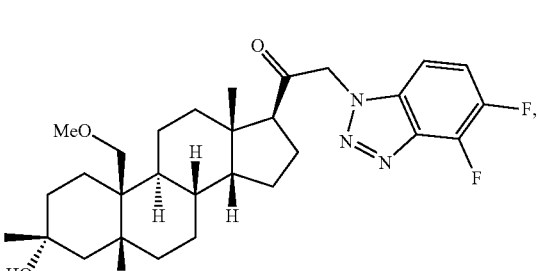
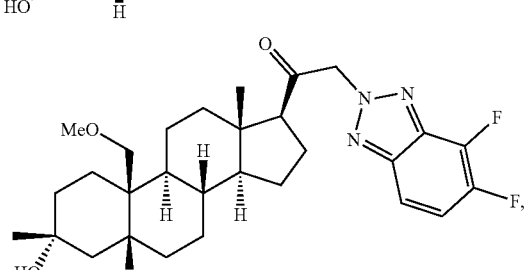
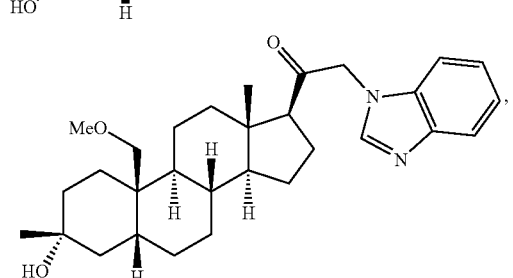
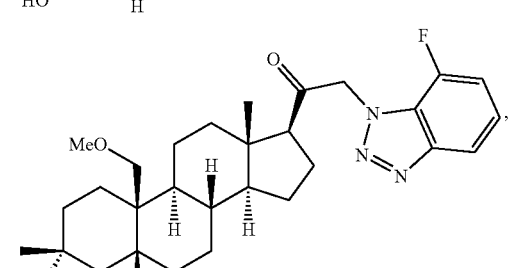
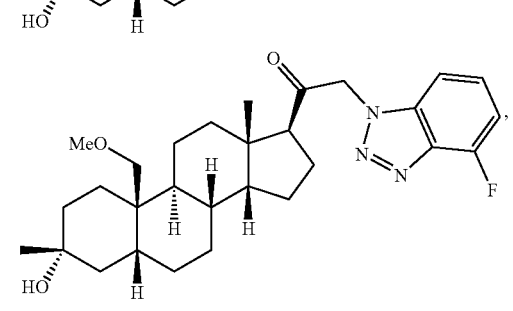

193
-continued
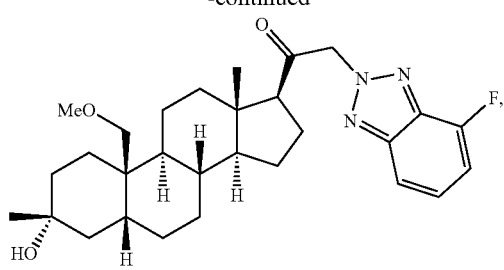
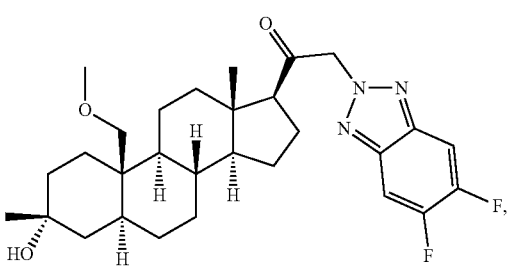
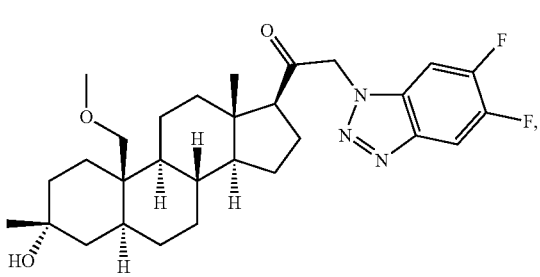
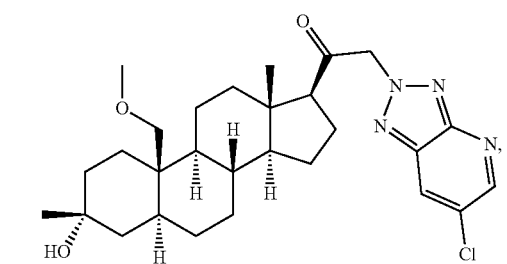
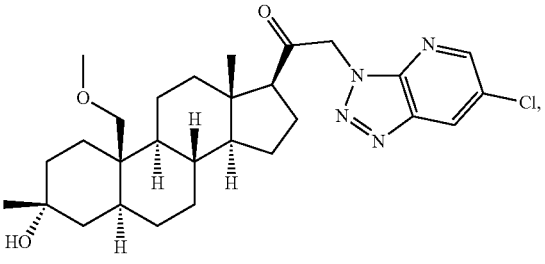
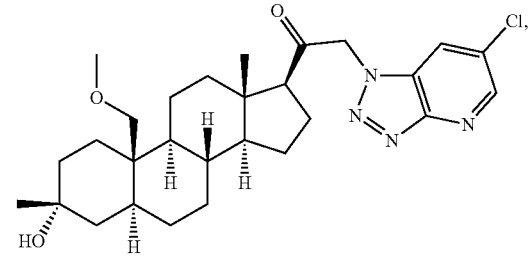
194
-continued
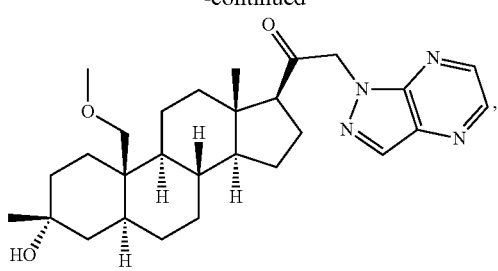
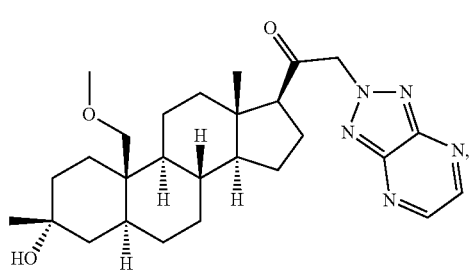
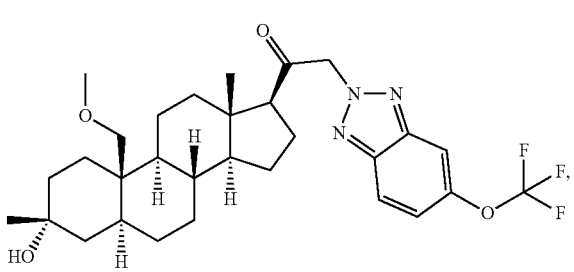
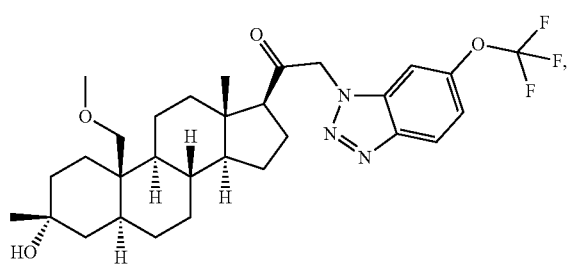
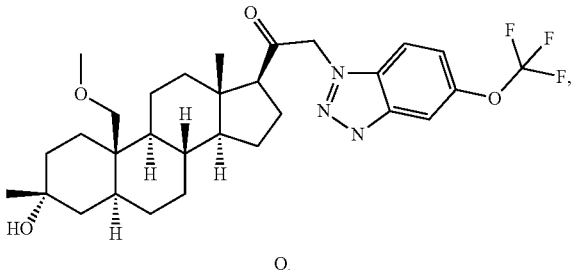
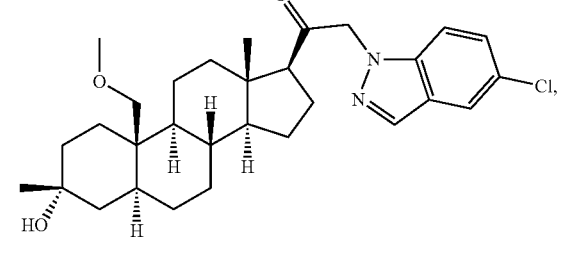

195
-continued
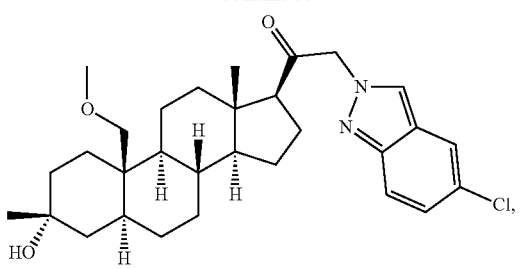
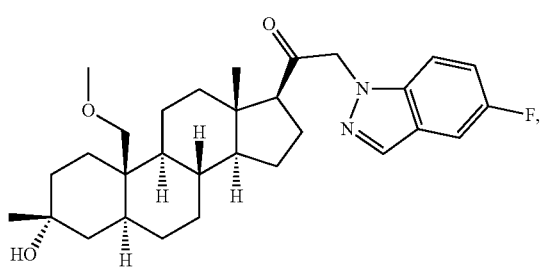
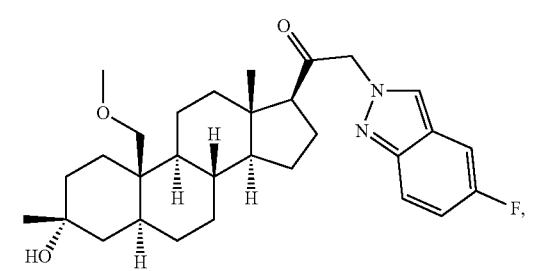
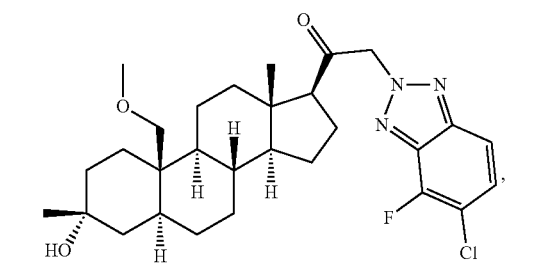
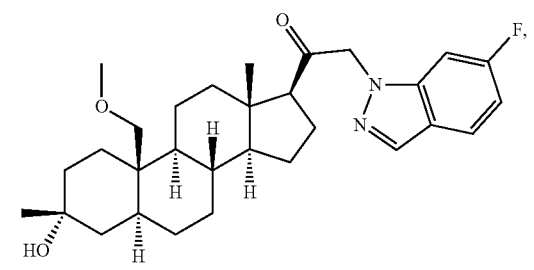
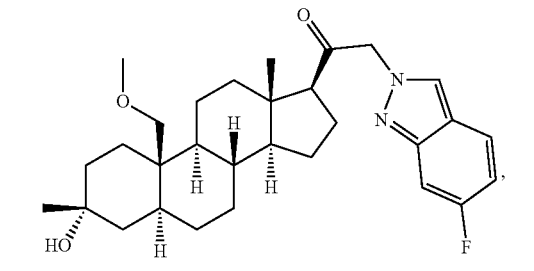
196
-continued
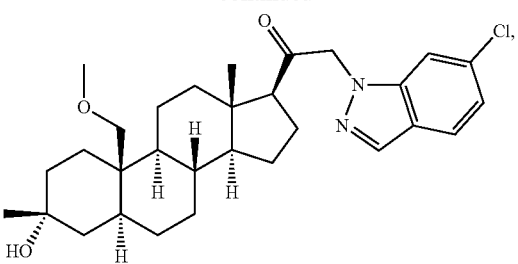
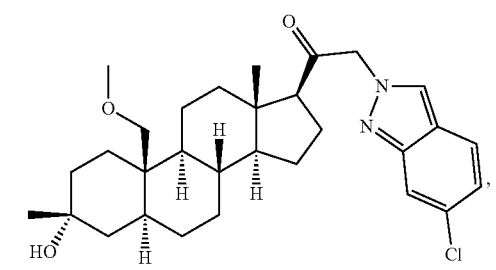
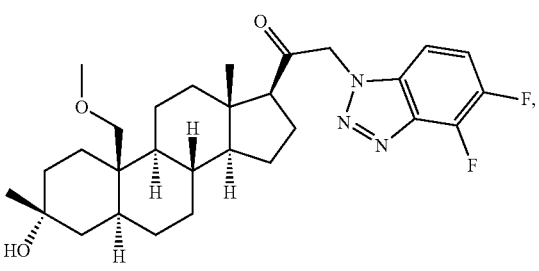
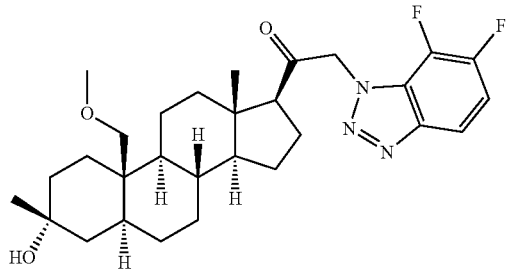
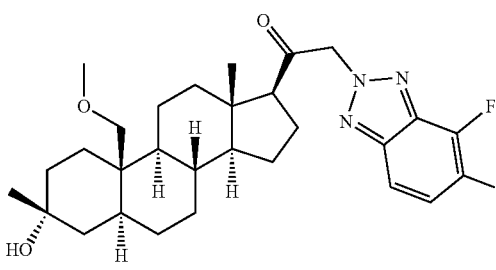
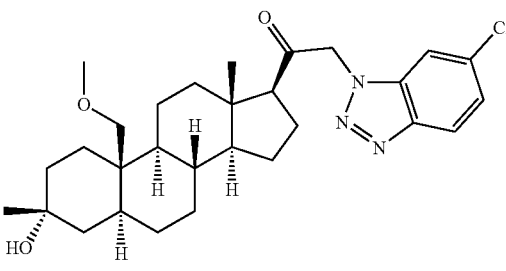

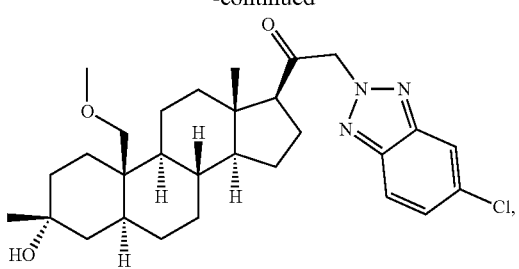
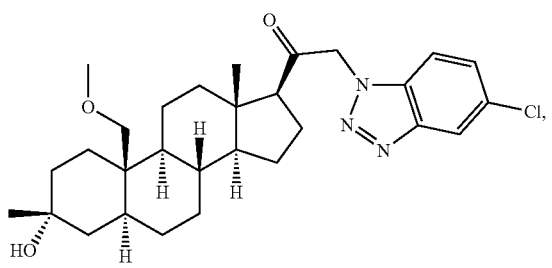
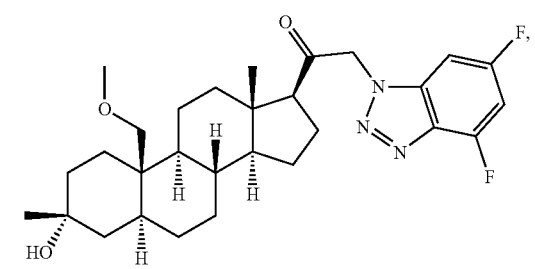
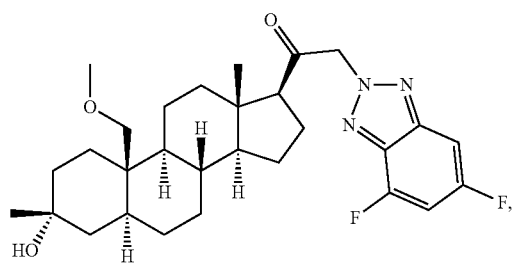
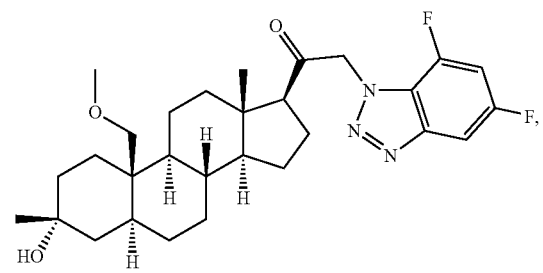
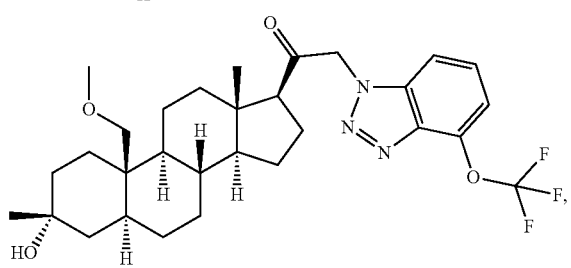
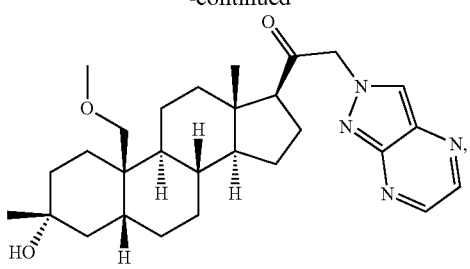
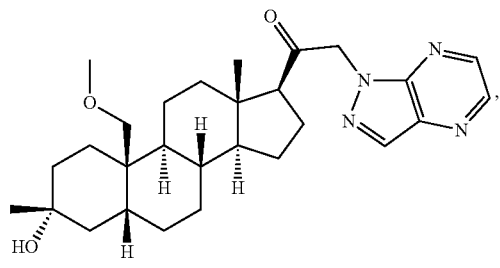
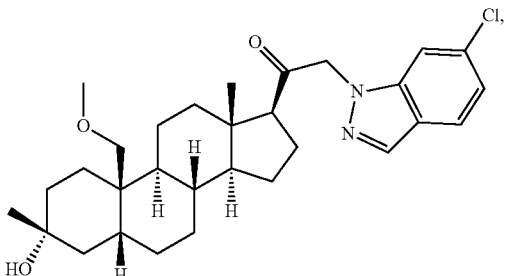
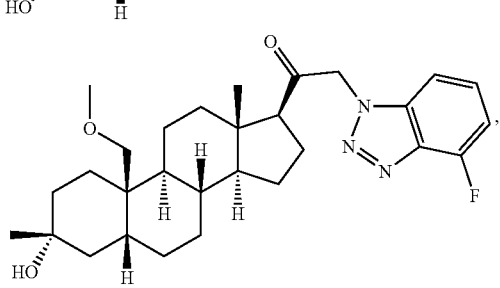
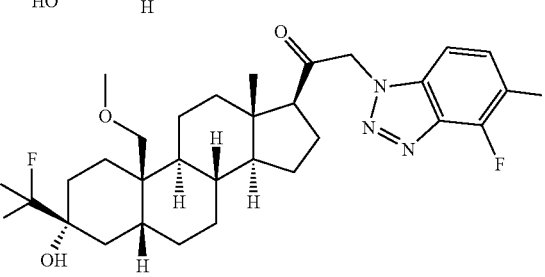
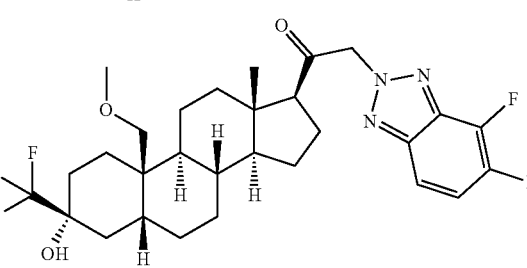

-continued
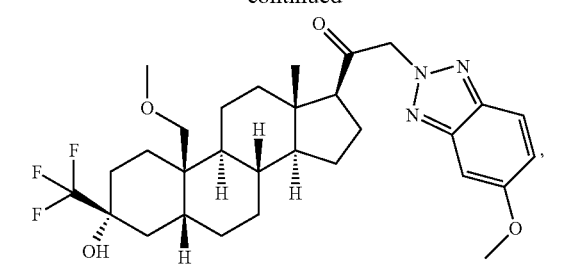
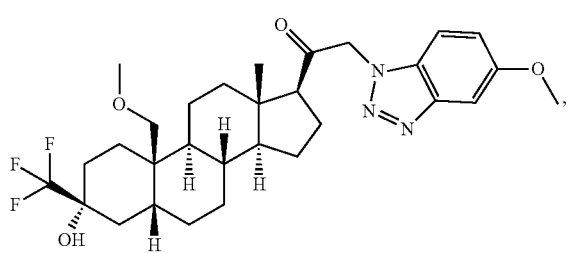
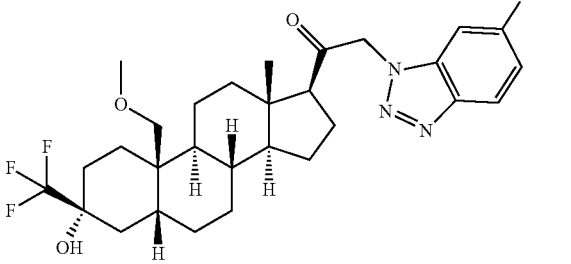
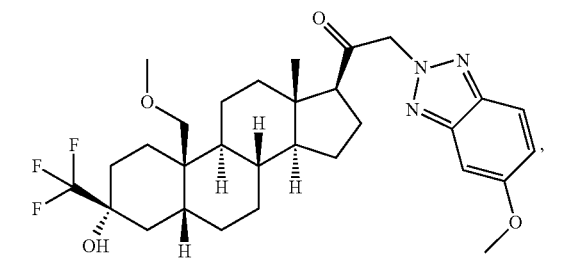
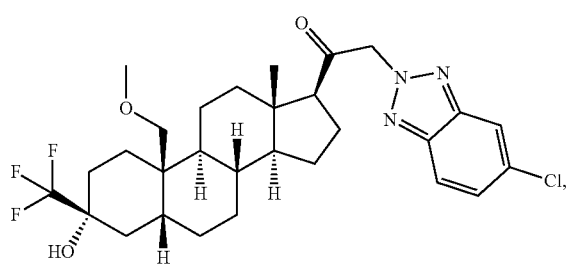
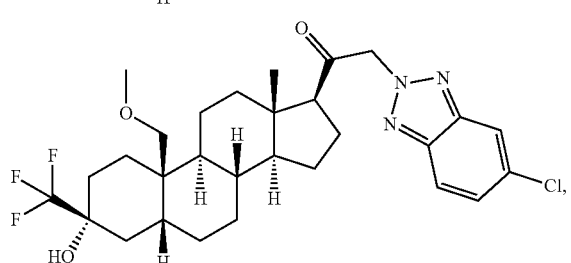
-continued
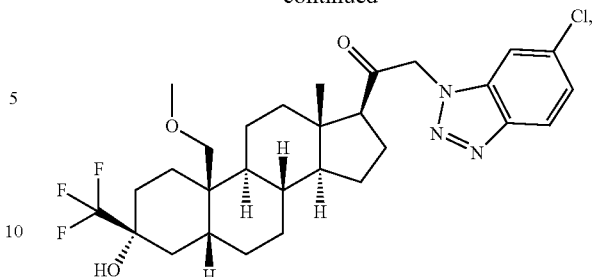
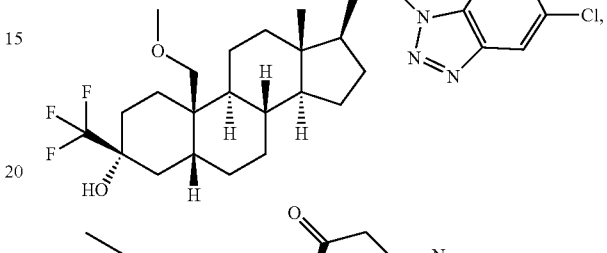
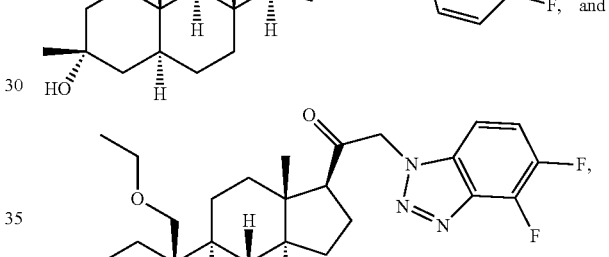
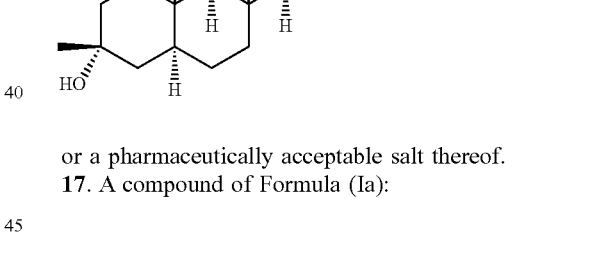
or a pharmaceutically acceptable salt thereof.
17. A compound of Formula (Ia):
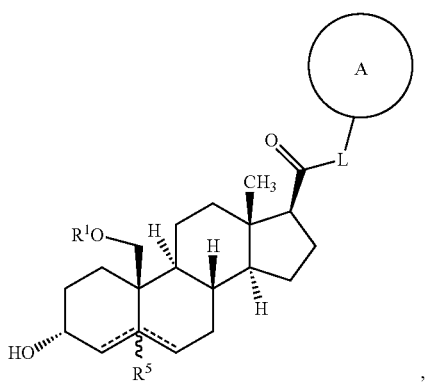
(Ia)
or a pharmaceutically acceptable salt thereof;
wherein:
Ring A is an optionally substituted 5-membered or 6-membered monocyclic heterocyclyl or an optionally substituted 5-membered or 6-membered monocyclic heteroaryl, wherein the heterocyclyl or heteroaryl of ring A comprises 1, 2, 3, or 4 nitrogen atoms and wherein the heterocyclyl or heteroaryl of ring A is linked through a nitrogen atom;

L is —C($R^3$)($R^3$)—, —O—, —S—, or —N$R^3$—;

$R^1$ is unsubstituted $C_1$-$C_6$ alkyl;

each $R^3$ is hydrogen;

$R^5$ is absent or hydrogen; and

----- is a single or double bond, wherein when one of ----- is a double bond, the other ----- is a single bond; and when one of the ----- is a double bond, $R^5$ is absent.

18. The compound or pharmaceutically acceptable salt of claim 17, wherein each ----- is a single bond and $R^5$ is hydrogen.

19. The compound or pharmaceutically acceptable salt of claim 18, wherein $R^1$ is methyl, ethyl, or isopropyl, each of which is unsubstituted.

20. The compound or pharmaceutically acceptable salt of claim 19, wherein $R^1$ is unsubstituted methyl or unsubstituted ethyl.

21. The compound or pharmaceutically acceptable salt of claim 17, wherein the compound of Formula (Ia) is a compound of Formula (Ia-1) or a compound of Formula (Ia-2):

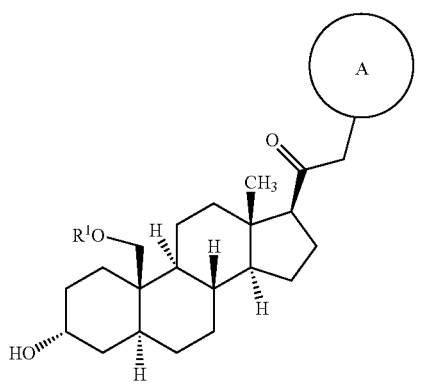

(Ia-1)

or

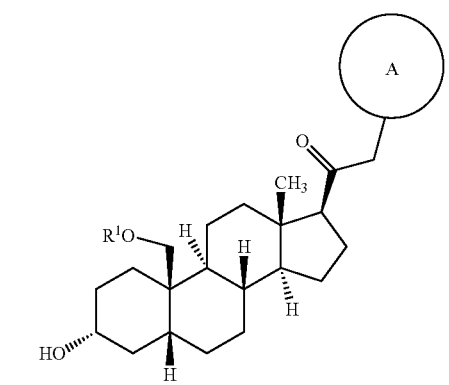

(Ia-2)

, or a pharmaceutically acceptable salt thereof.

22. The compound or pharmaceutically acceptable salt of claim 17, wherein ring A is an optionally substituted 5-membered or 6-membered monocyclic heteroaryl, wherein the heteroaryl of ring A comprises 2, 3, or 4 nitrogen atoms and wherein the heteroaryl of ring A is linked through a nitrogen atom.

23. The compound or pharmaceutically acceptable salt of claim 17, wherein the compound of Formula (Ia) is a compound of Formula (Ia-3) or a compound of Formula (Ia-4):

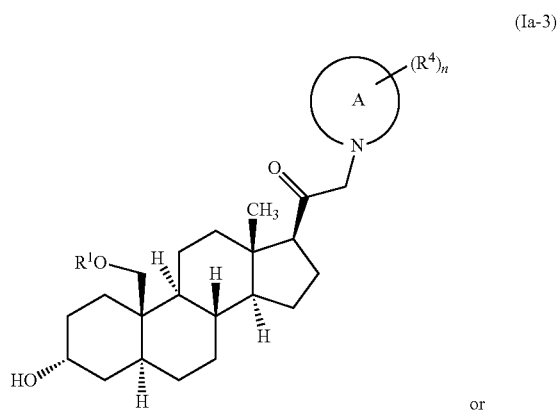

(Ia-3)

or

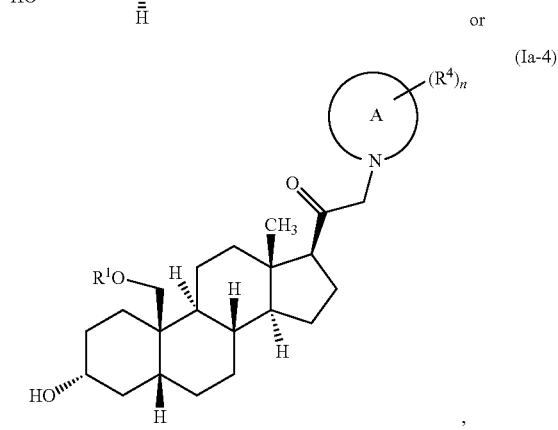

(Ia-4)

, or a pharmaceutically acceptable salt thereof, wherein $R^4$ is cyano, nitro, hydroxy, halo, $C_1$-$C_6$ alkyl, $C_1$-$C_6$ alkoxy, —C(O)$R^a$, —C(O)N($R^b$)($R^c$), —C(O)O$R^a$, —N($R^b$)($R^c$), —OC(O)N($R^b$)($R^c$), —OC(O)O$R^a$, —OC(O)$R^a$, —S(O)$_{0-2}R^a$, —S(O)$_{0-2}$O$R^a$, or —S(O)$_{0-2}$N($R^b$)($R^c$);

each $R^a$ is independently hydrogen or $C_{1-6}$ alkyl;

each $R^b$ and $R^c$ is independently hydrogen, $C_{1-6}$ alkyl, carbocyclyl, heterocyclyl, aryl, heteroaryl, or $R^b$ and $R^c$, together with the nitrogen atom to which they are bound to form a ring; and n is 0, 1, 2, or 3.

24. The compound or pharmaceutically acceptable salt of claim 23, wherein n is 0, and ring A is

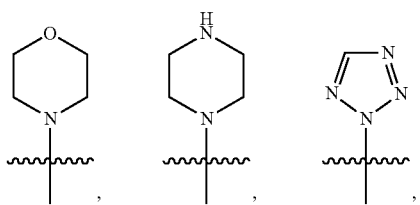

,

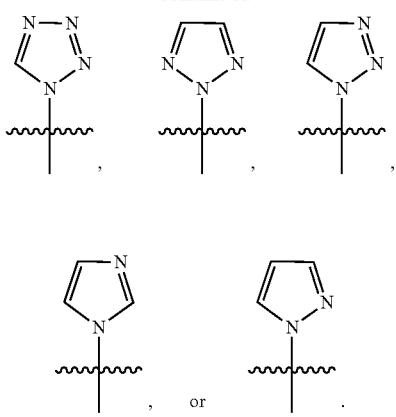

, or .

25. The compound or pharmaceutically acceptable salt of claim 24, wherein n is 0, and ring A is

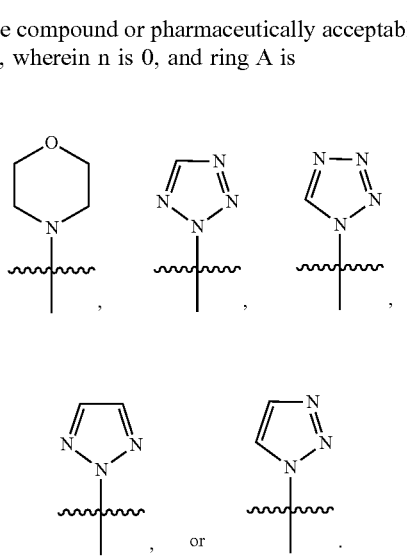

, or .

26. The compound or pharmaceutically acceptable salt of claim 23, wherein n is 1 or 2, and each $R^4$ is independently cyano, halo, $C_{1-6}$ alkyl, $C_{1-6}$ alkoxy, —C(O)$R^a$, or —S(O)$_{0-2}R^a$.

27. The compound or pharmaceutically acceptable salt of claim 26, wherein n is 1, and $R^4$ is —C(O)CH$_3$, —S(O)$_2$CH$_3$, cyano, halo, or $C_{1-6}$ alkyl.

28. A compound selected from

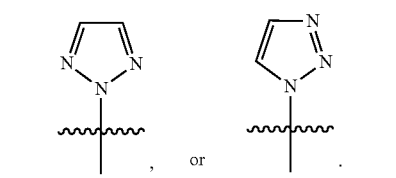

-continued

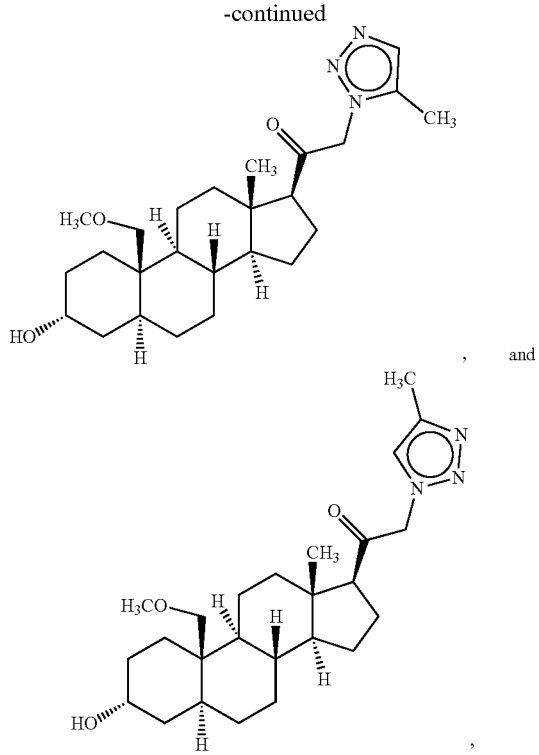

, and or a pharmaceutically acceptable salt thereof.

29. A pharmaceutical composition comprising a compound according to claim 1, or a pharmaceutically acceptable salt thereof and a pharmaceutically acceptable excipient.

30. A method of (a) therapeutically treating depression, insomnia, seizure, epilepsy, tremor or generalized anxiety disorder or (b) inducing sedation or anesthesia in a human subject in need thereof, comprising administering to the human subject a therapeutically effective amount of a compound or pharmaceutically acceptable salt according to claim 1.

31. The method of claim 30, wherein the depression is postnatal depression.

32. The method of claim 30, wherein the compound or pharmaceutically acceptable salt thereof is administered orally.

33. The method of claim 30, wherein the compound or pharmaceutically acceptable salt thereof is administered intramuscularly.

* * * * *